US008399187B2

(12) United States Patent
Murtaugh et al.

(10) Patent No.: US 8,399,187 B2
(45) Date of Patent: Mar. 19, 2013

(54) IDENTIFYING VIRALLY INFECTED AND VACCINATED ORGANISMS

(75) Inventors: Michael P. Murtaugh, Shoreview, MN (US); Craig R. Johnson, Eagan, MN (US)

(73) Assignee: Regents of the University of Minnesota, St. Paul, MN (US)

(*) Notice: Subject to any disclaimer, the term of this patent is extended or adjusted under 35 U.S.C. 154(b) by 44 days.

(21) Appl. No.: 12/576,067

(22) Filed: Oct. 8, 2009

(65) Prior Publication Data

US 2010/0035276 A1 Feb. 11, 2010

Related U.S. Application Data

(63) Continuation of application No. 11/155,830, filed on Jun. 17, 2005, now Pat. No. 7,611,717.

(60) Provisional application No. 60/656,192, filed on Feb. 25, 2005, provisional application No. 60/581,325, filed on Jun. 18, 2004.

(51) Int. Cl.
*C12Q 1/70* (2006.01)
(52) U.S. Cl. .......................................... 435/5; 435/7.1
(58) Field of Classification Search ........................ None
See application file for complete search history.

(56) References Cited

U.S. PATENT DOCUMENTS

| | | | |
|---|---|---|---|
| 3,137,631 A | 6/1964 | Soloway | |
| 3,959,457 A | 5/1976 | Speaker et al. | |
| 4,015,100 A | 3/1977 | Gnanamuthu et al. | |
| 4,122,167 A | 10/1978 | Buynak et al. | |
| 4,205,060 A | 5/1980 | Monsimer et al. | |
| 4,224,412 A | 9/1980 | Dorofeev et al. | |
| 4,452,747 A | 6/1984 | Gersonde et al. | |
| 4,468,346 A | 8/1984 | Paul et al. | |
| 4,554,159 A | 11/1985 | Roizman et al. | |
| 4,606,940 A | 8/1986 | Frank et al. | |
| 4,636,485 A | 1/1987 | van der Smissen | |
| 4,744,933 A | 5/1988 | Rha et al. | |
| 4,753,884 A | 6/1988 | Kit et al. | |
| 4,810,493 A | 3/1989 | Patrick et al. | |
| 4,908,305 A | 3/1990 | Snyder | |
| 4,921,706 A | 5/1990 | Roberts et al. | |
| 4,927,637 A | 5/1990 | Morano et al. | |
| 4,944,948 A | 7/1990 | Uster et al. | |
| 4,683,195 B1 | 11/1990 | Mullis et al. | |
| 5,008,050 A | 4/1991 | Cullis et al. | |
| 5,009,956 A | 4/1991 | Baumann | |
| 5,132,117 A | 7/1992 | Speaker et al. | |
| 5,143,825 A | 9/1992 | Chacko et al. | |
| 5,206,163 A | 4/1993 | Renard et al. | |
| 5,213,759 A | 5/1993 | Castberg et al. | |
| 5,223,409 A | 6/1993 | Ladner et al. | |
| 5,374,530 A | 12/1994 | Nuzzolo et al. | |
| 5,419,907 A | 5/1995 | Paul et al. | |
| 5,476,778 A | 12/1995 | Chladek et al. | |
| 5,498,551 A | 3/1996 | de Jaeger et al. | |
| 5,510,258 A | 4/1996 | Sanderson et al. | |
| 5,580,859 A | 12/1996 | Felgner et al. | |
| 5,587,164 A | 12/1996 | Sanderson et al. | |
| 5,597,721 A | 1/1997 | Brun et al. | |
| 5,620,691 A | 4/1997 | Wensvoort et al. | |
| 5,663,286 A | 9/1997 | Ahmed et al. | |
| 5,674,500 A | 10/1997 | Peeters et al. | |
| 5,677,429 A | 10/1997 | Benfield | |
| 5,683,865 A | 11/1997 | Collins et al. | |
| 5,690,940 A | 11/1997 | Joo | |
| 5,695,766 A | 12/1997 | Paul et al. | |
| 5,698,203 A | 12/1997 | Visser et al. | |
| 5,789,388 A | 8/1998 | Visser et al. | |
| 5,840,563 A | 11/1998 | Chladek et al. | |
| 5,846,805 A | 12/1998 | Collins et al. | |
| 5,858,729 A | 1/1999 | Van Woensel et al. | |
| 5,866,401 A | 2/1999 | Hesse | |
| 5,888,513 A * | 3/1999 | Duran et al. | 424/186.1 |
| 5,910,310 A | 6/1999 | Heinen et al. | |
| 5,925,359 A | 7/1999 | Van Woensel et al. | |
| 5,968,525 A | 10/1999 | Fitzgerald et al. | |
| 5,976,537 A | 11/1999 | Mengeling et al. | |
| 5,977,429 A | 11/1999 | Phillips et al. | |
| 5,989,563 A | 11/1999 | Chladek et al. | |
| 5,998,601 A * | 12/1999 | Murtaugh et al. | 536/23.72 |
| 6,001,370 A | 12/1999 | Burch et al. | |
| 6,015,663 A | 1/2000 | Wesley et al. | |
| 6,033,844 A | 3/2000 | Visser et al. | |

(Continued)

FOREIGN PATENT DOCUMENTS

| | | |
|---|---|---|
| CA | 2103460 A1 | 12/1992 |
| CA | 2290906 C | 12/1992 |

(Continued)

OTHER PUBLICATIONS

Oleksiewicz et al, Journal of Virology, Apr. 2001, vol. 75, No. 7, pp. 3277-3290.*
Oleksiewicz et al, Journal of General Virology, 2002, vol. 83, pp. 1407-1418.*
Oleksiewicz et al, Veterinary Microbiology, 2001, pp. 109-125.*
Klovins et al., "A Long-range Pseudoknot in Qb RNA is Essential for Replication". Journal of Molecular Biology, vol. 294, 1999, pp. 875-884.
Klump et al., "Complete Nucleotide Sequence of Infectious Coxsackievirus B3 cDNA: Two Initial 5' Uridine Residues Are Regained during Plus-Strand RNA Synthesis". Journal of Virology, vol. 64, No. 4, Apr. 1990, pp. 1573-1583.
Klupp, Barbara G. et al., "Sequence and Expression of the Glycoprotein gH Gene of pseudorabies Virus", Virology 182:732-741, 1991.

(Continued)

*Primary Examiner* — Shanon A Foley
(74) *Attorney, Agent, or Firm* — Davis, Brown, Koehn, Shors & Roberts, P.C.; Sean D. Solberg

(57) ABSTRACT

This document provides methods and materials related to assessing organisms for the presence or absence of anti-virus antibodies. For example, this document provides methods and materials that can be used to determine whether or not an organism (e.g., a member of a swine species such as a pig) contains anti-PRRS virus antibodies. In other embodiments, this document provides methods and materials that can be used to determine if a particular organism received a vaccine version of a virus, was infected with a naturally-occurring version of the virus, or is naïve with respect to the virus.

7 Claims, 50 Drawing Sheets

U.S. PATENT DOCUMENTS

| | | | |
|---|---|---|---|
| 6,042,830 A | 3/2000 | Chladek et al. | |
| 6,080,570 A | 6/2000 | Chladek et al. | |
| 6,110,467 A | 8/2000 | Paul et al. | |
| 6,110,468 A | 8/2000 | Collins et al. | |
| 6,194,389 B1 | 2/2001 | Johnston et al. | |
| 6,197,310 B1 | 3/2001 | Wensvoort et al. | |
| 6,241,990 B1 | 6/2001 | Collins et al. | |
| 6,251,397 B1 | 6/2001 | Paul et al. | |
| 6,251,404 B1 | 6/2001 | Paul et al. | |
| 6,268,199 B1 | 7/2001 | Meulenberg et al. | |
| 6,380,376 B1 | 4/2002 | Paul et al. | |
| 6,391,314 B1 | 5/2002 | Allan et al. | |
| 6,455,245 B1 | 9/2002 | Wensvoort et al. | |
| 6,495,138 B1 | 12/2002 | van Nieuwstadt et al. | |
| 6,498,008 B2 | 12/2002 | Collins et al. | |
| 6,500,662 B1 | 12/2002 | Calvert et al. | |
| 6,592,873 B1 | 7/2003 | Paul et al. | |
| 6,641,819 B2 | 11/2003 | Mengeling et al. | |
| 6,660,513 B2 | 12/2003 | Mengeling et al. | |
| 6,773,908 B1 | 8/2004 | Paul et al. | |
| 6,806,086 B2 | 10/2004 | Wensvoort et al. | |
| 6,841,364 B2 | 1/2005 | Yuan et al. | |
| 6,855,315 B2 | 2/2005 | Collins et al. | |
| 6,982,160 B2 | 1/2006 | Collins et al. | |
| 7,018,638 B2 | 3/2006 | Chu et al. | |
| 7,041,443 B2 | 5/2006 | Faaberg et al. | |
| 7,081,342 B2 | 7/2006 | Mengeling et al. | |
| 7,109,025 B1 | 9/2006 | Eloit et al. | |
| 7,122,347 B2 | 10/2006 | Verheije et al. | |
| 7,132,106 B2 | 11/2006 | Calvert et al. | |
| 7,169,394 B2 | 1/2007 | Chu et al. | |
| 7,211,379 B2 | 5/2007 | Ellis et a | |
| 7,232,680 B2 | 6/2007 | Calvert et al. | |
| 7,264,804 B2 * | 9/2007 | Collins et al. | 424/130.1 |
| 7,273,617 B2 | 9/2007 | Yuan et al. | |
| 7,312,030 B2 | 12/2007 | van Rijn et al. | |
| 7,335,361 B2 | 2/2008 | Liao et al. | |
| 7,335,473 B2 | 2/2008 | Wensvoort et al. | |
| 7,368,117 B2 | 5/2008 | Fetzer et al. | |
| 7,611,717 B2 | 11/2009 | Murtaugh et al. | |
| 7,632,636 B2 | 12/2009 | Roof et al. | |
| 7,691,389 B2 | 4/2010 | Calvert et al. | |
| 7,722,878 B2 | 5/2010 | Vaughn et al. | |
| 7,897,343 B2 | 3/2011 | Wensvoort et al. | |
| 8,110,390 B2 | 2/2012 | Faaberg et al. | |
| 2002/0012670 A1 * | 1/2002 | Elbers et al. | 424/204.1 |
| 2002/0098573 A1 | 7/2002 | Meulenberg et al. | |
| 2002/0172690 A1 | 11/2002 | Calvert et al. | |
| 2003/0049274 A1 | 3/2003 | Meulenberg et al. | |
| 2003/0118608 A1 | 6/2003 | Wensvoort et al. | |
| 2003/0157689 A1 | 8/2003 | Calvert et al. | |
| 2003/0219732 A1 | 11/2003 | van Rijn et al. | |
| 2004/0009190 A1 * | 1/2004 | Elbers et al. | 424/199.1 |
| 2004/0132014 A1 | 7/2004 | Wensvoort et al. | |
| 2004/0197872 A1 | 10/2004 | Meulenberg et al. | |
| 2004/0213805 A1 | 10/2004 | Verheije | |
| 2004/0224327 A1 | 11/2004 | Meulenberg et al. | |
| 2004/0253270 A1 | 12/2004 | Meng et al. | |
| 2006/0063151 A1 | 3/2006 | Roof et al. | |
| 2006/0205033 A1 | 9/2006 | Meulenberg et al. | |
| 2006/0240041 A1 | 10/2006 | Meulenberg et al. | |
| 2006/0286123 A1 | 12/2006 | Fetzer et al. | |
| 2007/0003570 A1 | 1/2007 | Murtaugh et al. | |
| 2007/0042000 A1 | 2/2007 | Mengeling et al. | |
| 2008/0268426 A1 | 10/2008 | Murtaugh et al. | |
| 2009/0148474 A1 | 6/2009 | Roof et al. | |
| 2010/0003278 A1 | 1/2010 | Roof et al. | |
| 2010/0028860 A1 | 2/2010 | Roof et al. | |
| 2010/0035276 A1 | 2/2010 | Murtaugh et al. | |
| 2010/0129398 A1 | 5/2010 | Klinge et al. | |
| 2010/0267929 A1 | 10/2010 | Faaberg et al. | |
| 2011/0104201 A1 | 5/2011 | Mengeling et al. | |
| 2011/0117129 A1 | 5/2011 | Roof et al. | |
| 2011/0195088 A1 | 8/2011 | Roof et al. | |

FOREIGN PATENT DOCUMENTS

| | | |
|---|---|---|
| CA | 2102036 C | 5/1994 |
| CA | 2410694 A1 | 12/1999 |
| DE | DD145705 A1 | 1/1981 |
| EP | 0208672 B1 | 1/1987 |
| EP | 0440219 A1 | 8/1991 |
| EP | 0529584 A2 | 3/1993 |
| EP | 0587780 B1 | 3/1994 |
| EP | 0595436 B1 | 5/1994 |
| EP | 0610250 B1 | 8/1994 |
| EP | 0676467 B1 | 10/1995 |
| EP | 0732340 B1 | 9/1996 |
| EP | 0835929 A1 | 4/1998 |
| EP | 0835930 B1 | 4/1998 |
| EP | 0839912 A1 | 5/1998 |
| EP | 1018557 B1 | 7/2000 |
| FR | 2602791 A1 | 2/1988 |
| GB | 2282811 A | 4/1995 |
| GB | 2289279 A | 11/1995 |
| JP | 62198626 A | 9/1987 |
| JP | 7501049 A | 2/1995 |
| JP | 7138186 A | 5/1995 |
| JP | 7289250 A | 11/1995 |
| JP | 9500544 A | 1/1997 |
| JP | 9503926 A | 4/1997 |
| JP | 11509087 B2 | 8/1999 |
| JP | 2002504317 A | 2/2002 |
| WO | WO8803410 A1 | 5/1988 |
| WO | WO8908701 A1 | 9/1989 |
| WO | WO9221375 A1 | 12/1992 |
| WO | WO9302556 A1 | 2/1993 |
| WO | WO9303760 A1 | 3/1993 |
| WO | WO9306211 A1 | 4/1993 |
| WO | WO9307898 A1 | 4/1993 |
| WO | WO9314196 A1 | 7/1993 |
| WO | WO9418311 A1 | 8/1994 |
| WO | WO9528227 A1 | 10/1995 |
| WO | WO9531550 A1 | 11/1995 |
| WO | WO9604010 A1 | 2/1996 |
| WO | WO9606619 A1 | 3/1996 |
| WO | WO9636356 A1 | 11/1996 |
| WO | WO9640932 A1 | 12/1996 |
| WO | WO9700696 A1 | 1/1997 |
| WO | WO9731651 A1 | 9/1997 |
| WO | WO9731652 A1 | 9/1997 |
| WO | WO9807898 A1 | 2/1998 |
| WO | WO9818933 A1 | 5/1998 |
| WO | WO9850426 A1 | 11/1998 |
| WO | WO9855625 A1 | 12/1998 |
| WO | WO9855626 A2 | 12/1998 |
| WO | WO9939582 A1 | 8/1999 |
| WO | WO0053787 A1 | 9/2000 |
| WO | WO0065032 A1 | 11/2000 |
| WO | WO0159077 A1 | 8/2001 |
| WO | WO0190363 A1 | 11/2001 |
| WO | WO02095040 A1 | 11/2002 |
| WO | WO03062407 A1 | 7/2003 |
| WO | WO2006002193 A2 | 1/2006 |
| WO | WO2006034319 A2 | 3/2006 |
| WO | WO2006074986 A2 | 7/2006 |
| WO | WO2008121958 A1 | 10/2008 |
| WO | WO2010025109 A1 | 3/2010 |
| WO | WO2011128415 A1 | 10/2011 |

OTHER PUBLICATIONS

Knowles et al., "Classification of porcine enteroviruses by antigenic analysis and cytopathic effects in tissue culture: Description of 3 new serotypes". Archives of Virology, vol. 62, No. 3, 1979, pp. 201-208.

Kolodziej et al., "Epitope tagging and protein surveillance". Methods in Enzymology, vol. 194, 1991, pp. 508-519.

Kouvelos et al., "Comparison of Bovine, Simian and Human Rotavirus Structural Glycoproteins". Journal of General Virology, vol. 65, Jul. 1984, pp. 1211-1214.

Kreutz, L.C., "Cellular membrane factors are the major determinants of porcine reproductive and respiratory syndrome virus tropism". Virus Research, vol. 53, 1998, pp. 121-128.

Krogh et al., "Predicting Transmembrane Protein Topology with a Hidden Markov Model: Application to Complete Genomes," J. Mol. Biol., 2001;305:567-580.

Kundin, W.D., "Hong Kong A-2 Influenza Virus Infection among Swine during a Human Epidemic in Taiwan". Nature, vol. 228, Nov. 1970, p. 857.

Kuo et al., "A Nested Set of Eight RNAs Is Formed in Macrophages Infected with Lactate Dehydrogenase-Elevating Virus", Journal of Virology, vol. 65, No. 9, Sept. 1991, pp. 5118-5123.

Kusanagi et al., "Isolation and Serial Propagation of Porcine Epidemic Diarrhea Virus in Cell Cultures and Partial Characterization of the Isolate". Journal of Veterinary Medical Science, Vol. 54, No. 2, 1992, pp. 313-318.

Kutsuzawa et al., "Isolation of Human Rotavirus Subgroups 1 and 2 in Cell Culture". Journal of Clinical Microbiology, vol. 16, No. 4, Oct. 1982, pp. 727-730.

Kwang et al., "Antibody and Cellular Immune Responses of Swine Following Immunisation with Plasmid DNA including the PRRS Virus ORF's 4,5,6 and 7", Short Communication. Research in Veterinary Science (1999) vol. 67, pp. 199-201.

Kwang et al., "Cloning, expression, and sequence analysis of the ORF4 gene of the porcine reproductive and respiratory syndrome virus MN-1b". Journal of Veterinary Diagnostic Investigation, vol. 6, No. 3, Jul. 1994, pp. 293-296.

Labarque et al., "Effect of cellular changes and onset of humoral immunity on the replication of porcine reproductive and respiratory syndrome virus in the lungs of pigs". Journal of General Virology, vol. 81, 2000, pp. 1327-1334.

Labarque et al., "Respiratory tract protection upon challenge of pigs vaccinated with attenuated porcine reproductive and respiratory syndrome virus vaccines". Veterinary Microbiology, vol. 95, 2003, pp. 187-197.

Laemmli, "Cleavage of structural proteins during the assembly of the head of bacteriophage T4," Nature, 1974, 227:680-684.

Lai et al., "Coronavirus: how a large RNA viral genome is replicated and transcribed". Infectious Agents and Disease, vol. 3, Nos. 2-3, 1994, pp. 98-105.

Lai et al., "Coronavirus: organization, replication and expression of genome". Annual Review of Microbiology, vol. 33, 1990, pp. 303-333.

Lai et al., "Infectious RNA transcribed from stably cloned full-length cDNA of dengue type 4 virus". Proceedings of the National Academy of Sciences, vol. 88, Jun. 1991, pp. 5139-5143.

Lai M.M.C., "Transcription, Replication, Recombination, and Engineering of Coronavirus Genes," Advances in Experimental Medicine and Biology Corona- and Related Viruses, New York, NY, 1995;463-472.

Larochelle et al., "Detection of porcine reproductive and respiratory syndrome virus in paraffin-embedded tissues: comparision of immunohistochemistry and in situ hybridization", Journal of Virological Methods. 1997; 63: 227-235.

Larochelle et al., "Evaluation of the presence of porcine reproductive and respiratory syndrome virus in packaged pig meat using virus isolation and plymerase chain reaction (PCR) method", Veterinary Microbiology. 1997; 58: 1-8.

Larochelle, R. et al., "Differentiation of North American and European porcine reproductive and respiratory syndrome virus genotypes by in situ hybridization", Journal of Virological Methods 68 (1997) 161-168.

Lawson et al., "Porcine reproductive and respiratory syndrome virus infection of gnotobiotic pigs: sites of virus replication and co-localization with MAC-387 staining at 21 days post-infection," Virus Res., 1997, 51:105-113.

Lazar et al., "Transforming Growth Factor a: Mutation of Aspartic Acid 47 and Leucine 48 Results in Different Biological Activities". Molecular and Cellular Biology, vol. 8, No. 3, Marc. 1988, pp. 1247-1252.

Lee et al., "A DNA-launched reverse genetics system for porcine reproductive and respiratory syndrome virus reveals that homodimerization of the nucleocapsid protein is essential for virus infectivity," Virol., 2005;331:47-62.

Lee et al., "Mutations within the nuclear localization signal of the porcine reproductive and respiratory syndrome virus nucleocapsid protein attenuate virus replication," Virol., 2006; 346:238-250.

Leitner et al., "DNA and RNA-based vaccines: principles, progress and prospects". Vaccine, vol. 18, 2000, pp. 765-777.

Levy et al., "Freeze-drying is an effective method for preserving infectious type C retroviruses". Journal of Virological Methods, Vol. 5, Nos. 3-4, Nov. 1982, pp. 165-171.

Liljestrom et al., "A New Generation of Animal Cell Expression Vectors Based on the Semliki Forest Virus Replicon". Nature Biotechnology, vol. 9, 1991, pp. 1356-1361.

Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.

Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.

Lin et al., "The 3' Untranslated Region of Coronavirus RNA Is Required for Subgenomic mRNA Transcription from a Defective Interfering RNA". Journal of Virology, vol. 70, No. 10, Oct. 1995, pp. 7236-7240.

Liu et al., "A Specific Host Cellular Protein Binding Element Near the 3? End of Mouse Hepatitis Virus Genomic RNA". Virology, vol. 232, No. 1, May 1997, pp. 74-85.

Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.

Loula, T., "Mystery Pig Disease", Agri-Practice, vol. 12, No. 1, Jan.-Feb. 1991, pp. 29-34.

Lowrie et al., "DNA Vaccines Methods and Protocols", Humana Press, Totowa, NJ (2000). Xix p. 529: ill.; 24 cm.

Luytjes et al., "Replication of Synthetic Defective Interfering RNAs Derived from Coronavirus Mouse Hepatitis Virus-A59". Virology, vol. 216, No. 1, Feb. 1996, pp. 174-183.

Lv et al., "An infectious cDNA clone of a highly pathogenic porcine reproductive and respiratory syndrome virus variant associated with porcine high fever syndrome". Journal of General Virology, vol. 89, 2008, pp. 2075-2079.

Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.

Madin, S.H. "Vesicular Exanthema Virus". Virus Infections of Porcines, Elsevier Science Publishers B.V., 1989, pp. 267-271.

Magar et al., "Antigenic Comparison of Canadian and US Isolates of Porcine Reproductive and Respiratory Syndrome Virus Using Monoclonal Antibodies to the Nucleocapsid Protein," Can J Vet. Res., 1995;59:232-234.

Magar et al., "Isolation and Experimental Oral Transmission in Pigs of a Porcine Reproductive and Respiratory Syndrome Virus Isolate", Corona- and reated viruses, 1994, Proceedings of the Sixth International Symposium on corona- and related viruses, Aug. 27, 1994-Sep. 1, 1994, pp. 139-144.

Makabe et al., "Hemagglutination with Ovine Rotavirus". Archives of Virology, vol. 90, 1986, pp. 153-158.

Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.

Makino et al., "Primary Structure and Translation of a Defective Interfering RNA of Murine Coronavirus". Virology, vol. 166, 1988, pp. 550-560.

Malet et al., "from RNA to quasispecies: a DNA polymerase with proofreading activity is highly recommended for accurate assessment of viral diversity," J Virol. Methods, 2003;109:161-170.

Mardassi et al., "Identification of major differences in the nucleosapsid protein genes of a Quebec strain and European strains of porcine reproductive and respiratory syndrome virus," J Gen Virol., 1994;75:681-685.

Mardassi et al., "Molecular analysis fo the Ofs 3 to 7 of procine reproductive and respiratory syndrome virus, Quebec reference strain", 1995 Arch Virol 140: 1405-1418.

Mardassi et al., "Structural Gene Analysis of a Quebec Reference Strain of Porcine Reproductive and Respiratory Syndrome Virus (PRRSV)", Corona- and reated viruses, 1994, Proceedings of the Sixth International Symposium on corona- and related viruses, Aug. 27, 1994-Sep. 1, 1994, pp. 277-281.

Mason, P.W., "Maturation of Japanese encephalitis virus glycoproteins produced by infected mammalian and mosquito cells". Virology, vol. 169, No. 2, Apr. 1989, pp. 354-364.

Masters et al., "Functions of the coronavirus nucleocapsid protein". Coronaviruses and Their Diseases, Plenum Press, New York, pp. 235-238.

Masurel, N., "Swine Influenza Virus and the Recycling of Influenza-A Viruses in Man". The Lancet, Jul. 31, 1976, pp. 244-247.

Mcauliffe et al., "Codon Substitution Mutations at Two Positions in the L Polymerase Protein of Human Parainfluenza Virus Type 1 Yield Viruses with a Spectrum of Attenuation in Vivo and Increased Phenotypic Stability in Vitro". Journal of Virology, vol. 78, No. 4, Feb. 2004, pp. 2029-2036.

McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.

McDaniel, H.A., "African Swine Fever". Diseases of Swine, 5th Edition, Chapter 18, The Iowa State University Press, Ames, Iowa, 1981, pp. 237-245.

Mcferran, J.B., "Reovirus Infection". Diseases of Swine, Fifth Edition, Chapter 28, The Iowa State University Press, Ames, Iowa, 1981, pp. 330-334.

McGuffin et al., "The PSIPRED protein structure prediction server," Bioinformatics Applications Note, 2000;16 (4):404-405.

McIntosh, "Diagnostic Virology". Fields Virology, Ch. 17, Second Edition, vol. 1, 1990, pp. 411-437.

McKinney, W.P., "Fatal Swine Influenza Pneumonia During Late Pregnancy". Archives of Internal Medicine, vol. 150, No. 1, Jan. 1990, pp. 213-215.

McQueen et al., "Influenza in animals". Advances in Veterinary Science, vol. 12, 1968, pp. 285-336.

MeikelJohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.

Melchers et al., "Cross-talk between orientation-dependent recognition determinants of a complex control RNA element, the enterovirus oriR". RNA, vol. 6, 2000, pp. 976-987.

Mendez et al., "Molecular Characterization of Transmissible Gastroenteritis Coronavirus Defective Interfering Genomes: Packaging and Heterogeneity". Virology, vol. 217, 1996, pp. 495-507.

Meng et al., "Characterization of a high-virulence US isolate of porcine reproductive and respiratory syndrome virus in a continuous cell line, ATCC CRL 11171," J Vet. Diagn. Invest., 1996;8:374-381.

Meng et al., "Molecular cloning and nucleotide sequencing of the 3'-terminal genomic RNA of the procine reproductive and respiratory syndrome virus", Journal of General Virology, vol. 75, No. 7, Jul. 1994, pp. 1795-1801.

Meng et al., "Phylogenetic analyses of the putative M (ORF 6) and N (ORF 7) genes of porcine reproductive and respiratory syndrome virus (PRRSV): implication for the existence of two genotypes ofPRRSV in the U.S.A. and Europe," Arch. Virol., 1995;140:745-755.

Meng, X.J., "Heterogeneity of porcine reproductive and respiratory syndrome virus: implications for current vaccine efficacy and future vaccine development". Veterinary Microbiology, vol. 74, 2000, pp. 309-329.

Mengeling et al., "An update of research at the National Animal Disease Center on current field strains of Porcine Reproductive and Respiratory Syndrome (PRRS) virus". Allen D. Leman Swine Conference, 1997, pp. 138-145.

Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.

Mengeling et al., "Clinical Effects of porcine reproductive and respiratory syndrome virus on pigs during the early postnatal interval". American Journal of Veterinary Research, vol. 59, No. 1, Jan. 1998, pp. 52-55.

Mengeling et al., "Comparative safety and efficacy of attenuated single-strain and multi-strain vaccines for porcine reproductive and respiratory syndrome". Veterinary Microbiology, vol. 93, 2003, pp. 25-38.

Mengeling et al., "Comparison among strains of porcine reproductive and respiratory syndrome virus for their ability to cause reproductive failure". American Journal of Veterinary Research, vol. 57, No. 6, Jun. 1996, pp. 834-839.

Mengeling et al., "Mystery Pig Disease: Evidence and Considerations for its Etiology". Proceedings of the Mystery Swine Disease Committee Meeting, Oct. 6, 1990, Denver, Colorado, Livestock Conservation Institute, Madison, WI, USA, pp. 88-90.

Mengeling et al., "Strain specificity of the immune response of pigs following vaccination with various strains of porcine reproductive and respiratory syndrome virus". Veterinary Microbiology, vol. 93, 2003, pp. 13-24.

Meredith, MJ, "Porcine Reproductive and Respiratory Syndrome (PRRS)", Pig Disease Information Center, 1st North American Edition, University of Cambridge, Aug. 1994, pp. 1-57.

Mettenleiter et al., "Isolation of a viable herpesvirus (pseudorabies virus) mutant specifically lacking all four known nonessential glycoproteins". Virology, vol. 179, No. 1, Nov. 1990, pp. 498-503.

Meulenberg et al. "Lelystad Virus, the Causative Agent of Porcine Epidemic Abortion and Respiratory Syndrome (PEARS), Is Related to LDC and EAV". Virology. 192:62-72, 1993.

Meulenberg et al., "An infectious cDNA clone of Porcine Reproductive and Respiratory Syndrome Virus". Coronaviruses and Arteriviruses (Advances in Experimental Medicine and Biology, vol. 440), Ch. 24, 1998, pp. 199-206.

Meulenberg et al., "Characterization of Proteins Encoded by ORFs 2 to 7 of Lelystad Virus". Virology, vol. 206, No. 1, Jan. 1995, pp. 155-163.

Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.

Meulenberg et al., "Infectious Transcripts from Cloned Genome-Length cDNA of Porcine Reproductive and Respiratory Syndrome Virus" Journal of Virology, vol. 72, No. 1, (Jan. 1998) pp. 380-387.

Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.

Meulenberg et al., "Molecular characterization of Lelystad virus". Veterinary Microbiology, vol. 55, 1997, pp. 197-202.

Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.

Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.

Meulenberg et al., "Subgenomic RNAs of Lelystad virus contain a conserved leader-body junction sequence". Journal of General Virology, vol. 74, 1993, pp. 1697-1701.

Meulenberg, J.J.M, PRRSV, The Virus, Veterinary Research, Jan. 2000, vol. 31, 11-21.

Molenkamp et al., "Isolation and Characterization of an Arterivirus Defective Interfering RNA Genome". Journal of Virology, vol. 74, No. 7, 2000, pp. 3156-3165.

Molenkamp et al., "The arterivirus replicase is the only viral protein required for genome replication and subgenomic mRNA transcription". Journal of General Virology, vol. 81, No. 10, 2000, pp. 2491-2496.

Moiling, "Naked DNA for Vaccine or Therapy", Journal of Molecular Medicine, vol. 75 (1997) pp. 242-246.

Montagnon, B.J., "Polio and rabies vaccines produced in continuous cell lines: a reality for Vero cell line". Dev Biol Stand., vol. 70, 1989, pp. 27-47.

Moore, C., "Porcine Proliferative and Necrotyzing Pneumonia Clinical Findings". Presented at American Association of Swine Practitioners, 22nd Annual Meeting, Mar. 3-5, 1991, pp. 443-453.

Moormann et al., "Hog cholera virus: identification and characterization of the viral RNA and the virus specific RNA synthesized in infected swine kidney cells". Virus Research, vol. 11, 1988, pp. 281-291.

Moormann et al., "Infectious RNA Transcribed from an Engineered Full-Length cDNA Template of the Genome of a Pestivirus". Journal of Virology, vol. 70, No. 2, Feb. 1996, pp. 763-770.

Moormann et al., "Molecular cloning and nucleotide sequence of hog cholera virus strain brescia and mapping of the genomic region encoding envelope protein E1". Virology, vol. 177, No. 1, Jul. 1990, pp. 184-198.

Morin et al., "Severe proliferative and necrotizing pneumonia in pigs: A newly recognized disease". Canadian Veterinary Journal, vol. 31, Dec. 1990, pp. 837-839.

Morozov et al., "Sequence analysis of open reading frames (ORFs) 2 to 4 of a U.S. isolate of porcine reproductive and respiratory syndrome virus". Archives of Virology, vol. 140, No. 7, 1995, pp. 1313-1319.

Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.

Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.

Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.

Mukamoto et al., "Immunogenicity in Aujeszky's disease virus structural glycoprotein gVI (gp50) in swine". Veterinary Microbiology, vol. 29, No. 2, Oct. 1991, pp. 109-121.

Murakami, et al., "Difference in growth behavior of human, swine, equine, and avian influenza viruses at a high temperature". Archives of Virology, vol. 100, Nos. 3-4, 1988, pp. 231-244.

Murphy et al., "Immunization Against Virus" in Virology, 2nd Edition, vol. 1, Fields, et al., eds. Raven Press, NY, 1990, pp. 469-502.

Murphy et al., "Virus Taxonomy". Chapter 2 in Fields Virology, 2nd. Edition, Fields, et al., eds, Raven Press, New York, 1990, pp. 9-35.

Murtaugh et al., "Comparison of the structural protein coding sequences of the VR-2332 and Lelystad virus strains of the PRRS virus," Arch. Virol., 1995;140: 1451-1460.

Murtaugh et al., "Genetic Variation in the PRRS Virus," Coronaviruses and Arteriviruses, New York, NY, 1998;787-794.

Murtaugh et al., "Immunological Responses of Swine to Porcine Reproductive and Respiratory Syndrome Virus Infection". Viral Immunology, vol. 15, No. 4, 2002, pp. 533-547.

Murtaugh et al., "Inflammatory cytokines and antigen presenting cell activation," Vet. Immunol. Immunopathol., 2002;87:109-121.

Murtaugh et al., "Role of Viral Proteases in PRRS Immunity, Project Period Sep. 1, 1997-Dec. 31, 2002, no cost extension Sep. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.

Murtaugh, M. "The Evolution of the Swine Veterinary Profession", presented on Swine conference, Sep. 11-14, 1993, The St. Paul Radisson Hotel, St. Paul, Minnesota.

Murtaugh, M.P., "Polymerase Chain Reaction (PCR) Applications in Swine Medicine and Diagnostics", Department of Veterinary PathoBiology.

Murtaugh, Michael P. et al., "Interrelatedness of PRRS virus isolates in North America", Allen D. Leman Swine Conference, vol. 24, 1997, College of Veterinary Medicine, University of Minnesota, pp. 146-149.

Myers et al., "Propagation of avian rotavirus in primary chick kidney cell and MA104 cell cultures". Avian Diseases, vol. 33, No. 3, Jul-Sep. 1989, pp. 578-581.

Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.

Narayanan et al., "Characterization of the Coronavirus M Protein and Nucleocapsid Interaction in Infected Cells". Journal of Virology, vol. 74, No. 17, Sep. 2000, pp. 8127-8134.

Needleman et al., "A General Method Applicable to the Search for Similarities in the Amino Acid Sequence of Two Proteins," J. Mol. Biol., 1970;48:443-453.

Nelsen et al., "Porcine reproductive and respiratory syndrome virus comparison: divergent evolution of two continents," J. Virol., 1999, 73:270-280.

Nelson et al., "Differentiation of U.S. and European Isolates of Porcine Reproductive and Respiratory Syndrome Virus by Monoclonal Antibodies", Journal of Clinical Microbiology, vol. 34, (1993), pp. 3184-3189.

Nelson et al., "High affinity interaction between nucleocapsid protein and leader/intergenic sequence of mouse hepatitis virus RNA". Journal of General Virology, vol. 81, 2000, pp. 181-188.

Nielsen et al., "Generation of an Infectious Clone of VR-2332, a Highly Virulent North American-Type Isolate of Porcine Reproductive and Respiratory Syndrome Virus," J. Virol., Mar. 2003;77(6):3702-3711.

Nishimura et al., "Replication and Synthesis of Japanese Encephalitis Virus Ribonucleic Acids in Vero Cells". Japanese Journal of Microbiology, vol. 15, No. 4, 1971, pp. 309-316.

Nodelijk et al., "A quantitative assessment of the effectiveness of PRRSV vaccination in pigs under experimental conditions". Vaccine, vol. 19, 2000, pp. 3636-3644.

Notice of Opposition by Akzo Nobel against European Patent No. 0 587 780, Nov. 28, 1995, EP.

Notice of Opposition by Cyanamid Iberica against European Patent No. 0 587 780, Nov. 28, 1995, EP.

Nuttall, P.A., "Growth Characteristics of Two Strains of Bovine Virus Diarrhoea Virus". Archives of Virology, vol. 66, 1980, pp. 365-369.

Office Action in CA 2,650,236 dated Feb. 9, 2011.

Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.

Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.

Oleksiewicz, M.B. et al., "Sensitive detection and typing of porcine reproductive and respiratory syndrome virus by RT-PCR amplification of whole viral genes", Veterinary Microbiology 64(1998) 7-22.

Olsthoorn et al., "A conformational switch at the 3' end of a plant virus RNA regulates viral replication". The EMBO Journal, vol. 18, No. 17, 1999, pp. 4856-4864.

Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.

Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.

Ostrowski et al., "Identification of Neutralizing and Nonneutralizing Epitopes in the Porcine Reproductive and Respiratory Syndrome Virus GP5 Ectodomain," J. Virol., May 2002; 76(9):4241-4250. Erratum in J. Virol., Jul. 2002:76 (13):6863.

Pan et al., "Replication of African swine fever virus in cell cultures". American Journal of Veterinary Research, vol. 41, No. 9, Sep. 1980, pp. 1357-1367.

Pardoll et al., "Exposing the Immunology of Naked Dna Vaccines", Immunity—Cambridge, MA, vol. 3, No. 2 (1995) pp. 165-169.

Park et al., "Pathogenesis of plaque variants of porcine reproductive and respiratory syndrome virus in pregnant sows," Am. J. Vet. Res., Mar. 1996;57 (3):320-323.

Parratt et al., "Radioimmunoassay of Antibody and its Clinical Applications". John Wiley & Sons, Chichester, 1982, p. 43.

Parsley et al., "Poly (rC) binding protein 2 forms a ternary complex with the 5'-terminal sequences of poliovirus RNA and the viral 3CD proteinase". RNA, vol. 3, 1997, pp. 1124-1134.

Paton et al., "'Blue ear'disease of pigs," Vet. Rec., 1991, 128:617.

Patriarca, et al., "Lack of Significant Person-to-Person Spread of Swine Influenza-Like Virus Following Fatal Infection in an Immunocomprised Child". American Journal of Epidemiology, Vol. 119, No. 2, 1984, pp. 152-158.

Pattnaik et al., "Comparison of liquid-phase and Mab-blocking ELISA for assessment of the reactivity of monoclonal antibodies to foot-and-mouth disease virus," J. Immunol. Methods, 1994;172:265-267.

Pattnaik et al., "Infectious Defective Interfering Particles of VSV from Transcripts of a cDNA Clone," Cell, Jun. 12, 1992;69:1011-1020.

Pearson et al., "Improved tools for biological sequence comparison". Proceedings of the National Academy of Sciences, vol. 85, Apr. 1988, pp. 2444-2448.

Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.

Pejsak et al., "Clinical signs and economic losses caused by porcine reproductive and respiratory syndrome virus in a large breeding farm". Veterinary Microbiology, vol. 44, 1997, pp. 317-322.

Peng et al., "Analysis of Second-Site Revertants of a Murine Coronavirus Nucleocapsid Protein Deletion Mutant and Construction of Nucleocapsid Protein Mutants by Targeted RNA Recombination". Journal of Virology, vol. 69, No. 6, Jun. 1995, pp. 3449-3457.

Penzes et al., "Characterization of a Replicating and Packaged Defective RNA of Avian Coronavirus Infectious Bronchitis Virus". vol. 203, No. 2, Sep. 1994, pp. 286-293.

Percy et al., "Expression of a Foreign Protein by Influenza A Virus". Journal of Virology, vol. 68, No. 7, Jul. 1994, pp. 4486-4492.

Shibata, Darryl K. et al., "Detection of Human Papilloma Virus in Paraffin-Embedded Tissue Using the Polymerase Chain Reaction", J. Exp. Med. 167:225-230, Jan. 1988.

Shieh et al., "The 5'-End Sequence of the Murine Coronavirus Genome: Implications of Multiple Fusion Sites in Leader-Primed Transcription". Virology, vol. 156, 1987, pp. 321-330.

Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.

Shope et al., "The Susceptibility of Swine to the Virus of Human Influenza". Annual Meeting of the Society of American Bacteriologists in New York, 1936, pp. 791-801.

Shortridge et al., "Geographical Distribution of Swine (HSw1N1) and Hong Kong (H3N2) Influenza Virus Variants in in Pigs in Southeast Asia". Intervirology, vol. 11, No. 1, 1979, pp. 9-15.

Skiadopoulos et al., "Identification of Mutations Contributing to the Temperature-Sensitive, Cold-Adapted, and Attenuation Phenotypes of the Live-Attenuated Cold-Passage 45 (cp45) Human Parainfluenza Virus 3 Candidate Vaccine". Journal of Virology, vol. 73, No. 2, Feb. 1999, pp. 1374-1381.

Smith et al., "Immunofluorescence in the Diagnosis of Bovine Fetal Leptospirosis", The Cornell Veterinarian, vol. 57 (1967) pp. 517-526.

Smith et al., "Isolation of Swine Influenza Virus from Autopsy Lung Tissue of Man". New England Journal of Medicine, vol. 294, Mar. 1976, pp. 708-710.

Smith et al., "San Miguel Sea Lion Virus Isolation, Preliminary Characterization and Relationship to Vesicular Exanthema of Swine Virus". Nature, vol. 244, Jul. 1973, pp. 108-110.

Snijder et al., "A 3'-Coterminal Nested Set of Independently Transcribed mRNAs Is Generated during Berne Virus Replication". Journal of Virology, vol. 64, No. 1, Jan. 1990, pp. 331-338.

Snijder et al., "Identification of a Novel Structural Protein of Arteriviruses". Journal of Virology, vol. 73, No. 8, Aug. 1999, pp. 6335-6345.

Snijder et al., "Non-structural proteins 2 and 3 interact to modify host cell membranes during the formation of the arterivirus replication complex". Journal of General Virology, vol. 83, 2001, pp. 985-994.

Snijder et al., "Proteolytic Processing of the Replicase ORF1a Protein of Equine Arteritis Virus". Journal of Virology, vol. 68, No. 9, Sept. 1994, pp. 5755-5764.

Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.

Snijder et al., "The molecular biology of arteriviruses," J Gen. Virol., 1998;79:961-979.

Snijder et al., "Toroviruses: replication, evolution and comparison with other members of the coronavirus-like superfamily". Journal of General Virology, vol. 74, 1993, pp. 2305-2316.

Spaan et al., "Coronaviruses: Structure and Genome Expression". Journal of General Virology, vol. 69, 1988, pp. 2939-2952.

Stephen et al., " Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.

Stephen et al., "Swine influenza virus vaccine: potentiation of antibody responses in rhesus monkeys". Science, vol. 197, No. 4310, 1977, pp. 1289-1290.

Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.

Stevenson et al., "Idiotypic DNA Vaccines Against B-cell Lymphoma", Immunology Reviews, vol. 145 (1995) pp. 211-228.

Stim, T.B., "Arbovirus Plaquing in Two Simian Kidney Cell Lines". Journal of General Virology, vol. 5, No. 3, Oct. 1969, pp. 329-338.

Suarez et al., "Direct Detection of the porcine reproductive and respiratory syndrome (PRRS) virus by reverse polymerase chain reaction (RT-PCR)" Arch. Vir. 135:89-99, 1994.

Suarez et al., "Phylogenetic relationships of European strains of porcine reproductive and respiratory syndrome virus (PRRSV) inferred from DNA sequences of putative ORF-5 and ORF-7 genes". Virus Research, vol. 42, Nos. 1-2, Jun. 1996, pp. 159-165.

Sumiyoshi et al., "Infectious Japanese Encephalitis Virus RNA Can Be Synthesized from in Vitro-Ligated cDNA Templates". Journal of Virology, vol. 66, No. 9, Sep. 1992, pp. 5425-5431.

Tahara et al., "Coronavirus Translational Regulation: Leader Affects mRNA Efficiency". Virology, vol. 202, No. 1, Aug. 1994, pp. 621-630.

Tao et al., "Host Range Restriction of Parainfluenza Virus Growth Occurs at the Level of Virus Genome Replication". Virology, vol. 220, 1996, pp. 69-77.

Tauraso et al., "Simian Hemorrhagic Fever: III. Characterization of a Viral Agent". The American Journal of Tropical Medicine and Hygiene, vol. 17, No. 3, May 1968, pp. 422-431.

Terpstra et al., "Experimental Reproduction of Porcine Epidemic Abortion and Respiratory Syndrome (Mystery Swine Disease) by Infection with Lelystad Virus: Koch's Postulates Fulfilled", The Veterinary Quarterly, vol. 13, (1991) pp. 131-136.

Thacker, B., "Clinical Manifestations of PRRS Virus". 2003 PRRS Compendium: Second Edition, National Pork Board, Des Moines, IA, 2003, pp. 7-15.

Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.

Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.

Theil et al., "Partial characterization of a bovine group a rotavirus with a short genome electropherotype". Journal of Clinical Microbiology, vol. 26, No. 6, Jun. 1988, pp. 1094-1099.

Thompson et al., "The CLUST AL_X windows interface: flexible strategies for multiple sequence alignment aided by quality analysis tools," Nucleic Acids Res., 1997 ;25(24):4876-4882.

Thomson et al., "Ontario. Proliferative and necrotizing pneumonia (PNP) of swine: the Ontario situation". Canadian Veterinary Journal, vol. 32, May 1991, p. 313.

Thouless et al., "Isolation of two lapine rotaviruses: Characterization of their subgroup, serotype and RNA electropherotypes". Archives of Virology, vol. 89, Nos. 1-4, 1986, pp. 161-170.

Tian et al.' "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.

Timony, P.J. "Equine Viral Arteritis", Manual of Standards for Diagnostic Tests and Vaccines, 1992, pp. 493-500.

Tobita et al., "Plaque Assay and Primary Isolation of influenza a Viruses in an Established Line of Canine Kidney Cells (MDCK) in the Presence of Trypsin". Medical Microbiology and Immunology, vol. 162, No. 1, Dec. 1975, pp. 9-14.

Todd et al., "Development of an adjuvant-active nonionic block copolymer for use in oil-free subunit vaccines formulations". Vaccine, vol. 15, No. 5, 1997, pp. 564-570.

Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.

Truong et al., "A highly pathogenic porcine reproductive and respiratory syndrome virus generated from an infectious cDNA clone retains the in vivo virulence and translnissibility properties of the parental virus," Virol., 2004;325:308-319.

Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.

Ulmer et al., "Enhancement of DNA vaccine potency using conventional aluminum adjuvants". Vaccine, vol. 18, 2000, pp. 18-28.

Urasawa et al., "Sequential Passages of Human Rotavirus in Ma-104 Cells". Microbiology and Immunology, vol. 25, No. 10, 1981, pp. 1025-1035.

Van Alstine, W.G., "Mystery Swine Disease in the United States". The New Pig Disease: Porcine Respiration and Reproductive Syndrome. A Report on the Seminar/Workshop Held in Brussels by the European Commission (Directorate-General for Agriculture), Apr. 29-30, 1991, pp. 65-70.

Van Alstine, W.G., "Past Diagnostic Approaches and Findings and Potentially Useful Diagnostic Strategies". Proceedings Mystery Swine Disease Committee Meeting, Oct. 6, 1990, pp. 52-58.

Van Berlo et al., "Equine Arteritis Virus-Infected Cells Contain Six Polyadenylated Virus-Specific RNAs". Virology, vol. 118, 1982, pp. 345-352.

Van Der Linden et al., "Virological kinetics and immunological responses to a porcine reproductive and respiratory syndrome virus infection of pigs at different ages". Vaccine, vol. 21, 2003, pp. 1952-1957.

Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.

Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.

Plagemann and Moennig, "Lactate Dehydrogenase-elevating virus, equine arteritis virus, and simian hemorrhagic fever virus: a new group of positive-strnad RNA viruses," Adv. Vir. Res., 1992 41:99-192.

Plagemann et al., "The primary neutralization epitope of porcine respiratory and reproductive syndrome virus strain VR-2332 is located in the middle of the GP5 ectodomain," Arch. Virol.,2002;147:2327-2347.

Plagemann P.G., "Complexity of the Single Linear Neutralization Epitope of the Mouse Arterivirus Lactate Dehydrogenase-Elevating Virus," Virology, 2001;290:11-20.

Plagemann, "Lactate Dehydrogenase-elevating virus and related viruses," Fields Virology, 1996, 3rd ed. Fields et al. (eds.), Philadelphia, Lippincott-Raven, p. 1105-1120.

Plotkin, Stanley A. MD et al., "New Technologies for Making Vaccines", Vaccines, 1988, 568-575.

Pol et al., "Pathological, ultrastructural, immunohistochemical changes caused by Lelystad virus in experimentally induced infections of mystery swine disease (synonym: porcine epidemic abortion and respiratory syndrome (PEARS))". Veterinary Quarterly, vol. 13, No. 3, Jul. 1991, pp. 137-143.

Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.

Polson et al., "Financial Implications of Mystery Swine Disease (MSD)". 1993, pp. 8-28.

Polson, DD, "Answers to Your Questions on PRRS". NOBL Laboratories, 1993, 18 pages.

Polson, DD, "RespPRRS a PRRS Vaccine Review", NOBL Laboratories, 1993, 22 pages.

Porcine reproductive and respiratory syndrome virus antibody test kit, 1997, IDEXX Laboratories, 4 pages.

Poser, C.M., "Swine Influenza Vaccination: Truth and Consequences". Archives of Neurology, vol. 42, No. 11, 1985, pp. 1090-1092.

Potgieter et al., "Isolation of Swine Influenza Virus in Oklahoma". Journal of the American Veterinary Medical Association, vol. 171, No. 8, 1977, pp. 758-760.

Potts et al., "Peroxidase-labeled primary antibody method for detection of pestivirus contamination in cell cultures". Journal of Virological Methods, vol. 26, No. 1, Oct. 1989, pp. 119-124.

Prager et al., "Widespread distribution of lysozyme g in egg white of birds," J. Biol. Chem., 1974, 249(22):7295-7297.

Quaife, T. "Mystery Agent Isolated! Isolation of the etiological agent behind mystery swine disease is a major breakthrough". Swine Practitioner, Mystery Disease: Part 8, Nov. 1991, pp. 4-7.

Reed et al., "A Simple Method of Estimating Fifty Per Cent Endpoints"., The American Journal of Hygiene, vol. 27, No. 3, May 1938, pp. 493-497.

Reed et al., "Persistent Respiratory Virus Infection in Tracheal Organ Cultures". British Journal of Experimental Pathology, vol. 50, 1969, pp. 378-388.

Response to Opposition to European Patent No. 0 587 780, Aug. 30, 1996.

Rice et al., "Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants". Journal of Virology, vol. 61, No. 12, Dec. 1987, pp. 3809-3819.

Roberts and Bazer, "The functions of uterine secretions," J. Reprod. Fert., 1988, 82:875-892.

Roberts et al., "Abortion in Swine". Veterinary Ostetrics and Genital Diseases, Edwards Brothers, Inc., Ann Arbor, 1986, pp. 180-192.

Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.

Ropp et al., "Characterization of Emerging European-Like Porcine Reproductive and Respiratory Syndrome Virus Isolates in the United States," J. Virol., Apr. 2004; 78(7):3684-3703.

Rossow et al., "Experimental porcine reproductive and respiratory syndrome virus infection in one-, four-, and 10-, week-old pigs". Journal of Veterinary Diagnostic Investigation, vol. 6, 1993, pp. 3-12.

Rossow et al., "Pathogenesis of Porcine Reproductive and Respiratory Syndrome Virus Infection in Gnotobiotic Pigs", Veterinary Pathology, vol. 32, No. 4, (1995) pp. 361-373.

Rossow K.D., "Porcine Reproductive and Respiratory Syndrome," Vet. Pathol., 1998;35:1-20.

Rost et al., "Topology prediction for helical transmembrane proteins at 86% accuracY,"Protein Sci., 1996;5:1704-1718.

Rost et al.,"The PredictProtein server," Nucleic Acids Res., 2004;32(Web Server issue):W321-326.

Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.

Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.

Rottier et al., "Predicted Membrane Topology of the Coronavirus Protein E1". Biochemistry, vol. 25, 1986, pp. 1335-1339.

Rovira et al., "Experimental Inoculation of Conventional Pigs with Porcine Reproductive and Respiratory Syndrome virus and Porcine Circovirus 2", J. Virol, Apr. 2002, vol. 76, No. 7, pp. 3232-3239.

Rowland et al., "The localization of porcine reproductive and respiratory syndrome virus nucleocapsid protein to the nucleolus of infected cells and identification of a potential nucleolar localization signal sequence," Virus Res., 1999;64:1-12.

Sagripanti et al., "The Cap Structure of Simian Hemorrhagic Fever Virion RNA". Virology, vol. 151, 1986, pp. 143-150.

Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.

Saif, L.J., "Coronavirus Immunogens". Veterinary Microbiology, vol. 37, No. 3-4, Nov. 1993, pp. 285-297.

Sambrook et al., Molecular Cloning: A Laboratory Manual, Books 1-3, Cold Spring Harbor Laboratory Press, Cold Spring Harbor, NY, 1989; title page, publisher's page and table of contents only (30) pgs.

Sarnow, P. "Role of 3'-End Sequences in Infectivity of Poliovirus Transcripts Made in Vitro". Journal of Virology, vol. 63, No. 1, Jan. 1989, pp. 467-470.

Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.

Schmidt et al., "Infection of Influenza a Viruses of Tracheal Organ Cultures Derived from Homologous and Heterologous Hosts". The Journal of Infectious Diseases, vol. 129, No. 1, 1974, pp. 28-36.

Scott, F.W., "Immunization against feline coronaviruses". Advances in Experimental Medicine and Biology, vol. 218, 1987, pp. 569-576.

Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.

Seal et al., "Isolation of caliciviruses from skunks that are antigenically and genotypically related to San Miguel sea lion virus Original Research". Virus Research, vol. 37, No. 1, Jun. 1995, pp. 1-12.

Seneca, H., "Influenza: epidemiology, etiology, immunization and management". Journal of American Geriatrics Society, vol. 28, No. 6, Jun. 1980, pp. 241-250.

Sethna et al., "Coronavirus subgenomic minus-strand RNAs and the potential for mRNA replicons". Proceedings of the National Academy of Sciences, vol. 86, Jul. 1989, pp. 5626-5630.

Setzer et al., "Size Heterogeneity in the 3' End of Dihydrofolate Reductase Messenger RNAs in Mouse Cells". Cell, vol. 22, Nov. 1980, pp. 361-370.

Shaw et al., "Experimental rotavirus infection in three-week-old pigs". American Journal of Veterinary Research, vol. 50, No. 11, Nov. 1989, pp. 1961-1965.

Shen et al., "Determination of the complete nucleotide sequence of a vaccine strain of porcine reproductive and respiratory syndrome virus and identification of the Nsp2 gene with a unique insertion," Arch. Virol.,2000;145:871-883.

"Dutch Team Isolates Mystery Pig Disease Agent", Animal Pharm, vol. 230, Abstract No. 00278268, Jun. 21, 1991, p. 21.

"For purification of viral RNA from Plasma, Serum, Cell-free body fluids, Cell-Culture supernatants". QIAamp® Viral RNA Mini Kit Handbook, QIAGEN, Jan. 1999, Cat #52906, pp. 1-35.

"Frontiers closing to mystery disease pigs". Animal Pharm., No. 228, May 24, 1991, p. 2.

"Revision of the taxonomy of the Coronavirus, Torovirus, and Arterivirus genera". Archives of Virology, vol. 135, 1994, pp. 227-239.

Abdallah et al., "Non-Viral Gene Transfer: Applications in Developmental Biology and Gene Therapy", Biology of the Cell, vol. 85, No. 1 (1995), pp. 1-7.

Abstracts of Papers Presented at the 71st Annual Meeting of the Conference of Research Workers in Animal Disease, No.'s 1-6, Nov. 5-6, 1990, 2 pages.

Aksenova et al., "Cultivation of the rabies virus in the continuous kidney cell line 4647 from the green marmoset". Vopr. Virusol., vol. 30, No. 2, 1985, pp. 180-182. (See Axenova for English Abstract).

Albina et al., "Immune responses in pigs infected with porcine reproductive and respiratory syndrome virus (PRRSV)". Veterinary Immunology and Immunopathology, vol. 61, 1998, pp. 49-66.

Albina, "Porcine reproductive and respiratory syndrome: Ten years of experience (1986-1996) with this undesirable virus infections," Veterinary Research (Paris), 1997, 28(4): 305-352.

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.

Allende et al., "Mutations in the genome of porcine reproductive and respiratory syndrome virus responsible for the attenuation phenotype," Arch. Virol., 2000, 145(6):1149-1161.

Allende et al., "North American and European porcine reproductive and respiratory syndrome viruses differ in non-structural protein coding regions," J. Gen. Virol., 1999;80:307-315.

Altschul et al., "Basic Local Alignment Search Tool". Journal of Molecular Biology, vol. 215, 1990, pp. 403-410.

Andreyev et al., "Genetic variation and phylogenetic relationships of 22 porcine reproductive and respiratory syndrome virus (PRRSV) field strains based on sequence analysis of open reading frame 5". Archives of Virology, vol. 142, 1997, pp. 993-1001.

Ashworth et al., "Antibody-dependent cell-mediated cytotoxicity (ADCC) in Aujeszky's disease". Archives of Virology, vol. 59, No. 4, 1979, pp. 307-318.

Ausubel et al. (eds.), "Purification of proteins by precipitation," Short Protocols in Molecular Biology, 1992, Ch. 10, Section VI, Green Publishing Associates and John Wiley & Sons.

Ausubel, et al., "Current Protocols in Molecular Biology" vol. 1, (1994), Table of Contents.

Axenova, T.A. "Propagation of Rabies Vaccine Virus in Continuous Green Monkey Kidney Cells 4647". Vopr. Virusol., vol. 30, No. 2, 1985, p. 182. (English Abstract of Aksenova Reference.).

Backstrom et al., "Respiratory Diseases of Swine". Veterinary Clinics of North America: Large Animal Practice, vol. 4, No. 2, Nov. 1982, pp. 259-276.

Bairoch et al., "The PROSITE database, its status in 1997," Nucleic Acids Res., 1997;25(1):217-221.

Baldo et al., "Comparison of different blocking agents and nitrocelluloses in the solid phase detection of proteins by labelled antisera and protein A," J. Biochem. Biophys. Meth., 1986, 12:271-279.

Bardfoed, Annette M. et al., DNA vaccination of pigs with open reading fram 107 of PRRS virus , Vaccine, vol. 22, 3628-3641, Apr. 10, 2004.

Barfoed et al., "DNA vaccination of pigs with open reading frame 1-7 of PRRS virus". Vaccine, vol. 22, 2004, pp. 3628-3641.

Baric et al., "Interactions between Coronavirus Nucleocapsid Protein and Viral RNAs: Implications for Viral Transcription". Journal of Virology, vol. 62, No. 11, Nov. 1988, pp. 4280-4287.

Baric et al., "Subgenomic Negative-Strand RNA Function during Mouse Hepatitis Virus Infection". Journal of Virology, vol. 74, No. 9, May 2000, pp. 4039-4046.

Bautista et al., "Comparison of porcine alveolar macrophages and CL 2621 for the detection of porcine reproductive and respiratory syndrome (PRRS) virus and anti-Prrs antibody," J. Vet. Diagn. Invest., 1993;5:163-165.

Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Beale, AJ, "Vaccines and antiviral drugs". Principles of bacteriology, virology and immunity, vol. 3, Ch. 86, 1984, pp. 147-161.
Beare et al., "Further Studies in Man of Man of HSw1N1 Influenza Viruses". Journal of Medical Virology, vol. 5, 1980, pp. 33-38.
Beghi et al., "Guillain-Barré Syndrome: Clinicoepidemiologic Features and Effect of Influenza Vaccine". Archives of Neurology, vol. 42, No. 11, 1985, pp. 1053-1057.
Bendtsen et al., "Improved Prediction of Signal Peptides: SignalP 3.0," J. Mol. Biol., 2004;340:783-795.
Benfield et al, Characterization of swine infertility and respiratory syndrome (SIRS) virus (isolate ATCC VR-2332), J. Vet. Diagn. Invest. 4:127-133, 1992.
Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.
Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.
Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.
Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.
Bierk et al., "Diagnostic investigation of chronic porcine reproductive and respiratory syndrome virus in a breeding herd of pigs," Vet. Rec., 2001, 148:687-690.
Bilodeau et al., "Porcine Reproductive and Respiratory Syndrome' in Quebec". The Veterinary Record, Aug. 3, 1991, p. 102.
Blackburn et al., "Use of human influenza vaccine to protect against blue-eared pig disease". Veterinary Record, vol. 129, No. 1, Jul. 1991, p. 19.
Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.
Bouillant et al., "Viral Susceptibility of a Cell Line Derived from the Pig Oviduct". Canadian Journal of Comparative Medicine, vol. 39, 1975, pp. 450-456.
Boursnell et al., "Sequence of the membrane protein gene from avian coronavirus IBV". Virus Research, vol. 1, 1984, pp. 303-313.
Boursnell et al., "Completion of the Sequence of the Genome of the Coronavirus Avian Infectious Bronchitis Virus". Journal of General Virology, vol. 68, 1987, pp. 57-77.
Bowie et al., "Deciphering the Message of Protein Sequences: Tolerance to Amino Acid Substitutions". Science, vol. 247, 1990, pp. 1306-1310.
Boyer et al., "Infectious Transcripts and cDNA Clones of RNA Viruses". Virology, vol. 198, No. 2, Feb. 1994, pp. 415-426.
Bramel-Verheije et al., "Expression of a Foreign Epitope by Porcine Reproductive and Respiratory Syndrome Virus". Virology, vol. 278, 2000, pp. 380-389.
Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.
Brenner et al., "A Negative Staining Method for High Resolution Electron Microscopy of Viruses". Biochimica Et Biophysica Acta, vol. 34, 1959, pp. 103-110.
Brinton-Darnell et al., "Structure and chemical-physical characteristics of lactate dehydrogenase-elevating virus and its RNA". Journal of Virology, vol. 16, No. 2, Aug. 1975, pp. 420-433.
Brinton-Darnell, M. "Lactate Dehydrogenase-Elevating, Equine Arteritis and Lelystad Viruses". Encyclopedia of Virology, vol. 2, 1999, pp. 763-771.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, pp. 37-38.
Wu et al., "A 10-kDa Structural Protein of Porcine Reproductive and Respiratory Syndrome Virus Encoded by ORF2b," Virology, 2001;287:183-191.
Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yang et al., "Developing Particle-Mediated Gene Transfer Technology for Research into Gene Therapy of Cancer", Molecular Medicine Today, vol. 2, No. Ref. (1996) pp. 476-481.
Yoon et al., "A modified serum neutralization test for the detection of antibody to porcine reproductive and respiratory syndrome virus in swine sera", J. Vet. Dign. Invest., 1994, 6:;289-292.
Yoon et al., "An Indirect Fluorescent Antibody Test for the Detection of Antibody to Swine Infertility and Respoiratory Syndrome Virus in Swine Area" Journal of Veterinary Diagnostic Investigation, vol. 4 (1992) pp. 144-147.
Yoon et al., "Characterization of the humoral immune response to porcine reproductive and respiratory syndrome (PRRS) virus infection," J. Vet. Diagn. Invest., 1995, 7:305-312.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Genetic and Antigenic Stability of PRRS Virus in Pigs. Field and experimental prospectives," The Nidoviruses (Coronaviruses and Arteriviruses), New York, NY, 2001, 25-30.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.
Yuan et al., "Characterization of heteroclite subgenomic RNAs associated with PRRSV infection," Virus Res., 2004;105:75-87.
Yuan et al., "Complete genome comparison of porcine reproductive and respiratory syndrome virus parental and attenuated strains," Virus Res., 2001;74:99-110.
Yuan et al., "Erratum to 'Complete genome comparison of porcine reproductive and respiratory syndrome virus parental and attenuated strains '[Virus Research 74 (2001) 99-110]". Virus Research, vol. 79, 2001, p. 187.
Yuan et al., "Heteroclite Subgenomic RNAs are Produced in Porcine Reproductive and Respiratory Syndrome Virus Infection," Virology, 2000;275: 158-169.
Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.
Yuan et al., "Recombination between North American strains of porcine reproductive and respiratory syndrome virus," Virus Res., 1999;61:87-98.
Yuan et al., American Society for Virology, 16th Annual Meeting, Bozeman, Montana, Jul. 19-23, 1997, Abstract P29-5, p. 229.
Zeijst, et al., "The Genome of Equine Arteritis Virus". Virology, vol. 68, 1975, pp. 418-425.
Zhou et al., "Generation of cytotoxic and humoral immune responses by nonreplicative recombinant Semliki Forest virus". Proceedings of the National Academy of Sciences, vol. 92, Mar. 1995, pp. 3009-3013.
Ziebuhr et al., "Virus-encoded proteinases and proteolytic processing in the Nidovirales," J. Gen. Virol., 2000;81:853-879.
Zimmerman et al., "General overview of PRRSV: A perspective from the United States". Veterinary Microbiology, vol. 55, Nos. 1-4, Apr. 1997, pp. 187-196.

Van Der Most et al., "A Domain at the 3' End of the Polymerase Gene Is Essential for Encapsidation of Coronavirus Defective Interfering RNAs". Journal of Virology, vol. 65, No. 6, Jun. 1991, pp. 3219-3226.
Van Dinten et al., "An infectious arterivirus cDNA clone: Identification of a replicase point mutation that abolished discontinuous mRNA transcription". Proceedings of the National Academy of Sciences, vol. 94, Feb. 1997, pp. 991-996.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase Is Mediated by nsp4 Serine Protease and Is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.
Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
vanNieuwstadt et al., "Proteins Enclosed by Open Reading Frames 3 and 4 of the Genome of Lelystad Virus (Arteriviridae) Are Structural Proteins of the Virion", Journal of Virology, vol. 70, No. 7, (1996) pp. 4767-4772.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Kissing Interaction between 3' Noncoding and Coding Sequences Is Essential for Porcine Arterivirus RNA Replication". Journal of Virology, vol. 76, No. 3, Feb. 2002, pp. 1521-1526.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins," Gene, 1991;100:189-194.
VIIIth International Symposium on Nidoviruses (Corona and Arteriviruses), May 20-25, 2000, 32 pages.
Visser, Nicolaas, "Declaration of Dr. N. Visser". Nov. 14, 1995, pp. 1-11.
Vogel et al., "Nucleic Acid Vaccines" Clinical Microbiology Reviews, vol. 8, No. 3 (1995) pp. 406-410.
Von Busse, F.W., Epidemiologic Studies on Porcine Reproductive and Respiratory Syndrome (PRRS). Tierarztliche Umschau, Dec. 1991, pp. 708-717 (Abstract in English p. 711).
Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.
Waltner-Toews et al., "A Field Trial to Evaluate the Efficacy of a Combined Rotavirus-Coronavirus/ Escherichia coli vaccine in Dairy Cattle.", Canadian Journal of Comparative Medicine, vol. 49, No. 1, 1985, pp. 1-9.

Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.
Wensvoort et al., "'Blue ear' disease in pigs". Veterinary Record, vol. 128, No. 24, Jun. 1991, p. 574.
Wensvoort et al., "Bovine viral diarrhoea virus infections in piglets born to sows vaccinated against swine fever with contaminated vaccine". Research in Veterinary Science, vol. 45, 1988, pp. 143-148.
Wensvoort et al., "Characterization of Porcine and Some Ruminant Pestiviruses by Cross-neutralization" vol. 20, 1989, pp. 291-306.
Wensvoort et al., "Lelystad virus, the cause of porcine epidemic abortion and respiratory syndrome: a review of mystery swine disease research at Lelystad," Vet. Microbiol.,1992;33:185-193.
Wensvoort et al., "Mystery swine disease in the Netherlands: the isolation of Lelystad virus," Vet Q., 1991, 13 (3):121-130.
Wensvoort et al., "Production of Monoclonal Antibodies Against Swine Fever Virus and Their Use in Laboratory Diagnosis". Veterinary Microbiology, vol. 12, 1986, pp. 101-108.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wensvoort, Gert et al., "Antigenic comparison of Lelystad virus and swine infertility and respiratory syndrome (SIRS) virus", J Vet Diagn Invest 4:134-138 (1992).
Wesley et al., "Differentiation of a porcine reproductive and respiratory syndrome virus vaccine strain from North American field strains by restriction fragment length polymorphism analysis of ORF 5," J Vet. Diagn. Invest., 1998;10: 140-144.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Westenbrink et al., "An enzyme-linked immunosorbent assay for detection of antibodies to porcine parvovirus". Journal of Virological Methods, vol. 23, 1989, pp. 169-178.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Witte, K.H. "The Situation of 'Epidemic Late Abortion of Swine' in the State of Northrhine-Westphalia". Workshop Seminar, Apr. 1991.
Woode, et al., "Porcine Rotavirus Infection". Diseases of Swine, Fifth Edition, Chapter 26, The Iowa State University Press, Ames, Iowa, 1981, pp. 310-322.
Woods et al., "Antigenicity of Inactivated Swine Influenza Virus Concentrated by Centrifugation". Research Communications in Chemical Pathology and Pharmacology, vol. 13, No. 1, 1976, pp. 129-132.
Woods et al., "Investigation of Four Outbreaks of Acute Respiratory Disease in Swine and Isolation of Swine Influenza Virus". Health Laboratory Science, vol. 5, No. 4, Oct. 1968, pp218-224.

Woods et al., "Experimental challenge of pregnant gilts with swine influenza virus after vaccination". Research Communications in Chemical Pathology and Pharmacology, vol. 15, No. 4, Dec. 1976, pp. 787-95.

Wootton et al., "Full-length sequence of a Canadian porcine reproductive and respiratory syndrome virus (PRRSV) isolate," Arch. Virol.,2000;145:2297-2323.

Wootton et al., "Homo-Oligomerization of the Porcine Reproductive and Respiratory Syndrome Virus Nucleocapsid Protein and the Role of Disulfide Linkages," J Virol., Apr. 2003;77(8):4546-4557.

de Antonio et al., "Quantitative Detection of Porcine Interferon-Gamma in Response to Mitogen, Superantigen and Recall Viral Antigen" Veterinary Immunology and Immunopathology, vol. 61, (1998) 265-277.

De Mazancourt et al., "Antibody response to the rubella virus structural proteins in infants with the congenital rubella syndrome". Journal of Medical Virology, vol. 19, No. 2, Jun. 1986, pp. 111-122.

De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.

De Vries et al., "The Genome Organization of the Nidovirales: Similarities and Differences between Arteri-, Toro-, and Coronaviruses". Seminars in Virology, vol. 8, 1997, pp. 33-47.

De Vries, et al., "All subgenomic mRNAs of equine arteritis virus contain a common leader sequence". Nucleic Acids Research, vol. 18, No. 11, 1990, pp. 3241-3247.

Dea et al., "Antigenic Variability among North American and European Strains of Porcine Reproductive and Respiratory Syndrome Virus as Defined by Monoclonal Antibodies to the Matrix Protein". Journal of Clinical Microbiology, vol. 34, No. 5, Jun. 1996, pp. 1488-1493.

Dea et al., "Antigenic variant of swine influenza virus causing proliferative and necrotizing pneumonia in pigs". Journal of Veterinary Diagnostic Investigation, vol. 4, No, 4, 1992, pp. 380-392.

Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.

Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.

Dea et al., "Isolation of encephalomyocarditis virus among stillborn and post-weaning pigs in Quebec". Archives of Virology, vol. 117, Nos. 1-2, 1991, pp. 121-128.

Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.

Dea et al., "Ultrastructural Characteristics and Morphogenesis of Porcine Reproductive and Respiratory Syndrome Virus propagated in the highly Permissive Marc-145 Cell Clone", Corona- and reated viruses, 1994, Proceedings of the Sixth International Symposium on corona- and related viruses, Aug. 27, 1994-Sep. 1, 1994, pp. 95-98.

Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.

Del Val et al., "Glycosylated components of African swine fever virus particles". Virology, vol. 152, No. 1, Jul. 1986, pp. 39-49.

den Boon et al., "Equine Arteritis virus is not a togavirus but belongs to the Coronaviruslike superfamily," J. Virol, 1991, 65(6)2910-2920.

den Boon et al., "Processing and Evolution of the N-Terminal Region of the Arterivirus Replicase ORF1a Protein: Identification of Two Papainlike Cysteine Proteases," J. Virol., Jul. 1995;69(7):4500-4505.

Deng et al., "An improved procedure for utilizing terminal transferase to add homopolymers to the 3' termini of DNA". Nucleic Acids Research, vol. 9, No. 16, 1981, pp. 4173-4188.

Derbyshire, J.B. "Porcine Enterovirus Infections". Diseases of Swine, Fifth Edition, Chapter 20, 1981, pp. 265-270.

Devereux et al., "A Comprehensive Set of Sequence Analysis Programs for VAX". Nucleic Acids Research, vol. 12, No. 1, 1984, pp. 387-395.

Diamond, "Real-space refinement of the structure of hen egg-white lysozyme," J. Mol. Biol., 1974, 82:371-391.

Dianzani et al., "Is Human Immunodeficiency Virus RNA Load Composed of Neutralized Immune Complexes". The Journal of Infectious Diseases, vol. 185, 2002, pp. 1051-1054.

Dildrop et al., "Immunoglobulin V region variants in hybridoma cells. II. Recombination between V genes". The EMBO Journal, vol. 1, No. 5, 1982, pp. 635-640.

Donnelly et al., "Protective Efficacy of Intramuscular Immunization with Naked DNA", Annuals New York Academy of Sciences DNA Vaccines: A New Era in Vaccinology, vol. 772 (1995), pp. 40-46.

Dreher, T.W., "Functions of the 3'-Untranslated Regions of Positive Strand RNA Viral Genomes". Annual Review of Phytopathology, vol. 37, 1999, pp. 151-174.

Drew et al., "Production, characterization and reactivity of monoclonal antibodies to porcine reproductive and respiratory syndrome virus". Journal of General Virology, vol. 76, 1995, pp. 1361-1369.

Drew, T., "Porcine Reproductive and Respiratory Syndrome Virus: A Review". Apr. 1996, 3 pages.

Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.

Duran et al. "Recombinant Baculovirus Vaccines Against Porcine Reproductive and Respiratory Syndrome (PRRS)". Abstracts PRRS, Aug. 9th to 10th, 1995, Copenhagen, Denmark, 2 pages.

Dykhuizen et al., "Determining the Economic Impact of the 'New' Pig Disease", Porcine Reproductive and Respiratory Syndrome, a Report on the Seminar Held in Brussels on Nov. 4-5, 1991 and Organized by the European Commission, pp. 53-60.

Easterday, B.C., (Part Two of Two—pp. 286-315), "Swine Influenza". Diseases of Swine, Sixth Edition, Iowa State University Press, 1986, pp. 244-315.. This NPL is too large for EFS submission. Therefore filing in two parts.

Easterday, B.C., "Swine Influenza". Diseases of Swine, Sixth Edition, Iowa State University Press, 1986, pp. 244-315. (Part One of Two—pp. 244-285). This NPL is too large for EFS submission. Therefore filing in two parts.

Easterday, et al., "Swine Influenza". In Diseases of Swine (8th Edition), Be Straw, S D'Allaire, WI. Mengeling, DJ Taylor, eds., Ames: Iowa State University Press, 1999, pp. 277-290.

Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, pp. 5227-5232.

Ehresmann et al., "RNA synthesized in calicivirus-infected cells is atypical of picornaviruses". Journal of Virology, vol. 22, No. 2, May 1977, pp. 572-576.

Ellis, R.W., "New Technologies for Making Vaccines". Vaccines, Chapter 29, Plotkin et al Eds., WB Saunders Company, Philadelphia, PA, 1988, pp. 568-575,.

Enjuanes et al., "Isolation and Properties of the DNA of African Swine Fever (ASF) Virus". Journal of General Virology, vol. 32, No. 3, Sep. 1976, pp. 479-492.

*Enzo Biochem Inc.* v. *Gen-Probe Incorporated et al.*, No. 01-01230; Decided Jul. 15, 2002.

Estes et al., "Simian rotavirus SA11 replication in cell cultures". Journal of Virology, vol. 31, No. 3, Sep. 1979, pp. 810-815.

Fang et al., "Heterogeneity in Nsp2 of European-like porcine reproductive and respiratory syndrome viruses isolated in the United States," Virus Res., 2004;100:229-235.

Fenner et al., "Immunization against Viral Diseases", Veterinary Virology, Ch. 14, 1992, pp. 265-271.

Fenner et al., "Viral Genetics and Evolution", Veterinary Virology, Ch. 5, 1992, pp. 89-95.

Ferrari et al., "Isolation of Cytopathic Strains of Rotavirus from Pigs". Microbiologica, vol. 9, No. 3, Jul. 1986, pp. 287-294.

Flint et al., "Virus Cultivation, Detection, and Genetics". Virology, Molecular Biology, Pathogenesis, and Control, Ch. 2, 2000, pp. 40-42.

Foss et al., "Adjuvant Danger Signals Increase the Immune Response to Porcine Reproductive and Respiratory Syndrome Virus". Viral Immunology, vol. 15, No. 4, 2002, pp. 557-566.

Frolov et al., "Alphavirus-based expression vectors: Strategies and applications". Proceedings of the National Academy of Sciences, vol. 93, Oct. 1996, pp. 11371-11377.

Fu et al., "Detection and survival of group A rotavirus in a piggery". Veterinary Record, vol. 125, 1989, pp. 576-578.

Fukuhara et al., "Evidence for endocytosis-independent infection by human rotavirus". Archives of Virology, vol. 97, Nos. 1-2, 1987, pp. 93-99.

Funkhouser et al., "Mutations in the 5'-noncoding, 2C and P3 Regions of the Genome Increase the Efficiency of Hepatitis a Virus Growth in MRC-5 Cells". Vaccines, vol. 94, Cold Springs Harbor Laboratory Press, 1994, pp. 345-349.

Gao et al., "Genomic characterization of two Chinese isolates of Porcine respiratory and reproductive syndrome virus," Arch. Virol., 2004;149: 1341-1351.

Garwes, D.J., "Transmissible gastroenteritis". Veterinary Record, vol. 122, 1988, pp. 462-463.

Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.

Bruner, D.W., "Table XXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.

Buchner et al., "A method for increasing the yield of properly folded recombinant fusion proteins: single-chain immunotoxins from renaturation of bacterial inclusion bodies," Anal. Biochem., 1992, 205(2):263-270.

Buck, K. W., "Comparison of the Replication of Positive-Stranded RNA Viruses of Plants and Animals". Advances in Virus Research, vol. 47, 1996, pp. 159-251.

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.

Burroughs, et al., "Relationship of San Miguel Sea Lion Virus to Other Members of the Calicivirus Group". Intervirology, vol. 10, 1978, pp. 51-59.

Cabasso et al., "Propagation of Infectious Canine Hepatitis Virus in Tissue Culture". Proceedings of the Society for Experimental Biology and Medicine, vol. 85, 1954, pp. 239-245.

Caeiro et al., "In vitro DNA replication by cytoplasmic extracts from cells infected with African swine fever virus". Virology, vol. 179, No. 1, Nov. 1990, pp. 87-94.

Callebaut et al., "Antigenic Differentiation between Transmissible Gastroenteritis Virus of Swine and a Related Porcine Respiratory Coronavirus". Journal of General Virology, vol. 69, 1988, pp. 1725-1730.

Carrascosa et al., "Relationship of San Miguel Sea Lion Virus to Other Members of the Calicivirus Group". Journal of Virological Methods, vol. 3, No. 6, Jan. 1982, pp. 303-310.

Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.

Cavanagh et al., "Recommendations of the Coronavirus Study Group for the Nomenclature of the Structural Proteins, mRNAs, and Genes of Corona viruses," Virol.,1990;176:306-307.

Cavanagh, D., "Nidovirales: a new order comprising Coronaviridae and Arteriviridae". Archives of Virology, vol. 142, No. 3, 1997, pp. 629-633.

Chang et al., "A cis-Acting Function for the Coronavirus Leader in Defective Interfering RNA Replication". Journal of Virology, vol. 68, No. 12, Dec. 1994, pp. 8223-8231.

Chang et al., "Evolution of Porcine Reproductive and Respiratory Syndrome Virus during Sequential Passages in Pigs," J. Virol., May 2002; 76(10):4750- 4763.

Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.

Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.

Chasey et al., "Replication of Atypical Ovine Rotavirus in Small Intestine and Cell Culture". Journal of General Virology, vol. 67, No. 3, Mar. 1986, pp. 567-576.

Chen et al., "Determination of the 5' end of the lactate dehydrogenase-elevating virus genome by two independent approaches," J. Gen. Virol., 1994;75:925-930.

Choi et al., "Identification of 5' and 3' cis-Acting Elements of the Porcine Reproductive and Respiratory Syndrome Virus: Acquisition of Novel 5' AU-Rich Sequences Restored Replication of a 5'-Proximal 7-Nucleotide Deletion Mutant," J. Virol., Jan. 2006;80(2):723-736.

Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.

Christianson et al., "Experimental reproduction of swine infertility and respiratory syndrome in pregnant sows". American Journal of Veterinary Research, vol. 53, No. 4, Apr. 1992, pp. 485-488.

Christianson et al., "Pathogenesis of Porcine Reproductive and Respiratory Syndrome Virus Infection in Mid-gestation Sows and Fetuses", Can J. Vet Res., 1993, 57:262-268.

Christianson et al., "Porcine reproductive and respiratory syndrome: A review"., Journal of Swine Health and Production, vol. 2, No. 2, Mar. and Apr. 1994, pp. 10-28.

Christianson et al., "Swine Infertility and Respiratory Syndrome". Pig Veterinary Journal, vol. 27, No. 9, Apr. 1991, pp. 9-12.

Christopher-Hennings et al., "Identification of Porcine Reproductive and Respiratory Syndrome Virus in Semen and Tissues from Vasectomized and Nonvasectomized Boars", Veterinary Pathology, vol. 35, No. 4, (1998) pp. 260-267.

Christopher-Hennings et al., "Persistence of porcine reproductive and respiratory syndrome virus in serum and semen of adult boars," J. Vet. Diag. Invest., 1995, 7:456-464.

Chutivongse et al., "One-year study of the 2-1-1 intramuscular postexposure rabies vaccine regimen in 100 severely exposed Thai patients using rabies immune globulin and Vero cell rabies vaccine". Vaccine, vol. 9, No. 8, Aug. 1991, pp. 573-576.

Clark et al., "Trypsin enhancement of rotavirus infectivity: mechanism of enhancement". Journal of Virology, vol. 39, No. 3, Sep. 1981, pp. 816-822.

Clark, "Refolding of recombinant proteins," Curr. Opin. Biotechnol., 1998, 9(2):157-163.

Coligan et al. (eds.), Curent Protocols in Immunology, Ch. 2, John Wiley & Sons (1996).

Coligan et al. (eds.), Curent Protocols in Immunology, Ch. 8 (Part 1 of 3), John Wiley & Sons (1996).

Coligan et al. (eds.), Curent Protocols in Immunology, Ch. 8 (Part 2 of 3) John Wiley & Sons (1996).

Coligan et al. (eds.), Curent Protocols in Immunology, Ch. 8 (Part 3 of 3) John Wiley & Sons (1996).

Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.

Collins et al., "Isolation of swine infertility and respiratory syndrome virus (isolate ATCC VR-2332) in North America and experimental reproduction of the disease in gnotobiotic pigs," J. Vet. Diagn. Invest., 1992, 4:117-126.

Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.

Collins et al., "Respiratory Disease in a Swine Herd Experiencing a Reproductive Failure Syndrome". Minnesota Swine Conference for Veterinarians, Sep. 16-18, 1990, pp. 206-207.

Collins et al., "Swine Diagnostic Pathology". Allen D. Leman Swine Conference, College of Veterinary Medicine, University of Minnesota, Sep. 18-22, 1998, pp. 1-4.

Collins et al., "Swine Infertility and Respiratory Syndrome (Mystery Swine Disease)". Minnesota Swine Conference for Veterinarians, St. Paul, MN, Sep. 15-17, 1991, pp. 200-205.

Collins, J.E., "Newly Recognized Respiratory Syndromes in North American Swine Herds". American Association of Swine Practitioners Newsletter, vol. 3, No. 7, Sep.-Oct. 1991, p. 7, 10-11.

Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.

Conzelmann et al. "Molecular Characterization of Porcine Reproductive and Respiratory Syndrome Virus, a Member of the Arterivirus Group". Virology. 193:329-339, 1993.

Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.

Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.

Dacso, et al., "Sporadic occurrence of zoonotic swine influenza virus infections". Journal of Clinical Microbiology, vol. 20, No. 4, Oct. 1984, pp. 833-835.

Database WPIL Week 8702, Derwent Publications Ltd., London, GB; AN 87-009295 [2] & EP, A,208672 (Regional Wallonne-Chiron Corp, Wallonne Regional) Jan. 14, 1987.

Database WPIL Week 8741, Derwent Publications Ltd., London, GB; AN 87-286929 [41] & EP, A,62, 198626 (Za Bieseibutsu Kagaku Ken) Sep. 2, 1987.

Database WPIL Week 8821, Derwent Publications Ltd., London, GB; AN 88-147502 [21] & WO,A,8 803 410 (Inst Pasteur) May 19, 1988.

Geisbert et al., "Use of Immunoelectron Microscopy to Show Ebola Virus During the 1989 United States Epizootic". Journal of Clinical Pathology, vol. 43, No. 10, Oct. 1990, pp. 813-816.

Girard et al., "Experimentally induced porcine proliferative and necrotising pneumonia with an influenza A virus". The Veterinary Record, vol. 130, Mar. 1992, pp. 206-207.

Godeny et al., "Map location of lactate dehydrogenase-elevating virus (LDV) capsid protein (Vpl) gene", Virology, vol. 177, No. 2, Aug. 1990, pp. 768-771.

Godeny et al., "Simian hemorrhagic fever virus: another ember of the Coronavirus-like superfamily," Proceedings of the 9th International Congress of Virology, Aug. 8-13, 1993, Glasgow, Scotland, p. 22, Abstract No. W4-8.

Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.

Goldfield et al., "Influenza in New Jersey in 1976: Isolations of Influenza A/New Jersey/76 Virus at Fort Dix". The Journal of Infectious Diseases, vol. 136, Supp. 3, 1977, pp. S347-S355.

Goldstein, et al., "Evaluation of Three Cell Culture Systems as Substrates for Influenza Virus Assay". Applied Microbiology, vol. 19, No. 4, Apr. 1970, pp. 580-582.

Gong et al., "Characterization of RNA synthesis during a one-step growth curve and of the replication mechanism of bovine viral diarrhoea virus". Journal of General Virology, vol. 77, 1996, pp. 2729-2736.

Gorbalenya et al., "Nidovirales: Evolving the largest RNA virus genome," Virus Res., 2006;117:17-37. Epub Feb. 28, 2006.

Gorcyca et al., RespPRRS: A new tool for the prevention and control of PRRS in pigs. Proceedings of the American Association of Swine Practitioners, Omaha, Nebraska, Mar. 1995, pp. 1-22.

Gourreau et al., "Diffusion du virus de la grippe du porc (H1N1=Hsw1N1) en France". Annales de l'Institut Pasteur/Virologie, vol. 132, No. 2, Apr.-Jun. 1981, pp. 287-294.

Goyal, S., "Porcine Reproductive and Respiratory Syndrome", Journal of Veterinary Diagnostic Investigation, vol. 5, No. 4, 1993, pp. 656-664.

Graham et al., "Characteristics of a Human Cell Line Transformed by DNA from Human Adenovirus Type 5", Journal of General Virology, vol. 36, (1977) pp. 59-72.

Gravell et al., "Differences among isolates of simian hemorrhagic fever (SHF) virus". Proceedings of the Society for Experimental Biology and Medicine, vol. 181, No. 1, 1986, pp. 112-119.

'Graves, J.H., "Swine Vesicular Disease". Diseases of Swine, Fifth Edition, Chapter 23, The Iowa State University Press, Ames, Iowa, 1958, pp. 288-293.

Grebennikova et al., "Genomic characterization of virulent, attenuated, and revertant passages of a North American porcine reproductive and respiratory syndrome virus strain". Virology, vol. 321, 2004, pp. 383-390.

Greiner et al., "Quantitative relationship of systemic virus concentration on growth and immune response in pigs". Journal of Animal Science, vol. 78, 2000, pp. 2690-2695.

Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.

Groot Bramel-Verheije et al., "Expression of a Foreign Epitope by Porcine Reproductive and Respiratory Syndrome Virus," Virol., 2000;278:380-389.

Grouse, L.D., "Swine Flue Sequelae"., Journal of the American Medical Association, vol. 243, No. 24, 1980, p. 2489.

Grunert et al., "Sensitivity of Influenza A/New Jersey/8/76 (HswINI) Virus to Amantadine-HCI". Journal of Infectious Diseases, vol. 136, No. 2, 1977, pp. 297-300.

Guan et al., "Requirement of a 5?-Proximal Linear Sequence on Minus Strands for Plus-Strand Synthesis of a Satellite RNA Associated with Turnip Crinkle Virus". Virology, vol. 268, No. 2, Mar. 2000, pp. 355-363.

Guarino, Helena et al., "Detection of procine reproductive and respiratory syndrome virus by reverse transcription-polymerase chain reaction using different regions of the viral genome", J. Vet Diagn Invest 11:27-33 (1999).

Gubler et al., "A simple and very efficient method for generating cDNA libraries". Gene, vol. 25, 1983, pp. 263-269.

Gustafson, D.P., "Pseudorabies". Diseases of Swine, Fifth Edition, Ch. 14, the Iowa State University Press, Ames, Iowa, 1981, pp. 209-223.

Halbur et al., "Comparative Pathogenicity of Nine US Porcine Reproductive and Respiratory Syndrome Virus (PRRSV) Isolates in a Five-Week-Old Cesarean-Derived, Colostrum-Deprived Pig Model", Journal of Veterinary Diagnositic Investigation, vol. 8, No. 1, (1996) pp. 11-20.

Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.

Halbur et al., "Immunohistochemical Identification of Porcine Reproductive and Respiratory Syndrome Virus (pRRSV) Antigen in the Heart and Lymphoid System of Three-week-old Colostrum-deprived Pigs," Vet. Pathol., 1995;32:200-204.

Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.

Halbur et al., "Viral Pneumonia in Neonatal and Nursery pigs. Experimental Work with SIRS Agent and Evidence of Another New Viral Agent". Agri-Practice, vol. 12, No. 1, Jan-Feb. 1991, pp. 23-34.

Hamajima et al., "Intranasal Administration ofIIV-Dna Vaccine Formulated with a Polymer, Carboxymethylcellulose, Augments Mucosal Antibody Production and Cell-Mediated Immune Response," Clin. Immunol. Immunopathol., Aug. 1998;88(2):205-210.

Han et al., "Complete genome analysis of RFLP 184 isolates of porcine reproductive and respiratory syndrome virus," Vir. Res., 2006;122: 175-182.

Han et al., "Identification of Nonessential Regions of the nsp2 Replicase Protein of Porcine reproductive and Respiratory Syndrome Virus Strain VR-2332 for Replication in Cell Culture", (Journal of Virology 81:9878-9890, 2007).

Hao et al., "Polymorphic genetic characterization of the ORF7 gene of porcine reproductive and respiratory syndrome virus (PRRSV) in China". Virology Journal, vol. 8:73, pp. 1-9.

Harlow et al., Antibodies: A Laboratory Manual, Cold Spring Harbor Labora~ory Press, Cold Spring Harbor, NY; title page, publisher's p., and table of contents only, 9 pages (1988).

Haynes et al., "Temporal and Morphologic Characterization of the Distribution of Porcine Reproductive and Respiratory Syndrome Virus (PRRSV) by in Situ Hybridization in Pigs Infected with Isolates of PRRSV that Differ in Virulence". Veterinary Pathology, vol. 34, 1997, pp. 39-43.

Heath, et al., "The Behaviour of Some Influenza Viruses in Tissue Cultures of Kidney Cells of Various Species". Archie. f. Virusforschung Bd. VIII, HS, 1958, pp. 577-591.

Hedger et al., "Swine Vesicular Disease Virus". Virus Infections of Porcines, Elsevier Science Publishers, B.V., 1989, pp. 241-250.

Hill, "Overview and history of mystery swine disease (swine infertility and respiratory syndrome)," Proceedings of the Mystery Swine Disease Committee Meeting, Oct. 6, 1990, Denver, CO, Livestock Conservation Institute, Madison, WI, p. 29-30.

Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.

Hofmann et al., "Propagation of the virus of porcine epidemic diarrhea in cell culture". Journal of Clinical Microbiology, vol. 26, No. 11, Nov. 1988, pp. 2235-2239.

Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.

Honda et al., "A Serological Comparison of 4 Japanese Isolates of Porcine Enteroviruses with the International Reference Strains". The Japanese Journal of Veterinary Science, vol. 52, No. 1, 1990, pp. 49-54.

Horowitz et al., "Anti-schistosome monoclonal antibodies of different isotypes—correlation with cytotoxicity". The EMBO Journal, vol. 2, No. 2, 1983, pp. 193-198.

Horsfall et al., "General Principles of Animal Virus Multiplication". Viral and Rickettsial Infections of Man, Fourth Edition, J.B. Lippincott Company, Philadelphia, 1965, pp. 239-241,.

Horzinek et al., "Studies on the Substructure of Togaviruses: II. Analysis of Equine Arteritis Rubella, Bovine Viral Diarrhea, and Hog Cholera Viruses". Archiv Fir die gesamte Virusforschung, vol. 33, 1971, pp. 306-318.

Hoshino et al., "Isolation and characterization of an equine rotavirus". Journal of Clinical Microbiology, vol. 18, No. 3, Sep. 1983, pp. 585-591.

Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.

Howard et al., Veterinary Immunology and Immunopathology, vol. 102, Issues 1-2 and 4, cover page, title page, and table of contents: 7 pgs.

Hsu et al., "Use of Avidin-Biotin-Peroxidase Complex (ABC) in Immunoperoxidase Techniques: A Comparison between ABC and Unlabeled Antibody (PAP) Procedures", Journal of Histochemistry and Cytochemistry, vol. 29, (1981) pp. 577-580.

Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.

Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.

Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.

Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.

Hyllseth, B., "Structural Proteins of Equine Arteritis Virus". Archiv Fïr die gesamte Virusforschung, vol. 30, 1973, pp. 177-188.

Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.

Imagawa et al., "Isolation of Foal Rotavirus in MA-104 Cells". Bulleting of Equine Research Institute, vol. 18, 1981, pp. 119-128.

Imoto et al., "Vertebrate Lysozymes", the Enzymes 1972, Chapter 21, 7:665-868, Academic Press NY.

International Preliminary Examination Report for PCT/NL02/00314 mailed Aug. 26, 2003.

International Search Report and Written Opinion for PCT/EP2006/050098 mailed on Oct. 2, 2007.

International Search Report and Written Opinion for PCT/US2005/021973 mailed on Jan. 4, 2006.

International Search Report and Written Opinion for PCT/US2005/33760 mailed on Apr. 5, 2006.

International Search Report and Written Opinion for PCT/US2008/58898 mailed on Jun. 26, 2008.

International Search Report and Written Opinion for PCT/US2009/054775 mailed Nov. 23, 2009.

International Search Report for PCT/NL1992/00096 mailed on Sep. 15, 1992.

International Search Report for PCT/NL1997/00593 mailed on Mar. 6, 1998.

International Search Report for PCT/NL2000/00152 mailed on Jul. 6, 2000.

International Search Report for PCT/NL2001/00382 mailed on Sep. 12, 2001.

International Search Report for PCT/NL2002/00314 mailed on Aug. 14, 2002.

International Search Report for PCT/US1992/06873 mailed on Nov. 25, 1992.

International Search Report for PCT/US1995/09927 mailed Oct. 19, 1995.

International Search Report for PCT/US1996/06800 mailed on Sep. 5, 1996.

International Search Report for PCT/US2000/10852 mailed on Aug. 3, 2000.

International Search Report for PCT/US92/07826 mailed on Feb. 25, 1993.

Ivanov et al., "Major genetic marker of nidoviruses encodes a replicative endoribonuclease," PNAS, Aug 24, 2004;101 (34):12694-12699.

Izeta et al., "Replication and Packaging of Transmissible Gastroenteritis Coronavirus-Derived Synthetic Minigenomes". Journal of Virology, vol. 73, No. 2, Feb. 1999, pp. 1535-1545.

Jackwood et al., "Replication of Infectious Bursal Disease Virus in Continuous Cell Lines". Avian Diseases, vol. 31, No. 2, Apr.-Jun. 1987, pp. 370-375.

Johnson et al., "Feline panleucopaenia virus. IV. Methods for obtaining reproducible in vitro results". Research in Veterinary Science, vol. 8, No. 2, Apr. 1967, pp. 256-264.

Johnson et al., "Pathogenic and humoral immune responses to porcine reproductive and respiratory syndrome virus (PRRSV) are related to viral load in acute infection," Vet. Immunol. Immunopathol., 2004, 102:233-247.

Johnson et al., "Replication of Flock House Virus RNAs from Primary Transcripts Made in Cells by RNA Polymerase II," J. Virol., 1997 Apr; 71 (4): 3323-3327.

Johnston et al., "Genetic to genomic vaccination". Vaccine, vol. 15, No. 8, 1997, pp. 808-809.

Joo et al., "Encephalomyocarditis Virus As a Potential Cause for Mystery Swine Disease", Livestock Conservation Institute, Proceedings of the Mystery Swine Disease Committee Meeting, Denver, CO, Oct. 6, 1990, pp. 62-66.
Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.
Jusa et al., "Effect of heparin on infection of cells by porcine reproductive and respiratory syndrome virus". American Journal of Veterinary Research, vol. 58, No. 5, May 1997, pp. 488-491.
Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.
Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.
Kapur et al., "Genetic variation in porcine reproductive and respiratory syndrome virus isolates in the midwestem United States," J. Gen. Virol., 1996;77:1271-1276.
Kasza et al., "Establishment, viral susceptibility and biological characteristics of a swine kidney cell line SK-6". Research in Veterinary Science, vol. 13, No. 1, Jan 1972, pp. 46-51.
Kasza et al., "Isolation and Characterization of a Rotavirus from Pits". Veterinary Record, vol. 87, 1970, pp. 681-686.
Katz et al., "Antigenic differences between European and American isolates of porcine reporductive and respiratory syndrome virus (PRRSV) are encloded by the carboxyterminal portion of viral open reading frame 3", Veterinary microbiology, vol. 44, 1995, pp. 65-76.
Keffaber, K, "Reproductive Failure of Unknown Etiology"., AASP Newsletter, vol. 1, No. 2, Sept.-Oct. 1989, pp. 1, 4-5, 8-10.
Keffaber, K.K., "Swine Reproductive Failure of Unknown Etiology". The George A. Young Swine Conference & Annual Nebraska SPF Swine Conference, Aug. 13-14, 1990, pp. 55-67.
Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Analysis of cis-Acting Sequences Essential for Coronavirus Defective Interfering RNA Replication". Virology, vol. 197, No. 1, Nov. 1993, pp. 53-63.
Kim et al., "Characterization of encephalomyocarditis virus isolated from aborted swine fetuses" Am J Vet Res., 1991, 52(10):1649-1652.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Kim et al., "Enhanced replication of porcine reproductive and respiratory syndrome (PRRS) virus in a homogeneous subpopulation ofMA-104 cell line," Arch. Virol., 1993;133:477-483.
Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.

* cited by examiner

FIG. 2

FIG. 3 pET 24b myc-NSP 4-His

```
                                                        Bgl II                              T7 Promoter
AGGCGCCAGCAACCGCACCTGTGGCGCCGGTGATGCCGGCCACGATGCGTTCCGGCGTAGAGGATCC|AGATCT|CGATCCCGGCGAAATT|AATACGACTCACT|    100
                                lac operator                           RBS       Nde 1    Myc Tag
ATA|GGGGAATTGTGAGCGGATAACAATTCC|CTCTAGA|AATAATTTGTTTAACTTT|AAGAAG|GAGATATA|CATATG|GAACAAAACTCATCTCAGAAGA         200
        Xba 1                                                                     Start   M  E  Q  K  L  I  S  E  E
          EcoR 1      Bamh 1                    NSP 4 (underlined)
GGATCTG|AATTC|GATCCAT|GAATTG|TAG|GGATCC|GGTGCTTTCAGAACTCGAAAGCCCTCACTGAAACGTCAATGTGATCGGGTCCTCCATGGGCTCT          300
 D  L  N  R  S  M  N   S  S   G   S   G  A   F  R  T  R  K  P   S  L   N   T  V  N  V  I   G  S  S  M  G  S
GGCGGGGGTGTTTACCATCGACGGGAAAGTCAAGTGCGTAACGGCACATGTCCTTGACGGGCAATTCAGCGTCCTCGGGTTCAATCAAA                        400
 G  G  G  V  F  T  I  D  G  K  V  K  C  V  T  A  A  H  V  L  T  G  N  S  A  R  V  S  G  V  G  F  N  Q
TGCTTGACTTTGACGTAAAGGGAGATTTCGCTATAGCTGATTGCCCGAATTGGCAAGGGGCTGCCCCCAAGACCCAGTTCTGCACGGATGGAGACTGG             500
 M  L  D  F  D  V  K  G  D  F  A  I  A  D  C  P  N  W  Q  G  A  A  P  K  T  Q  F  C  T  D  G  W  T  G
CCGTGCCTATTGGCTAACATCCTCGGGCGTCGAACCGGGTCATTGAAAAGGATTCGGCTTCTCACCGCATGTGGCCCCTTCCAGGCCCAGTTTTGTAATGTGGCAC     600
 R  A  Y  W  L  T  S  S  G  V  E  P  G  V  I  G  K  G  F  A  F  C  F  T  A  C  G  D  S  G  S  P  V
ATCACCGAGGCCGGTGAGCTTGTCGGCGTTCACGGTCAGCAACAAGGGGGCGGGGGGATCGAATAAAACAAGGAGCT                                   700
 I  T  E  A  G  E  L  V  G  V  H  T  G  S  N  K  Q  G  G  I  V  T  R  P  S  G  Q  F  C  N  V  A
CCATCAAGCTAAGCGAATTAAGTGAATTCTTTGCTGGGCCTAAGGTCCCGCTCGGTGATGAAAGACATAAGGAGCT                                    800
 P  I  K  L  S  E  L  S  E  F  F  A  G  P  K  V  P  L  G  D  V  K  V  G  S  H  I  I  K  D  I  S  E  V
                                                                      Xho I        His Tag
GCCTTTCAGATCTTTGTGCCTTGCTGCTGCCAAACCTGAACTGAG|CTCGAG|CTGGAGCTGGAGCTGGAGCACCACCACCACCACCAC|TGA|ATCGGCTGCTAACAAAGCCCGAAAG    900
 P  S  D  L  C  A  L  L  A  A  K  P  E  L  E  L   E  L  E  H  H  H  H  H  H  Stop
                        Bpu1102 I                           T7 Terminator
GAAGCTGAGTTGGCTGCTGCCACC|GCTGAGC|AATAACTAGCAT|AACCCCTTGGGGCCTCTAAACGGGTCTTGAGGGG|TTTTTT|GCTGAAAGGAGGAACTA       1000
TATCCGGATATTGGCGAATGGACGCGCCCTGTAGCGGCGCATTAAGCGCG                                                             1049
```

FIG. 4

VR 2332 (MLV) Positive Serum

MN 30100 Positive Serum

FIG. 13

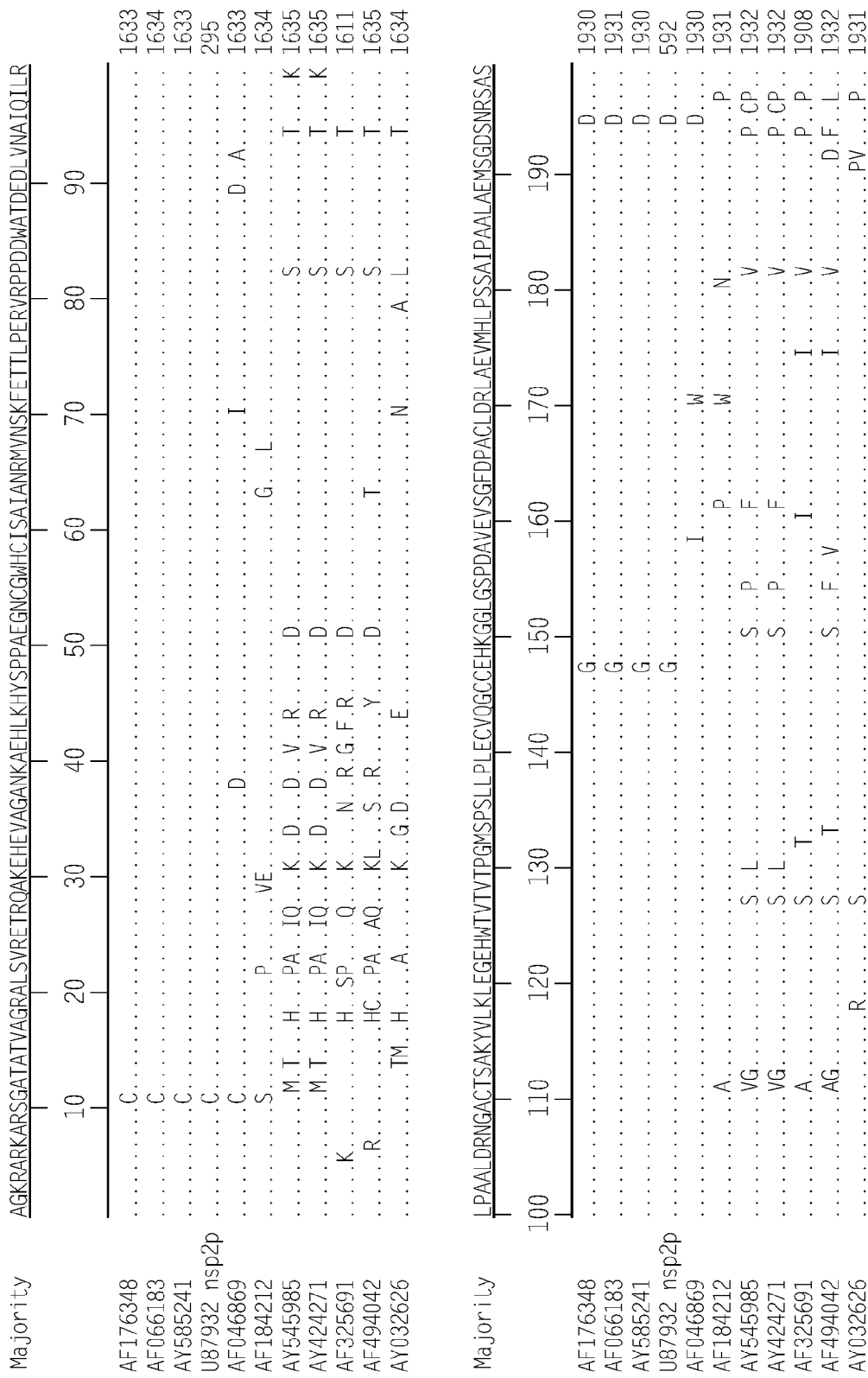
FIG. 14 Page 1

FIG. 14 Page 2

FIG. 14 Page 3

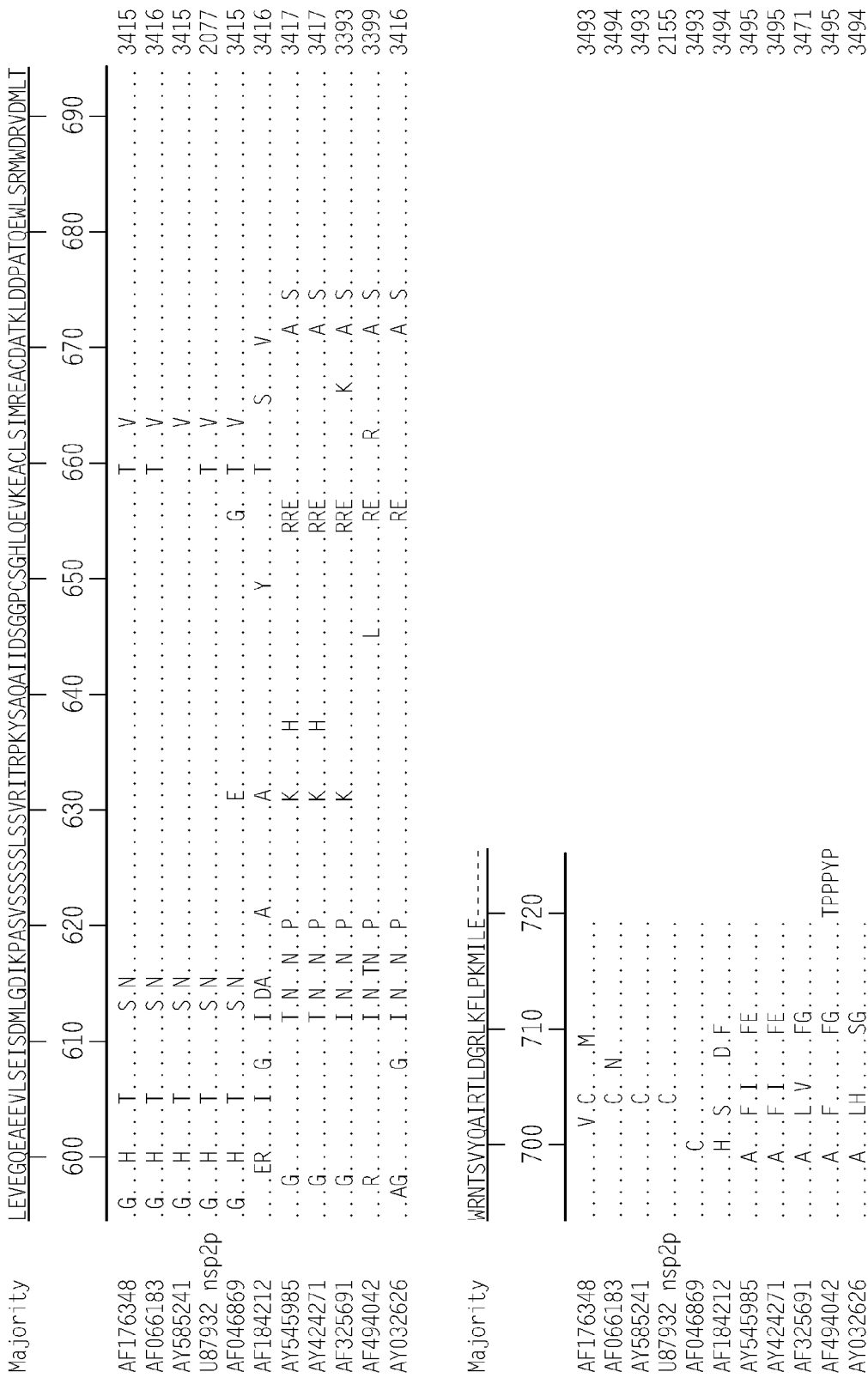
FIG. 14 Page 4

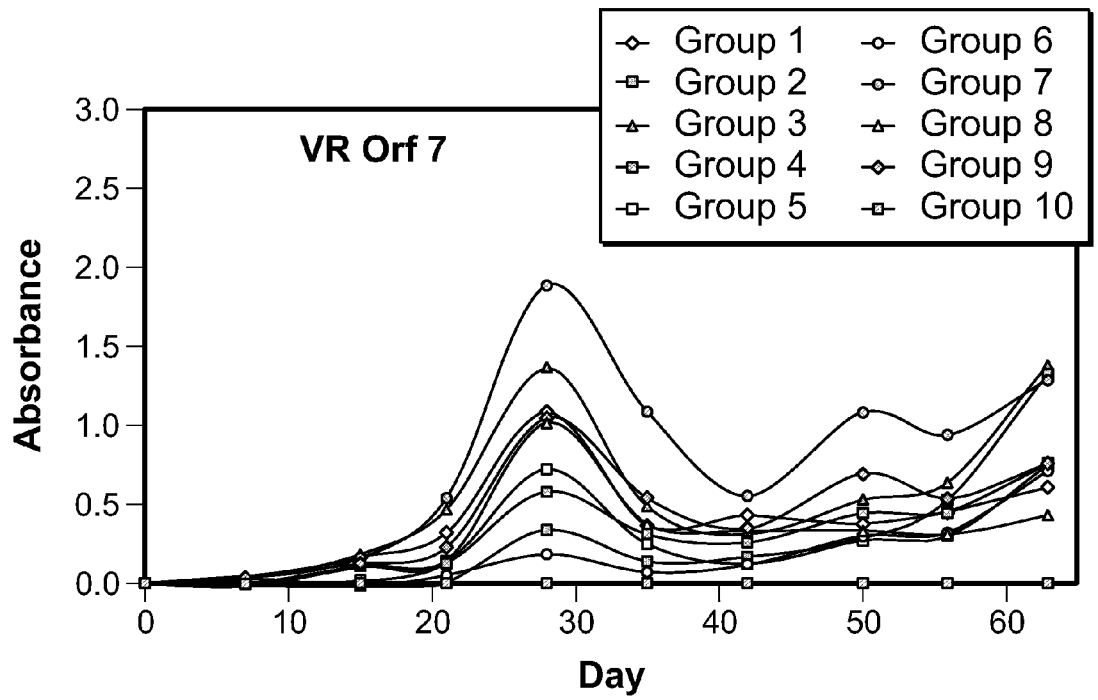
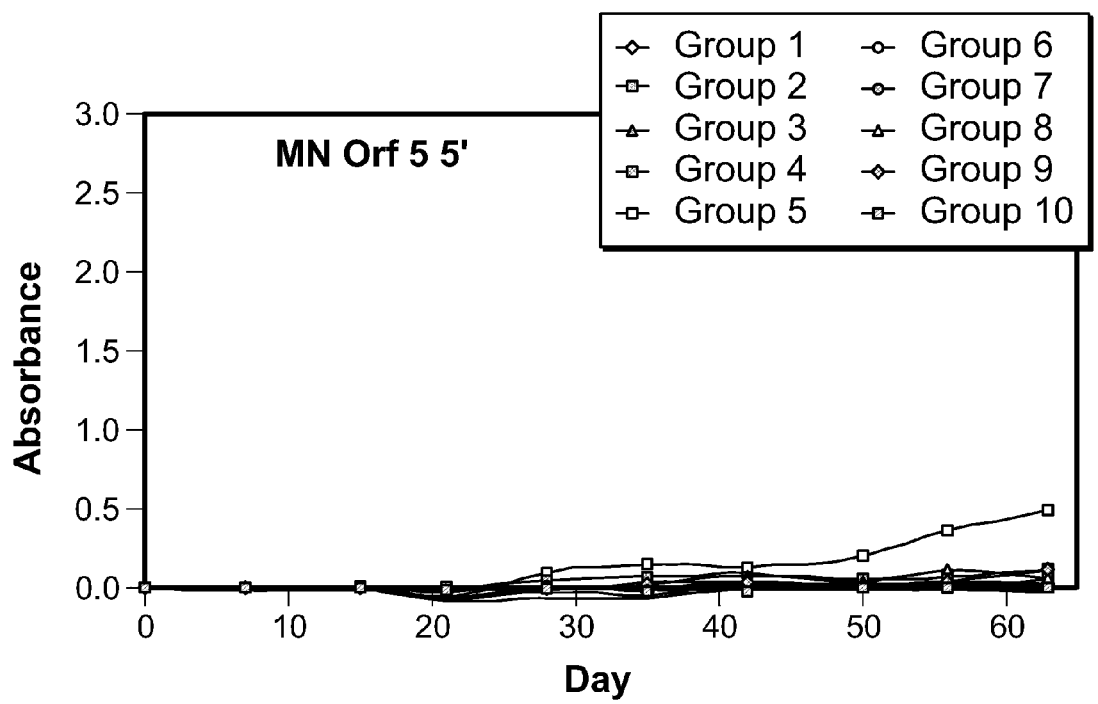
FIG. 18 (Page 1 of 5)

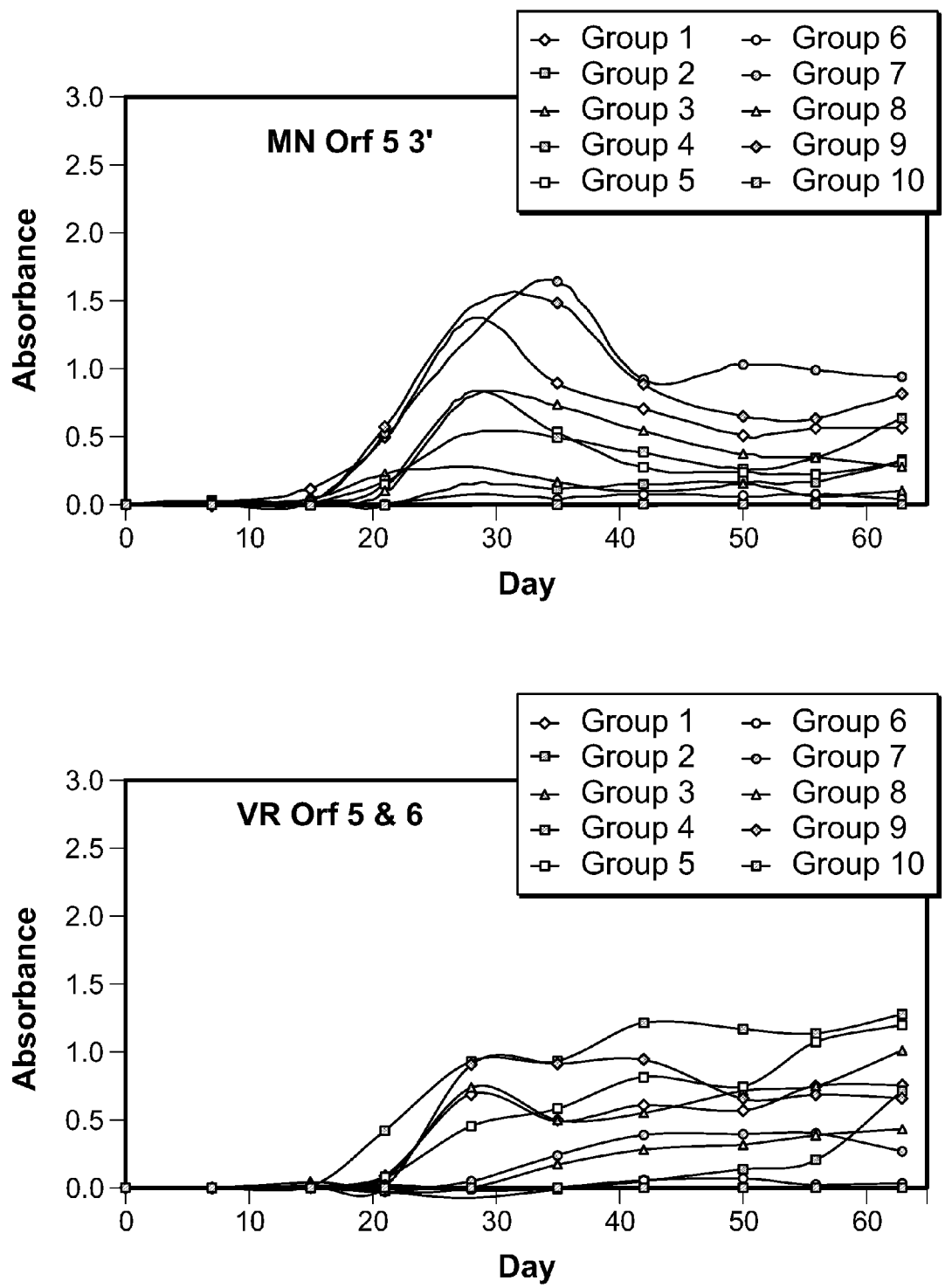
FIG. 18 (Page 2 of 5)

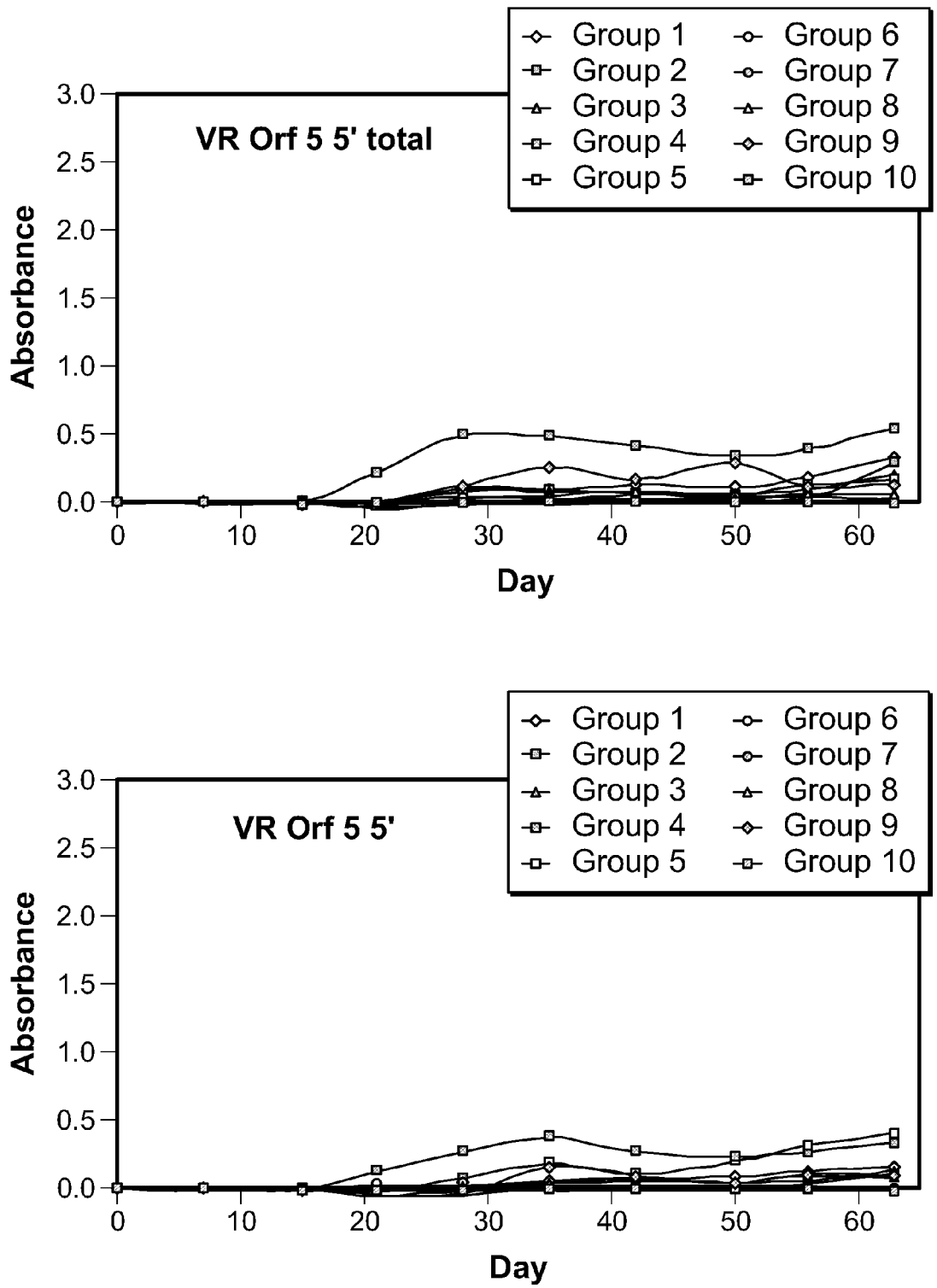
FIG. 18 (Page 3 of 5)

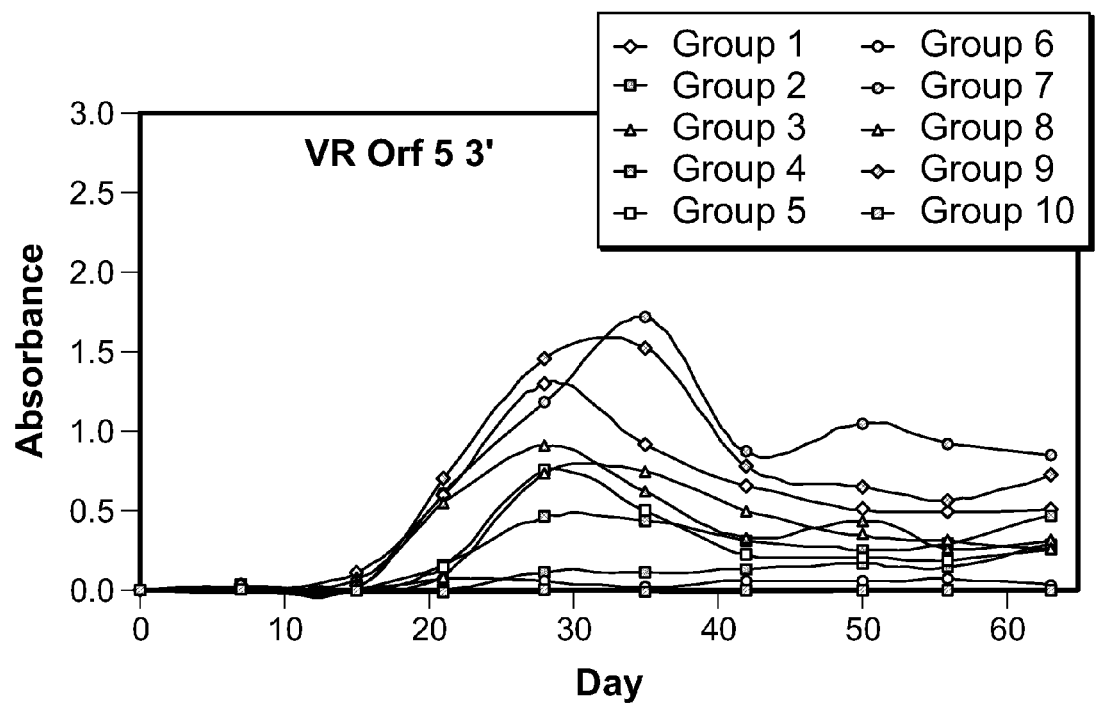
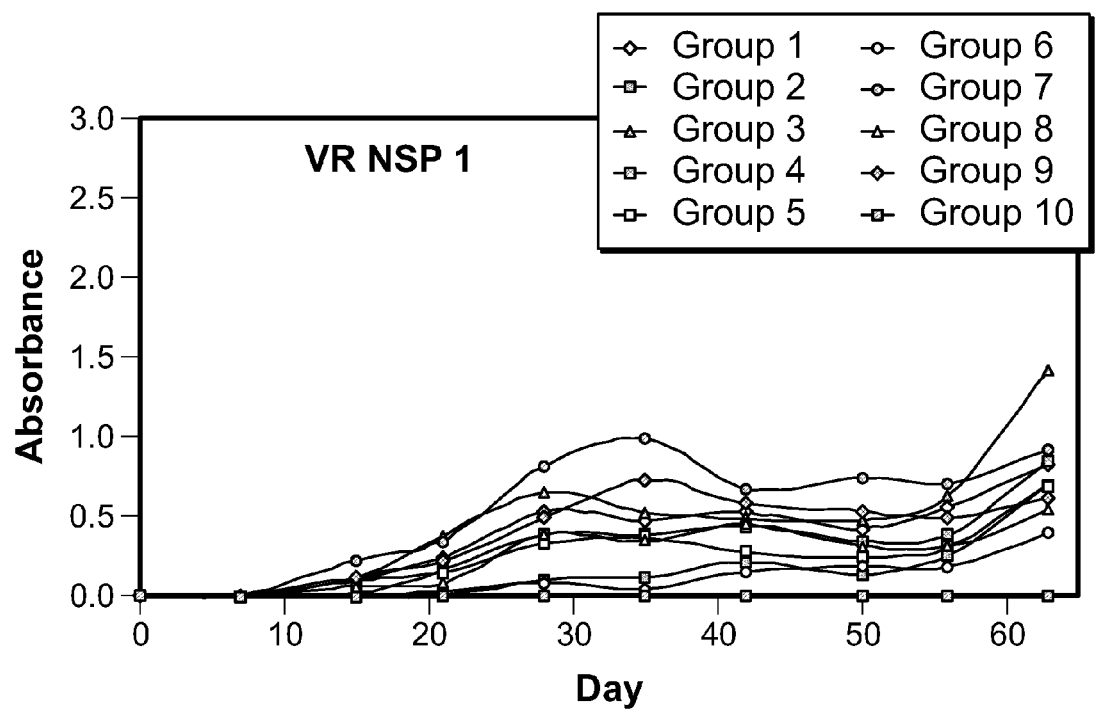
FIG. 18 (Page 4 of 5)

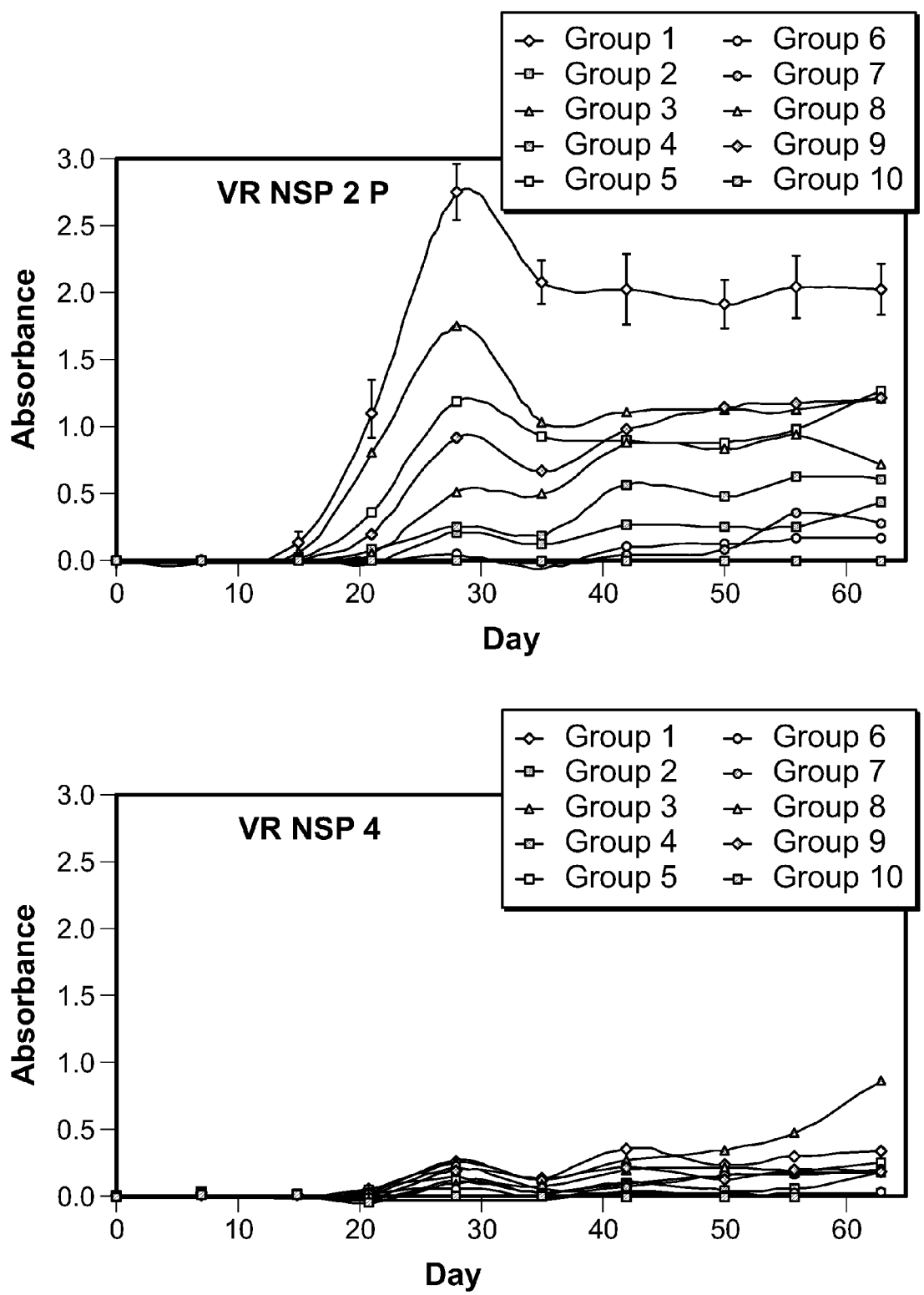
FIG. 18 (Page 5 of 5)

FIG. 19 pET 24b myc-ORF 5 5'-His (MN30100)

```
AGGGCGCCAGCAACCGCACCTGTGGGCGCCGGTGATGCCGGCCCGGCGTAGAGGATCCGGCGTCCGGCGTAGAGGATCCCGGGAAAT
                                                        Bgl II                    T7 Promoter
                                                                          AATACGACTCACT  100
         lac operator         Xba 1                 RBS         Nde 1           Myc Tag
ATAGGGAATTGTGAGCGGATAACAATTCCCGTCTAGAAATAATTTTGTTTAACTTTAAGAAGGAGATATACATATGGAACAAAAACTCATCTCAGAAGA  200
                                                                     Start M E Q K L I S E E
             Ecor 1    BamH I                MN ORF5 5' (underlined)
GAATCGATCCATGAGTCGGATCCATGAACGCCAACAGCAGCAGCTCACATTTCAGTTGATTTATAACTTGACGTATGCGAGCTG  300
 L  N  R  S  M  N  S  S  G  S  M  N  A  N  S  T  S  S  S  H  F  Q  L  I  Y  N  L  T  L  C  E  L
                                            Xho I            His Tag                   Stop
AATGGCACAGATTGGCTGGCTGGAAAGTTTGATTGGGCAGTGCTCGAGCACCACCACCACCACCACTGAGATCCGGCTGCTAACAAAGCCCGAAAGGAAG  400
  N  G  T  D  W  L  A  G  K  F  D  W  A  V  L  E  H  H  H  H  H  H  Stop
      Bpu1102 I                                  T7 Terminator
CTGAGTTGGCTGCTGCCACCGCTGAGCAATAACTAGCATAACCCCTTGGGGCCTCTAAACGGGTCTTGAGGGGTTTTTTGCTGAAAGGAGGAACTATATC  500

CGGATTGGCGAATGGGACGCGCCCTGTAGCGGCGCATTAAGCGCG                                                    545
```

FIG. 20 pET 24b myc-ORF 5 5'-His (VR-2332)

``` pET 24b myc-ORF 5 total-His (VR-2332)

AGGCGCCAGCAACCGCAC pET 24b myc-ORF 5 3'-His (VR-2332)

```
                                                                          T7 Promoter
AGGGCGCCAGCAACCGCACCTGTGGCGCCGGCTGATGCCGCCACGATGCGTCCGGCGTAGAGGATCGAGATCTCGATCCCGCGAAATAATACGACTCACT  100
                                                  Bgl II
      lac operator                    Xba 1                RBS       Nde 1      Myc Tag
ATAGGGGAAT pET 24b myc-ORF 5 3'-His (MN30100)

```
                                                                                          T7 Promoter
AGGGGCCCAGCAACCGCACCTGTGGCGCCGGTGATGCGGCCAGATGCGTCCGGCGTAGAGGATGCGAGATCTCGATCCCGCGAAAT TAATACGACTCACT  100
                                lac operator             Xba 1         RBS             Nde 1    Myc Tag
ATAGGGGAATTGTGAGCGGATAACAATTCCCTCTAGAAATAATTTTGTTTAACTTTAAGAAGGAGATATACATATGGAACAAAAACTCATCTCAGAAGA  200
                                                                                   Start M  E  Q  K  L  I  S  E  E
                             Ecor 1         BamH I             MN ORF5 3' Endodomain (underlined)
GGATCTCGAATCGATCCATGGATCCATGAAGAACTGTCCTGGCGCTATTCATGTACCAGATACCACCAACTTCCTCCTAGACACTAAG              600
 D  L  N  R  S  M  D  P  M  K  N  C  S  W  R  Y  S  C  T  R  Y  T  N  F  L  L  D  T  K
GGCAGACTCTATGTTGGCGGGTGCCCTGTCATTATAGAGAAAGGGGGTAAGGTTGAGGTCGAAGGCCACCTGATGACTCAAAAGAGTGTGCTTGATG  700
 G  R  L  Y  V  G  G  C  P  V  I  I  E  K  G  G  K  V  E  V  E  G  H  L  I  D  L  K  R  V  V  L  D
                                                                  Xho 1        His Tag
GTTCCGTGGCAACATGGGTTTAACCAGAGTTTCAGCGGAACAATGGGGTCGTCCTCGAGCACCACCACCACCACCACTGATCCGGCTGCTAACAAAGC  500
 G  S  V  A  T  P  L  T  R  V  S  A  E  Q  W  G  R  P  L  E  H  H  H  H  H  H  Stop
                                                             Bpu1102 I              T7 Terminator
CCGAAAGGAAGCTGAGTTGGCTGCTGCCACCGCTGAGGAATAACTAGCATAACCCCCTTGGGGCCTCTAAACGGGTCTTGAGGGGTTTTTTGCTGAAAGGA  600
GGAACTATATCCGGATTGGCGAATGGGACGGCGCCCTGTAGCGGGGCATTAAGCGCG  656
```

FIG. 24 pET 24b myc-ORF 5+6-His (VR-2332)

```
                                                                                                    Bgl II            T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT  100 lac operator         Xba 1                    RBS            Nde 1       Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                                                                      Start M  E  Q  K  L  I  S  E  E EcoR 1   BamH I                   ORF5 5' Ectodomain 1
GGATCTGAATCGATCCATGAATTCTAGTGGATCCATGAACGCCAGCAACGACAGCAGCTCCCATCTACAGCTGATTTACAACTTGACGCTATGTGAGCTG  300
  D  L  N  R  S  M  N  S  S  G  S  M  N  A  S  N  D  S  S  S  H  L  Q  L  I  Y  N  L  T  L  C  E  L Xho1 GGGGS Linker    ORF5 5' Ectodomain 2       GGGGS Linker
AATGGCACAGATTGGCTAGCTAACAAATTTGATTGGGCAGTGCTCGAGGGAGGAGGCGGCAGCGGGTTTGTTCACGGGCGGTATGTCCTAAGTGGAGGAG  400
 N  G  T  D  W  L  A  N  K  F  D  W  A  V  L  E  G  G  G  G  S  G  F  V  H  G  R  Y  V  L  S  G  G ORF6  Ectodomain  2                             GGGGS  Linker   ORF6   Ectodomain  2
GCGGCAGCATGGGGTCGTCCTTAGATGACTTCTGTCATGATAGCACGGCTCCACAAAAGGTGCTTGGAGGAGGCGGCAGCGCGCACTTTCAGAGTACAAA  500
G  G  S  M  G  S  S  L  D  D  F  C  H  D  S  T  A  P  Q  K  V  L  G  G  G  G  S  A  H  F  Q  S  T  N Xho  1    His Tag                                                                  Bpu1102 I
TAAGCTCGAGCACCACCACCACCACCACTGAGATCCGGCTGCTAACAAAGCCCGAAAGGAAGCTGAGTTGGCTGCTGCCACCGCTGAGCAATAACTAGCA  400
  K  L  E  H  H  H  H  H  H Stop T7 Terminator
TAACCCCTTGGGGCCTCTAAACGGGTCTTGAGGGGTTTTTTGCTGAAAGGAGGAACTATATCCGGATTGGCGAATGGGACGCGCCCTGTAGCGGCGCATT  500
```

FIG. 25 pET 24b myc-ORF 7-His (VR-2332)

Bgl II T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator Xba 1 Ribz Nde 1 Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
Start M E Q K L I S E E Ecor 1 BamH I ORF 7 (underline)
GGATCTGAATCGATCCATGAATTCTAGTGGATCCATGCCAAATAACAACGGCAAGCAGCAGAAGAGAAAGAAGGGGGATGGCCAGCCAGTCAATCAGCTG 300
D L N R S M N S S G S M P N N N G K Q Q K R K K G D G Q P V N Q L TGCCAGATGCTGGGTAAGATCATCGCTCAGCAAAACCAGTCCAGAGGCAAGGGACCGGGAAAGAAAAATAAGAAGAAAAACCCGGAGAAGCCCCATTTTC 400
C Q M L G K I I A Q Q N Q S R G K G P G K K N K K K N P E K P H F CTCTAGCGACTGAAGATGATGTCAGACATCACTTTACCCCTAGTGAGCGGCAATTGTGTCTGTCGTCAATCCAGACCGCCTTTAATCAAGGCGCTGGGAC 500
P L A T E D D V R H H F T P S E R Q L C L S S I Q T A F N Q G A G T TTGCACCCTGTCAGATTCAGGGAGGATAAGTTACACTGTGGAGTTTAGTTTGCCTACGCATCATACTGTGCGCCTGATCCGCGTCACAGCATCACCCTCA 600
C T L S D S G R I S Y T V E F S L P T H H T V R L I R V T A S P S Xho I His Tag Bpu1102 I
GCACTCGAGCACCACCACCACCACCACTGAGATCCGGCTGCTAACAAAGCCCGAAAGGAAGCTGAGTTGGCTGCTGCCACCGCTGAGCAATAACTAGCAT 700
A L E H H H H H H Stop

T7 Terminator
AACCCCTTGGGGCCTCTAAACGGGTCTTGAGGGGTTTTTTGCTGAAAGGAGGAACTATATCCGGATTGGCGAATGGGACGCGCCCTGTAGCGGCGCATTA 800

AGCGCG 806

FIG. 26 pET 24b myc-NSP 2HP-His (VR-2332)

```
                                                                          Bgl II               T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT  100 lac operator          Xba 1                     RBS            Nde 1      Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                                                                          Start  M  E  Q  K  L  I  S  E  E Ecor 1   BamH I                     NSP  2HP (underlined)
GGATCTGAATCGATCCATGAATTCTAGTGGATCCGGCAGCCCGGTTTCATTAGGCGGCGATGTCCCTAACAGTTGGGAAGATTTGGCTGTTAGTAGCCCC  300
  D  L  N  R  S  M  N  S  S  G  S  G  S  P  V  S  L  G  G  D  V  P  N  S  W  E  D  L  A  V  S  S  P TTTGATCTCCCGACCCCACCTGAGCCGGCAACACCTTCAAGTGAGCTGGTGATTGTGTCCTCACCGCAATGCATCTTCAGGCCGGCGACACCCTTGAGTG  400
 F  D  L  P  T  P  P  E  P  A  T  P  S  S  E  L  V  I  V  S  S  P  Q  C  I  F  R  P  A  T  P  L  S AGCCGGCTCCAATTCCCGCACCTCGCGGAACTGTGTCTCGACCGGTGACACCCTTGAGTGAGCCGATCCCTGTGCCCGCACCGCGGCGTAAGTTTCAGCA  500
E  P  A  P  I  P  A  P  R  G  T  V  S  R  P  V  T  P  L  S  E  P  I  P  V  P  A  P  R  R  K  F  Q  Q GGTGAAAAGATTGAGTTCGGCGGCGGCAATCCCACCGTACCAGGACGAGCCCCTGGATTTGTCTGCTTCCTCACAGGCTGAATATGAGGCCTCTCCCCCA  600
  V  K  R  L  S  S  A  A  A  I  P  P  Y  Q  D  E  P  L  D  L  S  A  S  S  Q  A  E  Y  E  A  S  P  P GCACCGCCGCAGAGCGGGGGCGTTCTGGGAGTAGAGGGGCATGAAGCTGAGGAAACCCTGAGTGAAATCTCGGACATGTCGGGTAACATTAAACCTGCGT  700
 A  P  P  Q  S  G  G  V  L  G  V  E  G  H  E  A  E  E  T  L  S  E  I  S  D  M  S  G  N  I  K  P  A Xho I   His Tag                                                                 Bpu1102 I
CCGTGTCATCACTCGAGCACCACCACCACCACCACTGAGATCCGGCTGCTAACAAAGCCCGAAAGGAAGCTGAGTTGGCTGCTGCCACCGCTGAGCAATA  800
S  V  S  S  L  E  H  H  H  H  H  H  Stop T7 Terminator
ACTAGCATAACCCCTTGGGGCCTCTAAACGGGTCTTGAGGGGTTTTTTGCTGAAAGGAGGAACTATATCCGGATTGGCGAATGGGACGCGCCCTGTAGCG  900

GCGCATT                                                                                               907
```

FIG. 27 pET 24b myc-NSP 2 S1 HP-His (VR-2332)

```
                                                                                   Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT  100 lac operator          Xba 1                      RBS             Nde 1     Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                                                                        Start  M  E  Q  K  L  I  S  E  E Ecor 1    BamH I                   NSP 2 S1 HP (underlined)
GGATCTGAATCGATCCATGAATTCTAGTGGATCCGCGACTGCTACAGTCGCTGGCCGCGCTTTGTCCGTTCGTGAAACCCGGCAGGCCAAGGAGCACGAG  300
   D  L  N  R  S  M  N  S  S  G  S  A  T  A  T  V  A  G  R  A  L  S  V  R  E  T  R  Q  A  K  E  H  E Xho 1       His Tag
GTTGCCGGCGCCAACAAGGCTGAGCACCTCAAACACCTCGAGCACCACCACCACCACCACTGAGATCCGGCTGCTAACAAAGCCCGAAAGGAAGCTGAGT  400
 V  A  G  A  N  K  A  E  H  L  K  H  L  E  H  H  H  H  H  H Stop Bpu1102 I                  T7 Terminator
TGGCTGCTGCCACCGCTGAGCAATAACTAGCATAACCCCTTGGGGCCTCTAAACGGGTCTTGAGGGGTTTTTTGCTGAAAGGAGGAACTATATCCGGATT  500

GGCGAATGGGACGCGCCCTGTAGCGGCGCATT                                                                      532
```

FIG. 28 pET 24b myc-NSP 2 S2 HP-His (VR-2332)

```
                                                                                                      Bgl II            T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator          Xba 1                              RBS              Nde 1      Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                         Start  M  E  Q  K  L  I  S  E  E Ecor 1     BamH I                      NSP 2 S2 HP (underlined)
GGATCTGAATCGATCCATGAATTCTAGTGGATCCGCAAAGATTGACCTGTACCTCCGTGGTGCAACAAATCTTGAAGAATGCTTGGCCAGGCTTGAGAAA 300
  D  L  N  R  S  M  N  S  S  G  S  A  K  I  D  L  Y  L  R  G  A  T  N  L  E  E  C  L  A  R  L  E  K Xho 1       His Tag
GCGCGCCCGCCACGCGTAATCGACACCTCCTTTGATTGGGATCTCGAGCACCACCACCACCACCACTGAGATCCGGCTGCTAACAAAGCCCGAAAGGAAG 400
 A  R  P  P  R  V  I  D  T  S  F  D  W  D  L  E  H  H  H  H  H  H Stop Bpu1102 I                            T7 Terminator
CTGAGTTGGCTGCTGCCACCGCTGAGCAATAACTAGCATAACCCCTTGGGGCCTCTAAACGGGTCTTGAGGGGTTTTTTGCTGAAAGGAGGAACTATATC 500

CGGATTGGCGAATGGGACGCGCCCTGTAGCGGCGCATT                                                                538
```

FIG. 29 pET 24b myc-ORF 6 5' total-His (VR-2332)

```
                                                                Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator        Xba 1                    RBS          Nde 1       Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA 200
                                                                      Start  M  E  Q  K  L  I  S  E  E Ecor 1   BamH I                 5' ORF6 Ectodomain 1                    GGGGS Linker
GGATCTGAATCGATCCATGAATTCTAGTGGATCCATGGGGTCGTCCTTAGATGACTTCTGTCATGATAGCACGGCTCCACAAAAGGTGCTTGGAGGAGGC 300
   D  L  N  R  S  M  N  S  S  G  S  M  G  S  S  L  D  D  F  C  H  D  S  T  A  P  Q  K  V  L  G  G  G 3' ORF6 Ectodomain 2    Xho 1      His Tag
GGCAGCGCGCACTTTCAGAGTACAAATAAGCTCGAGCACCACCACCACCACCACTGAGATCCGGCTGCTAACAAAGCCCGAAAGGAAGCTGAGTTGGCTG 400
 G  S  A  H  F  Q  S  T  N  K  L  E  H  H  H  H  H  H Stop Bpu1102 I                T7 Terminator
CTGCCACCGCTGAGCAATAACTAGCATAACCCCTTGGGGCCTCTAAACGGGTCTTGAGGGGTTTTTTGCTGAAAGGAGGAACTATATCCGGATTGGCGAA 500

TGGGACGCGCCCTGTAGCGGCGCATT                                                                           526
```

FIG. 30 pET 24b myc-ORF 6 3'-His (VR-2332)

Bgl II; T7 Promoter

AGGCGCCAGCAACCGCACCTGTGGCGCCGGTGATGCCGGCCACGATGCGTCCGGCGTAGAGGATCGAGATCTCGATCCCGCGAAATTAATACGACTCACT 100 lac operator; Xba 1; RBS; Nde 1; Myc Tag

ATAGGGGAATTGTGAGCGGATAACAATTCCCCTCTAGAAATAATTTTGTTTAACTTTAAGAAGGAGATATACATATGGAACAAAAACTCATCTCAGAAGA 200

Start M E Q K L I S E E

EcoR 1; BamH I; ORF 6 3' (underline)

GGATCTGAATCGATCCATGAATTCTAGTGGATCCTCAGCCATAGAAACCTGGAAATTCATCACCTCCAGATGCCGTTTGTGCTTGCTAGGCCGCAAGTAC 300

D L N R S M N S S G S S A I E T W K F I T S R C R L C L L G R K Y

ATTCTGGCCCCTGCCCACCACGTTGAAAGTGCCGCACGGTTTCATCCGATTGCGGCAAATGATAACCACGCATTTGTCGTCCGGCGTCCCGGCTCCACTA 400

I L A P A H H V E S A A R F H P I A A N D N H A F V V R R P G S T

CGGTCAACGGCACATTGGTGCCCGGGTTAAAAAGCCTCGTGTTGGGTGGCAGAAAAGCTGTTAAACAGGGAGTGGTAAACCTTGTCAAATATGCCAAACT 500

T V N G T L V P G L K S L V L G G R K A V K Q G V V N L V K Y A K L

Xho 1; His Tag; Bpu1102 I

CGAGCACCACCACCACCACCACTGAGATCCGGCTGCTAACAAAGCCCGAAAGGAAGCTGAGTTGGCTGCTGCCACCGCTGAGCAATAACTAGCATAACCC 600

E H H H H H H Stop

T7 Terminator

CTTGGGGCCTCTAAACGGGTCTTGAGGGGTTTTTTGCTGAAAGGAGGAACTATATCCGGATTGGCGAATGGGACGCGCCCTGTAGCGGCGCATT 694

FIG. 31

VR 2332 Protein Coated Plate

FIG. 32A pET 24b myc-ORF 7-His (Lelystad)

```
                                                   Bgl II                T7 Promoter
AGGCGCCAGCAACCGCACCTGTGGCGCCGGTGATGCCGGCCACGATGCGTCCGGCGTAGAGGATCGAGATCTCGATCCCGCGAAATTAATACGACTCACT  100 lac operator            Xba 1                Ribz         Nde 1    Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                                                                  Start   M  E  Q  K  L  I  S  E  E EcoR 1   BamH I      ORF 7 (underline)
GGATCTGAATCGATCCATGAATTCTAGTGGATCCATGGCCGGTAAAAACCAGAGCCAGAAGAAAAAGAAAAGTACAGCTCCGATGGGGAATGGCCAGCCA  300
 D  L  N  R  S  M  N  S  S  G  S  M  A  G  K  N  Q  S  Q  K  K  K  K  S  T  A  P  M  G  N  G  Q  P GTCAATCAACTGTGCCAGTTGCTGGGTGCAATGATAAAGTCCCAGCGCCAGCAACCTAGGGGAGGACAGGCCAAAAAGAAAAAGCCTGAGAAGCCACATT  400
 V  N  Q  L  C  Q  L  L  G  A  M  I  K  S  Q  R  Q  Q  P  R  G  G  Q  A  K  K  K  K  P  E  K  P  H TTCCCCTGGCTGCTGAAGATGACATCCGGCACCACCTCACCCAGACTGAACGCTCCCTCTGCTTGCAATCGATCCAGACGGCTTTCAATCAAGGCGCAGG  500
F  P  L  A  A  E  D  D  I  R  H  H  L  T  Q  T  E  R  S  L  C  L  Q  S  I  Q  T  A  F  N  Q  G  A  G AACTGCGTCGCTTTCATCCAGCGGGAAGGTCAGTTTTCAGGTTGAGTTTATGCTGCCGGTTGCTCATACAGTGCGCCTGATTCGCGTGACTTCTACATCC  600
  T  A  S  L  S  S  S  G  K  V  S  F  Q  V  E  F  M  L  P  V  A  H  T  V  R  L  I  R  V  T  S  T  S Xho I    His Tag                                                          Bpu1102 I
GCCAGTCAGGGTGCAAGTCTCGAGCACCACCACCACCACCACTGAGATCCGGCTGCTAACAAAGCCCGAAAGGAAGCTGAGTTGGCTGCTGCCACCGCTG  700
 A  S  Q  G  A  S  L  E  H  H  H  H  H  H  Stop T7 Terminator
AGCAATAACTAGCATAACCCCTTGGGGCCTCTAAACGGGTCTTGAGGGGTTTTTTGCTGAAAGGAGGAACTATATCCGGATTGGCGAATGGGACGCGCCC  800

TGTAGCGGCGCATTAAGCGCG   821
```

FIG. 36

FIG. 37 pET 24b myc-NSP 2P-His (Lelystad)

```
AGGCGCCAGCAACCGCAC

FIG. 38 pET 24b myc-NSP 2HP-His (ATP)

```
                                                                                              Bgl II              Nde 1       Myc Tag                T7 Promoter
AGGGCCAGCAACCGGCACCTGTGGCGCCGGTGAGCCGGCCACGATGGCTCCGGCGTAGAGGATCGGAGATCTCGATCCCGCGAAATTAATACGACTCACT   100
                                          lac operator                  Xba 1                           RBS           AAGAAGGAGATATACATATGGAACAAAAACTCATCTCAGAAGAA   200
ATAGGGAATTGTGAGCGGATAACAATTCCCGTCTAGAAATAATTTTGTTTAACTTT                                                                Start  M  E  Q  K  L  I  S  E  E
                                                                                                              NSP 2HP (underlined)
                                                     EcoR 1      BamH 1                                                                                                      P
                                                                                                                                                                                  300
GAGATTTGCCTGTTGGTGGCCCCGATTTGATGGGCGACAATGTTCCTGACGGTCGGGAAGATTTGCCTGTTGGTGGCCCC
 E  Q  K  L  I  S  E  E                                                                                           E  D  L  P  V  G  G  P 400
GGATCTGAATCGATCCATGAGTAGTGGATCCGGCAGCCGGATTTGATGGGCGACAATGTTCCTGACGGTCGGGAAGATTTGCCTGTTGGTGGCCCC
 D  L  N  R  S  M  N  S  S  G  S  G  S  G  S  P  I  L  M  G  D  N  V  P  D  G  R  E  D  L  P  V  G  G  P 500
CTTGATCTTTGACACCATCCGAGCGATGACACCTCTGAGTGAGCCTATGCCACCTCTGAGTGAGCCGGCCCCCTTGAGTGAGCCGGTACCGACCTGTGCTGACAGTGTCCGACCGGCGTAGAAC
 L  D  L  S  T  P  S  E  P  M  T  P  L  S  E  P  A  P  M  P  A  L  Q  Y  I  S  R  P  V  T  P  L  S 600
AGCTGGGCCCCAGTACCTGACCGGCGTAGAACTGTGTCCGACCGGCGTAGAACTGTCCGACCGGCGAACAATGCTGACGCAACAATGCTGACGCAACAATGCTGA
 E  L  A  P  V  P  A  P  R  R  T  V  S  R  P  V  T  P  L  S  E  P  I  F  V  S  A  P  R  H  K  F  R  Q 700
GGTGGAAGAAGCGAATCTGGCGGCAACAATGCTGACGCACCAGGATGAGCCGCTGGATCTGAGTGCATCGAGTCAGACTGAATATGAGGCTTCTCCCTA
 V  E  E  A  N  L  A  A  T  M  L  T  H  Q  D  E  P  L  D  L  S  A  S  S  Q  T  E  Y  E  A  S  P  L Xho 1         His Tag                              Bpu1102 I                                                                 800
ACACCACTGCAGAGAACATGGGTATTCTTGAGGTGGGGGGCCAAGAAGAAGTCTGAGTGAAGAAACTGAAGAAACTGAATGACATCAACCCTGCAC  AAGAAGGAGAACTATATCCGGATTGGCCGAATGGGACGCCGCCCTGTAG  900
 T  P  L  Q  N  M  G  I  L  E  V  G  G  Q  E  A  E  E  V  L  S  E  N  S  D  T  L  N  D  I  N  P  A 900
CTGTGTCATCACTGAGCGTGAGATCCGGCTGCTAACAAAGCCCGAAAGGAAGCTGAGTTGGCTGCTGCCACGGCTGAGCAAT GCTGAAAGGAGGAACTATATCCGGATTGGCCGAATGGGACGCCGCCCTGTAG
 P  V  S  S  L  E  H  H  H  H  H  H  Stop T7 Terminator
AACTAGCATAACCCCCTTGGGGCCTCTAAACGGGTCTTTTTGCTGAAAGGAGGAACTATATCCGGATTGGCCGAATGGGACGCCGCCCTGTAG

CGGGCGCATT  909
```

FIG. 39 pET 24b myc-ORF 5 3'-His (Lelystad)

```
                                                                                          T7 Promoter
AGGGCGCCAGCAACCGCACCTGTGGCGCCGGTGATGCCGGCCACGATGCGTTCCGGCGTAGAGGATCGAGATCTCGATCCCGCGAAATTAATACGACTCACT  100
              lac operator                                        Bgl II
                                                 RBS                        Nde 1       Myc Tag
ATAGGGGAATTGTGAGCGGATAACAATTCCCCTCTAGAAATAATTTTGTTTAACTTTAAGAAGGAGATATACATATGGAACAAAAACTCATCTCAGAAGA  200
                             Xba 1                                                  Start M  E  Q  K  L  I  S  E  E
                       Ecor 1    BamH I                   ORF 5 3' (underline)
GGATCTGAATCGATCCATGAGTGGATCCTGCATGGCCTGCCGCTACGCCCGGTTACCAACTTCATTGTGGACGACCGGGGAGAGTT  300
 D  L  N  R  S  S  M  N  S  S  G  S  C  M  A  C  R  Y  A  R  T  R  F  T  N  F  I  V  D  D  R  G  R  V
CATCGATGGAAGTCTCCAATAGTGGTAGAAAAATTGGGCAAGGCAAAGGCCAAAGCCGAAGTCGATGGCAATCTGGTCACCATCAAACATGTCGTCCTCGAAGGGGTTAAAG  400
 H  R  W  K  S  P  I  V  V  E  K  L  G  K  A  E  V  D  G  N  L  V  T  I  K  H  V  V  L  E  G  V  K
                                                                       Xho I   His Tag
CTCAACCCTTGACGACGAGGACTTCGGCTGAGCAATGGGAGGCCCTCGAGCACCACCACCACCACCACTGAGATCCGGCTGCTAACAAAGCCCGAAAGGAAGC  500
 A  Q  P  L  T  R  T  S  A  E  Q  W  E  A  L  E  H  H  H  H  H  H  *  Stop
           Bpu1102 I                                  T7 Terminator
TGAGTTGGCTGCTGCCACCGCTGAGCAATAACTAGCATAACCCCTTGGGGCCTCTAAACGGGTCTTGAGGGGTTTTTTGCTGAAAGGAGGAACTATATC  600

CGGATTGGCGAATGGGACGCGCCCTGTAGCGGCGCATTAAGCGCG                                                         645
```

FIG. 40 pET 24b myc-Orf 6 3'-His (Lelystad)

```

PRRSV Strains Used to Inoculate Pigs
- MN 184
- SDSU 73
- VR 2332
- Control
- MLV
- Euro PRRSV Lelystad Virus NSP2P

IDENTIFYING VIRALLY INFECTED AND VACCINATED ORGANISMS

CROSS-REFERENCE TO RELATED APPLICATIONS

This application is a continuation of U.S. application Ser. No. 11/155,830, filed Jun. 17, 2005, now U.S. Pat. No. 7,611, 717, which claims the benefit of U.S. Provisional Application Ser. No. 60/656,192, filed on Feb. 25, 2005, now expired, and U.S. Provisional Application Ser. No. 60/581,325, filed on Jun. 18, 2004, now expired. The disclosures of the prior applications are considered part of (and are incorporated by reference in) the disclosure of this application.

BACKGROUND

1. Technical Field

This document relates to methods and materials involved in identifying virally infected or vaccinated organisms (e.g., vertebrates and mammals). For example, this document relates to methods and material for identifying a mammal (e.g., a pig) having antibodies against a virus such as a porcine reproductive and respiratory syndrome (PRRS) virus.

2. Background Information

Organisms infected with a virus can mount an immune response against that infecting virus. Such an immune response can include the production of antibodies that bind to the virus. The presence of antibodies against a virus can indicate that the organism was exposed to that virus. For example, pigs infected with a PRRS virus can contain pig antibodies that bind PRRS virus.

PRRS is a viral disease of pigs, characterized by reproductive failure in sows (e.g., late-term abortions and stillbirths in sows) and respiratory difficulties in piglets (e.g., interstitial pneumonia in nursery pigs) (Collins et al., *J. Vet. Diagn. Invest.*, 4:117-126 (1992) and Wensvoort et al., *Vet Q.*, 13:121-130 (1991)). It was detected in North America in 1987 (Keffaber, *Am. Assoc. Swine Pract. Newsl.*, 1:1-9 (1989) and Hill, Overview and History of Mystery Swine Disease (Swine Infertility and Respiratory syndrome). In: Proceedings of the Mystery Swine Disease Committee Meeting, October 6, Denver Co., pp. 29-30. Livestock Conservation Institute, Madison, Wis. (1990)) and in Europe in 1990 (Paton et al., *Vet Rec.*, 128:617 (1991)). The causative agent is a small, enveloped positive-stranded RNA virus that is recovered primarily from alveolar macrophages and blood of infected swine. It is a member of the Arteriviridae, which includes equine arteritis virus (EAV; den Boon et al., *J. Virol.*, 65:2910-2920 (1991)), lactate dehydrogenase elevating virus of mice (LDV; Plagemann and Moennig, *Adv. Vir. Res.*, 41:99-192 (1992)), and simian hemorrhagic fever virus (SHFV; Godeny et al., In Proceedings of the 9th International Congress of Virology, p 22, August 8-13, Glasgow, Scotland (1993) and Plagemann, In Fields Virology, 3$^{rd}$ ed., pp. 1105-1120. Edited by B. N. Fields, D. M. Knipe and P. M. Howley. Philadelphia: Lippincott-Raven (1996)), in the Order Nidovirales (Cavanagh, *Arch. Virol.*, 142:629-633 (1997)). Like other arteriviruses, PRRS virus infects predominantly macrophages and establishes a persistent infection in resident macrophages of numerous tissues (Lawson et al., *Virus Res.*, 51:105-113 (1997) and Christopher-Hennings et al., *J. Vet. Diag. Invest.*, 7:456-464 (1995)).

SUMMARY

This document involves methods and materials related to assessing organisms to determine whether or not the organisms were exposed to a viral vaccine or viral infection. For example, this document provides methods and materials that can be used to determine whether or not an organism (e.g., a member of a swine species such as a pig) contains anti-PRRS virus antibodies. Determining whether or not, for example, pigs contain anti-PRRS virus antibodies can allow pig farmers to identify pigs that can be infected with PRRS virus. This can allow the farmer to separate pigs suspected to be infected with a PRRS virus from those pigs believed to be uninfected. Also, identifying pigs that do not contain anti-PRRS virus antibodies can allow pig farmers to vaccinate the previously uninfected population of pigs as opposed to an entire herd, which could include many previously infected pigs.

In one embodiment, this document provides methods and materials that can be used to determine if a particular organism received a vaccine version of a virus, was infected with a naturally-occurring version of the virus, or is naïve with respect to the virus. Differentiating between vaccinated organisms and organisms infected with a naturally-occurring version of the virus can allow clinicians, in the case of humans, and farmers, in the case of farm animals, to determine the immunological origin of each organism's immunity to the virus. For example, a farmer receiving a herd of pigs can determine if the pigs of the herd received a PRRS virus vaccine, were infected with a naturally-occurring version of the virus (e.g., a field isolate of PRRS virus), or are naïve with respect to the virus. With this information, the farmer can determine whether the herd need not be vaccinated or whether any uninfected pigs are at risk of being infected from, for example, pigs that were infected with a naturally-occurring version of the virus.

In general, this document features a kit for detecting a swine anti-PRRS virus antibody. The kit includes (a) a polypeptide having an amino acid sequence present in a PRRS virus polypeptide selected from the group consisting of NSP 2 polypeptides and ORF 5 polypeptides, wherein the polypeptide contains an epitope for the swine anti-PRRS virus antibody; and (b) an anti-swine Ig antibody. The polypeptide can be at least eight amino acid residues in length. The polypeptide can contain an amino acid sequence at least 100 amino acids in length that is at least about 80 percent identical to an amino acid sequence encoded by the nucleic acid sequence set forth in SEQ ID NO:5 over the length. The polypeptide can contain an amino acid sequence at least 100 amino acids in length that is at least about 90 percent identical to an amino acid sequence encoded by the nucleic acid sequence set forth in SEQ ID NO:5 over the length. The polypeptide can contain an amino acid sequence at least 20 amino acids in length that is at least about 80 percent identical to a sequence set forth in SEQ ID NO:22 over the length. The polypeptide can contain an amino acid sequence at least 20 amino acids in length that is at least about 90 percent identical to a sequence set forth in SEQ ID NO:22 over the length. The polypeptide can contain the amino acid sequence encoded by the nucleic acid sequence set forth in SEQ ID NO:11. The polypeptide can contain an amino acid sequence of SEQ ID NO:32. The polypeptide can contain an amino acid sequence of SEQ ID NO: 16, 19, 22, 26, 29, 32, 39, 45, 61, or 64. The polypeptide can be a recombinant polypeptide produced in cells not infected with a PRRS virus. The anti-swine Ig antibody can be an anti-swine IgG or IgM antibody. The anti-swine Ig antibody can be a goat anti-swine Ig antibody. The kit can contain a polypeptide having an amino acid sequence present in a PRRS virus NSP 2 polypeptide and a polypeptide having an amino acid sequence present in a PRRS virus ORF 5 polypeptide. The kit can contain a polypeptide having an amino acid sequence present in a PRRS virus ORF 7 polypeptide (e.g., a polypeptide containing an amino acid sequence of SEQ ID NO:36 or 54). The kit can contain a polypeptide having an amino acid sequence present in a PRRS virus ORF 6 polypeptide (e.g., a polypeptide containing an amino acid sequence of SEQ ID NO:32, 48, 51, or 67). The anti-swine Ig antibody can contain an enzyme. The kit can contain a polypeptide having an amino acid sequence present in a PRRS virus NSP 1 polypeptide. The kit can contain a control sample containing swine anti-PRRS virus antibody. The kit can contain a control sample containing swine serum lacking swine anti-PRRS virus antibodies.

In another embodiment, this document features a method for determining whether or not a sample contains a swine anti-PRRS virus antibody. The method includes (a) contacting a polypeptide with the sample under conditions wherein the polypeptide forms a polypeptide:swine anti-PRRS virus antibody complex with an antibody, if present, within the sample, wherein the polypeptide contains an amino acid sequence present in a PRRS virus polypeptide selected from the group consisting of NSP 2 polypeptides and ORF 5 polypeptides, wherein the polypeptide contains an epitope for the swine anti-PRRS virus antibody; and (b) detecting the presence or absence of the complex, wherein the presence of the complex indicates that the sample contains the swine anti-PRRS virus antibody. The sample can be a pig serum sample. The polypeptide can be at least eight amino acid residues in length. The polypeptide can contain an amino acid sequence at least 100 amino acids in length that is at least about 80 percent identical to an amino acid sequence encoded by the nucleic acid sequence set forth in SEQ ID NO:5 over the length. The polypeptide can contain an amino acid sequence at least 20 amino acids in length that is at least about 80 percent identical to a sequence set forth in SEQ ID NO:22 over the length. The polypeptide can contain the amino acid sequence encoded by the nucleic acid sequence set forth in SEQ ID NO:11. The polypeptide can contain an amino acid sequence of SEQ ID NO:32. The polypeptide can contain an amino acid sequence of SEQ ID NO: 16, 19, 22, 26, 29, 32, 39, 45, 61, or 64. The polypeptide can be a recombinant polypeptide produced by cells not infected with a PRRS virus. The step (b) can include contacting the complex with an anti-swine Ig antibody. The anti-swine Ig antibody can contain an enzyme. The step (a) can include contacting the sample with polypeptides within a kit, wherein the kit contains a polypeptide having an amino acid sequence present in a PRRS virus NSP 2 polypeptide and a polypeptide having an amino acid sequence present in a PRRS virus ORF 5 polypeptide. The kit can contain a polypeptide containing an amino acid sequence present in a PRRS virus ORF 7 polypeptide (e.g., a polypeptide containing an amino acid sequence of SEQ ID NO:36 or 54), a polypeptide containing an amino acid sequence present in a PRRS virus ORF 6 polypeptide (e.g., a polypeptide containing an amino acid sequence of SEQ ID NO:32, 48, 51, or 67), and a polypeptide containing an amino acid sequence present in a PRRS virus NSP 1 polypeptide. The method can include contacting the sample with an additional polypeptide to form a polypeptide:swine anti-PRRS virus antibody complex, wherein the additional polypeptide contains an amino acid sequence present in a PRRS virus ORF 7 polypeptide, a PRRS virus ORF 6 polypeptide, or a PRRS virus NSP 1 polypeptide.

In another aspect, this document features a kit for determining whether an animal received a vaccine version of a virus or was infected with a naturally-occurring version of the virus. The kit includes (a) a first polypeptide having an amino acid sequence such that antibodies made against the vaccine version of the virus bind the first polypeptide and antibodies made against the naturally-occurring version of the virus bind the first polypeptide, and (b) a second polypeptide having an amino acid sequence such that antibodies made against the vaccine version of the virus bind the second polypeptide and antibodies made against the naturally-occurring version of the virus do not bind the second polypeptide. The animal can be a vertebrate (e.g., an avian or mammalian species). The animal can be a pig or a human. The virus can be a PRRS virus. The vaccine version can be an attenuated PRRS virus. The vaccine version can be the RespPRRS vaccine. The first polypeptide can contain an amino acid sequence present in a C-terminal portion of an ORF 5 polypeptide of a VR2332 or RespPRRS PRRS virus. The second polypeptide can contain an amino acid sequence present in the N-terminal half of an ORF 5 polypeptide of a VR2332 or RespPRRS PRRS virus.

In another embodiment, this document features a method for determining the immunological state of an animal with respect to a virus, wherein the immunological state is that (1) the animal received a vaccine version of the virus, (2) the animal was infected with a naturally-occurring version of the virus, or (3) the animal is immunologically naive with respect to the virus. The method includes (a) contacting a first sample from the animal with a first polypeptide under conditions wherein the first polypeptide forms a first polypeptide:antibody complex with an antibody, if present, within the first sample, wherein the first polypeptide contains an amino acid sequence such that antibodies made against the vaccine version of the virus bind the first polypeptide and antibodies made against the naturally-occurring version of the virus bind the first polypeptide; (b) contacting a second sample from the animal with a second polypeptide under conditions wherein the second polypeptide forms a second polypeptide:antibody complex with an antibody, if present, within the second sample, wherein the second polypeptide contains an amino acid sequence such that antibodies made against the vaccine version of the virus bind the second polypeptide and antibodies made against the naturally-occurring version of the virus do not bind the second polypeptide; and (c) detecting the presence or absence of the first polypeptide:antibody complex and the presence or absence of the second polypeptide:antibody complex, wherein the presence of the first polypeptide:antibody complex and the presence of the second polypeptide:antibody complex indicates that the animal received the vaccine version of the virus, wherein the presence of the first polypeptide:antibody complex and the absence of the second polypeptide:antibody complex indicates that the animal was infected with the naturally-occurring version of the virus, and wherein the absence of the first polypeptide:antibody complex and the absence of the second polypeptide:antibody complex indicates that the animal is immunologically naive with respect to the virus. The animal can be a vertebrate (e.g., an avian or mammalian species). The animal can be a pig or a human. The virus can be a PRRS virus. The vaccine version can be an attenuated PRRS virus. The vaccine version can be the RespPRRS vaccine. The first polypeptide can contain an amino acid sequence present in a C-terminal portion of an ORF 5 polypeptide of a VR2332 or RespPRRS PRRS virus. The second polypeptide can contain an amino acid sequence present in the N-terminal half of an ORF 5 polypeptide of a VR2332 or RespPRRS PRRS virus.

Another aspect of this document features a substantially pure polypeptide having the amino acid sequence of a PRRS virus NSP 2 polypeptide or a fragment of the PRRS virus NSP 2 polypeptide, wherein the fragment is greater than 20 amino acid residues in length.

Another aspect of this document features a substantially pure polypeptide having the amino acid sequence of a PRRS virus NSP 4 polypeptide or a fragment of the PRRS virus NSP 4 polypeptide, wherein the fragment is greater than 20 amino acid residues in length.

Another aspect of this document features a host cell that expresses a PRRS virus NSP 1, NSP 2, or NSP 4 polypeptide. The cell can be a prokaryotic cell (e.g., a bacterial cell).

Another aspect of this document features a method of reducing background signals in an assay capable of detecting PRRS virus antibodies in a swine sample. The assay includes contacting a solid support containing PRRS virus polypeptides with the swine sample. The method includes treating the solid support with a blocking solution at a pH value greater than 8.0 (e.g., greater than 8.5, 9.0, 9.5, 10.0, or 10.5). The blocking solution can be milk (e.g., nonfat dry milk in PBS), protein solutions, or animal serum.

Another aspect of this document features a solid support containing PRRS virus polypeptides. The solid support was treated with a blocking solution at a pH value greater than 8.0 (e.g., greater than 8.5, 9.0, 9.5, 10.0, or 10.5). The blocking solution can be milk (e.g., nonfat dry milk in PBS), protein solutions, or animal serum. The solid support can be a plastic plate (e.g., a 96 well plate), a glass slide, glass or plastic beads, or the like.

Another aspect of this document features a method of increasing the ability of a polypeptide attached to a solid support to react with an antibody that binds the polypeptide. The method includes contacting the solid support with the polypeptide and a lysozyme. The polypeptide can be a PRRS virus polypeptide. The polypeptide can be a PRRS virus ORF 7 polypeptide. The polypeptide can be a recombinant polypeptide produced by cells not infected with a PRRS virus. The antibody can be an anti-PRRS virus polypeptide antibody. The lysozyme can be a chicken egg lysozyme. The polypeptide and the lysozyme can be contacted with the solid support at a ratio of at least 4 ng of the polypeptide per 1 ng of the lysozyme. The lysozyme and the polypeptide can be contacted with the solid support at a ratio of at least 1 ng of the lysozyme per 1 ng of the polypeptide.

Another aspect of this document features a solid support that was treated with a PRRS virus polypeptide and a lysozyme. The polypeptide can be a PRRS virus ORF 7 polypeptide. The polypeptide can be a recombinant polypeptide produced by cells not infected with a PRRS virus. The lysozyme can be a chicken egg lysozyme. The polypeptide and the lysozyme can be contacted with the solid support at a ratio of at least 4 ng of the polypeptide per 1 ng of the lysozyme. The lysozyme and the polypeptide can be contacted with the solid support at a ratio of at least 1 ng of the lysozyme per 1 ng of the polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 is a listing of a nucleic acid sequence (SEQ ID NO:1) of a pET 24b myc-polypeptide-His construct with the polypeptide being an NSP 1 polypeptide from the VR-2332 strain of PRRS virus. The underlined nucleic acid sequence (SEQ ID NO:2) encodes an NSP 1 polypeptide from the VR-2332 strain of PRRS virus. The shown amino acid sequence (SEQ ID NO:3) is the amino acid sequence from the start site to the start of the NSP 1 polypeptide-encoding region.

FIG. 3 is a listing of a nucleic acid sequence (SEQ ID NO:4) of a pET 24b myc-polypeptide-His construct with the polypeptide being an NSP 2 polypeptide from the VR-2332 strain of PRRS virus. The underlined nucleic acid sequence (SEQ ID NO:5) encodes an NSP 2 polypeptide. The shown amino acid sequence (SEQ ID NO:6) is the amino acid sequence from the start site into the myc tag-encoding region. The LEHHHHHH sequence (SEQ ID NO:13) includes a his tag.

FIG. 4 is a listing of a nucleic acid sequence (SEQ ID NO:7) of a pET 24b myc-polypeptide-His construct with the polypeptide being an NSP 4 polypeptide from the VR-2332 strain of PRRS virus. The underlined nucleic acid sequence (SEQ ID NO:8) encodes an NSP 4 polypeptide. The shown amino acid sequence (SEQ ID NO:9) is an amino acid sequence for a myc-NSP 4-His polypeptide.

FIG. 13 contains two bar graphs plotting the absorbance for samples obtained from animals exposed to MLV or MN30100 PRRS viruses. The absorbance values were detected using an ELISA with the indicated polypeptide.

FIG. 14 contains a sequence alignment of PRRS virus NSP 2 polypeptides (SEQ ID NOS: 70-81, respectively, in order of appearance). The nucleic acid encoding the NSP 2 polypeptide of VR-2332 PRRS virus was truncated using a naturally-occurring XhoI restriction site at nucleotides 3490-3495 to generate nucleic acid encoding a truncated NSP 2 polypeptide referred to as an NSP 2P polypeptide.

FIG. 18 contains graphs plotting the absorbance for ELISAs containing the indicated polypeptide. The groups are as set forth in Table 6.

FIG. 19 is a listing of a nucleic acid sequence (SEQ ID NO:10) of a pET 24b myc-polypeptide-His construct with the polypeptide being an NSP 2P polypeptide from the VR-2332 strain of PRRS virus. The underlined nucleic acid sequence (SEQ ID NO:11) encodes an NSP 2P polypeptide. The first amino acid sequence (SEQ ID NO:12) is an amino acid sequence of the myc tag region of a myc-NSP 2P-His polypeptide, while the second amino acid sequence (SEQ ID NO:13) is an amino acid sequence of the His tag region of a myc-NSP 2P-His polypeptide.

FIG. 20 is a listing of a nucleic acid sequence (SEQ ID NO:14) of a pET 24b myc-polypeptide-His construct with the polypeptide being an ORF 5 5' polypeptide from the MN30100 strain of PRRS virus. The underlined nucleic acid sequence (SEQ ID NO:15) encodes an ORF 5 5' polypeptide. The amino acid sequence (SEQ ID NO:16) is an amino acid sequence for a myc-ORF 5 5'-His polypeptide.

FIG. 21 is a listing of a nucleic acid sequence (SEQ ID NO:17) of a pET 24b myc-polypeptide-His construct with the polypeptide being an ORF 5 5' polypeptide from the VR-2332 strain of PRRS virus. The underlined nucleic acid sequence (SEQ ID NO:18) encodes an ORF 5 5' polypeptide. The amino acid sequence (SEQ ID NO:19) is an amino acid sequence for a myc-ORF 5 5'-His polypeptide.

FIG. 22 is a listing of a nucleic acid sequence (SEQ ID NO:20) of a pET 24b myc-polypeptide-His construct with the polypeptide being an ORF 5 5' total polypeptide from the VR-2332 strain of PRRS virus. The underlined nucleic acid sequence (SEQ ID NO:21) encodes an ORF 5 total polypeptide. The amino acid sequence (SEQ ID NO:22) is an amino acid sequence for a myc-ORF 5 total-His polypeptide. A linker amino acid sequence (GGGGS; SEQ ID NO:23) is located between the first and second ectodomains of the 5' region of the ORF 5 polypeptide.

FIG. 23 is a listing of a nucleic acid sequence (SEQ ID NO:24) of a pET 24b myc-polypeptide-His construct with the polypeptide being an ORF 5 3' polypeptide from the VR-2332 strain of PRRS virus. The underlined nucleic acid sequence (SEQ ID NO:25) encodes an ORF 5 3' polypeptide. The amino acid sequence (SEQ ID NO:26) is an amino acid sequence for a myc-ORF 5 3'-His polypeptide.

FIG. 24 is a listing of a nucleic acid sequence (SEQ ID NO:27) of a pET 24b myc-polypeptide-His construct with the polypeptide being an ORF 5 3' polypeptide from the MN30100 strain of PRRS virus. The underlined nucleic acid sequence (SEQ ID NO:28) encodes an ORF 5 3' polypeptide. The amino acid sequence (SEQ ID NO:29) is an amino acid sequence for a myc-ORF 5 3'-His polypeptide.

FIG. 25 is a listing of a nucleic acid sequence (SEQ ID NO:30) of a pET 24b myc-polypeptide-His construct with the polypeptide being an ORF 5+6 polypeptide from the VR-2332 strain of PRRS virus. The underlined nucleic acid sequence (SEQ ID NO:31) encodes an ORF 5+6 polypeptide. The amino acid sequence (SEQ ID NO:32) is an amino acid sequence for a myc-ORF 5+6-His polypeptide. A first linker amino acid sequence (GGGGS; SEQ ID NO:23) is located between the first and second ectodomains of the 5' region of the ORF 5 polypeptide. A second linker amino acid sequence is located between the second ectodomain of the 5' region of the ORF 5 polypeptide and the first ectodomain of the 5' region of the ORF 6 polypeptide. A third linker amino acid sequence is located between the first and second ectodomains of the 5' region of the ORF 6 polypeptide.

FIG. 26 is a listing of a nucleic acid sequence (SEQ ID NO:34) of a pET 24b myc-polypeptide-His construct with the polypeptide being an ORF 7 polypeptide from the VR-2332 strain of PRRS virus. The underlined nucleic acid sequence (SEQ ID NO:35) encodes an ORF 7 polypeptide. The amino acid sequence (SEQ ID NO:36) is an amino acid sequence for a myc-ORF 7-His polypeptide.

FIG. 27 is a listing of a nucleic acid sequence (SEQ ID NO:37) of a pET 24b myc-polypeptide-His construct with the polypeptide being an NSP 2HP polypeptide from the VR-2332 strain of PRRS virus. The underlined nucleic acid sequence (SEQ ID NO:38) encodes an NSP 2HP polypeptide. The amino acid sequence (SEQ ID NO:39) is an amino acid sequence for a myc-NSP 2HP-His polypeptide.

FIG. 28 is a listing of a nucleic acid sequence (SEQ ID NO:40) of a pET 24b myc-polypeptide-His construct with the polypeptide being an NSP 2 S1 HP polypeptide from the VR-2332 strain of PRRS virus. The underlined nucleic acid sequence (SEQ ID NO:41) encodes an NSP 2 S1 HP polypeptide. The amino acid sequence (SEQ ID NO:42) is an amino acid sequence for a myc-NSP 2 S1 HP-His polypeptide.

FIG. 29 is a listing of a nucleic acid sequence (SEQ ID NO:43) of a pET 24b myc-polypeptide-His construct with the polypeptide being an NSP 2 S2 HP polypeptide from the VR-2332 strain of PRRS virus. The underlined nucleic acid sequence (SEQ ID NO:44) encodes an NSP 2 S2 HP polypeptide. The amino acid sequence (SEQ ID NO:45) is an amino acid sequence for a myc-NSP 2 S2 HP-His polypeptide.

FIG. 30 is a listing of a nucleic acid sequence (SEQ ID NO:46) of a pET 24b myc-polypeptide-His construct with the polypeptide being an ORF 6 5' total polypeptide from the VR-2332 strain of PRRS virus. The underlined nucleic acid sequence (SEQ ID NO:47) encodes an ORF 6 5' total polypeptide. The amino acid sequence (SEQ ID NO:48) is an amino acid sequence for a myc-ORF 6 5' total-His polypeptide. A linker amino acid sequence (GGGGS; SEQ ID NO:23) is located between the first and second ectodomains of the 5' region of the ORF 5 polypeptide.

FIG. 31 is a listing of a nucleic acid sequence (SEQ ID NO:49) of a pET 24b myc-polypeptide-His construct with the polypeptide being an ORF 6 3' polypeptide from the VR-2332 strain of PRRS virus. The underlined nucleic acid sequence (SEQ ID NO:50) encodes an ORF 6 3' polypeptide. The amino acid sequence (SEQ ID NO:51) is an amino acid sequence for a myc-ORF 6 3'-His polypeptide.

FIG. 36 is a listing of a nucleic acid sequence (SEQ ID NO:52) of a pET 24b myc-polypeptide-His construct with the polypeptide being an ORF 7 polypeptide from the Lelystad virus strain of PRRS virus. The underlined nucleic acid sequence (SEQ ID NO:53) encodes an ORF 7 polypeptide. The amino acid sequence (SEQ ID NO:54) is an amino acid sequence for a myc-ORF 7-His polypeptide.

FIG. 37 is a listing of a nucleic acid sequence (SEQ ID NO:55) of a pET 24b myc-polypeptide-His construct with the polypeptide being an NSP 2P polypeptide from the Lelystad virus strain of PRRS virus. The underlined nucleic acid sequence (SEQ ID NO:56) encodes an NSP 2P polypeptide. The shown amino acid sequence is the amino acid sequence from the start site to the start of the NSP 2P polypeptide-encoding region (SEQ ID NO:3) and from the end of the NSP 2P polypeptide-encoding region through the his tag (SEQ ID NO:13).

Figure 38:
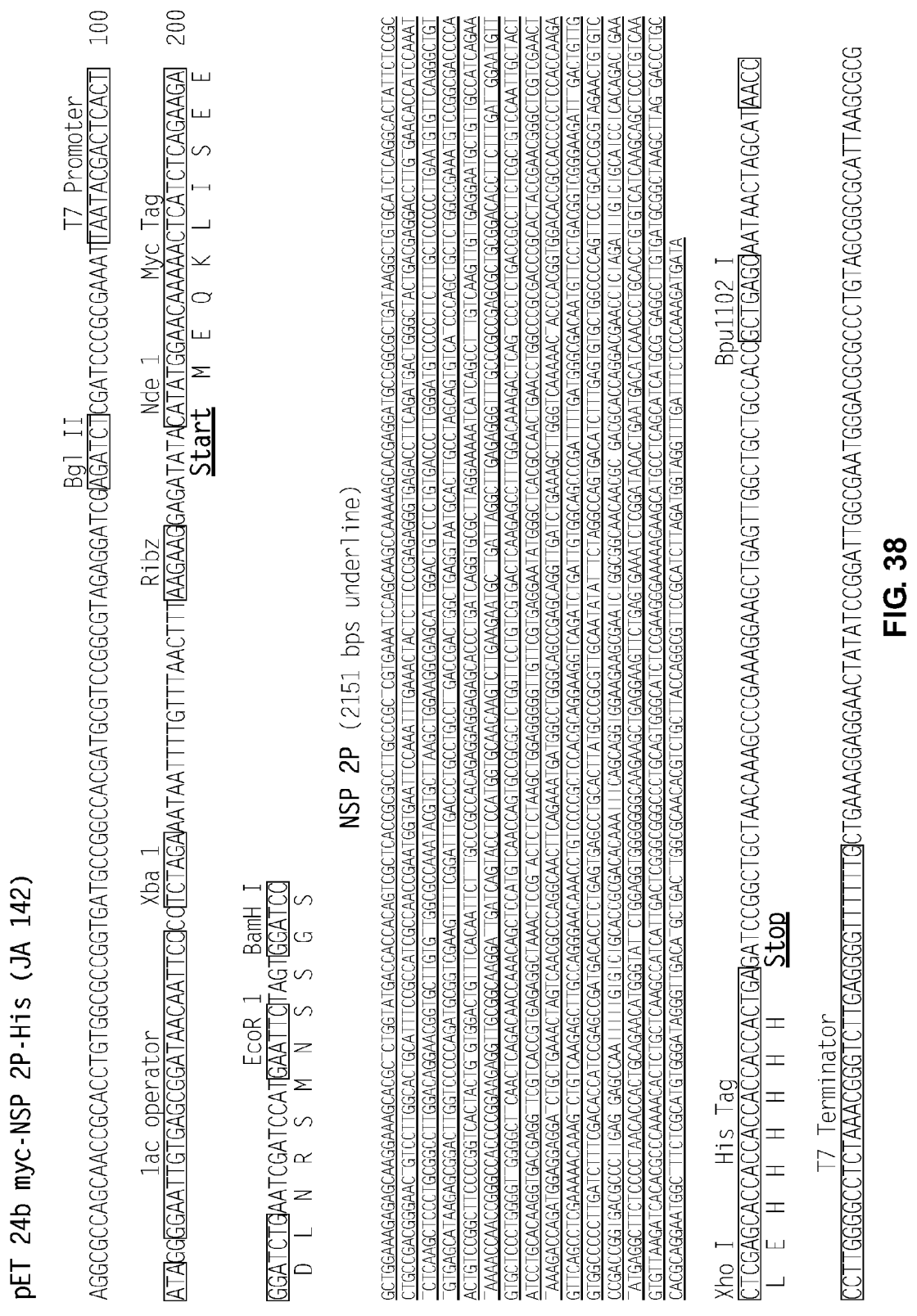

FIG. 38 is a listing of a nucleic acid sequence (SEQ ID NO:57) of a pET 24b myc-polypeptide-His construct with the polypeptide being an NSP 2P polypeptide from the JA 142 virus strain of PRRS virus. The underlined nucleic acid sequence (SEQ ID NO:58) encodes an NSP 2P polypeptide. The shown amino acid sequence is the amino acid sequence from the start site to the start of the NSP 2P polypeptide-encoding region (SEQ ID NO:3) and from the end of the NSP 2P polypeptide-encoding region through the his tag (SEQ ID NO:13).

FIG. 39 is a listing of a nucleic acid sequence (SEQ ID NO:59) of a pET 24b myc-polypeptide-His construct with the polypeptide being an NSP 2HP polypeptide from the Boehringer Ingelheim Ingelvac ATP virus strain of PRRS virus. The underlined nucleic acid sequence (SEQ ID NO:60) encodes an NSP 2HP polypeptide. The amino acid sequence (SEQ ID NO:61) is an amino acid sequence for a myc-NSP 2HP-His polypeptide.

FIG. 40 is a listing of a nucleic acid sequence (SEQ ID NO:62) of a pET 24b myc-polypeptide-His construct with the polypeptide being an ORF 5 3' polypeptide from the Lelystad virus strain of PRRS virus. The underlined nucleic acid sequence (SEQ ID NO:63) encodes an ORF 5 3' polypeptide. The amino acid sequence (SEQ ID NO:64) is an amino acid sequence for a myc-ORF 5 3'-His polypeptide.

FIG. 41 is a listing of a nucleic acid sequence (SEQ ID NO:65) of a pET 24b myc-polypeptide-His construct with the polypeptide being an ORF 6 3' polypeptide from the Lelystad virus strain of PRRS virus. The underlined nucleic acid sequence (SEQ ID NO:66) encodes an ORF 6 3' polypeptide. The amino acid sequence (SEQ ID NO:67) is an amino acid sequence for a myc-ORF 6 3'-His polypeptide.

DETAILED DESCRIPTION

Figure 1:
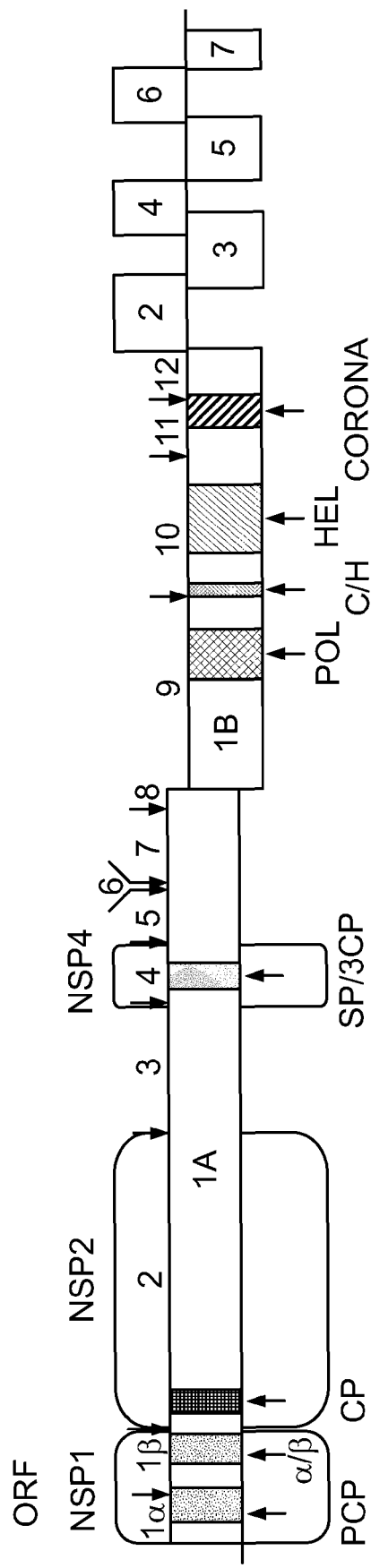
FIG. 1 is a diagram of a PRRS virus genome. Genomic regions shaded in gray were PCR amplified from VR2332 viral RNA, cloned, and expressed in *E. coli* BL21(DE3RP) cells.

This document provides methods and materials related to assessing organisms to determine whether or not the organisms were exposed to viral antigens via, for example, a viral vaccination (e.g., vaccination with a vaccine of recombinant viral polypeptides or a vaccine of attenuated virus) or a viral infection. For example, this document provides polypeptides, nucleic acid encoding such polypeptides, methods for making such polypeptides, host cells that express such polypeptides, methods for making such host cells, kits for detecting anti-PRRS virus antibodies, methods for detecting anti-PRRS virus antibodies, kits for assessing an organism's immunological state with respect to a virus, and methods for assessing an organism's immunological state.

Polypeptides

In one embodiment, this document provides polypeptides that can be used to detect anti-PRRS virus antibodies present in a sample from an organism (e.g., pigs). The anti-PRRS virus antibodies can be any type of anti-PRRS virus antibody. For example, the anti-PRRS virus antibodies can be IgA, IgD, IgE, IgG, or IgM antibodies. Such antibodies can be formed in an organism when that organism is exposed to a PRRS virus antigen such as a PRRS virus polypeptide, an attenuated PRRS virus vaccine, or a pathogenic PRRS virus. In addition, the anti-PRRS virus antibodies can be antibodies that bind to any type of PRRS virus including, without limitation, a VR-2332 PRRS virus (GenBank® Accession No. PRU87392; U.S. Pat. Nos. 5,846,805 and 5,683,865), an MN30100 PRRS virus (Bierk et al., *Vet. Rec.*, 148:687-690 (2001)), an attenuated PRRS virus such as a RespPRRS virus (GenBank® Accession No. AF066183), a 16244B PRRS virus (GenBank® Accession No. AF046869), a PA8 PRRS virus (GenBank® Accession No. AF176348), an SP PRRS virus (GenBank® Accession No. AF184212), an NVSL 97-7985 IA 1-4-2 PRRS virus (GenBank® Accession No. AF325691), a P129 PRRS virus (GenBank® Accession No. AF494042), a CH-1a PRRS virus (GenBank® Accession No. AY032626), a JA142 PRRS virus (GenBank® Accession No. AY424271), an NVSL 97-7895 PRRS virus (GenBank®

Accession No. AY545985), or a PL97-1 PRRS virus (GenBank® Accession No. AY585241). Likewise, the anti-PRRS virus antibodies can be antibodies that bind to field isolates or naturally-occurring versions of a PRRS virus including, without limitation, isolates and naturally-occurring versions of PRRS viruses from North America, Europe, or elsewhere (e.g., China).

The polypeptides provided herein can be used to detect anti-PRRS virus antibodies present in a sample from an organism that is susceptible to a PRRS virus infection. Such organisms include, without limitation, swine species such as domestic and feral pigs and wild boars. In some cases, the polypeptides provided herein can be used to detect anti-PRRS virus antibodies present in a sample from an organism that is not susceptible to a PRRS virus infection. For example, the polypeptides provided herein can be used to detect anti-PRRS virus antibodies present in a sample from a rabbit or mouse that was exposed to a PRRS virus antigen via, for example, injection of a PRRS virus polypeptide, an attenuated PRRS virus vaccine, or a pathogenic PRRS virus. When making anti-PRRS virus antibodies in a rabbit or mouse, detecting anti-PRRS virus antibodies in a rabbit or mouse serum sample can help scientists identify rabbits or mice that produce anti-PRRS virus antibodies.

Any sample can be obtained from an organism and assessed for the presence or absence of an anti-PRRS virus antibody. Such samples include, without limitation, blood samples, serum samples, tissue samples (e.g., lymph tissue, muscle tissue, and skin tissue). For example, blood samples can be obtained from pigs and assessed for the presence or absence of pig anti-PRRS virus antibodies.

The polypeptides provided herein can be any length (e.g., between 8 and 2500 amino acid residues). In some embodiments, the polypeptide can contain at least eight amino acid residues. For example, the length of a polypeptide can be greater than 8, 9, 10, 11, 12, 13, 14, 15, 20, 25, 30, 50, 75, 100, 150, 200, 250, 300, 400, 500, 600, 700, 800, 900, 1000, or more amino acid residues. In other embodiments, the length of the polypeptide can be between 25 and 800 amino acid residues, between 50 and 800 amino acid residues, between 50 and 450 amino acid residues, between 50 and 400 amino acid residues, between 50 and 300 amino acid residues, between 100 and 400 amino acid residues, or between 100 and 300 amino acid residues.

The polypeptides can have any amino acid sequence. For example, a polypeptide can contain an amino acid sequence present in a PRRS virus polypeptide (e.g., an NSP 1, NSP 2, NSP 3, NSP 4, NSP 5, NSP 6, pol, C/H, HEL, CORONA, ORF 2, ORF 2b, ORF 3, ORF 4, ORF 5, ORF 6, or ORF 7 polypeptide). In some embodiments, the polypeptide can be a PRRS virus NSP 2 polypeptide that lacks a hydrophobic region such as the region encoded by nucleotides 1339 to 3495 of the sequence set forth in GenBank accession number PRU87392. In other embodiments, the polypeptide can be an ectodomain of a PRRS virus ORF 5 or ORF 6 polypeptide. For example, a polypeptide can contain the first ectodomain from the 5' end of a PRRS virus ORF 5 polypeptide (ORF 5 5' ectodomain 1), the second ectodomain from the 5' end of a PRRS virus ORF 5 polypeptide (ORF 5 5' ectodomain 2), the first ectodomain from the 5' end of a PRRS virus ORF 6 polypeptide (ORF 6 5' ectodomain 1), the second ectodomain from the 5' end of a PRRS virus ORF 6 polypeptide (ORF 6 5' ectodomain 2), or combinations thereof. When a polypeptide contains more than one (e.g., two, three, four, five, six, or more) ectodomain, the ectodomains can be next to each other or separated by a linker sequence (e.g., a GGGGS (SEQ ID NO: 23) amino acid linker sequence).

The polypeptides provided herein can contain additional amino acid sequences including those commonly used as tags (e.g., poly-histidine tags, myc tags, GFP tags, and GST tags). For example, a 50 amino acid fragment of a PRRS virus NSP 2 polypeptide can contain the amino acid sequence of a poly-histidine tag (e.g., HHHHHH, SEQ ID NO:33).

A polypeptide provided herein can contain an amino acid sequence having (1) a length, and (2) a percent identity to an identified amino acid sequence over that length. Likewise, an isolated nucleic acid provided herein can encode such a polypeptide or can contain a nucleic acid sequence having (1) a length, and (2) a percent identity to an identified nucleic acid sequence over that length. Typically, the identified nucleic acid or amino acid sequence is a sequence referenced by a particular sequence identification number or a particular GenBank accession number or is a particular PRRS virus nucleic acid or polypeptide (e.g., a PRRS virus NSP 2 polypeptide). The nucleic acid or amino acid sequence being compared to the identified sequence typically is referred to as the target sequence. For example, an identified sequence can be a PRRS virus ORF 5 polypeptide sequence set forth in SEQ ID NO:16, 19, or 22.

A length and percent identity over that length for any nucleic acid or amino acid sequence is determined as follows. First, a nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the State University of New York—Old Westbury campus library (catalog number: QH 447.M6714) as well as from Fish & Richardson's web site ("fr" dot "com/blast/") or from the U.S. government's National Center for Biotechnology Information web site ("ncbi" dot "nlm" dot "nih" dot "gov"). Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides or amino acid residues from the target sequence presented in alignment with sequence from the identified sequence starting with any matched position and ending with any other matched position. A matched position is any position where an identical nucleotide or amino acid residue is presented in both the target and identified sequence. Gaps presented in the target sequence are not counted since gaps are not nucleotides or amino acid residues. Likewise, gaps presented in the identified sequence are not counted since target sequence nucleotides or amino acid residues are counted, not nucleotides or amino acid residues from the identified sequence.

The percent identity over a determined length is determined by counting the number of matched positions over that length and dividing that number by the length followed by multiplying the resulting value by 100. For example, if (1) a 1000 nucleotide target sequence is compared to a PRRS virus NSP 2 polypeptide sequence, (2) the Bl2seq program presents 200 nucleotides from the target sequence aligned with a region of the PRRS virus NSP 2 polypeptide sequence where the first and last nucleotides of that 200 nucleotide region are matches, and (3) the number of matches over those 200 aligned nucleotides is 180, then the 1000 nucleotide target sequence contains a length of 200 and a percent identity over that length of 90 (i.e., 180÷200*100=90).

It will be appreciated that a single nucleic acid or amino acid target sequence that aligns with an identified sequence can have many different lengths with each length having its own percent identity. For example, a target sequence containing a 20 nucleotide region that aligns with an identified sequence as follows has many different lengths including those listed in Table A.

```
                       1                    20
Target Sequence:    AGGTCGTGTACTGTCAGTCA  (SEQ ID NO: 68)
                    | || ||| |||| |||| |
Identified Sequence: ACGTGGTGAACTGCCAGTGA  (SEQ ID NO: 69)
```

TABLE A

| Starting Position | Ending Position | Length | Matched Positions | Percent Identity |
|---|---|---|---|---|
| 1 | 20 | 20 | 15 | 75.0 |
| 1 | 18 | 18 | 14 | 77.8 |
| 1 | 15 | 15 | 11 | 73.3 |
| 6 | 20 | 15 | 12 | 80.0 |
| 6 | 17 | 12 | 10 | 83.3 |
| 6 | 15 | 10 | 8 | 80.0 |
| 8 | 20 | 13 | 10 | 76.9 |
| 8 | 16 | 9 | 7 | 77.8 |

It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It is also noted that the length value will always be an integer.

In some embodiments, the polypeptide can have an amino acid sequence at least about 70 percent (e.g., at least about 75, 80, 85, 90, 95, or 99 percent) identical to the sequence set forth in SEQ ID NO:9, 16, 19, 22, 26, 29, 32, 36, 39, 42, 45, 48, 51, 54, 61, 64, or 67 over a length such as 20, 30, 40, 50, 60, 70, 80, 90, 100, 110, 120, 130, 140, 150, 160, 170, 180, 190, 200, or more amino acid residues.

The polypeptides provided herein can be substantially pure. The term "substantially pure" as used herein with reference to a polypeptide means the polypeptide is substantially free of other polypeptides, lipids, carbohydrates, and nucleic acid with which it is naturally associated. For example, a substantially pure polypeptide is any polypeptide that is removed from its natural environment and is at least 60 percent pure. The term "substantially pure" as used herein with reference to a polypeptide also includes chemically synthesized polypeptides. A substantially pure polypeptide can be at least about 65, 70, 75, 80, 85, 90, 95, or 99 percent pure. Typically, a substantially pure polypeptide will yield a single major band on a non-reducing polyacrylamide gel.

Any method can be used to obtain a polypeptide or a substantially pure polypeptide. For example, common polypeptide purification techniques such as affinity chromatography and HPLC as well as polypeptide synthesis techniques can be used. In addition, any material can be used as a source to obtain a substantially pure polypeptide. For example, cultured cells engineered to over-express a particular polypeptide of interest can be used to obtain substantially pure polypeptide. Such cells can be prokaryotic cells (e.g. bacterial cells such as E. coli cells) or eukaryotic cells (e.g., yeast cells, insect cells, mammalian cells). A polypeptide can be designed to contain an amino acid sequence that allows the polypeptide to be captured onto an affinity matrix. For example, a tag such as c-myc, hemagglutinin, poly histidine, or Flag™ tag (Kodak) can be used to aid polypeptide purification. Such tags can be inserted anywhere within the polypeptide including at either the carboxyl or amino termini. Other fusions that could be useful include enzymes that aid in the detection of the polypeptide, such as alkaline phosphatase.

The polypeptides provided herein can be formulated into a polypeptide composition that contains additional ingredients. For example, a polypeptide provided herein can be combined with other polypeptides to form a composition that contains more than one different polypeptide (e.g., two, three, four, five, six, seven, eight, nine, ten, or more different polypeptides). For example, a composition can contain a PRRS virus NSP 2 polypeptide and a PRRS virus NSP 1 polypeptide. A composition containing one or more of the polypeptides provided herein can contain one or more carriers such as a solvent, suspending agent, or any other vehicle. Carriers can be liquid or solid, and can be selected with the desired use in mind so as to provide for the desired bulk, consistency, and other pertinent transport and chemical properties. Typical carriers include, without limitation, water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Nucleic Acids

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism or virus from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, all non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally occurring can be exogenous to a particular cell. For example, an entire chromosome isolated from a cell of person X is an exogenous nucleic acid with respect to a cell of person Y once that chromosome is introduced into Y's cell.

An isolated nucleic acid can encode any of the polypeptides provided herein. For example, an isolated nucleic acid can encode a PRRS virus NSP 2 polypeptide that lacks a hydrophobic region (e.g., amino acid residues 1 to 722 of a VR-2332 PRRS virus NSP 2 polypeptide) normally present in a PRRS virus NSP 2 polypeptide. In some embodiments, the nucleic acid can encode a polypeptide having an amino acid sequence at least about 70 percent (e.g., at least about 75, 80, 85, 90, 95, or 99 percent) identical to the sequence set forth in SEQ ID NO: 9, 16, 19, 22, 26, 29, 32, 36, 39, 42, 45, 48, 51, 54, 61, 64, or 67 over a length such as 20, 30, 40, 50, 60, 70, 80, 90, 100, 110, 120, 130, 140, 150, 160, 170, 180, 190, 200, or more amino acid residues. In other embodiments, the nucleic acid can have a nucleic acid sequence at least about 70 percent (e.g., at least about 75, 80, 85, 90, 95, or 99 percent) identical to the sequence set forth in SEQ ID NO:2, 5, 8, 11, 15, 18, 21, 25, 28, 31, 35, 38, 41, 44, 47, 50, 53, 56, 58, 60, 63, or 66 over a length such as 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1000, or more nucleotides.

The isolated nucleic acids provided herein can be at least about 5 bases in length (e.g., at least about 5, 6, 7, 8, 9, 10, 15, 20, 25, 30, 40, 50, 60, 100, 250, 500, 750, 1000, 1500, 2000, 3000, 4000, or 5000 bases in length) and hybridize, under hybridization conditions, to the sense or antisense strand of a nucleic acid that encodes a polypeptide provided herein (e.g., a PRRS virus NSP 2P polypeptide or a PRRS virus ORF 5/ORF 6 chimeric polypeptide). The hybridization conditions can be moderately or highly stringent hybridization conditions.

For the purpose of this invention, moderately stringent hybridization conditions mean the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about $5×10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about $5×10^7$ cpm/µg), while the washes are performed at about 65° C. with a wash solution containing 0.2×SSC and 0.1% sodium dodecyl sulfate.

Isolated nucleic acids can be obtained using any method including, without limitation, common molecular cloning and chemical nucleic acid synthesis techniques. For example, PCR can be used to obtain an isolated nucleic acid containing a nucleic acid sequence sharing similarity to a PRRS virus nucleic acid sequence provided, for example, in GenBank® (e.g., GenBank® Accession No. PRU87392). PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

In addition, nucleic acid and amino acid databases (e.g., GenBank®) can be used to obtain an isolated nucleic acid. For example, any nucleic acid sequence having some homology to a nucleic acid sequence that encodes a polypeptide provided herein can be used as a query to search GenBank®.

Host Cells

A host cell can be designed to contain an isolated nucleic acid described herein. Such cells can be prokaryotic cells (e.g., bacterial cells such as *E. coli, B. subtilis,* or *Agrobacterium tumifaciens, Streptomyces* species cells) or eukaryotic cells (e.g., fungal cells such as yeast cells including, without limitation, *Saccharomyces* species cells and *Pichia pastoris* cells; insect cells; or mammalian cells). Cells It is noted that cells containing an isolated nucleic acid provided herein are not required to express a polypeptide. In addition, the isolated nucleic acid can be integrated into the genome of the cell or maintained in an episomal state. Thus, host cells can be stably or transiently transfected with a construct containing an isolated nucleic acid provided herein. Typically, a host cell contains an exogenous nucleic acid molecule that encodes a polypeptide provided herein and expresses that encoded polypeptide.

Any methods can be used to introduce an isolated nucleic acid molecule into a cell. For example, calcium phosphate precipitation, electroporation, heat shock, lipofection, microinjection, and viral-mediated nucleic acid transfer are common methods that can be used to introduce an isolated nucleic acid molecule into a cell.

Detecting Anti-PRRS Virus Antibodies

The methods and materials provided herein can be used to detect anti-PRRS virus antibodies within an organism (e.g., a pig). In general, anti-PRRS virus antibodies are detected by contacting a PRRS virus polypeptide provide herein with a sample from an organism under conditions wherein the PRRS virus polypeptide can bind to an anti-PRRS virus antibody, if present within the sample, to form an antibody-polypeptide complex. Such complexes can be detected using, for example, labeled-antibodies that bind to that organism's antibodies.

Any of the PRRS virus polypeptides provided herein can be used to detect anti-PRRS virus antibodies. Furthermore, multiple different PRRS virus polypeptides provided herein can be used in combination to detect anti-PRRS virus antibodies. For example, a kit containing PRRS virus NSP 1, NSP 2, NSP 4, and ORF 7 polypeptides can be used to detect anti-PRRS virus antibodies.

Typically, the PRRS virus polypeptides are immobilized on solid substrates such as dipsticks, microtiter plates, particles (e.g., beads), affinity columns, and immunoblot membranes. See, U.S. Pat. Nos. 5,143,825; 5,374,530; 4,908,305; and 5,498,551 for exemplary descriptions of solid substrates and methods for their use. For example, PRRS virus polypeptides can be immobilized on a solid substrate, such as a 96-well plate, using known methodologies, then contacted with a sample from a pig under conditions such that anti-PRRS virus antibodies present within the sample can bind to the immobilized PRRS virus polypeptides to form antibody-polypeptide complexes. Suitable conditions include incubation in an appropriate buffer (e.g., sodium phosphate buffer, pH 7.2 to 7.4) at room temperature from about at least 10 minutes to about 10 hours (e.g., from about 1 to about 2.5 hours). Thereafter, unbound material is washed away, and antibody-polypeptide complexes can be detected.

Detecting the presence of such antibody-polypeptide complexes can be indicative of a PRRS virus infection. Any method can be used to detect the antibody-polypeptide complexes. For example, an indicator molecule having binding affinity for the antibody-polypeptide complex can be used to detect an antibody-polypeptide complex. As used herein, an "indicator molecule" is any molecule that allows the presence of a given polypeptide, antibody, or antibody-polypeptide complex to be visualized, either with the naked eye or an appropriate instrument. Typically, the indicator molecule is an antibody having binding affinity for antibodies from the organism (e.g., a pig) from which the sample was obtained, e.g., anti-pig IgG antibodies. Indicator molecules can be detected either directly or indirectly by standard methodologies. See, e.g., *Current Protocols in Immunology*, Chapters 2 and 8, Coligan et al., (eds.), John Wiley & Sons (1996). For direct detection, the indicator molecule can be labeled with a radioisotope, fluorochrome, other non-radioactive label, or any other suitable chromophore. For indirect detection methods, enzymes such as horseradish peroxidase (HRP) and alkaline phosphatase (AP) can be attached to the indicator molecule, and the presence of the antibody-polypeptide complex can be detected using standard assays for HRP or AP. Alternatively, the indicator molecule can be attached to avidin or streptavidin, and the presence of the antibody-polypeptide complex can be detected with biotin conjugated to, for example, a fluorochrome, or vice versa. Thus, assay formats for detecting antibody-polypeptide complexes can include enzyme-linked immunoassays (ELISA) such as competitive ELISAs, radioimmunoassays (RIA), fluorescence assays, chemiluminescent assays, immunoblot assays (Western blots), particulate-based assays, and other known techniques. In some embodiments, antibody-polypeptide complexes are formed in solution. Such complexes can be detected by immunoprecipitation. See, e.g., *Short Protocols in Molecular Biology*, Chapter 10, Section VI, Ausubel et al., (eds.), Green Publishing Associates and John Wiley & Sons (1992).

Kits for Detecting Anti-PRRS Virus Antibodies

The PRRS virus polypeptides provided herein can be used to make kits for detecting anti-PRRS virus antibodies. Such kits can contain one, two, three, four, five, six, seven, eight, nine, ten, or more different PRRS virus polypeptides. For example, a kit can contain a PRRS virus NSP 1 polypeptide, a PRRS virus NSP 2 polypeptide, a PRRS virus NSP 4 polypeptide, a PRRS virus ORF 5 polypeptide, a PRRS virus ORF 6 polypeptide, a PRRS virus ORF 7 polypeptide, or any combination thereof. In some embodiments, the kit can contain a PRRS virus NSP 2P polypeptide and an ORF 7 polypeptide.

The kit containing PRRS virus polypeptides can contain other components including, without limitation, packaging materials (e.g., written instructions), indicator molecules (e.g., anti-swine Ig antibodies), buffers, positive control samples (e.g., a sample containing swine anti-PRRS virus antibodies), and negative control samples (e.g., a sample containing swine serum lacking swine anti-PRRS virus antibodies).

Assessing an Organism's Immunological State

The methods and materials provided herein can be used to determine an organism's immunological state with respect to a virus. Such methods and materials can be used to determine an immunological state in any organism. For example, the immunological state of a pig, dog, cat, bird (e.g., chicken, turkey, or duck), sheep, cow, horse, goat, monkey, or human can be determined using the methods and materials provided herein. In addition, an organism's immunological state with respect to any virus can be determined. For example, an organism's immunological state with respect to a PRRS virus, a circovirus, an influenza virus, a herpes virus, an adenovirus, a parvovirus, a coronavirus, a picornavirus, a parainfluenza virus, or a filovirus can be determined.

In one embodiment, the methods and materials provided herein can be used to determine whether an organism's immunological state is such that (1) the organism received a vaccine version of a virus, (2) the organism was infected with a naturally-occurring version of the virus, or (3) the organism is immunologically naive with respect to the virus. In some cases, the methods and materials provided herein can be used to differentiate between organisms having either an immunological state such that (1) the organism received a vaccine version of a virus or (2) the organism was infected with a naturally-occurring version of the virus.

Figure 14:
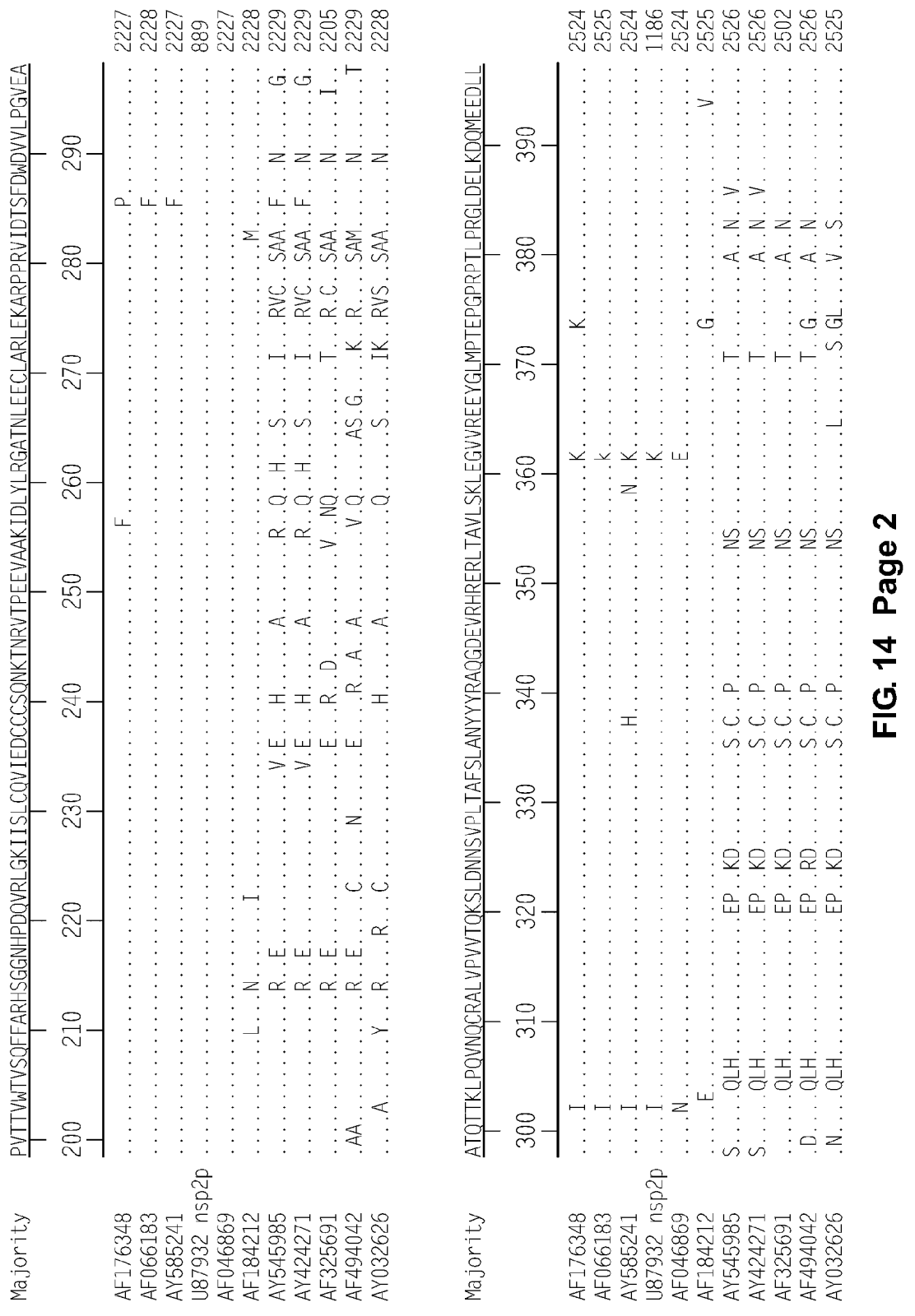
Figure 14:
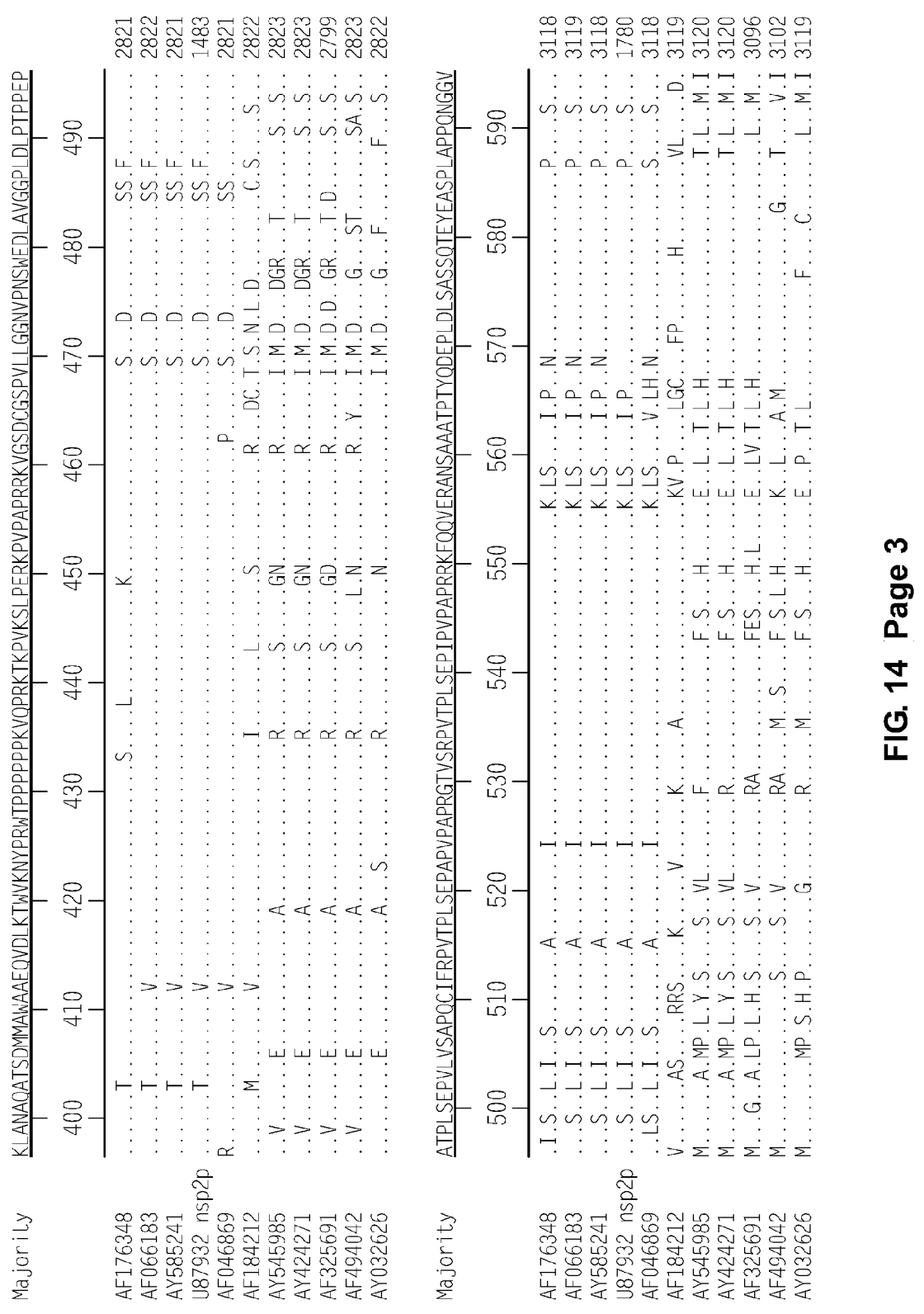
Figure 15:
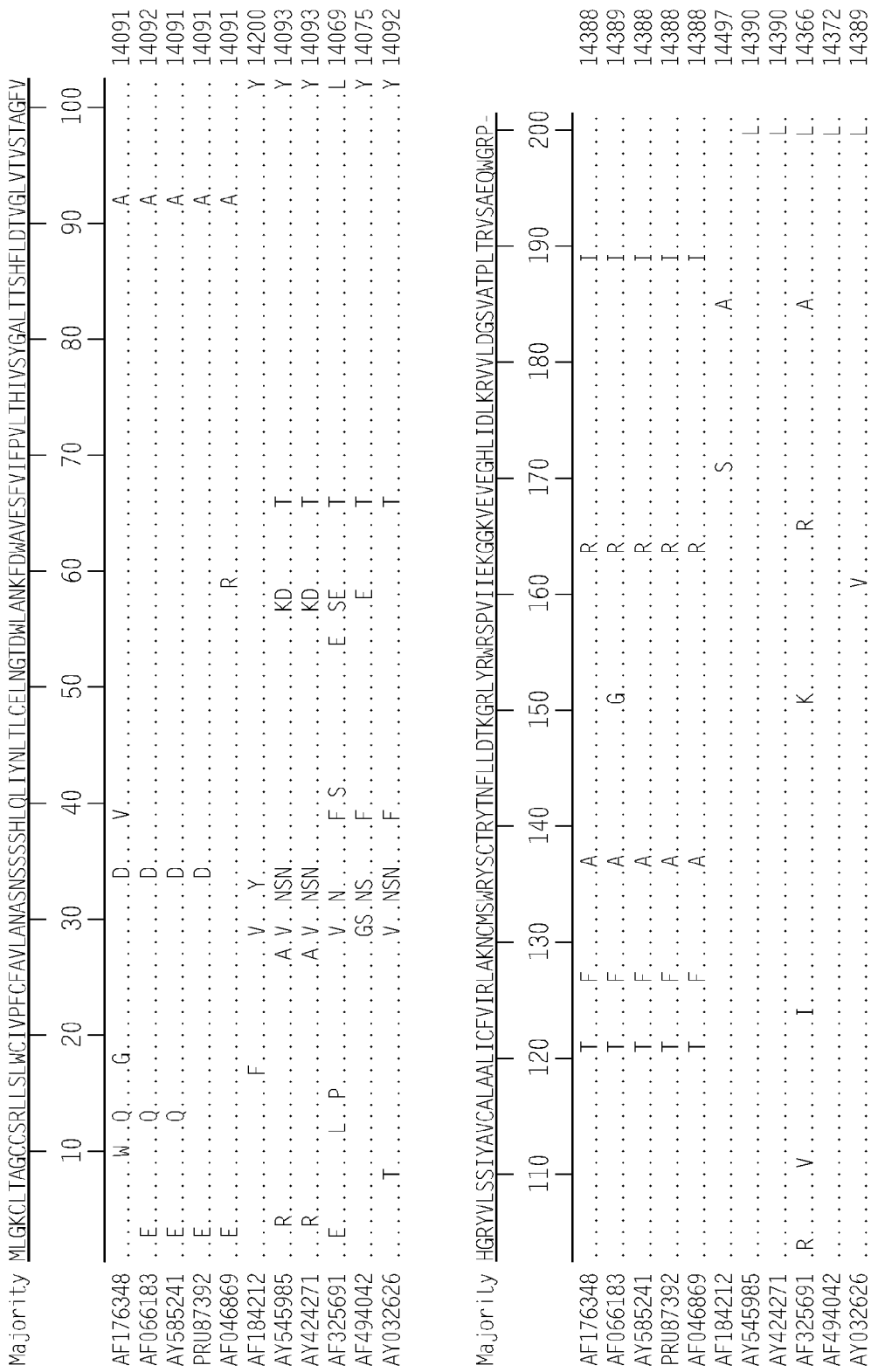
FIG. 15 contains a sequence alignment of PRRS virus ORF 5 polypeptides (SEQ ID NOS: 82-93, respectively, in order of appearance).
Figure 16:
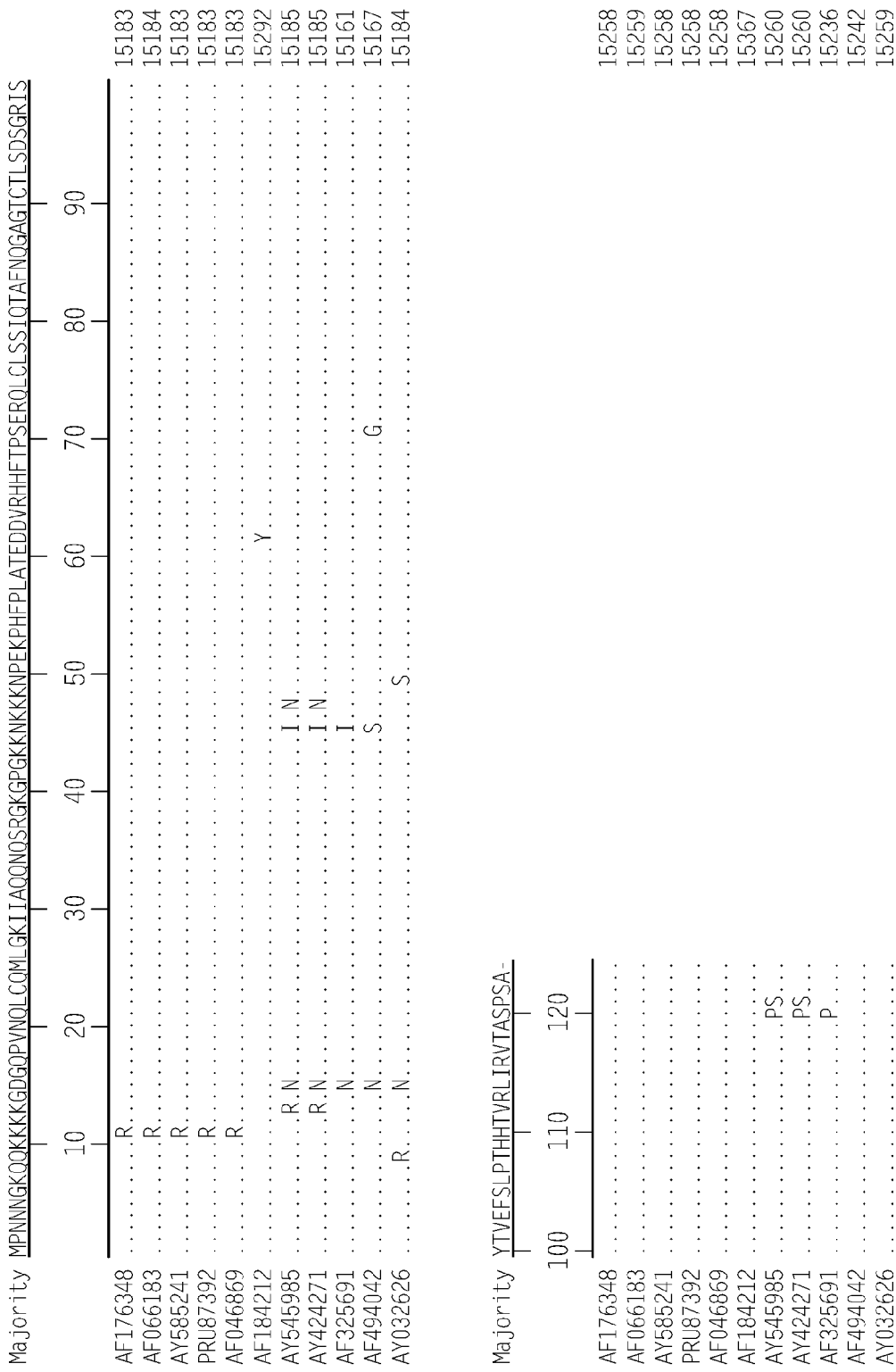
FIG. 16 contains a sequence alignment of PRRS virus ORF 7 polypeptides (SEQ ID NOS: 94-105, respectively, in order of appearance).
Figure 17:
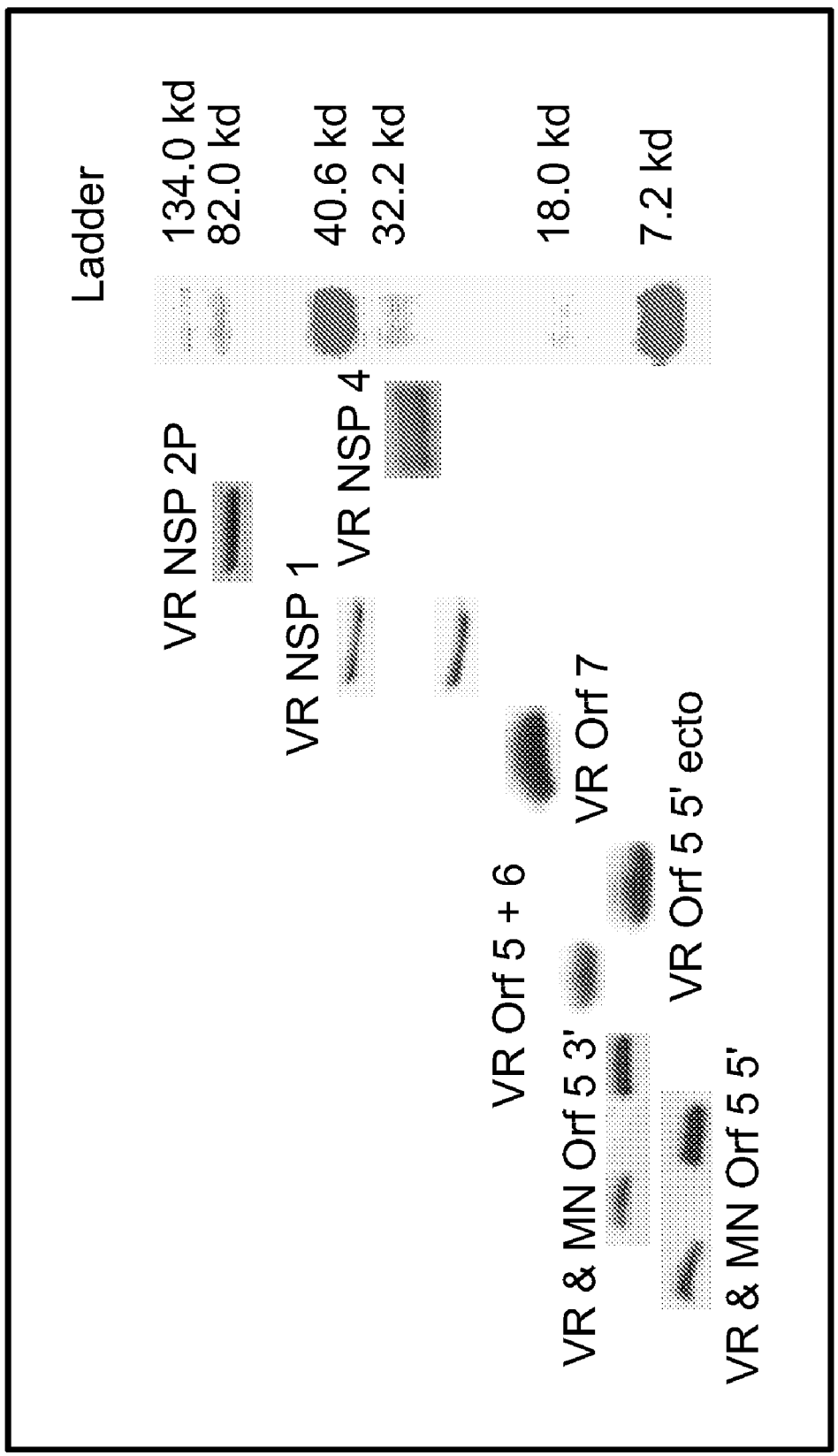
FIG. 17 contains photographs of gels of the indicated purified PRRS virus polypeptides.

In general, at least two polypeptides are used to assess an organism's immunological state. The first polypeptide can be a polypeptide having an amino acid sequence that is conserved (e.g., highly conserved or, in some cases, completely conserved) between a vaccine version of a virus and naturally-occurring versions of the virus. For example, the first polypeptide can have an amino acid sequence such that antibodies made against a vaccine version of the virus bind the first polypeptide and antibodies made against naturally-occurring versions of the virus bind the first polypeptide. When assessing the immunological state of a pig with respect to a PRRS virus, the first polypeptide can be a polypeptide having an amino acid sequence that is conserved among vaccine and naturally-occurring versions of PRRS viruses such as a C-terminal region of a PRRS ORF 5 polypeptide. Other amino acid sequences conserved among vaccine and naturally-occurring versions of PRRS viruses can be obtained from standard sequence alignments (FIGS. 14-16).

The second polypeptide can be a polypeptide having an amino acid sequence that is not well conserved (e.g., a variable sequence) between a vaccine version of a virus and naturally-occurring versions of the virus. The second polypeptide can have a sequence that is similar or identical to a sequence present in a vaccine version of the virus. For example, the second polypeptide can have an amino acid sequence such that antibodies made against a vaccine version of the virus bind the second polypeptide and antibodies made against naturally-occurring versions of the virus do not bind the second polypeptide. When assessing the immunological state of a pig with respect to a PRRS virus, the second polypeptide can be a polypeptide having an amino acid sequence that is variable among vaccine and naturally-occurring versions of PRRS viruses such as an N-terminal region of a PRRS ORF 5 polypeptide. The amino acid sequence of such a second polypeptide can be from a VR-2332 or RespPRRS PRRS virus. Other amino acid sequences not conserved among vaccine and naturally-occurring versions of PRRS viruses can be obtained from standard sequence alignments (FIGS. 14-16).

To assess an organism's immunological state with respect to a virus, the first and second polypeptides can be contacted with a sample from the organism under conditions such that the first and second polypeptides can bind to anti-virus antibodies, if present within the sample, to form either (1) first polypeptide-antibody complexes or (2) first polypeptide-antibody complexes and second polypeptide-antibody complexes. The formation of first polypeptide-antibody complexes and not second polypeptide-antibody complexes can indicate that the sample is from an organism that was exposed to a naturally-occurring version of the virus. The formation of both first polypeptide-antibody complexes and second polypeptide-antibody complexes can indicate that the sample is from an organism that was exposed to a vaccine version of the virus. The failure to detect either first polypeptide-antibody complexes or second polypeptide-antibody complexes can indicate that the sample is from an organism that is naïve with respect to the virus.

In the case of assessing a pig's immunological state with respect to PRRS virus, the first and second polypeptides can be contacted with a blood sample from the pig under conditions such that the first and second polypeptides can bind to anti-PRRS virus antibodies, if present within the blood sample, to form either (1) first polypeptide-antibody complexes or (2) first polypeptide-antibody complexes and second polypeptide-antibody complexes. The formation of first polypeptide-antibody complexes and not second polypeptide-antibody complexes can indicate that the sample is from a pig that was exposed to a naturally-occurring version of PRRS virus. The formation of both first polypeptide-antibody complexes and second polypeptide-antibody complexes can indicate that the sample is from a pig that was exposed to a vaccine version of PRRS virus. The failure to detect either first polypeptide-antibody complexes or second polypeptide-antibody complexes can indicate that the sample is from a pig that is naïve with respect to the virus.

Typically, the virus polypeptides are immobilized on solid substrates such as dipsticks, microtiter plates, particles (e.g., beads), affinity columns, and immunoblot membranes. See, U.S. Pat. Nos. 5,143,825; 5,374,530; 4,908,305; and 5,498,551 for exemplary descriptions of solid substrates and methods for their use. For example, PRRS virus polypeptides (e.g., one polypeptide with a PRRS virus sequence limited to a conserved PRRS virus amino acid sequence and another polypeptide with a PRRS virus sequence limited to a divergent PRRS virus amino acid sequence) can be immobilized on a solid substrate, such as a 96-well plate, using known methodologies, then contacted with a sample for a pig under conditions such that anti-PRRS virus antibodies present within the sample can bind to the immobilized PRRS virus polypeptides to form polypeptide-antibody complexes. Suitable conditions include incubation in an appropriate buffer (e.g., sodium phosphate buffer, pH 7.2 to 7.4) at room temperature from about at least 10 minutes to about 10 hours (e.g., from about 1 to about 2.5 hours). Thereafter, unbound material is washed away, and polypeptide-antibody complexes can be detected as described herein.

Kits for Assessing an Organism's Immunological State

A first polypeptide having an amino acid sequence such that antibodies made against a vaccine version of the virus can bind that first polypeptide and antibodies made against naturally-occurring versions of the virus can bind that first polypeptide can be combined with a second polypeptide to make a kit for assessing an organism's immunological state. The second polypeptide can have a sequence that is similar or identical to a sequence present in a vaccine version of the virus. In addition, the second polypeptide can have an amino acid sequence such that antibodies made against a vaccine version of the virus bind that second polypeptide and antibodies made against naturally-occurring versions of the virus do not bind that second polypeptide. Such kits can contain additional polypeptides. For example, a kit can contain two, three, four, five, six, seven, eight, nine, ten, or more different polypeptides with each having a different sequence that is conserved among vaccine and naturally-occurring versions of the virus. Likewise, a kit can contain two, three, four, five, six, seven, eight, nine, ten, or more different polypeptides with each having a different viral sequence that is not conserved among vaccine and naturally-occurring versions of the virus.

The kit can contain other components including, without limitation, packaging materials (e.g., written instructions), indicator molecules (e.g., anti-organism Ig antibodies), buffers, positive control samples, and negative control samples.

In some cases, a solid support can be contacted with a polypeptide and a lysozyme to increase the ability of the polypeptide attached to the solid support to react with an antibody that binds the polypeptide. Any polypeptide can be attached to a solid support including, without limitation, the PRRS virus polypeptides provided herein (e.g., a PRRS virus ORF 7 polypeptide). Any lysozyme can be used. Typically, a lysozyme can be a hydrolytic enzyme that degrades $\beta$-1,4 glucosidic linkages between N-acetylmuramic acid and N-acetylglucosamine in cell walls of certain bacteria, particularly Gram-positive bacteria. A lysozyme can be found in animal secretions and tissues, including, without limitation, saliva, tears, milk, urine, cervical mucus, leucocytes, and kidneys. For example, a lysozyme can be found in uterine secretions of the pig (Roberts and Bazer, *J. Reprod. Fertil.*, 82:875-892 (1988)). Lysozyme from chicken egg white has been extensively studied, and was the first enzyme for which a crystal structure was solved (Diamond, *J. Mol. Biol.*, 82:371-391 (1974)). Lysozyme is widely distributed in egg white of birds (Prager et al., *J. Biol. Chem.*, 249:7295-7297 (1974)). Structure-function relationships of lysozymes are described elsewhere (Imoto et al., *J. Vertebrate Lysozymes*, The Enzymes 7, P. Boyer, Academic Press, NY, 1972)).

Any ratio of polypeptide to lysozyme can be used. For example, a polypeptide and a lysozyme can be contacted with a solid support at a ratio of at least 4 ng of the polypeptide per 1 ng of the lysozyme (e.g., 4:1, 5:1, 6:1, 7:1, or more). In some cases, a lysozyme and a polypeptide can be contacted with a solid support at a ratio of at least 1 ng of the lysozyme per 1 ng of the polypeptide (e.g., 1:1, 2:1, 3:1, 4:1, 5:1, or more).

The solid support can be any type of solid support including, without limitation, glass slides, plastic plates, 96-well plates, beads, and the like.

The invention will be further described in the following examples, which do not limit the scope of the invention described in the claims.

EXAMPLES

Example 1

Production of Recombinant PRRS Virus Polypeptides

Methods and Materials

Plasmid cloning vectors pET24b, pET25b, and pETBlue2 were obtained from Novagen (Madison, Wis.) and pGEM-T was obtained from Promega (Madison, Wis.). *E. coli* BL21 (DE3) cells were obtained from Novagen. *E. coli* BL21(DE3) strains Tuner, RP, and ABLE-K were obtained from Stratagene (La Jolla, Calif.). DH5α cells were obtained from Invitrogen (Carlsbad, Calif.). Plasmid and DNA purification kits were obtained from Qiagen (Valencia, Calif.). PCR reagents were obtained from Applied Biosystems (Roche Molecular Systems, Branchburg, N.J.). Standard lab supplies, bacterial growth media, and electrophoresis chemicals were obtained from Sigma Chemical Co. (St. Louis, Mo.). PRRS virus cDNA fragments for cloning were obtained by reverse transcriptase-PCR amplification of regions of VR-2332 genomic RNA encoding NSP 1α and 1β, NSP 2, and NSP 4.

PCR Amplification, Cloning of DNA Fragments, and Restriction Analysis

Primers for PCR were designed using Primer3 (Whitehead Institute for Biomedical Research, Cambridge, Mass.) and PRRS virus strain VR2332 sequence (GenBank accession number U87392 or PRU87392) (Table 1). Primers were synthesized, purified, and quantified by Integrated DNA Technologies, Inc. (Coralville, Iowa). PCR reactions used the Applied Biosystems heat activated AmpliTaq Gold® kit (Roche Molecular Systems, Branchburg, N.J.). The reaction mixtures (50 µL total volume) contained 10× Buffer II (1× concentration), 1.5 mM $MgCl_2$, 200 µM each of dATP, dCTP, dGTP, dTTP; 0.2 µM each primer pair (Table 1); 1.0 U AmpliTaq Gold®, and the appropriate cDNA. Upon mixing, the solutions were immediately placed in the thermocycler (GeneAmp PCR system 2400, Perkin Elmer, Shelton, Conn.). Temperature cycle: 1 cycle (95° C. for 10 minutes); 35 cycles (94° C. for 30 seconds, 55° C. for 30 seconds, 72° C. for 45 seconds); 1 cycle (72° C. for 7 hold). The resulting amplified DNA was then separated using an agarose gel. Bands corresponding to the predicted product sizes were gel extracted (Gel Extraction Kit, Qiagen) and then further purified using a PCR Purification Kit. The isolated products were then cloned into pGEM-T vector and transformed into DH5α cells, which were spread on LB 100 µg/mL ampicillin (Amp) agar plates with IPTG and X-Gal. White colonies were selected and grown. The nucleic acid from the selected colonies was sequenced using the standard T7 and SP6 primers (Advanced Genetic Analysis Center, University of Minnesota, St, Paul Minn.). After an initial BLAST search screening (GeneBank NCBI, Bethesda, Md.), trace files were edited to remove vector sequence (Seqman, DNASTAR, Inc., Madison, Wis.) and aligned (Megalign, DNASTAR).

A specialized vector based on pET 24b (Novagen, Madison, Wis.) containing a myc tag 5' leader sequence and a terminal 3' His tag was engineered for high efficiency polypeptide expression and isolation. This plasmid (pET 24b myc His) contains a Bam HI site immediately 3' to the myc tag and a Xho I site preceding the terminal 6× His tag. The vector was prepared for insertion by digestion with BamHI and Xho I, followed by dephosphorylation with calf intestinal alkaline phosphatase (CIAP) (Promega). PCR conditions, insert isolation, and purification were as described above followed by restriction digestion (BamHI, Xho I) to prepare the insert for ligation. Ligation reactions typically contained 100 ng of dephosphorylated vector, 20 ng insert, 1× ligation buffer, and 400 Units T4 ligase (New England Biolabs, Beverly, Mass.), total volume 10 µL. The ligation reaction was placed at 16° C. for 16 hours before transformation into DH5α cells. Colonies were selected as previously described and grown. The nucleic acid from the selected colonies was sequenced and analyzed (yielding plasmid pET 24b myc-polypeptide-His).

Test Protein Expression

To test polypeptide expression, recombinant plasmids were transformed into BL21 (DE3)-RP cells, which contain eukaryotic tRNA's for arginine and proline and are chloramphenicol (cam) resistant. Transformed cells were spread on kanamycin 30 µg/mL (kan 30), chloramphenicol 35 µg/mL (cam 35) LB plates and screened by colony PCR using the T7 and SP6 primers for the pET 24b plasmid. Ten positive colonies were grown overnight at 30° C. in 2 mL of 2×YT media (kan 30, cam 35). 200 µL of each of the overnight cultures were used to inoculate ten temperature equilibrated (30° C.) 10 mL aliquots of 2×YT (kan 30). These cultures were grown at 30° C. to an $OD_{600}$ of 0.4, 200 μL was remove for SDS-PAGE analysis, and IPTG was added to a final concentration of 1.0 mM. The induced samples were allowed to grow at 30° C. for 4 hours, and then 200 μL were removed for SDS-PAGE analysis.

Large Scale Polypeptide Expression and Purification

Polypeptides were purified using a modification of the Qiagen Ni-NTA agarose affinity isolation procedure for native His tagged proteins. Briefly, the induced bacterial cells from a 1-liter culture were pelleted at 4000 g for 20 minutes at 4° C., and supernatant was decanted. The pellet was resuspended in 30 mL of lysis buffer (50 mM $NaH_2PO_4$, 300 mM NaCl, 10 mM imidazole, 1 μM pepstatin A, 1 μM leupeptin, and 1 mM PMSF, at pH 8.0), and then lysozyme was added to a final concentration of 1.0 mg/mL. The solution was incubated on ice for 60 minutes, followed by sonication on ice using six 10-second bursts of 250 W at 10-second intervals. RNAse A (10 μg/mL final) and DNAse 1 (5 μg/mL final) were then added, and the solution was incubated on ice for an additional 15 minutes to further degrade nucleic acids. The lysate was then centrifuged (4° C.) for 30 minutes at 10,000×g to pellet the insoluble aggregates and cellular debris. The pellet contained the majority of expressed recombinant polypeptide in the form of inclusion bodies and was isolated in the denatured form to be refolded later. Immediately following centrifugation, this pellet was resuspended in 30 mL of a solution containing 100 mM $NaH_2PO_4$, 10 mM Tris-HCl, and 8 M urea, at pH 8.0. The resuspended pellet was rotated (200 rpm) at room temperature for 30 minutes and then placed at 4° C. for later processing.

The supernatant containing various levels of soluble polypeptide was decanted into 6 mL of 50% Ni-NTA slurry and gently rotated (200 rpm) for 1 hour at 4° C. The supernatant-Ni-NTA mixture was then poured into a 1.5×30 cm column and drained by gravity. The column was washed twice with 20 mL of a solution containing 50 mM $NaH_2PO_4$, 300 mM NaCl, 20 mM imidazole, 1 μM pepstatin A, 1 μM leupeptin, and 1 mM PMSF at pH 8.0. The polypeptide was eluted with four 3-mL aliquots of elution buffer containing 50 mM $NaH_2PO_4$, 300 mM NaCl, 250 mM imidazole, 1 μM pepstatin A, 1 μM leupeptin, and 1 mM PMSF at pH 8.0. Purified polypeptides were concentrated by either tangential flow filtration cassette (Pellicon XL Ultracel PLC 5 kD, Millipore, Bedford Mass.) or a YM-3 Amicon Centriprep® centrifugal filter device (Millipore Corp. Bedford, Mass.), followed by dialysis (Spectra/Por MWCO® 6-8,000, Spectrum Laboratories, Rancho Dominguez, Calif.) against 50% glycerol and 20 mM Tris HCl, pH 7.5. Polypeptide concentrations were determined using the Bio-Rad RC DC protein assay kit (Bio-Rad, Hercules, Calif.). Purified polypeptide solutions were stored at −20° C.

The denatured insoluble recombinant polypeptide mixture stored at 4° C. was centrifuged at 4° C. for 30 minutes at 10,000×g to pellet cellular debris. The supernatant contained high levels of previously insoluble denatured recombinant polypeptide and was decanted into 6 mL of 50% Ni-NTA slurry and gently rotated (200 rpm) for 1 hour at 4° C. The supernatant-Ni-NTA mixture was then poured into a 1.5×30 cm column and allowed to drain. The column was washed twice with 20 mL of a solution containing 100 mM $NaH_2PO_4$, 10 mM Tris-HCl, and 8 M urea, at pH 6.3. The polypeptide was then eluted 4 times with 3 mL aliquots of elution buffer containing 100 mM $NaH_2PO_4$, 10 mM Tris-HCl, and 8 M urea, pH 5.9. SDS gel analysis, concentration of the polypeptide, dialysis into PBS, and the concentration determinations were done as described above.

Polypeptide Refolding

Refolding of the denatured recombinant polypeptide was performed using a variation of the methods described elsewhere (Buchner et al., *Anal. Biochem.*, 205:263-270 (1992) and Clark, *Curr. Opin. Biotechnol.*, 9:157-163 (1998)). Briefly, denatured polypeptide solutions containing purified polypeptide were pooled and dialyzed (Spectra/Por MWCO® 6-8,000, Spectrum Laboratories, Rancho Dominguez, Calif.) for 4 hours at 4° C. against 500 mL of 0.1 M Tris, pH 8.0, 6 M guanidine-HCl, and 2 mM EDTA. The dialysis was then repeated with fresh buffer for an additional 4 hours. After adjusting the polypeptide concentration to 3 mg/mL (concentration determined with the Bio-Rad RC DC protein assay kit, Bio-Rad, Hercules, Calif.), dithiothreitol (DTT) was added to a final concentration of 300 mM DTT. The resulting 5-mL solution was stirred at room temperature for 2 hours followed by filtration using a 0.45 μm filter (Syringe Filter, Fisher Scientific, Pittsburgh, Pa.). The reduced polypeptide solution was then added rapidly at 4° C. with moderate stirring into 500 mL of refolding buffer (100 mM Tris HCl, pH 8.0, 0.5 M L-arginine, 8 mM oxidized glutathione, 2 mM EDTA, 10 μM pepstatin A, 10 μM leupeptin, and 1 mM PMSF) corresponding to a final dilution of about 1:100. The resulting solution was then filtered through a 0.22 μm membrane (Steritop, Millipore, Bedford Mass.) to remove particulates and stirred overnight. Purified polypeptide was concentrated by tangential flow filtration cassette (Pellicon XL Ultracel PLC 5 kD, Millipore, Bedford Mass.) to a volume of 10 mL followed by dialysis (Spectra/Por MWCO® 6-8,000, Spectrum Laboratories) against 50% glycerol and 20 mM Tris HCl, pH 7.5. Polypeptide concentrations were determined using the Bio-Rad RC DC protein assay kit (Bio-Rad, Hercules, Calif.). Purified polypeptide solutions were stored at −20° C.

Gel Electrophoresis and Immunoblotting

Bacterial lysates, purification fractions, and purified polypeptides were analyzed on SDS-polyacrylamide gels with the Laemmli buffer system (Laemmli, *Nature*, 227:680-684 (1974). Protein bands were visualized by staining with 0.025% Coomassie blue. For immunoblotting, gels were electroblotted onto supported nitrocellulose membranes (MSI Separations, Westbrook Mass.). Membranes were incubated with anti-myc monoclonal antibody 9E10 for 1 hour at room temperature. Antibody binding was detected using alkaline phosphatase-conjugated goat-anti-mouse IgG and visualized with the ECL Western Blotting system (Amersham Pharmaciea Biotech, Piscataway, N.J.).

ELISA

ELISA plates were coated with individual PRRS virus polypeptides in 100 μL carbonate buffer (15 mM $Na_2CO_3$ and 35 mM $NaHCO_3$), pH 9.6, or buffer alone overnight and washed 6 times with PBS-Tween (0.1% Tween-20). Two hundred μL of PBS-Tween containing 2.5% nonfat dried milk was added for 1 hour at room temperature to block previously unbound sites, and the plates were washed 5 times. One hundred μL of pig serum at various dilutions was added in duplicate for 2 hours at room temperature, and plates were washed 4 times with PBS-Tween. Levels of specific antibody were determined by incubation of wells in horseradish peroxidase-conjugated goat-anti swine IgG (heavy+light chains) (KPL, Gaithersburg Md.) diluted 1:5000 for 1 hour. Wells were washed 5 times, and color was developed with 100 μL of TMB substrate (KPL). Reactions were stopped after 15 minutes with 100 μL 1 M phosphoric acid, and the plates read at 450 nm.

pETBlue2 (Novagen)

Clones in pGEM-T were transformed into DH5α cells. Colonies were grown overnight, and plasmids were isolated with Qiagen Miniprep Purification Kits. The purified plasmids and 2 µg of pETBlue2 were digested individually with Nco I and Not I for 4 hours. pETBlue2 was dephosphorylated with CIAP for the last 20 minutes of digestion. Insert fragments and linearized pETBlue2 were gel purified with the Qiagen Gel Purification Kit and then ligated in an about 1:2 ratio of vector to insert.

The ligations were transformed into DH5α cells. Two colonies per plate were cultured overnight, and a plasmid preparation was performed on the cultures to isolate the plasmids. The purified plasmids were then transformed into BL-21 (DE3) RP cells. Two colonies per clone were cultured and induced with 400 µM of IPTG for 4 hours at 30° C. A subsequent SDS-PAGE gel of the whole cell lysates showed no evidence of specific polypeptide induction. Similarly, ELISA tests of induced cell lysates coated on microtiter plates and reacted with PRRS+ and PRRS− swine sera did not reveal evidence of PRRS virus polypeptide. Evaluation of pETBlue2 for PRRS virus polypeptide expression was stopped at this point.

pET24d/pET25b (Novagen)

2 µg of pET24d was digested with Nco I and Not I and dephosphorylated with CIAP. The fragment was then purified with a Qiagen PCR Purification Kit. An agarose gel was used to further purify the fragment, and a QIAquick Gel Extraction Kit was used to extract the vector fragment from the gel. The pET24d fragment was then ligated to the clone fragments in an about 2:1 insert to vector ratio. Transformation of these plasmids into DH5α cells did not result in colony growth. Similar results were obtained after cloning into pET24d vector that was not dephosphorylated or into pET25d that was or was not dephosphorylated.

Cloning

PCR was used to amplify the three PRRS virus proteases that were identified by their active sites, at the following amino acid positions in ORF 1a of PRRS virus strain VR2332: papain-like cysteine protease α and β (PCP α/β) (amino acids 74-146 and 268-339), unusual cysteine protease (amino acids 435-506), and the poliovirus 3C-like serine protease (amino acids 1840-1946). The location of these functional protease domains in the PRRS virus genome is shown graphically in FIG. 1. Table 1 lists the nucleotide sequence regions of PRRS virus strain VR2332 that were PCR amplified and summarizes the overall results.

TABLE 1

PRRS virus NSP fragments cloned.

| Nonstructural protein (NSP) | Region Amplified | Restriction Sites | Results |
|---|---|---|---|
| 1 (PCPα/β) | 174-1322 | AccIII, BamHI NdeI, XhoI XhoI, NcoI | PCR band, digestion product, transformed bacterial colonies positive by PCR screening, no plasmid |
| 2 (unusual cysteine protease) | 1339-4922 | BamHI, NcoI NdeI, XhoI | PCR band, digestion product, PCR-positive colonies, no plasmid |
| 4 (poliovirus 3C-like serine protease) | 5598-6209 | NdeI, XhoI | PCR band, digestion product, transformed bacterial colony, plasmid with insert, point mutation in protein |

Nonstructural Protein 1 (NSP 1)

Ligation products of this fragment and pET24b yielded colonies following transformation of E. coli DH5α cells. Colonies grew slowly and typically required 48 hours at 37° C. to be visible. Screening of colonies by PCR gave positive results consistent with the presence of a cloned fragment. Efforts to recover recombinant plasmid from bacteria grown in broth were unsuccessful. It appeared that recombinant plasmids were unstable. To overcome this problem, a variety of E. coli strains were used as plasmid recipients: DH5α, JM109, HB101, SURE (Stratagene), and ABLE (Stratagene). Transformation plates and broth cultures were incubated at 37°, 30°, and 22° C. Culture volumes of 1, 2, 5, 10, and 25 mL were performed. Various methods of plasmid purification were attempted, including Qiagen miniprep, standard alkaline lysis with phenol/chloroform extraction, and boiling lysis with lithium chloride/isopropanol precipitation. None of these conditions and treatments resulted in the recovery of recombinant plasmid. In all, 353 transformants were screened by colony PCR, with about 70 reactions yielding bands. Plasmid purifications yielded no visible bands or a high molecular weight band, which upon diagnostic restriction digestion disappeared from the gel. This result is consistent with the behavior of genomic DNA.

Nonstructural Protein 2 (NSP 2)

The same results were obtained as with NSP 1. Transformed colonies were obtained on LB agar plates that were positive by PCR, but attempts to isolate plasmid DNA were unsuccessful.

Nonstructural Protein 4 (NSP 4)

The results with NSP 4 were identical to the experiences with NSP 1 and NSP 2 with one exception. Plasmid DNA was successfully recovered from a clone and was shown by DNA sequencing to contain the predicted NSP 4. A point mutation was noted that changed amino acid 16 from isoleucine to threonine.

Cloning of NSP Fragments in pET24bmycHis

Figure 2:
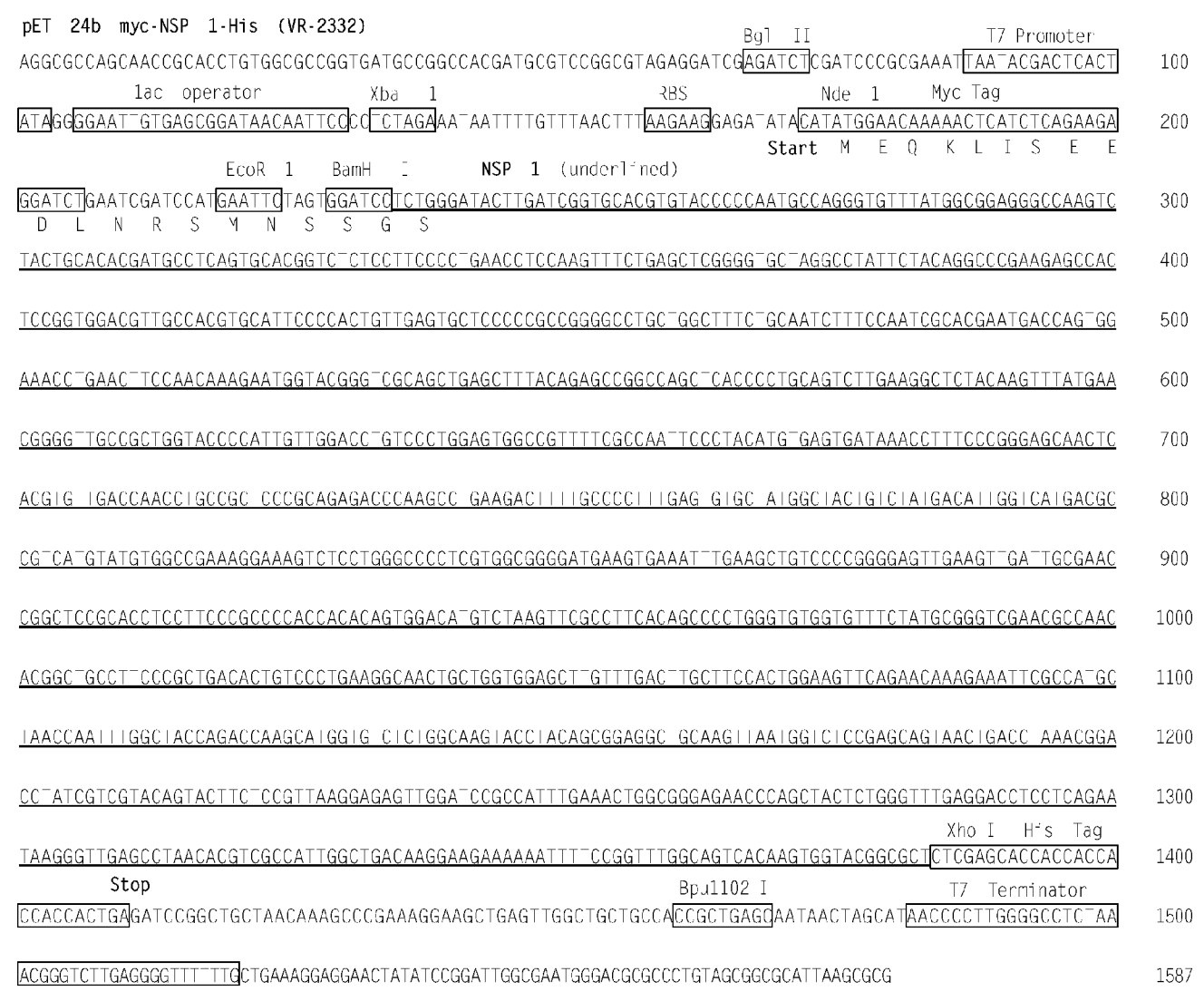
Figure 3:
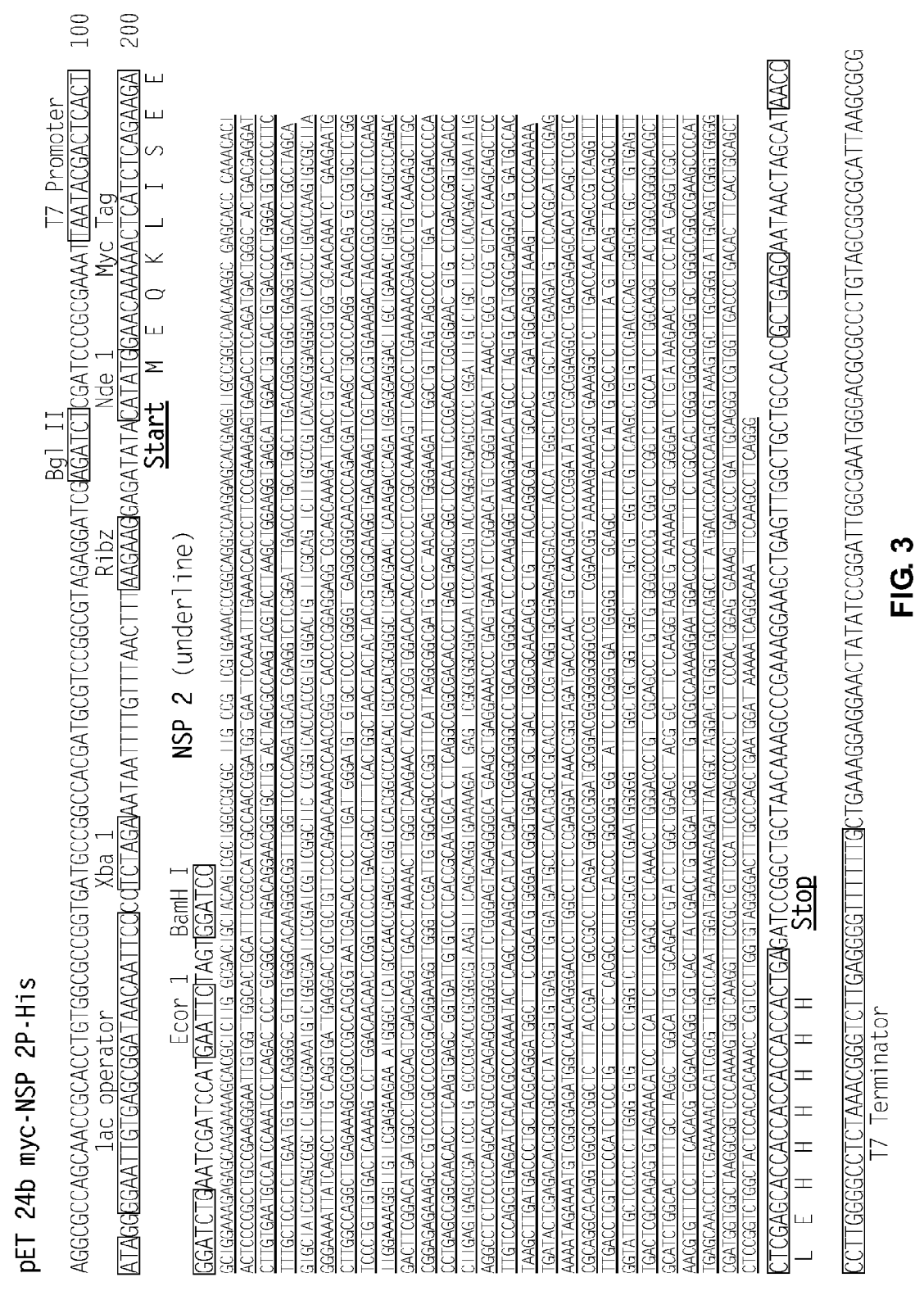

DNA fragments corresponding to NSP 1, NSP 2, and NSP 4 were amplified by PCR and cloned into pET24b-mycHis (FIGS. 2, 3, and 4). Functionally positive clones were identified by small-scale test induction of individual colonies, and a single, high expressing clone was picked, grown, purified, and sequenced. Each clone contained EcoR1 and BamHI sites at the 5'-end and an XhoI site at the 3'-end. The encoded polypeptides contained an amino terminal myc tag and a carboxyl terminal 6×His tag.

Recombinant NSP Expression and Purification

Figure 5:
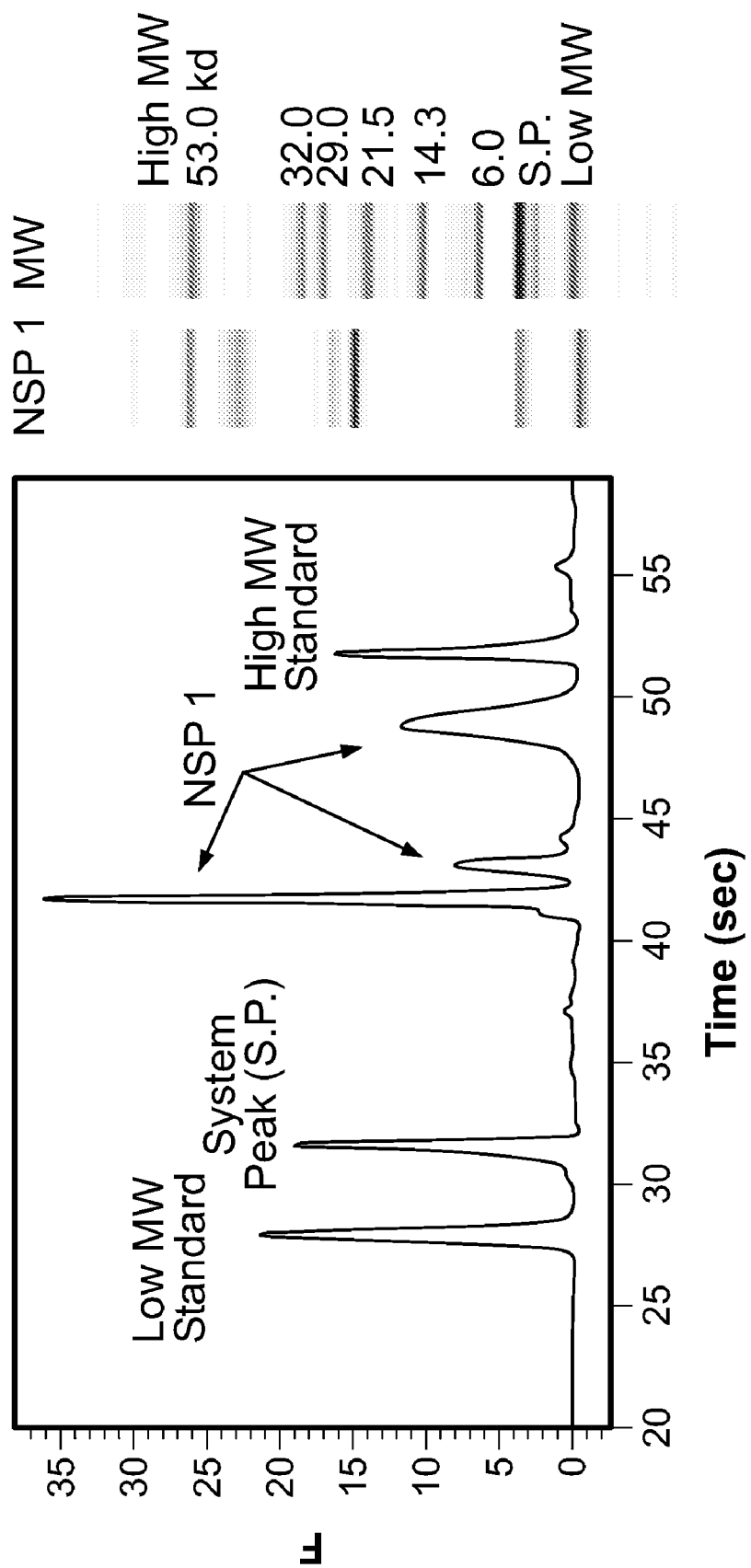
FIG. 5 is a graph plotting the fluorescence level of refolded NSP 1 polypeptides detected using an Agilent bioanalyzer. Purified and refolded NSP 1 polypeptide was applied to an Agilent 2100 Bioanalyzer (Agilent Technologies, Palo Alto, Calif.) and analyzed according to the standard protocol on the Protein 50 Assay LabChip kit. The NSP 1 polypeptide resulted in peaks corresponded to 46 kD (intact polypeptide) and 24 and 22 kD PCP1α and PCP1β, respectively.
Figure 6:
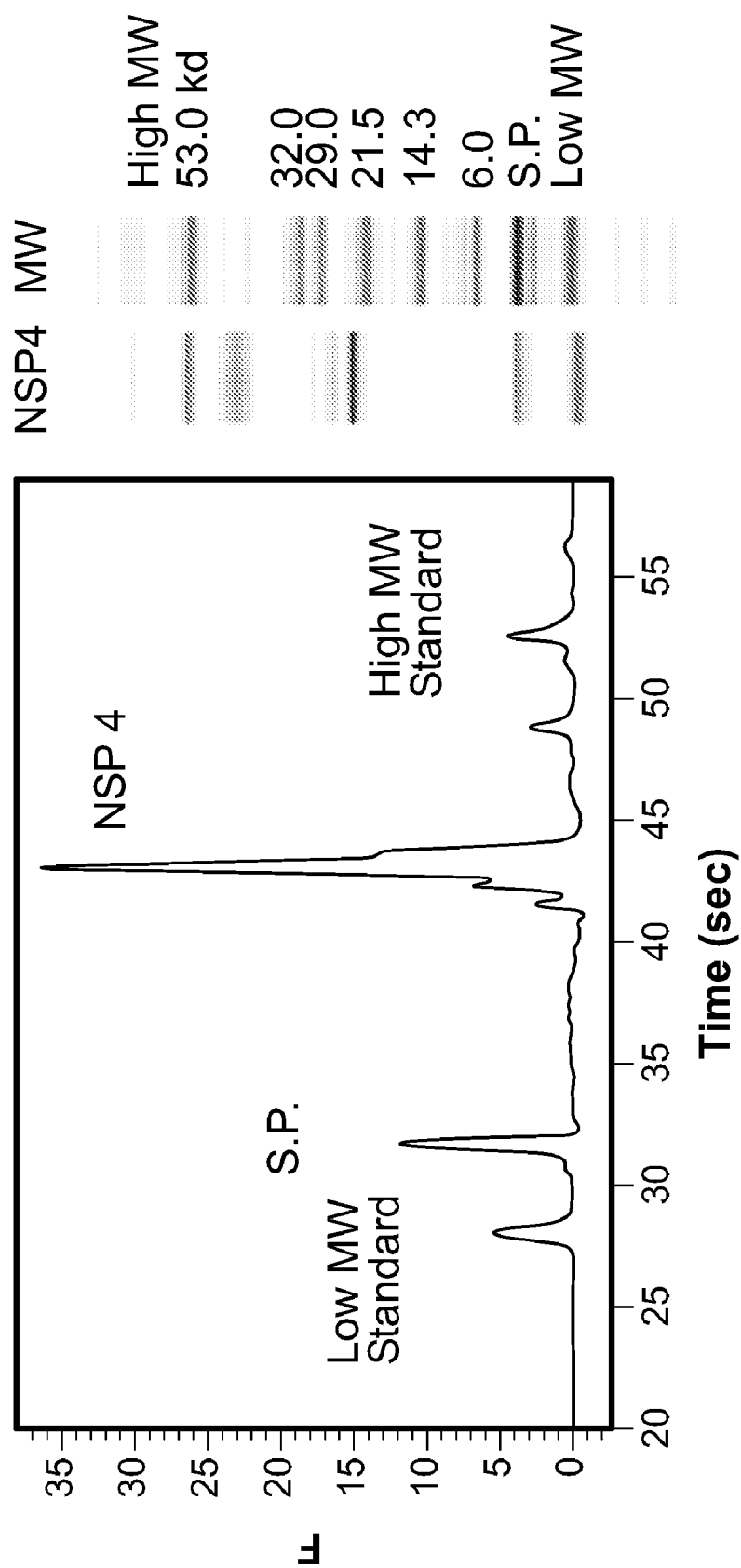
FIG. 6 is a graph plotting the fluorescence level of refolded NSP 4 polypeptides detected using an Agilent bioanalyzer. Purified and refolded NSP 4 polypeptide was applied to an Agilent 2100 Bioanalyzer (Agilent Technologies, Palo Alto, Calif.) and analyzed according to the standard protocol on the Protein 50 Assay LabChip kit. The NSP 4 polypeptide resulted in a single peak at 26 kD.

Individual colonies were grown and induced for polypeptide expression as described herein. Polypeptides were purified by Ni-NTA immobilized metal affinity chromatography. Recombinant NSP 1 and NSP 4 were readily expressed at mg/L levels in shake flasks under the described conditions, and about 50% of the polypeptide was recovered following affinity chromatography and refolding (Table 2). The purified and refolded polypeptides were homogeneous and contained fragment sizes consistent with predicted protease activities. The NSP 1 and NSP 4 polypeptides consisted of homogeneous polypeptides in which the NSP 1 preparation contain intact polypeptide and two fragments autoproteolytically cleaved into PCP1α and PCP1β, whereas the NSP 4 preparation was a single band (FIGS. 5 and 6).

TABLE 2

Polypeptide expression yields.

| Nonstructural protein (NSP) | Total expressed (mg/L culture) | Ni-NTA purified (mg/L culture) | After Refolding (mg/L culture) |
| --- | --- | --- | --- |
| NSP 1 (pcpα/pcpβ) | 20 | 10 | 9 |
| NSP 4 | 25 | 14 | 13 |

The NSP 2 polypeptide was expressed at low levels that could not be visualized in whole cell lysates on SDS polyacrylamide gels stained with Coomassie blue, but it was observed by western blot detection with anti-myc antibody. The presence of multiple bands at sizes lower than the encoded polypeptide sequence of 132 kD indicated that proteolytic degradation had occurred either during bacterial growth and polypeptide expression or during cell lysis and sample handling. Further evidence that the western blot band contained PRRS virus NSP 2 was obtained from test ELISA results in which microtiter plate wells were coated with induced bacterial lysates from clones expressing NSP 1, NSP 2, or NSP 4. Wells containing NSP 2 polypeptide reacted strongly and in a specific and dilution-dependent fashion. The low level of expression of NSP 2 polypeptide may be due to the presence of a hydrophobic region toward the carboxyl end of the polypeptide.

Effect of Refolding on ELISA Reactivity

Apparent differences in antibody reactivity among the three NSP polypeptides were observed in the preliminary test ELISA, raising the possibility that the conformation of the purified, recombinant polypeptides might be variable and might affect immunoreactivity. Recombinant nucleocapsid (N) varied in immunoreactivity depending on the conditions of expression, purification, and refolding. Therefore, the immunoreactivity of NSP 1 and NSP 4 was evaluated before and after refolding.

Figure 7:
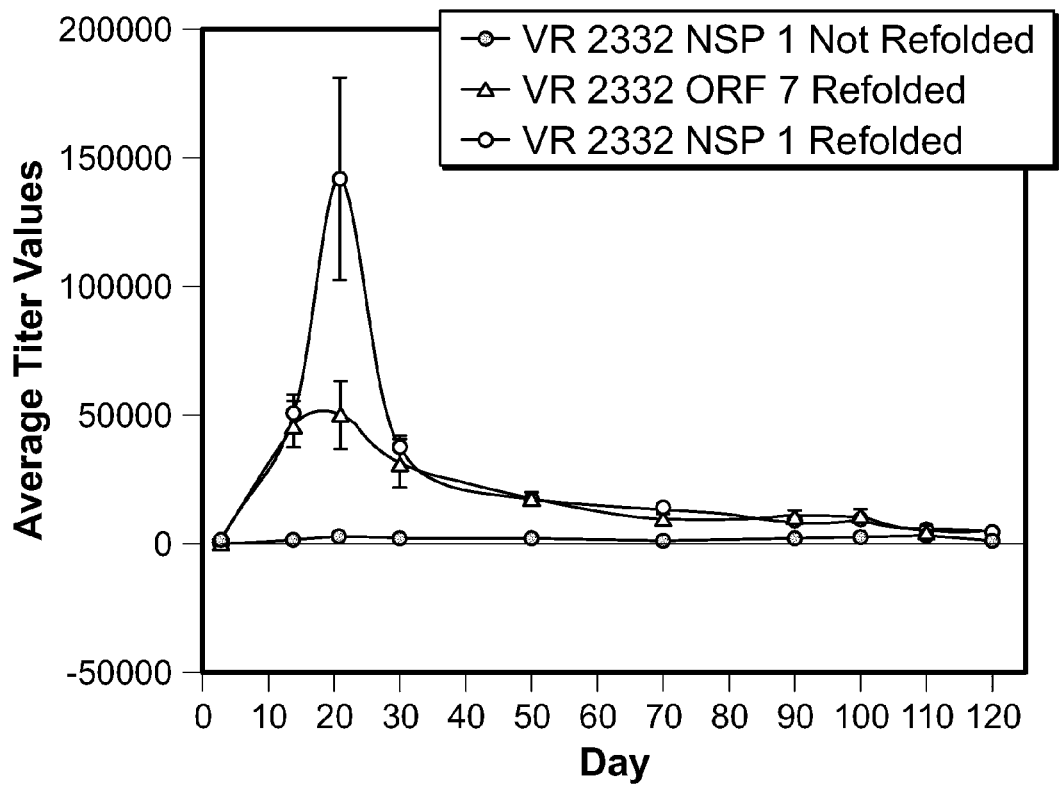
FIG. 7 is a graph plotting the average titer values for antibodies reactive against NSP1 polypeptides (not refolded), NSP 1 polypeptides (refolded), and nucleocapsid (ORF 7) polypeptides (refolded). The time course of anti-NSP 1 or anti-N antibody response was performed using a cohort of 14 pigs that were infected with PRRS virus strain MN30100 and bled at the indicated times.

Refolding had an effect on the immunoreactivity of NSP 1 (FIG. 7). Affinity purified NSP 1 polypeptide that was not refolded was essentially non-reactive to serum obtained from pigs during a 120 day period after PRRS virus infection.

Figure 8:
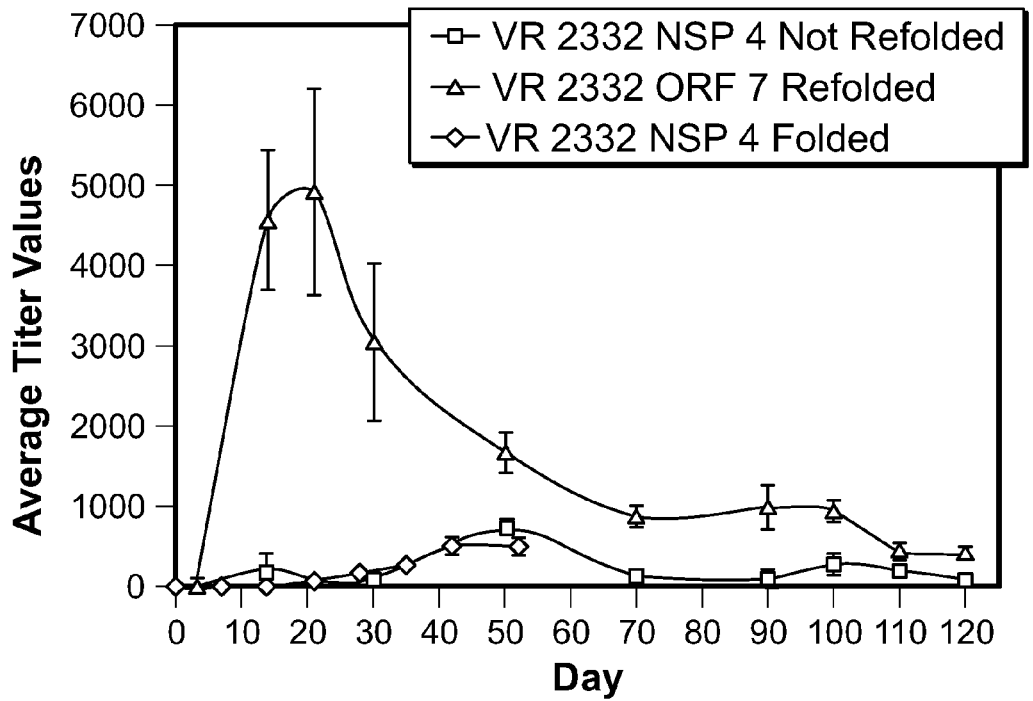
FIG. 8 is a graph plotting the average titer values for antibodies reactive against NSP 4 polypeptides (not refolded), NSP 4 polypeptides (folded), and nucleocapsid (ORF 7) polypeptides (refolded). The time course of anti-NSP 4 (not refolded) and anti-ORF 7 antibody responses were performed using a cohort of 14 pigs that were infected with PRRS virus strain MN30100, while the anti-NSP 4 (folded) responses were performed in pigs immunized with Ingelac MLV vaccine.

By contrast, there was no substantial difference in anti-NSP 4 antibody titers against non-refolded or refolded NSP 4 polypeptides (FIG. 8). The analysis of refolded polypeptide reactivity was terminated at 52 days since it was apparent that there was no difference in the two forms for NSP 4. The lack of effect of refolding was further emphasized by the choice of serum samples for analysis. The maximum antibody response was predicted to occur in animals immunized with homologous virus (VR2332 is the parental strain to Ingelvac MLV vaccine) and tested with refolded, presumably native, polypeptide. The minimum response was predicted to occur in animals infected with a heterologous strain (MN30100) and tested with non-refolded polypeptide. Under these conditions, no differences were observed.

These results demonstrate that polypeptide refolding affects immunoreactivity in the case of NSP 1 and is insignificant for NSP 4. Each recombinant NSP polypeptide, however, is routinely refolded and stored in soluble form in glycerol to maintain a uniform product.

Induction and Duration of Antibody Responses to NSP Recombinant Polypeptide

Figure 9:
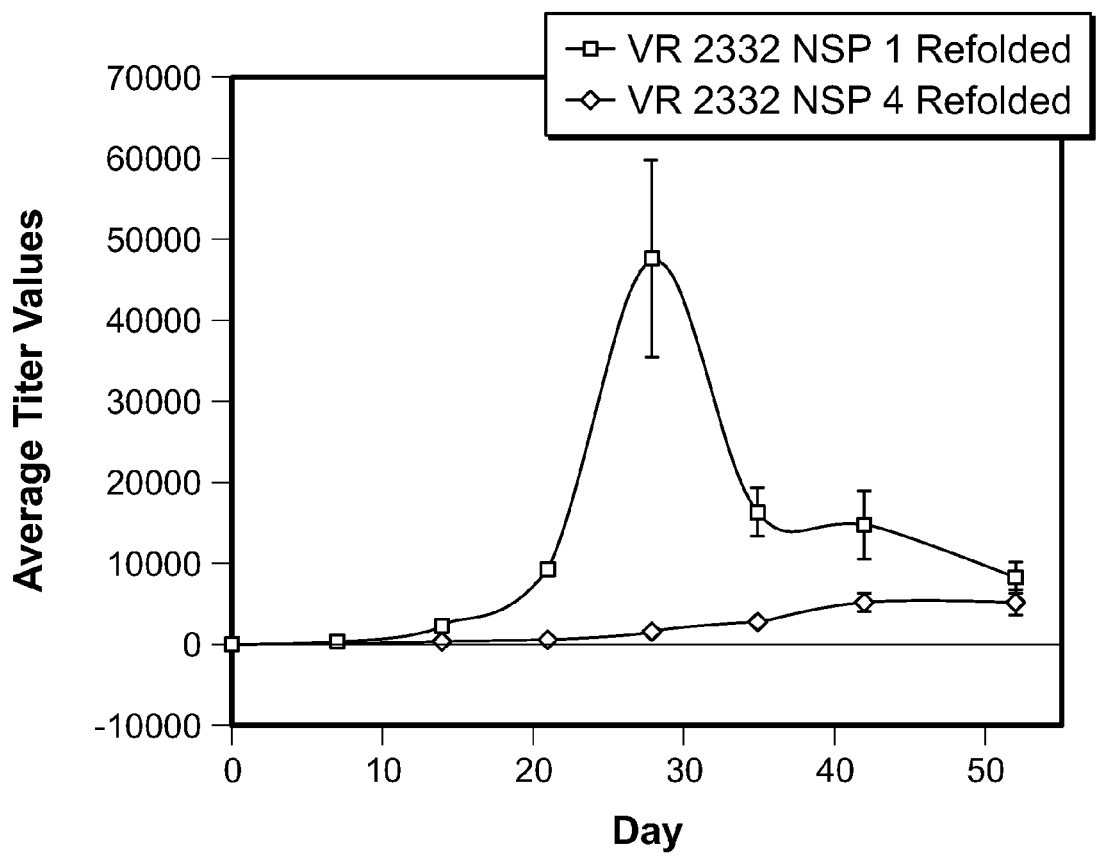
FIG. 9 is a graph plotting the average titer values for antibodies reactive against refolded NSP 1 and NSP 4 polypeptides in pigs immunized with Ingelvac MLV.

The kinetics of anti-NSP 1 antibody response were similar to the response to N in 4-month old gilts. The anti-NSP 1 titer was about 1/50,000 at 14 days after infection and peaked at 21 days after infection at about 1/140,000. Antibody levels declined rapidly and were equivalent to N (ORF 7) from 28-120 days after infection. In a small group of young pigs (4-6 weeks of age) immunized with Ingelvac MLV, antibody titers to NSP 1 showed a similar sharp peak and rapid decline, but the peak occurred at 28 days instead of 21 days after infection (FIG. 9).

In gilts, the antibody response to NSP 4 was weak in comparison to N and to NSP 1. There was evidence of an increase in titer at 40-55 days after infection, and again, possibly at 100-110 days after infection. In young pigs, there was a similar late and modest increase in anti-NSP 4 titers starting at about 28-35 days after immunization (FIG. 9). This time frame corresponds to the period in which acute infection is resolved.

Cross-Reactivity of Swine Anti-NSP Antibodies to VR2332 NSP Recombinant Polypeptide Purified and refolded NSP 1 and 4 polypeptides, derived from the VR2332 strain of PRRS virus and expressed in bacteria, reacted equivalently with antiserum from pigs exposed to a homologous strain (Ingelvac MLV) and a heterologous strain (MN30100) of PRRS virus.

Example 2

Production of Additional Recombinant PRRS Virus Polypeptides

Figure 19:
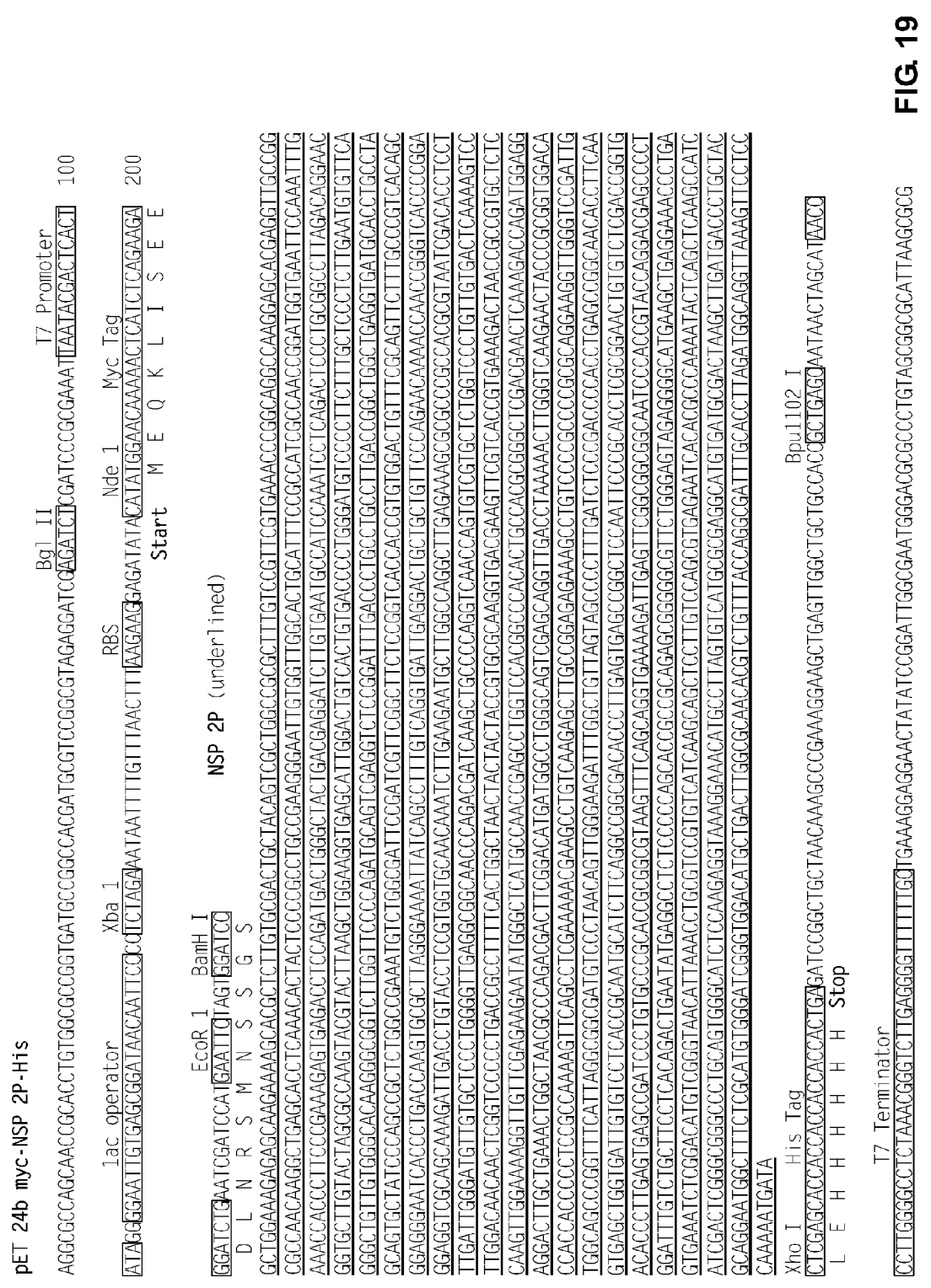

The following polypeptides were produced: a PRRS virus NSP 2P polypeptide (FIG. 19), a PRRS virus first N-terminal ectodomain ORF 5 polypeptide (ORF 5 5'; FIGS. 20 and 21), a PRRS virus first and second N-terminal ectodomains ORF 5 polypeptide (ORF 5' total; FIG. 22), a PRRS virus endodomain ORF 5 polypeptide (ORF 5 3'; FIGS. 23 and 24), a chimeric polypeptide combining a PRRS virus first and second N-terminal ectodomains ORF 5 polypeptide with a PRRS virus first and second N-terminal ectodomains ORF 6 polypeptide (ORF 5+6; FIG. 25), and a PRRS virus ORF 7 polypeptide. The nucleic acid encoding the polypeptides were from the nucleotide sequences in the VR-2332 strain of PRRS virus (GenBank® Accession No. PRU87392) or the MN30100 strain of PRRS virus.

PCR Amplification and Cloning

Fragments for cloning were obtained from plasmids prepared as described elsewhere (Nelsen et al., *J. Virol.*, 73:270-280 (1999)). The desired fragments were isolated with appropriate cloning sites by PCR. Primers were designed using Primer3 (Whitehead Institute for Biomedical Research, Cambridge, Mass.). The oligonucleotide primers were obtained from IDT (Coralville, Iowa). The nucleic acid encoding the ORF 7, ORF 5 5', and ORF 5 3' polypeptides were PCR amplified in separate reactions using the AmpliTaq Gold® kit (Roche Molecular Systems, Branchburg, N.J.). The nucleic acid encoding the ORF 5 5' total and ORF 5+6 polypeptide were constructed both by PCR of cDNA and subsequent oligo annealing, PCR amplification, and ligation. The reaction mixtures (50 µL total volume) contained 10× Buffer II (1× concentration), 1.5 mM $MgCl_2$, 200 µM each of dATP, dCTP, dGTP, and dTTP; 0.2 µM each primer pair; 1.0 U AmpliTaq Gold®, and the appropriate serially diluted (1:10 . . . 1:10, 000) mRNA derived cDNA. Upon mixing, the solutions were immediately placed in the thermocycler (GeneAmp PCR system 2400, Perkin Elmer, Shelton, Conn.). Temperature cycle; 1 cycle (95° C. for 10 min); 35 cycles (94° C. for 30 sec, 55° C. for 30 sec, 72° C. for 45 sec); 1 cycle (72° C. for 7 min, 4° C. hold). The resulting amplified DNAs were then separated on an agarose gel. Bands corresponding to the predicted product sizes were gel extracted (Gel Extraction Kit®, Qiagen, Valencia, Calif.) then further purified using the Qiagen PCR Purification Kit® (Qiagen, Valencia, Calif.).

The isolated products were then cloned into pGEM®T vector (Promega, Madison, Wis.) transformed into DH5α cells (Invitrogen Corp., Carlsbad, Calif.), which were spread on LB 100 mg/mL ampicillin (Amp) agar plates with IPTG and X-Gal. Colonies were color-selected and grown, and the nucleic acid sequenced (Advanced Genetic Analysis Center, University of Minnesota, St, Paul Minn.). After an initial BLAST search screening (GeneBank NCBI, Bethesda, Md.), trace files were edited to remove vector sequence (Seqman® DNASTAR, Inc., Madison, Wis.), and overlapping sequences were aligned (Megalign® DNASTAR, Inc., Madison, Wis.). The nucleic acid encoding the NSP 2P polypeptide was obtained by digesting the clone pET 24b myc-NSP 2-His (FIG. 3) with XhoI and relegating the vector.

Sub-Cloning into the Expression Plasmid

Clones were amplified using the appropriate PGEM®T constructs as templates for primers having terminal BamHI and Xho I sites. The PCR conditions and the insert isolation and purification were standard, followed by restriction digestion (BamHI, XhoI) to prepare the insert for ligation. Ligation conditions were: 100 ng of dephosphorylated vector, 20 ng insert, 1× ligation buffer, and 400 U T4 ligase (New England Biolabs), total volume 10 μL. The ligation reaction was placed at 16° C. for 16 hours before transformation into DH5α cells (Invitrogen Corp., Carlsbad, Calif.). Colonies were selected as previously described and grown, and the nucleic acid sequenced and analyzed (yielding plasmid pET 24b myc-polypeptide-His).

Nucleic acid constructs encoding polypeptides similar to ORF 5 5' and ORF 5 3' were also made from MN30100 PRRS virus sequences (Bierk et al., *Vet. Rec.*, 148:687-690 (2001)) starting from cell culture supernatants containing the virus. Viral RNA was obtained from the media by standard procedures. Viral RNA was isolated using the QIAamp viral RNA kit (Qiagen) and stored at −80° C. Purified RNA was converted to cDNA with random hexamers using the GeneAmp RNA PCR kit (Applied Biosystems, Roche Molecular Systems, Branchburg, N.J.). Briefly, 1 μL of a 50 μM solution of random hexamers was combined with 3.0 μg of total RNA to a total volume of 4 μL. The solution was heated at 68° C. for 10 minutes, then quick chilled on ice. 16 μL of a master mix solution was added for a final concentration that contained 10× Buffer II (1× concentration final); 5 mM $MgCl_2$, 1.0 mM each of dATP, dCTP, dGTP, and dTTP; 20 U/μL Rnase inhibitor, and 25 U/μL reverse transcriptase. This solution was immediately incubated at 25° C. for 10 minutes, 42° C. for 30 minutes, 99° C. for 5 minutes, then 4° C. for 5 minutes. The resulting cDNA was stored at −20° C. and used for PCR amplification.

Protein Expression

Plasmids pET 24b myc-polypeptide-His were transformed into BL21™ (DE3)-RP cells (Stratagene, River Creek, Tex.), which contain eukaryotic tRNA's for arginine and proline as well as chloramphenicol (cam) resistance. Transformed cells were spread on Kanamycin 30 μg/mL (kan 30), chloramphenicol 35 μg/mL (cam 35) LB plates and screened by colony PCR using the T7, T7 termination primers for the pET 24b plasmid. Ten positive colonies each were grown overnight at 30° C. in 2 mL of 2×YT media (kan 30, cam 35). 200 μL of each of the overnight cultures were used to inoculate ten temperature equilibrated (30° C.) 10 mL aliquots of 2×YT (kan 30). These cultures were grown at 30° C. to an $OD_{\lambda=600}$ of 0.3; 200 μL was remove for SDS-PAGE analysis; and IPTG was added to a final concentration of 1.0 mM. The induced samples were allowed to grow at 30° C. for 4 hours, then 200 μL was removed for SDS-PAGE analysis. SDS-PAGE gels indicated that all of the colonies expressed polypeptides of the predicted size at high levels (>2 mg/liter media). Expression on a larger scale was done in the same manner scaling up by 100× for a total of 1 liter of media.

Polypeptide Purification

The polypeptides were purified using a modification of the Qiagen Ni-NTA agarose affinity isolation procedure for denatured His tagged polypeptides (Qiagen, Valencia, Calif.). Briefly, 1 liter of induced plasmid containing bacterial cells was pelleted at 4000 g for 20 minutes at 4° C., and the supernatant was decanted off. Immediately following centrifugation, the pellet was resuspended in 30 mL of a solution containing 100 mM $NaH_2PO_4$, 10 mM Tris-HCl, 8 M Urea, at pH 8.0, and rotated gently at room temperature for 30 minutes. The resulting suspensions were then centrifuged (4° C.) for 30 minutes at 10,000 g to pellet the cellular debris. The supernatant contained high levels of denatured polypeptide and was decanted into 6 mL of 50% Ni-NTA slurry and gently rotated for 1 hour at 4° C. The supernatant-Ni-NTA mixture was then poured into a 1.5 cm ID×30 cm length column and allowed to drain. The column was then washed twice with 20 mL of a solution containing 100 mM $NaH_2PO_4$, 10 mM Tris-HCl, 8 M Urea, at pH 6.3. The polypeptide was then eluted 4 times with 3 mL aliquots of elution buffer containing 100 mM $NaH_2PO_4$, 10 mM Tris-HCl, 8 M Urea, at pH 5.9. SDS gel analysis and protein concentration were determined as described above (FIG. 17).

Polypeptide Refolding

Refolding of the denatured recombinant polypeptides was performed using a variation of the method described elsewhere (Buchner et al., *Anal. Biochem.*, 205(2):263-70 (1992) and Clark, *Curr. Opin. Biotechnol.*, 9(2):157-63 (1998)). First, denatured polypeptide solutions containing pure polypeptide were pooled and dialyzed (Spectra/Por MWCO® 6-8,000, Spectrum Laboratories, Rancho Dominguez, Calif.) for 4 hours at 4° C. against 500 mL of 0.1 M Tris, pH 8.0, 6 M guanidine-HCl, and 2 mM EDTA. The dialysis was then repeated with fresh buffer for an additional 4 hours. After adjusting the polypeptide concentration to 3 mg/mL (concentration determination using the Bio-Rad RC DC protein assay kit, Bio-Rad, Hercules, Calif.), dithiothreitol (DTT) was added yielding a final concentration of 300 mM DTT. This solution (5 mL) was allowed to stir at room temperature for 2 hours followed by filtration using a 0.45 μm filter (Syringe Filter, Fisher Scientific, Pittsburgh, Pa.). The reduced polypeptide solution was then added rapidly at 4° C. with moderate stirring into 500 mL of refolding buffer (100 mM Tris at pH 8.0, 0.5 M L-Arginine, 8 mM oxidized glutathione, 2 mM EDTA, 10 μM pepstatin A, 10 μM leupeptin, 1 mM PMSF) corresponding to a final dilution of about 1:100. The resulting solution was then filtered through a 0.22 μm membrane (Steritop, Millipore, Bedford Mass.) to remove particulates and left to stir overnight. The purified polypeptide was concentrated by tangential flow filtration cassette (Pellicon XL Ultracel PLC 5 kd, Millipore, Bedford Mass.) to a volume of 10 mL followed by dialysis (Spectra/Por MWCO® 6-8,000, Spectrum Laboratories, Rancho Dominguez, Calif.) against 20 mM Tris HCl, at pH 8.0. Polypeptide concentrations were determined using the Bio-Rad RC DC protein assay kit (Bio-Rad, Hercules, Calif.), quantitative SDS gel, and the Agilent 2100 bioanalyzer (Protein LabChip® Kit, Agilent Technologies, Palo Alto, Calif.). Purified polypeptide solutions were stored at −80° C. The polypeptides ORF 5 5', ORF 5 3', and ORF 5 total were not routinely refolded because refolding did not affect ELISA reactivity.

ELISA

Polypeptides were diluted in carbonate buffer (15 mM $Na_2CO_3$, 35 mM $NaHCO_3$, pH 9.6) to a concentration of 1 µg/mL. Each of the ELISA plate wells (COSTAR 3590, 96 Well EIA/RIA plate, Corning Inc., Corning, N.Y.) was then coated with 100 µL of the appropriate polypeptide carbonate solution (providing 100 ng of polypeptide per well), then incubated at 4° C. overnight. Samples were run in duplicate. A set of wells was left uncoated for determination of serum and secondary antibody background effects (found to be less that 0.005 Absorbance units). The plates were then washed (EL-404 Microplate Washer, Bio-Tek Instruments Inc. Winooski, Vt.) six times with PBS-Tween-20 (0.1%) at room temperature. Non-specific binding sites were blocked with 300 µL/well of PBS-Tween (0.1%) containing 3% nonfat dried milk (NFDM) for 2 hour at room temperature. The plates were then washed as described above. Serum samples were then diluted 1:2000 with PBS-Tween-20 (0.1%) containing 3% NFDM, then 100 µL was added to the appropriate wells, and the plates equilibrated at room temperature for 2 hours. The titer values using serial dilution indicated that 1:2000 serum dilutions demonstrated similar data trends (within error). The wells were then washed as before. Secondary detection antibody (peroxidase labeled goat anti-swine IgG (H+L), Kirkegaard & Perry Laboratories Inc. (KPL) Gaithersburg, Md.) was diluted 1:5000 in PBS-Tween (0.1%) containing 3% NFDM, 100 µL of the diluted solution was added to each well. After incubating for 1 hour at room temperature, the plates were again washed. Tetra methyl benzidine (TMB cat #50-76-00 Kirkegaard & Perry Laboratories Inc. (KPL) Gaithersburg, Md.) was used to perform the calorimetric analysis. Equal volumes of TMB peroxidase (solution A) and peroxidase (solution B) were mixed together, and 100 µL was added to each well. The solution was allowed to develop for 15 minutes at room temperature (blue color). The reactions were then quenched by adding 100 µL of 1 M phosphoric acid (yellow color). Plates were read at 450 nm (Thermo Max microplate reader, Molecular Devices, Sunnyvale, Calif.).

Example 3

PRRS Virus Antibody Responses Following Repeated Homologous Wild-Type Virus Challenges Serology has been the cornerstone of veterinary disease monitoring and control. The presence of specific antibodies in serum indicates prior exposure to disease, and may also confirm that the animal possesses protective immunity. Currently available PRRS virus ELISA antibody tests may not be sensitive for all possible situations found in infected groups of pigs, particularly re-infected animals. Many animals return to seronegative status within 4 to 6 months after initial infection (Yoon et al., *J. Vet. Diagn. Invest.*, 7:305-312 (1995)). In addition, there have been reports of animals returning to and remaining ELISA antibody negative during multiple repeated vaccinations with a modified live PRRS virus vaccine (Baker et al., Proc. Allen D. Leman Swine Conference, vol. 26 (suppl.) p. 31 (1999)). If loss of ELISA antibody response were to occur after repeated frequent exposures to the same wild-type PRRS virus, it might alter the way veterinarians interpret PRRS virus ELISA test results for their clients when monitoring herds for continued virus circulation.

The following experiment was performed to (1) determine whether PRRS virus ELISA seronegative animals can be induced by multiple low-dose immunizations with wild-type virus and (2) characterize the expression timeline for PRRS virus serum neutralizing antibodies and antibodies to individual recombinant ORF polypeptides.

Sixty-eight PRRS virus-negative 6 month old barrows were injected twice, one month apart, and then every other month approximating a 6/60 type schedule for a total of 6 immunizations using $10^{2.5}$ field strain SD 28983 PRRS viruses per dose. The animals were bled 3 weeks following each immunization, and the samples tested for PRRS virus ELISA and serum neutralizing antibodies. Four months after the last immunization (12 months after initial exposure), the animals were challenged again with SD 28983.

The blood samples were tested for serum neutralization antibodies by fluorescent focus neutralization (strain 23983 virus as assay inoculum) and for antibodies to recombinant PRRS virus polypeptides obtained as described herein. Briefly, PRRS virus rORF polypeptides were produced by inserting the desired cDNA nucleic acid fragments into *E. coli* for expression. The polypeptides produced included nucleocapsid (an ORF 7 polypeptide) and a chimera polypeptide fragment that contained the ectodomain regions of both an ORF 5 envelope polypeptide and an ORF 6 matrix polypeptide, which co-localize within the viral envelope. ELISA plates were coated with each polypeptide and serum samples were tested by limiting dilution. Results were recorded as titers rather than optical density ratios. The blood samples also were tested using a commercially available PRRS virus ELISA (2XR PRRS virus antibody test kit; IDEXX Laboratories).

The PRRS virus 2XR ELISA antibody levels dropped sharply after initial sero-conversion, even in the face of repeated injections with virulent 28983 strain PRRS virus. Nearly all animals developed solidly positive antibody responses initially. 75 percent of these animals, however, returned to sero-negative status 4 months after the 6th injection with live virus. This is similar to that observed in sows following multiple vaccinations with MLV PRRS virus vaccine (Baker et al., Proc. Allen D. Leman Swine Conference, vol. 26 (suppl.) p. 31 (1999)). Conversely, the serum neutralization test detected antibody later following initial infection, and all animals remained serum neutralization antibody positive at the end of the experiment.

The rORF ELISAs revealed temporal antibody curves. The assay using recombinant nucleocapsid polypeptides resulted in a curve that followed the IDEXX 2XR ELISA response curve closely, falling to low levels at 4 months. Conversely, the envelope chimera ORF 5 and ORF 6 polypeptide ELISA followed a temporal pattern nearly identical to the PRRS serum neutralization antibody response curve. Thus, it appears that pigs initially produce strong antibody responses directed predominantly against nucleocapsid polypeptides, but over time the antibody response is redirected to the envelope polypeptides. It appears that the immune response to PRRS virus is slow to shift to immunologically protective serum neutralization antibodies.

These results demonstrate that an effective diagnostic kit can include ORF 5 polypeptides and ORF 6 polypeptides. These results also demonstrate that a weak IDEXX PRRS virus ELISA antibody response following vaccination or re-exposure may paradoxically indicate that the animal has a protective immune response against that vaccine or virus, since the IDEXX PRRS virus ELISA kit appears to be limited to detecting antibodies that bind PRRS virus nucleocapsid polypeptides.

Example 4

Comparative Antibody Responses to Virulent and Attenuated Strains of PRRS Virus

The following experiment was performed to (1) characterize the antibody response of pigs to individual PRRS virus polypeptides, (2) determine the antibody responses to viral isolates that vary in virulence, and (3) determine the relationship between antibody response and protection to challenge.

One hundred PRRS-negative 3-4 week-old piglets were divided into groups. Ten pigs per group were inoculated intranasally with $2 \times 10^3$ $TCID_{50}$ PRRS virus strains characterized as highly or moderately virulent (SDSU73, MN 184, JA 142, and 17198-6), low virulent (VR2332 and ABST-1), or avirulent (Ingelvac PRRS and Ingelvac ATP). One group of ten pigs received a cocktail containing equal amounts of all viruses, and ten control pigs received no virus. After animals were fully recovered from acute infection, they were challenged with MN 184. Clinical signs were recorded throughout the experiment and necropsies were performed 14 days after challenge. Animals were bled weekly, and antibody levels were determined by ELISA to purified nonstructural and structural polypeptides that were produced by inserting the desired cDNA fragments into E. coli for expression and purification. The polypeptides included a VR2332 PRRS virus ORF 7 polypeptide (a nucleocapsid polypeptide), a VR2332 PRRS virus NSP 1 polypeptide, a VR2332 PRRS virus NSP 2P polypeptide, a VR2332 PRRS virus NSP 4 polypeptide, a VR2332 ORF 5 5' ectodomain 1 polypeptide, an MN30100 VR2332 ORF 5 5' ectodomain 1 polypeptide, a VR2332 ORF 5 3' endodomain polypeptide, an MN30100 ORF 5 3' endodomain polypeptide, a VR2332 ORF 5 5' ectodomains 1 and 2 polypeptide, and a VR2332 ORF 5/ORF 6 chimeric polypeptide (ORF 5 5' ectodomains 1 and 2 plus ORF 6 5' ectodomains 1 and 2; also referred to as a GP5-M chimeric ectodomain polypeptide). ELISA plates were coated with each polypeptide, and the serum samples were tested at a dilution of 1/2000. Specific antibody levels were expressed as background-corrected optical density values.

Clinical responses to PRRS virus inoculation ranged from no or minimal observed effects in animals given avirulent or lowly virulent strains, to death in about 50 percent of animals administered MN 184. Antibody responses to animals inoculated with highly and moderately virulent strains were pronounced. Antibodies usually first appeared at 21 days and peaked at 28 days after infection. The level of antibodies to nucleocapsid declined dramatically after day 28, whereas the response to other viral polypeptides tended to be maintained at high levels to the end of the experiment. Antibody responses to nonstructural polypeptides NSP 1 and NSP 2 were as high or higher than the response to nucleocapsid, but the response to NSP 4, encoding a viral protease, was low at all time points.

Although the humoral response to viral administration was IDEXX-positive in all treatment groups, marked variations in the intensity of antibody responses were apparent. Avirulent and lowly virulent strains elicited less robust antibody responses as compared to moderate or highly virulent strains. These differences were present across all antigens tested. However, response to challenge was similar among all treatment groups.

In summary, differences in antibody response to various structural and nonstructural PRRS virus polypeptides were observed. In addition, variation in antibody responses to virulent strains of PRRS virus as compared to their attenuated forms were observed. The differences in antibody responses, however, were not associated with protection against re-infection with a heterologous, highly virulent challenge strain. These findings are the first characterization of antibody responses to individual PRRS virus polypeptides throughout acute infection and following virulent challenge.

Example 5

Detecting Antibodies to PRRS Virus using Individual PRRS Virus Polypeptides Versus a Commercially Available ELISA Kit The following experiment was performed to determine whether particular polypeptide ELISAs can detect PRRS virus positive samples under conditions of multiple exposure and extended time periods in which the IDEXX ELISA changes from positive to negative. PRRS-negative 6 month old barrows were injected with $10^{2.5}$ tissue culture infective dose 50% ($TCID_{50}$) of field strain SD 28983 PRRS virus initially, then at one, two, four, six, and eight months for a total of 6 inoculations. Animals were bled preceding each inoculation, and serum was collected. The blood samples were tested using (1) a commercially available PRRS virus ELISA (2XR PRRS virus antibody test kit; IDEXX Laboratories) or (2) an ELISA containing particular PRRS virus polypeptides. The IDEXX 2XR HerdChek® ELISA was performed according to the manufacturer's directions on serum samples diluted 1/40. Data are presented as means and standard deviation of all samples in each group. Group size varied from 19-23 samples from 23 pigs per group.

Figure 10:
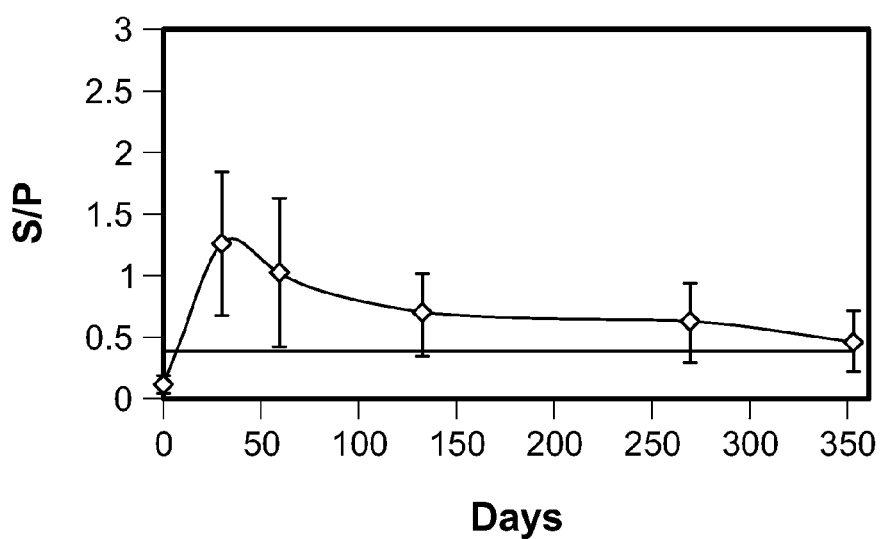
FIG. 10 is a graph plotting the sample/positive ratio (S/P ratio) for samples analyzed using a commercially available ELISA kit (IDEXX 2XR kit). The horizontal line intersecting the Y-axis at 0.4 shows the cutoff value for a positive result.

About half the animals analyzed using the IDEXX kit were found to be negative at the 353 day time point (Table 3 and FIG. 10). An S/P ratio greater than 0.4 indicated that the sample was positive for antibodies to PRRS virus, while an S/P ratio less than 0.4 indicated that the sample was negative for antibodies to PRRS virus.

TABLE 3

Analysis of samples using the IDEXX kit.

| Days | Average S/P | Number Samples Positive | Number Samples Negative |
| --- | --- | --- | --- |
| 0 | 0.124 | 0 | 22 |
| 29 | 1.273 | 22 | 1 |
| 59 | 1.033 | 20 | 1 |
| 132 | 0.697 | 17 | 2 |
| 270 | 0.629 | 18 | 4 |
| 353 | 0.480 | 11 | 11 |

The same samples were analyzed using either recombinant GP5 endodomain polypeptides or recombinant GP5-M chimeric polypeptides in ELISAs. Briefly, plates were coated with 100 ng polypeptide per well in carbonate pH 9.6 overnight. Sera were diluted 1/1000 and tested in duplicate. For the GP5 endodomain polypeptide ELISAs, data are presented as the sample/positive ratio of unadjusted OD values of all samples in each group and the number of samples with a mean greater than (Positive) or less than (Negative) 0.21. For the GP5-M chimeric polypeptide ELISAs, data are presented as the sample/positive ratio of unadjusted OD values of all samples in each group and the number of samples with a mean greater than (Positive) or less than (Negative) 0.5. The sample/positive ratio was determined as the sample OD minus OD of control wells without antigen/positive control OD minus OD of control wells without antigen.

Figure 11:
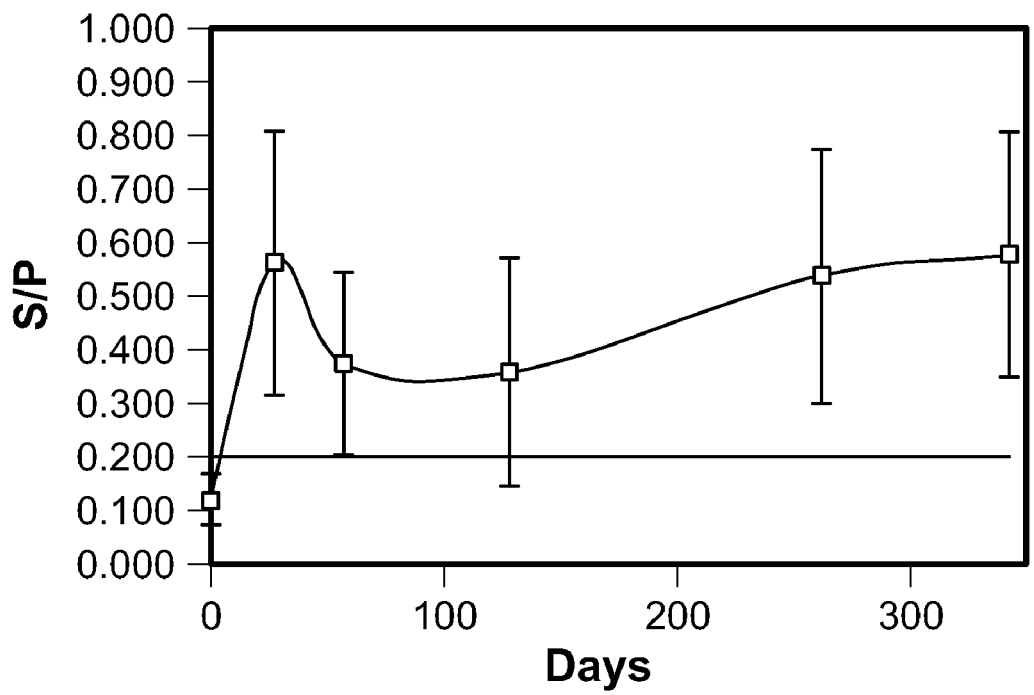
FIG. 11 is a graph plotting the S/P ratios for samples analyzed using a 3' polypeptide fragment of PRRS virus ORF 5 in an ELISA. The horizontal line intersecting the Y-axis at 0.21 shows the cutoff value for a positive result.
Figure 12:
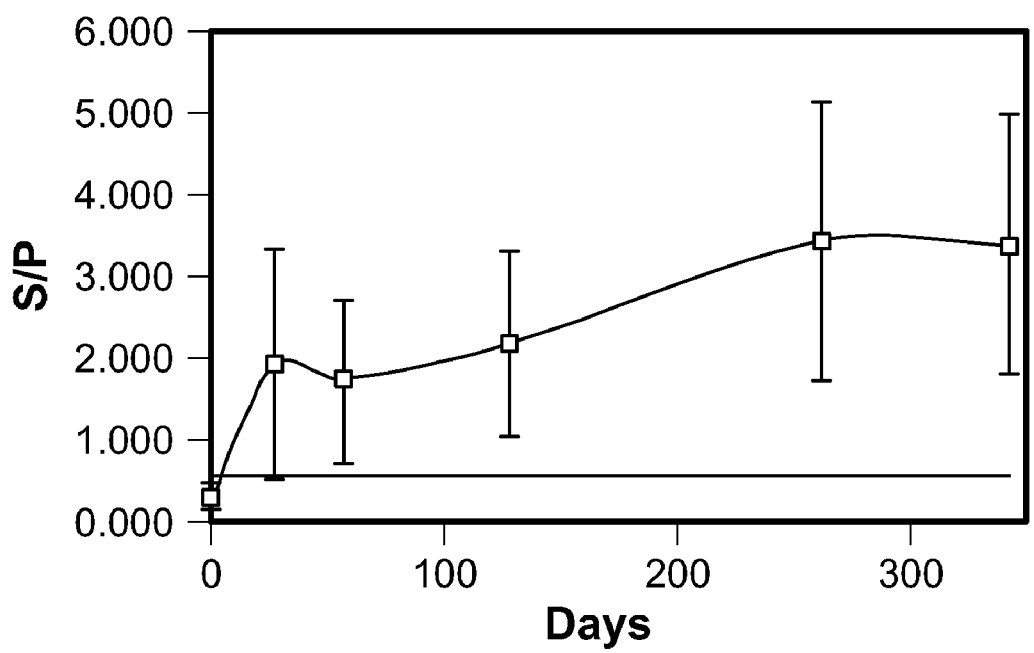
FIG. 12 is a graph plotting the S/P ratios for samples analyzed using a GP5-M chimeric polypeptide in an ELISA. The horizontal line intersecting the Y-axis at 0.5 shows the cutoff value for a positive result.

Two samples were found to be negative for antibodies to the tested PRRS virus GP5 endodomain polypeptide at the 353-day time point (Table 4 and FIG. 11). When the GP5-M chimeric polypeptide was used, all the tested samples were found to be positive at the 353-day time point (Table 5 and FIG. 12). These results demonstrate that assays using GP5 polypeptides can detect anti-PRRS virus antibodies in situations where the commercially available IDEXX kit can not.

TABLE 4

Analysis of samples using a GP5 endodomain polypeptide in an ELISA.

| Days | Months | Average S/P | Number Samples Positive | Number Samples Negative |
|---|---|---|---|---|
| 0 | 0.000 | 0.123 | 0 | 22 |
| 29 | 1.000 | 0.565 | 23 | 0 |
| 59 | 2.000 | 0.374 | 19 | 2 |
| 132 | 4.400 | 0.360 | 15 | 4 |
| 270 | 9.000 | 0.537 | 23 | 0 |
| 353 | 11.800 | 0.576 | 20 | 2 |

TABLE 5

Analysis of samples using a GP5-M chimeric polypeptide in an ELISA.

| Days | Months | Average S/P | Number Samples Positive | Number Samples Negative |
|---|---|---|---|---|
| 0 | 0.000 | 0.333 | 0 | 22 |
| 29 | 1.000 | 1.929 | 21 | 2 |
| 59 | 2.000 | 1.722 | 20 | 1 |
| 132 | 4.400 | 2.157 | 19 | 0 |
| 270 | 9.000 | 3.378 | 23 | 0 |
| 353 | 11.800 | 3.318 | 22 | 0 |

Example 6

Detecting Antibodies to PRRS Virus Using a Mixture of PRRS Virus Polypeptides Versus a Commercially Available ELISA Kit Ten weaned pigs per group were each inoculated intranasally with 2 mL of tissue culture media containing 3.0 $\text{Log}_{10}$ $\text{TCID}_{50}$/mL of the virus isolates listed in Table 6. The pool was a mixture of equal portions of each of the eight isolates. The control was tissue culture media alone.

TABLE 6

PRRS virus isolates.

| Isolate | Group number | Virulence |
|---|---|---|
| VR 2332 | 1 | Moderate |
| Ingelvac ® PRRS MLV* | 2 | Attenuated VR2332 |
| JA 142 | 3 | High |
| Ingelvac ® PRRS ATP* | 4 | Attenuated JA 142 |
| SDSU 73 | 5 | High |
| Abst-1* | 6 | Attenuated SDSU 73 |
| MN 184 | 7 | High |
| 17198 | 8 | High |
| Pool** | 9 | High |
| Control | 10 | N/A |

*Attenuated PRRS virus isolates.
**Mixture containing all of the eight isolates.

To compare the IDEXX ELISA kit with a recombinant polypeptide ELISA, sera were selected blindly from five pigs per group at day 7 after inoculation. Four of the five samples were also tested on day 14. For the IDEXX ELISA kit, an S/P ratio ≧0.4 indicated that the sample was positive, while an S/P ratio <0.4 indicated that the sample was negative. The same samples were analyzed using the IDEXX ELISA kit and the recombinant polypeptide ELISA.

For the recombinant polypeptide ELISA, the following polypeptides were expressed and purified as described herein: an ORF 7 polypeptide, a ORF 5+6 chimeric ectodomains polypeptide, an NSP 2P polypeptide, and an ORF 5 3' endodomain polypeptide. The purified polypeptide concentrations were determined by agreement among $\text{OD}_{280}$ absorbance, Agilent bioanalyzer analysis, SDS PAGE, and RC DC Lowry protein assay. Microtiter plates were coated with 150 ng of each polypeptide for a total of 600 ng in 100 μL carbonate, pH 9.6, coating buffer. ELISAs were performed on serum samples at a 1/500 dilution. The day 7 and day 14 samples are the identical samples as were analyzed by IDEXX ELISA. In addition, 7 animals per group (5 in the MN184 and pool groups) were analyzed at day 50. Control animals were negative at all times. Seven pigs in group 10 were tested and were negative at all tested days.

Only one of the tested samples collected on day 7 was positive when analyzed using the IDEXX kit (Table 7). In addition, thirteen samples collected on day 14 were negative for PRRS virus antibodies. Twenty-three of the 36 samples collected on day 14 were positive for PRRS virus antibodies.

TABLE 7

Results with IDEXX ELISA kit.

| Day | Average S/P | Number Samples Positive | Number Samples Negative |
|---|---|---|---|
| 7 | 0.116374 | 1 | 44 |
| 14 | 0.753558 | 23 | 13 |

In contrast, 14 of the tested 45 samples collected on day 7 were positive when analyzed using the ELISA containing the mixture of PRRS virus polypeptides (Table 8). In addition, only eight of the 36 samples collected on day 14 were negative for PRRS virus antibodies. Twenty-eight of the 36 samples collected on day 14 were positive for PRRS virus antibodies. Further, 54 of the 59 samples collected on day 50 were positive for PRRS virus antibodies (Table 8).

TABLE 8

Results with ELISA containing the mixture of PRRS virus polypeptides.

| Days | Average S/P | Number Samples Positive | Number Samples Negative | Cutoff value |
|---|---|---|---|---|
| 7 | 0.558178 | 14 | 31 | 0.4 |
| 14 | 1.549222 | 28 | 8 | 0.4 |
| 50 | 3.024511 | 54 | 5 | 0.55 |

These results demonstrate that mixtures of PRRS virus polypeptides can be used to detect PRRS virus antibodies in animals exposed to PRRS virus at time points that are not only early but also late with respect to the time of PRRS virus exposure. For example, positive samples were detected at day 7, 14, and 50 following PRRS virus exposure.

The samples for each group were also tested using ELISAs with an individual PRRS virus polypeptide obtained as described herein (FIG. 18).

Example 7

Differentiating between Animals Exposed to Vaccine or Field Strains of PRRS Virus Twenty-eight days after vaccination with the Ingelvac MLV (also referred to as RespPRRS; GenBank® Accession Number AF066183), serum samples were obtained from 5 pigs, diluted 1/300, and analyzed in duplicate on ELISA plates coated with 200 ng of a 5' ectodomain ORF 5 polypeptide from PRRS virus strain VR2332, a 5' ectodomain ORF 5 polypeptide from PRRS virus isolate MN30100, a 3' endodomain ORF 5 polypeptide from PRRS virus strain VR2332, or a 3' endodomain ORF 5 polypeptide from PRRS virus isolate MN30100. Twenty-eight days after inoculation with PRRS virus isolate MN30100, serum samples were obtained from 5 pigs and analyzed in the same manner. The 5' ectodomain of PRRS virus ORF 5 polypeptides contains an amino acid sequence that is variable among PRRS virus isolates, while the 3' endodomain of PRRS virus ORF 5 polypeptides contains an amino acid sequence that is conserved among PRRS virus isolates.

Figure 13:
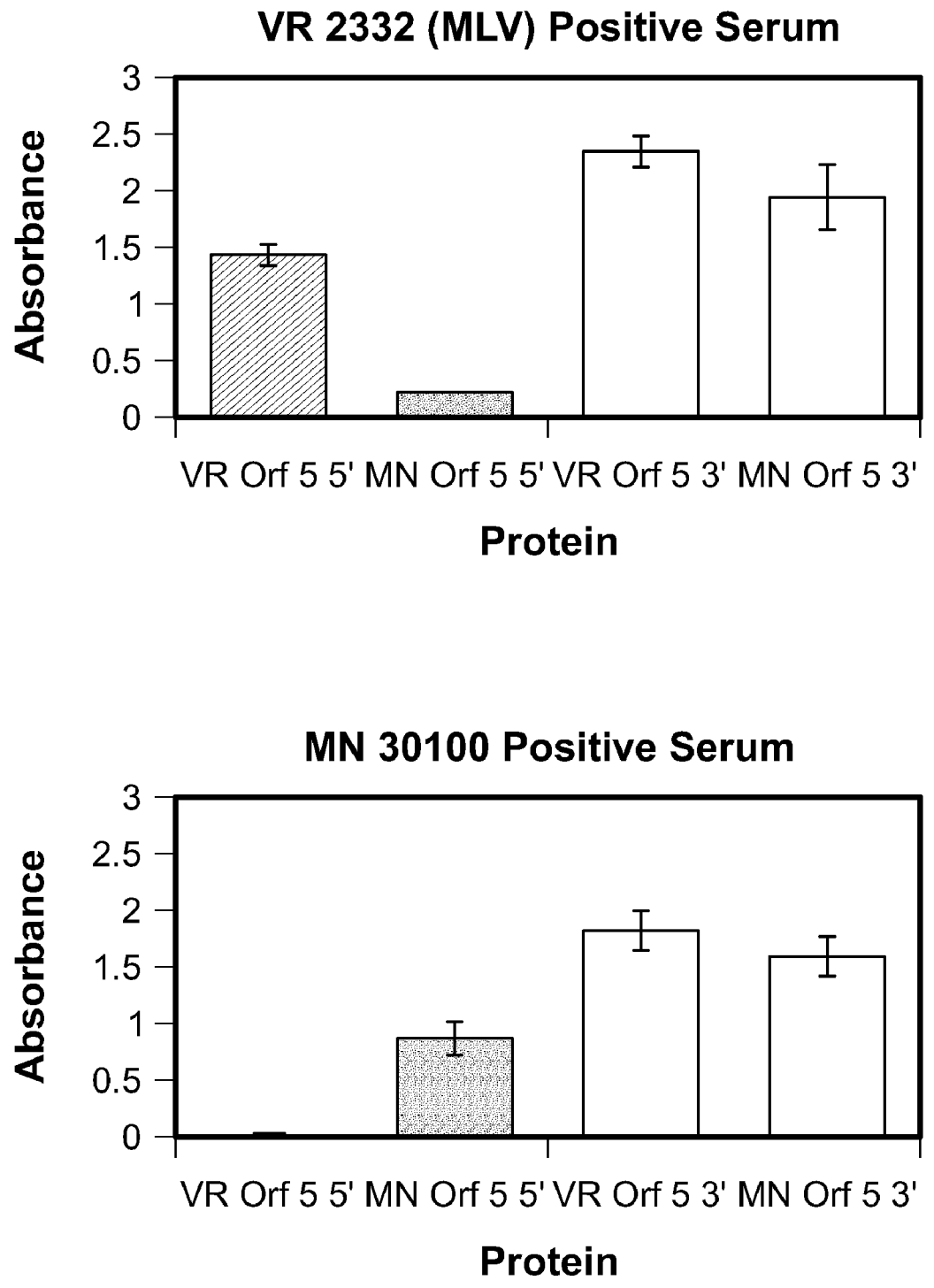

The ELISAs containing the 3' endodomain ORF 5 polypeptides (either the 3' endodomain ORF 5 polypeptide from VR2332 or the 3' endodomain ORF 5 polypeptide from MN30100) detected PRRS virus antibodies in samples obtained from animals exposed to either the vaccine strain (Ingelvac MLV) or the field isolate (MN30100) of PRRS virus (Table 9 and FIG. 13). These results demonstrate that a polypeptide limited to a PRRS virus sequence that is conserved among PRRS viruses, whether from a vaccine version or a wild-type version of PRRS virus, can be used to detected animals exposed to any type of PRRS virus (e.g., a vaccine version or wild-type version of PRRS virus).

TABLE 9

ELISA results of serum samples obtained from pigs exposed to PRRS virus Ingelvac MLV or MN30100 and reacted with polypeptide fragments from either PRRS virus Ingelvac MLV or MN30100.

| Polypeptide for ELISA: | Virus animal exposed to: | Average* | Standard Deviation | SEM |
|---|---|---|---|---|
| 5' ORF 5 (VR2332) | MN30100 | 0.009 | 0.05303 | 0.037 |
|  | MLV | 1.443 | 0.11172 | 0.079 |
| 5' ORF 5 (MN30100) | MN30100 | 0.946 | 0.22273 | 0.157 |
|  | MLV | 0.193 | 0.00636 | 0.004 |
| 3' ORF 5 (VR2332) | MN30100 | 1.985 | 0.26269 | 0.185 |
|  | MLV | 2.336 | 0.19940 | 0.141 |
| 3' ORF 5 (MN30100) | MN30100 | 1.726 | 0.27930 | 0.197 |
|  | MLV | 1.932 | 0.42426 | 0.300 |

*The data are specific OD values after subtraction of background.

The ELISAs containing the 5' ectodomain ORF 5 polypeptide from VR2332 detected PRRS virus antibodies in samples obtained from animals exposed to the vaccine strain (Ingelvac MLV) and did not detect PRRS virus antibodies in samples obtained from animals exposed to the field isolate (MN30100) of PRRS virus (Table 9 and FIG. 13). Likewise, the ELISAs containing the 5' ectodomain ORF 5 polypeptide from MN30100 detected PRRS virus antibodies in samples obtained from animals exposed to the field isolate (MN30100) of PRRS virus and did not detect PRRS virus antibodies in samples obtained from animals exposed to the vaccine strain (Ingelvac MLV) (Table 9). These results demonstrate that a polypeptide limited to a PRRS virus sequence from a vaccine version of a PRRS virus that is variable among PRRS viruses can be used to identify animals exposed to the vaccine version of PRRS virus as opposed to animals exposed to a wild-type version of PRRS virus.

Example 8

Producing Additional Recombinant PRRS Virus Polypeptides from Vaccine Strains and Field Isolates The following polypeptides were produced: a PRRS virus ORF 7 polypeptide (FIG. 26), a PRRS virus NSP 2HP polypeptide (FIG. 27), a PRRS virus NSP 2 S1 HP polypeptide (FIG. 28), a PRRS virus NSP 2 S2 HP polypeptide (FIG. 29), a PRRS virus first and second N-terminal ectodomains ORF 6 polypeptide (ORF 6 5' total; FIG. 30), and a PRRS virus endodomain ORF 6 polypeptide (ORF 6 3'; FIG. 31). In each case, the polypeptides contained a myc sequence followed by the PRRS virus sequence followed by a polyhistidine sequence. The nucleic acid encoding the PRRS virus sequence of these polypeptides was from the nucleotide sequence in the VR-2332 strain of PRRS virus (GenBank® Accession No. PRU87392). In addition, a myc-ORF 7-His polypeptide, a myc-ORF 5 3'-His polypeptide, a myc-ORF 6 3'-His polypeptide, and a myc-NSP 2-His polypeptide was produced. The nucleic acid encoding the PRRS virus sequence of these polypeptides were from the nucleotide sequence in the Lelystad Virus (LV) strain of PRRS virus (GenBank® Accession No. M96292). A myc-NSP 2 HP-His polypeptide also was produced. The nucleic acid encoding the PRRS virus sequence of this polypeptide was from the nucleotide sequence in the Boehringer Ingelheim vaccine strain ATP. GenBank® Accession No. AY424271 for PRRS virus strain JA142 was used to obtain the ATP sequences since PRRS virus strain JA142 is the parental virus strain of the Boehringer Ingelheim vaccine strain ATP.

The polypeptides containing a PRRS sequence of VR-2332 were constructed as described in Example 2. For plasmids containing sequences of PRRS virus strains LV or ATP, viruses were isolated from cell culture lysates by centrifugation through a sucrose cushion. Viral RNA was extracted with a Qiagen kit. Primers were designed to amplify the desired sequences and to contain necessary restriction sites. PCR products were cleaned up with the Qiagen PCR Purification kit and ligated into pGEM-T vector. Plasmids were amplified in *E. coli* DH5α, purified, and digested with BamHI and Xho1. The insert was purified and recloned into the pET 24b myc His vector.

Recombinant polypeptides were expressed from plasmids in BL21 (DE3)-RP cells. After transformation, cells were spread on LB agar plates containing kanamycin (30 µg/mL) and chloramphenicol (35 µg/mL) and incubated overnight at 37° C. A single colony was picked and grown in 20 mL 2×YT medium containing kanamycin and chloramphenicol as above and grown overnight with shaking at 225 rpm. The 20 mL culture was transferred to 1 liter of 2×YT medium with antibiotics at 30° C. with shaking until the $OD_{600}$ reached 0.3. IPTG was added to 1 mM, and the flask agitated for 4 to 5 hours at 30° C. Two hundred µL of culture was removed for gel analysis.

The remaining culture was centrifuged at 4000×g for 20 minutes at 4° C. to pellet bacteria. The pellet was resuspended in 30 mL of 100 mM $NaH_2PO_4$, 10 mM Tris HCl, 8 M urea, pH 8.0. PMSF was added to 1 mM, and the mixture was rotated gently at room temperature for 2 hours. The mixture was centrifuged at 10,000×g for 30 minutes at 4° C. to pellet cellular debris. Six mL of a 50% slurry of Ni-NTA agarose (Qiagen, Valencia Calif.) was added to the supernatant containing denatured protein and rotated gently for 1 hour at room temperature. The mixture was then placed in a glass column 1.5 cm ID×40 cm and allowed to drain. The column was washed twice with 20 mL of 100 mM $NaH_2PO_4$, 10 mM Tris HCl, 8 M urea, pH 6.3. Recombinant protein was eluted with three to four 4-mL aliquots of 100 mM $NaH_2PO_4$, 10 mM Tris HCl, 8 M urea, pH 5.5-5.7. Proteins were stored at −20° C. until refolding.

Proteins were refolded by adding 231.3 mg of dithiothreitol to the pooled protein solution and stirring gently for 2 hours. Then, the solution was rapidly diluted into 500 mL of refolding buffer (100 mM Tris HCl, pH 8.0, 0.5 M L-arginine, 8 mM oxidized glutathione, 2 mM EDTA, 10 µM pepstatin A, 10 µM leupeptin, 1 mM PMSF) and stirred gently overnight at 4° C. Protein was reconcentrated by tangential flow filtration (Pellicon XL Ultracel PLC 5 kd, Millipore, Bedford Mass.) and dialyzed (Spectra/Por MWCO 3,000) overnight at 4° C. against 10 mM Na phosphate, pH 8.0. Solutions were concentrated by centrifugation (Centriprep, Millipore) at 3,800 rpm for 30 minutes at 4° C. as needed. Proteins were stored in aliquots at −80° C. Protein concentrations and purity were assessed by SDS-polyacrylamide gel electrophoresis.

Example 9

Detecting Antibodies to North American and European Genotype PRRS Viruses Using Mixtures of PRRS Virus Polypeptides from Either or Both Genotypes The following experiments were performed to (1) determine if ELISAs using polypeptides from a North American type PRRS virus (e.g., VR-2332) are capable of detecting PRRS virus positive samples from pigs inoculated with a European type PRRS virus (e.g., Lelystad virus) and (2) determine if ELISAs using polypeptides from a European type PRRS virus (e.g., Lelystad virus) are capable of detecting PRRS virus positive samples from pigs inoculated with a North American type PRRS virus (e.g., VR-2332). The following experiments also were performed to determine if ELISAs using a combination of polypeptides from both North American and European type viruses are capable of detecting PRRS virus positive samples from pigs infected with either type of virus.

The following polypeptides in 15 mM $Na_2CO_3$, 35 mM $NaHCO_3$, pH 9.6, were used to coat ELISA plates (COSTAR 3590, 96 well EIA/RIA plate, Corning N.Y.): myc-ORF 7-His (VR-2332), myc-ORF 6 3'-His (VR-2332), myc-ORF 5 3'-His (VR-2332), myc-ORF 7-His (LV), myc-ORF 6 3'-His (LV), and myc-ORF 5 3'-His (LV). These polypeptides were expressed from the respective plasmids containing all or portions of ORF 7 (N), ORF 6 (M), or ORF 5 (GP5). Wells were coated with solutions containing either 100 ng each of the three VR-2332 polypeptides/100 µL, or 100 ng each of the three LV polypeptides/100 µL, or 50 ng each of all six polypeptides/100 µL. Thus, all wells contained 300 ng of polypeptide.

Plates were incubated with coating solution overnight at 4° C. Plate wells were washed one time with PBS, 0.05% Tween 20, pH 7.3-7.5 and blocked with 300 µL of 5% nonfat dry milk in PBS, 0.05% Tween 20, pH 9.4-9.6, per well for 2 hours. Plates were washed 5 times in PBS, 0.05% Tween 20, pH 7.3-7.5, and 100 µL of test serum diluted 1/500 in PBS, 0.05% Tween 20, 5% nonfat dry milk was added to duplicate wells for 1 hour. Plates were washed 5 times, and 100 µL of peroxidase-labeled affinity purified antibody to swine IgG (H+L) (KPL, Gaithersburg Md.) diluted 1/5000 in PBS, 0.05% Tween 20, 5% nonfat dry milk was added for 1 hour. Plates were washed 5 times, and enzyme substrate was added for 5 minutes. Enzyme substrate consisted of 100 µL per well of equal portions of TMB peroxidase substrate solution A and peroxidase $H_2O_2$ substrate solution B (TMB Peroxidase Substrate System, KPL, Gaithersburg Md.) mixed together. Reactions were stopped with 100 µL of 2 M phosphoric acid, and results were read at 450 nm in a Thermo Max Microplate Reader, Molecular Devices, Sunnyvale Calif.

Figure 32A:
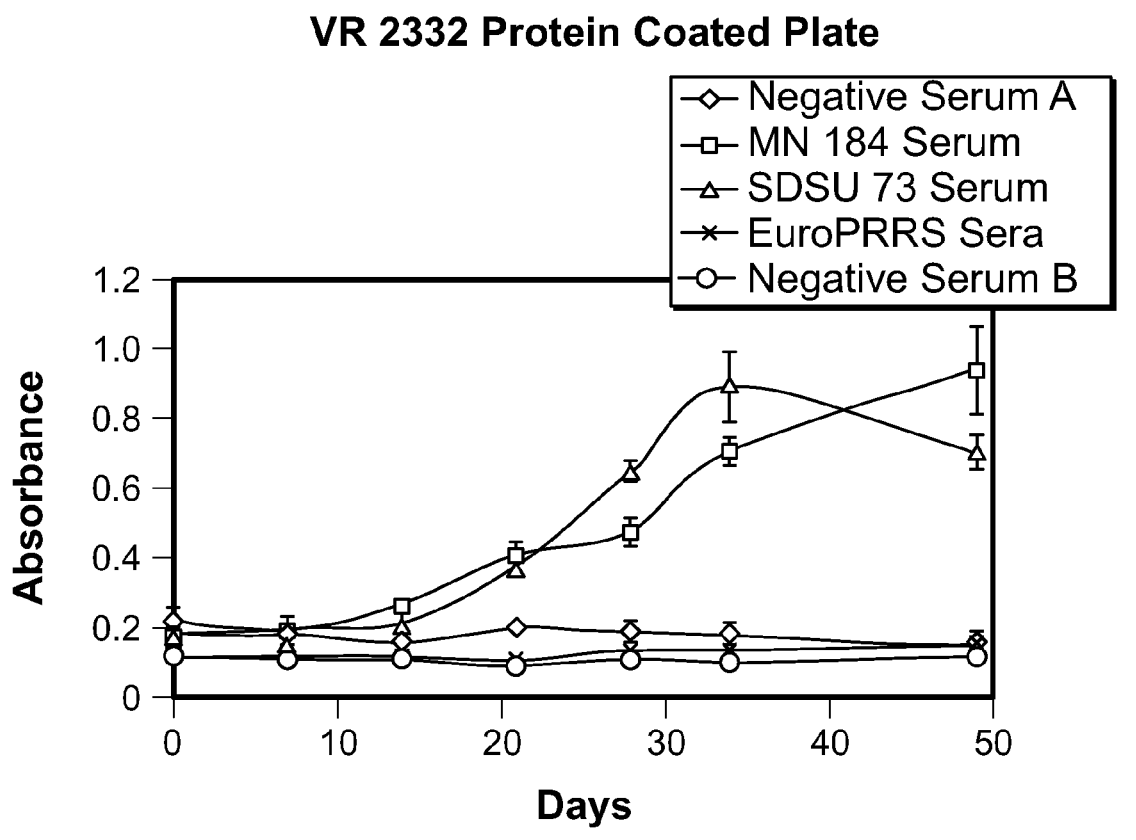
Figure 32B:
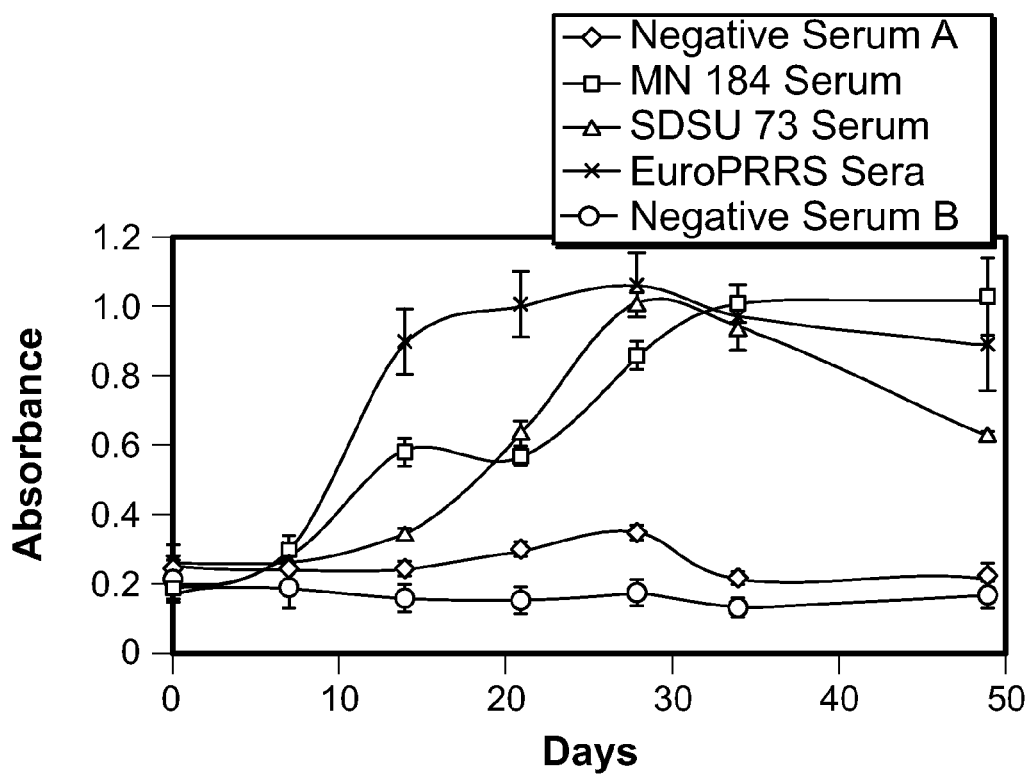
FIG. 32 contains three graphs plotting the absorbance for samples obtained from animals exposed to MN 184, SDSU 73, or EuroPRRS as well as two controls. The absorbance values were detected using an ELISA of VR-2332 polypeptides (A), LV polypeptides (B), or a mixture of both (C).
Figure 32C:
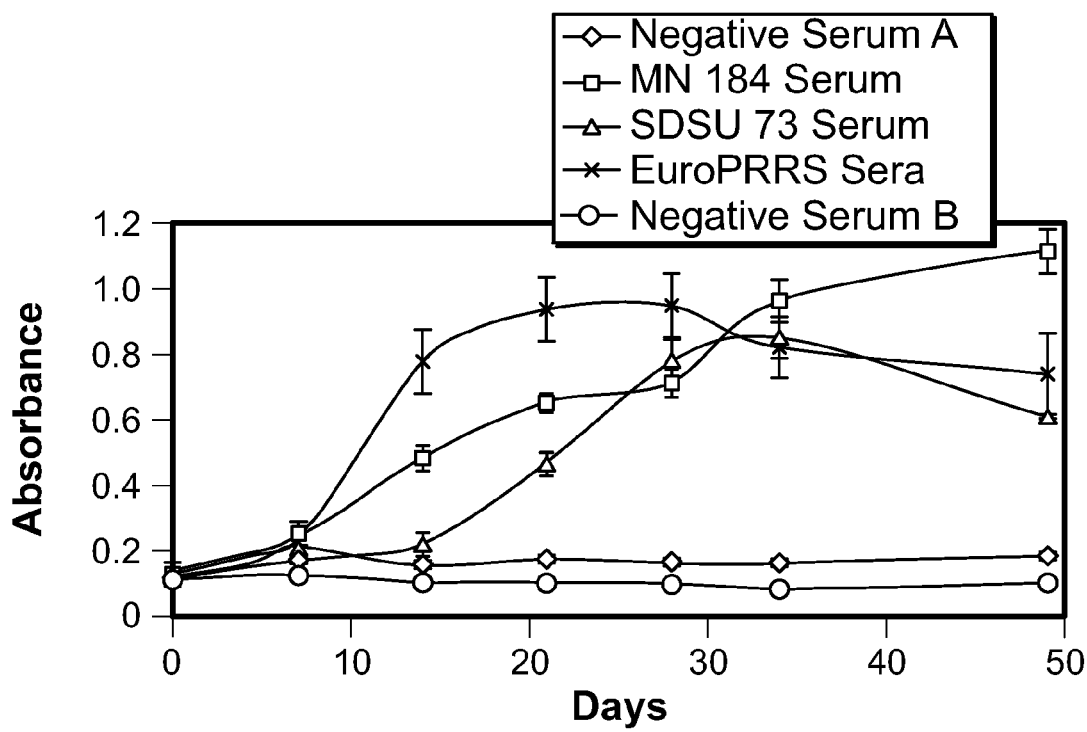

Serum samples were obtained from pigs that were uninfected (negative sera A and negative serum B), infected with a European type PRRS virus (n=9), and either of two North American PRRS virus strains, MN 184 or SDSU 73 (Johnson et al., *Vet. Immunol. Immunopathol.*, 102:233-247 (2004)) (n=1 each). Samples were obtained at approximately 0, 7, 14, 21, 28, 35, and 49 days after infection. The mixture of VR-2332 polypeptides detected anti-PRRS virus antibodies in sera of pigs exposed to MN184 or SDSU 73 at 14 days after infection and at all time points thereafter (FIG. 32; panel A). The VR-2332 polypeptides did not detect anti-PRRS virus antibodies in sera of pigs infected with a European PRRS virus.

The mixture of LV polypeptides detected antibodies in sera of pigs exposed to a European genotype PRRS virus at 7 days of infection and at high levels at all time points thereafter (FIG. 32; panel B). The LV polypeptides also detected antibodies in pigs exposed to North American PRRS viruses at day 14 and later (FIG. 32; panel B). The combination of LV and VR-2332 polypeptides detected anti-PRRS virus antibodies in sera of exposed pigs similarly to LV polypeptides alone except that there was a tendency to higher values in the animal exposed to MN 184 (FIG. 32; panel C).

These results indicate that LV polypeptides, such as the mixture of ORF 5 3', ORF 6 3', and ORF 7 polypeptides, can detect an antibody response in pigs exposed to European and North American genotype PRRS viruses as early as 7 days after infection. VR-2332 polypeptides specifically recognized sera of pigs exposed to North American type PRRS viruses, and not to sera from pigs exposed to the European type virus. Thus, with the appropriate mixtures of polypeptides, one can detect serological responses to all PRRS viruses and can differentiate between responses to European and North American types.

Example 10

Figure 33A:
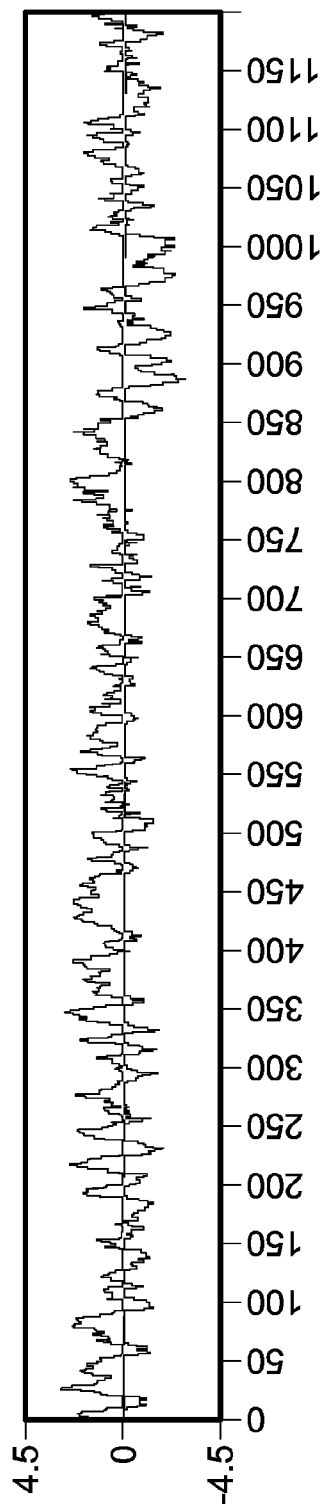
FIG. 33A contains a Kyte-Doolittle hydrophilicity profile of an NSP 2 polypeptide.
Figure 33B:
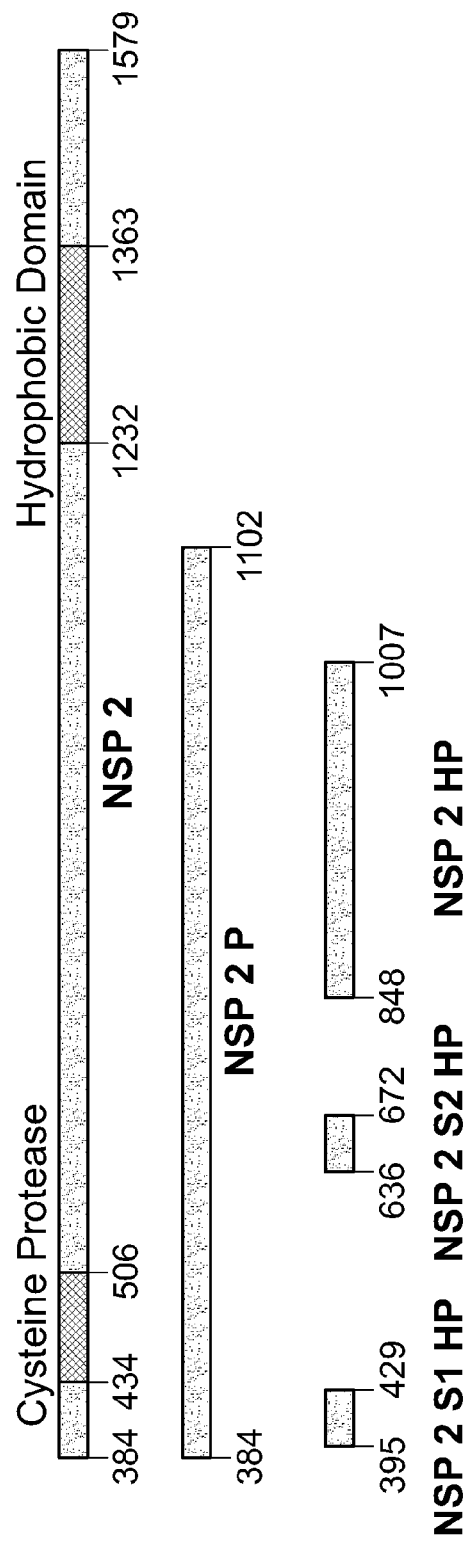
FIG. 33B is a diagram of NSP 2 and fragments of NSP 2. The amino acid numbering is according to VR-2332 orf 1 (GenBank® accession number U87392). The cysteine protease catalytic site and the hydrophobic domain are labeled.
Figure 34A:
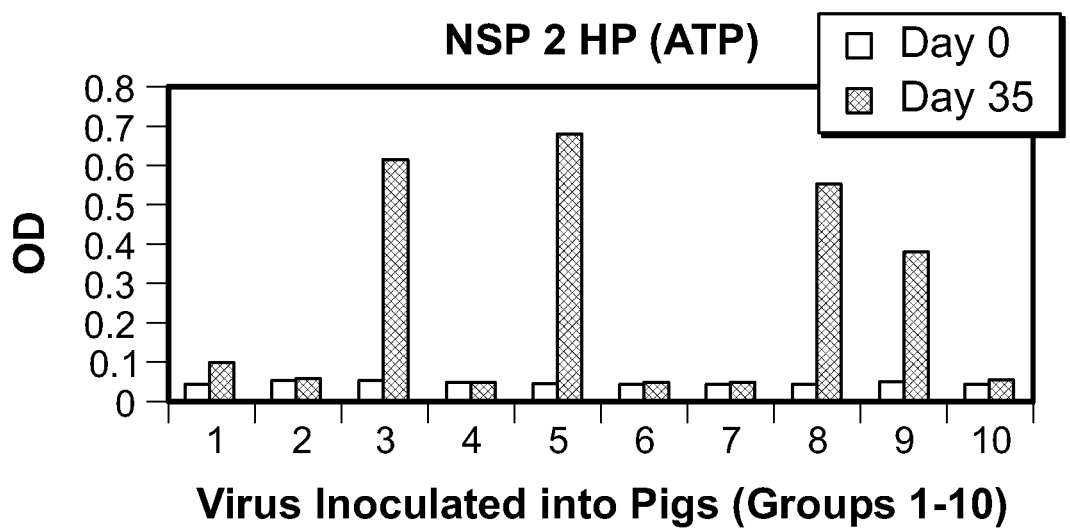
FIG. 34 contains two graphs plotting the absorbance for samples obtained from animals treated as indicated. The absorbance values were detected using an ELISA of NSP 2 HP (ATP) polypeptides (A) or NSP 2P (VR-2332) polypeptides (B).
Figure 34B:
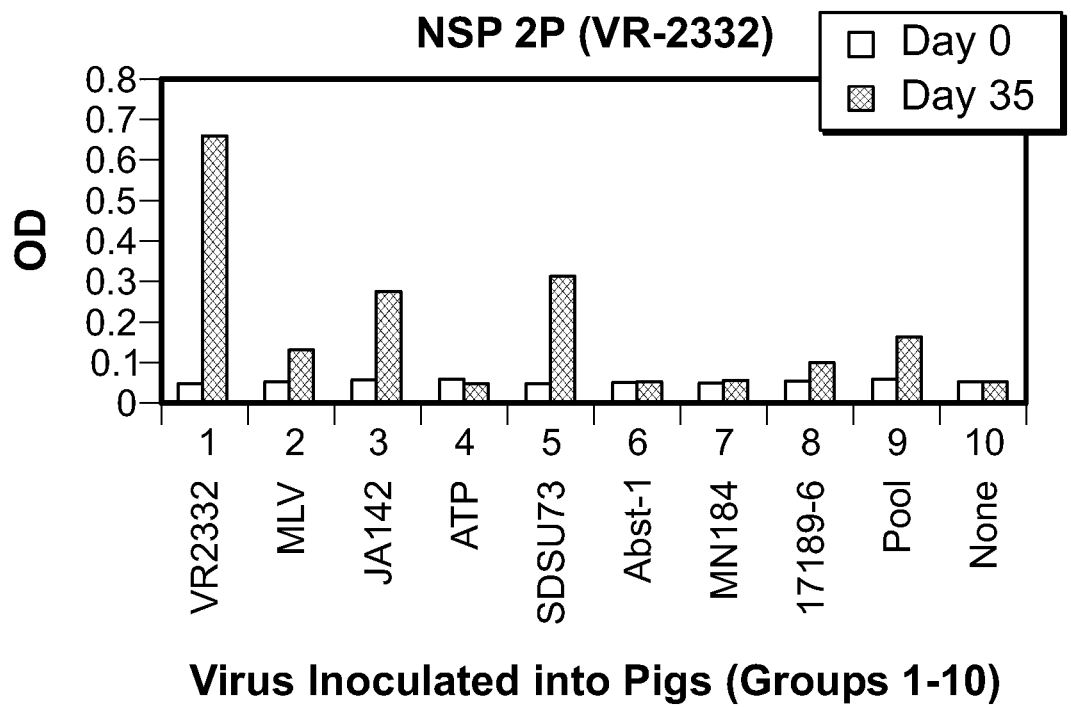
Figure 35A:
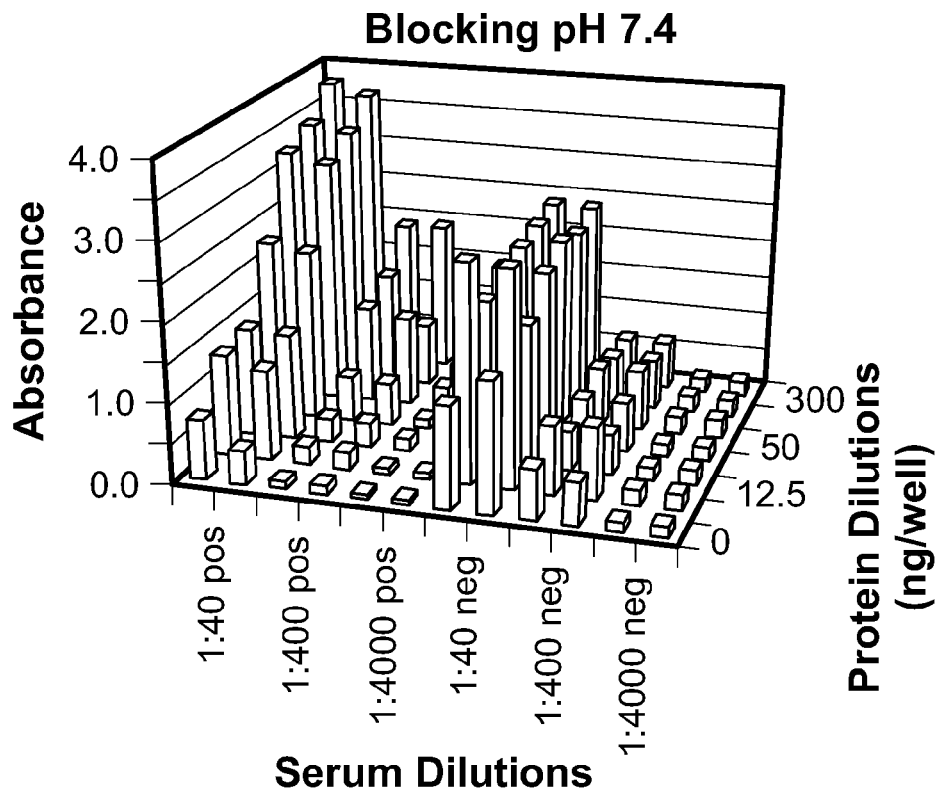
FIG. 35 contains two 3D graphs plotting the absorbance for positive and negative samples diluted as indicated and assessed with wells having the indicated amount of polypeptide. The pH during the blocking step was either 7.4 (A) or 9.6 (B).
Figure 35B:
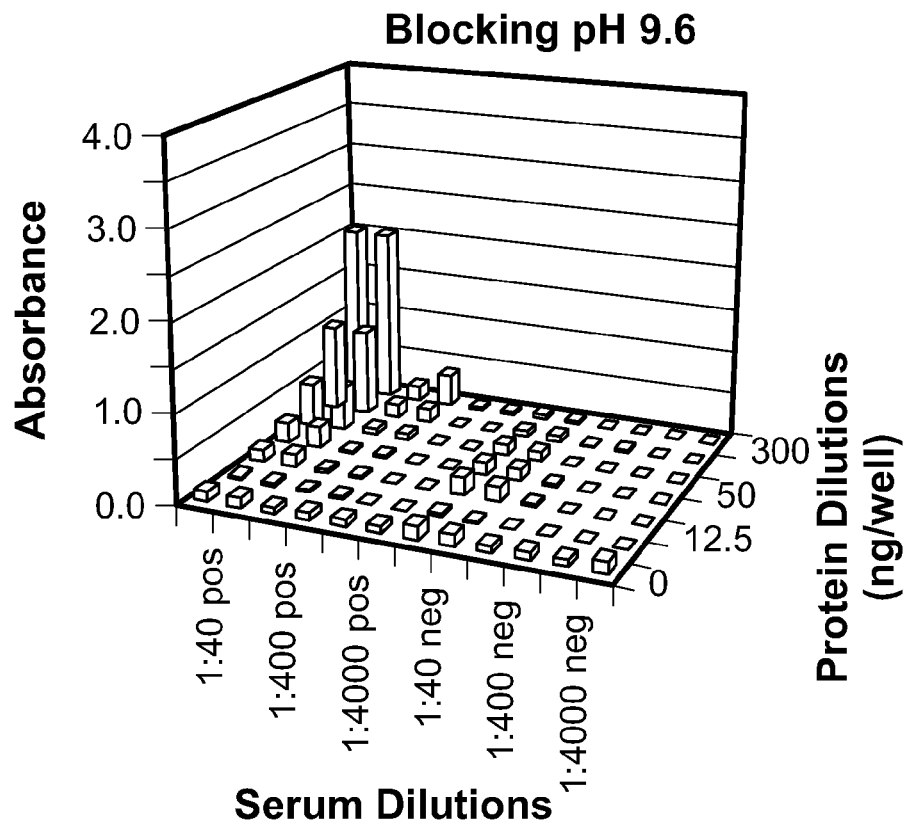

Differentiating Between Animals Exposed to a Vaccine or Field Strains of PRRS Virus Using Nonstructural Protein Polypeptides Example 4 demonstrated that swine antibody responses to PRRS viruses can be greater to the nonstructural proteins than to structural proteins such as N. Since detection of NSP's might result in a more sensitive assay, the following experiments were performed to determine if ELISAs comprised of polypeptides derived from a nonstructural protein from VR-2332 or the Ingelvac ATP vaccine strain of PRRS virus would differentiate pigs vaccinated with the Ingelvac MLV or Ingelvac ATP strains from pigs exposed to field strains of PRRS virus. Various polypeptides were produced containing portions of NSP 2 (FIG. 33).

In the first experiment, serum samples from pigs exposed to field viruses or the Ingelvac MLV vaccine virus for 28 days were incubated in microtiter plates coated with myc-NSP 2 P-His (VR-2332) or myc-NSP 2HP-His (VR-2332) polypeptides. Serum from pigs inoculated with MLV vaccine, which was derived from the VR-2332 strain, reacted strongly with both myc-NSP 2P-His and myc-NSP 2 HP-His polypeptides. Positive signals in serum samples diluted 1/1000 from seven pigs ranged from 0.8 to 3.6 OD units against NSP 2P and from 0.7 to 3.1 OD units against NSP 2HP. The relative percent difference $(1-(OD_{NSP\ 2HP}/OD_{NSP\ 2P}))$ after background subtraction, ranged from 9.9 to 23.2 percent. By contrast, serum from pigs inoculated with any of five different wild-type field viruses reacted more strongly with myc-NSP 2P-His polypeptides than with myc-NSP 2HP-His polypeptides. Positive signals among 35 pigs exposed to five different viruses ranged from 0.54 to 3.3 OD units against NSP 2P and from 0.22 to 1.9 OD units against NSP 2HP. The relative percent difference ranged from 36.6 to 85.1 percent.

These results indicate that the NSP 2HP (VR-2332) polypeptide is different from other PRRS virus NSP 2HP polypeptides such that its derived vaccine virus, MLV, elicits antibodies in pigs that react selectively with the NSP 2HP (VR-2332) polypeptide. In addition, the pronounced reactivity of serum samples from field virus-exposed pigs with NSP 2P (VR-2332) indicates that this polypeptide can be used as a diagnostic polypeptide. The relative specificity of the NSP 2 HP polypeptide for the MLV vaccine indicates that a test that compares the relative serological reactivity of a test serum to both VR-2332 NSP 2P and NSP 2HP can differentiate swine vaccinated with Ingelvac MLV from pigs that were exposed to field viruses.

In a second experiment, additional portions from the NSP 2 (VR-2332) polypeptide that showed variation in amino acid sequence among the PRRS virus sequences in GenBank were evaluated for specific reactivity with serum from pigs exposed to Ingelvac MLV vaccine or field viruses as in the previous experiment. ELISA plates were coated with myc-NSP 2P-His (VR-2332) polypeptides or with myc-NSP 2 S1 HP-His (VR-2332) or myc-NSP 2 S2 HP-His (VR-2332) polypeptides.

All pig sera, both from vaccinated and field virus-exposed animals and diluted 1/1000 (n=42), reacted with NSP 2P with high OD values as in the previous experiment. However, the sera reacted weakly with both NSP 2 S1 HP and NSP 2 S2 HP. The OD values of more than 90 percent of the samples were below 0.1. These results indicate that polypeptides of about 30 to 40 amino acids may not encompass sufficient immunoreactivity to discriminate different serological reactivities to a viral infection even though the amino acid sequence variability in the polypeptide is high.

In a third experiment, microtiter plates were coated as described in Example 9 with myc-NSP 2HP-His (ATP) or myc-NSP 2P-His (VR-2332) polypeptides. ELISA assays were performed with serum samples from pigs exposed to vaccine and field viruses as described in Example 4. The assay was performed as described in Example 9 with the exception that serum samples were diluted 1/1000, and color development reactions were stopped after 3 minutes. As shown herein, serum samples from pigs exposed to field viruses or the MLV vaccine react positively with NSP 2P (VR-2332) (FIG. 34). Serum from pigs exposed to Abst-1 or the vaccine strain ATP did not react positively, due to use at doses that elicited a low or negligible immune response. The NSP 2HP (ATP) polypeptide reacted strongly with serum from a pig exposed to JA142, the parental virus of the vaccine, but also to serum from pigs exposed to field viruses SDSU73 and 17198-6. These results demonstrate that the use of non-structural polypeptides such as NSP 2HP and NSP 2 P from different PRRS virus strains such as Ingelvac ATP and VR-2332 did not result in a serological test that was specific for exposure of swine to a particular strain or isolate. The NSP 2HP (ATP) polypeptide may not be uniquely different from other PRRS virus NSP 2 HP polypeptides in the way that NSP 2HP (VR-2332) is.

Example 11

Increasing pH During the Blocking Step Reduces Background Signals

High nonspecific backgrounds in ELISA tests is a commonly encountered problem in swine serology, especially with serum at low dilutions and from older animals such as six months and above. The levels of specific and nonspecific reactivity of positive and negative swine sera were determined on ELISA plates that were blocked at pH 7.4 or 9.6. Wells were coated with equal amounts of N, ORF 5 and ORF 6 ectodomains, and ORF 5 endodomain (all from VR-2332) at zero to 300 ng/well, and positive or negative sera were applied at dilutions of 1/40 to 1/4000. The positive serum samples were obtained from a 7 week-old pig at 3 weeks after exposure to VR-2332. The negative serum samples were obtained from a 6 month-old pig. Blocking was performed with 5% nonfat dry milk in PBS, 0.05% Tween 20 at pH 7.4 or 9.6.

Serum concentration-dependent color development was observed in PRRS virus-positive serum at pH 7.4, but nonspecific color development in PRRS virus-negative serum wells was even higher than specific reactivity at moderate and low levels of antigen on the plate (FIG. 35). At a blocking pH value of 9.6, the nonspecific reactivity was nearly completely abolished. Specific reactivity was reduced by about 50 percent, but the overall signal-to-noise ratio was greatly increased (FIG. 35).

These results indicate that blocking solutions (e.g., protein solutions) applied to ELISA plates at neutral pH do not completely neutralize the protein-binding capacity, resulting in nonspecific binding of swine immunoglobulins and high OD values. The problem is exacerbated at low serum dilutions which would otherwise increase assay sensitivity. Increasing the pH of the blocking solution above 7.4 (e.g., greater than 9) reduced or abolished nonspecific reactivity across a wide range of antigen coating amounts and serum dilutions.

Example 12

Producing Recombinant PRRS Virus Polypeptides

The following polypeptides were produced using methods and materials similar to those described in Example 2: a PRRS virus (Lelystad strain) ORF 7 polypeptide (FIG. 36), a PRRS virus (Lelystad strain) NSP 2P polypeptide (FIG. 37), a PRRS virus (JA 142 strain) NSP 2P polypeptide (FIG. 38), a PRRS virus (ATP strain) NSP 2HP polypeptide (FIG. 39), a PRRS virus (Lelystad strain) endodomain ORF 5 polypeptide (ORF 5 3'; FIG. 40), and a PRRS virus (Lelystad strain) endodomain ORF 6 (ORF 6 3'; FIG. 41) polypeptide.

Example 13

Adding Lysozyme to Coating Buffer Increases Reactivity to Nucleocapsid

Lysozyme was included as a control in coating of wells with recombinant polypeptides. Briefly, ELISA wells were coated with 100 ng of polypeptides (e.g., refolded myc-ORF 7-His polypeptide) alone or with various amounts of chicken egg lysozyme (Sigma) in 100 μL carbonate buffer. ELISA was performed with serum samples from two pigs 21 days after infection with PRRS virus strain VR2332 or two uninfected control pig serum.

Figure 42:
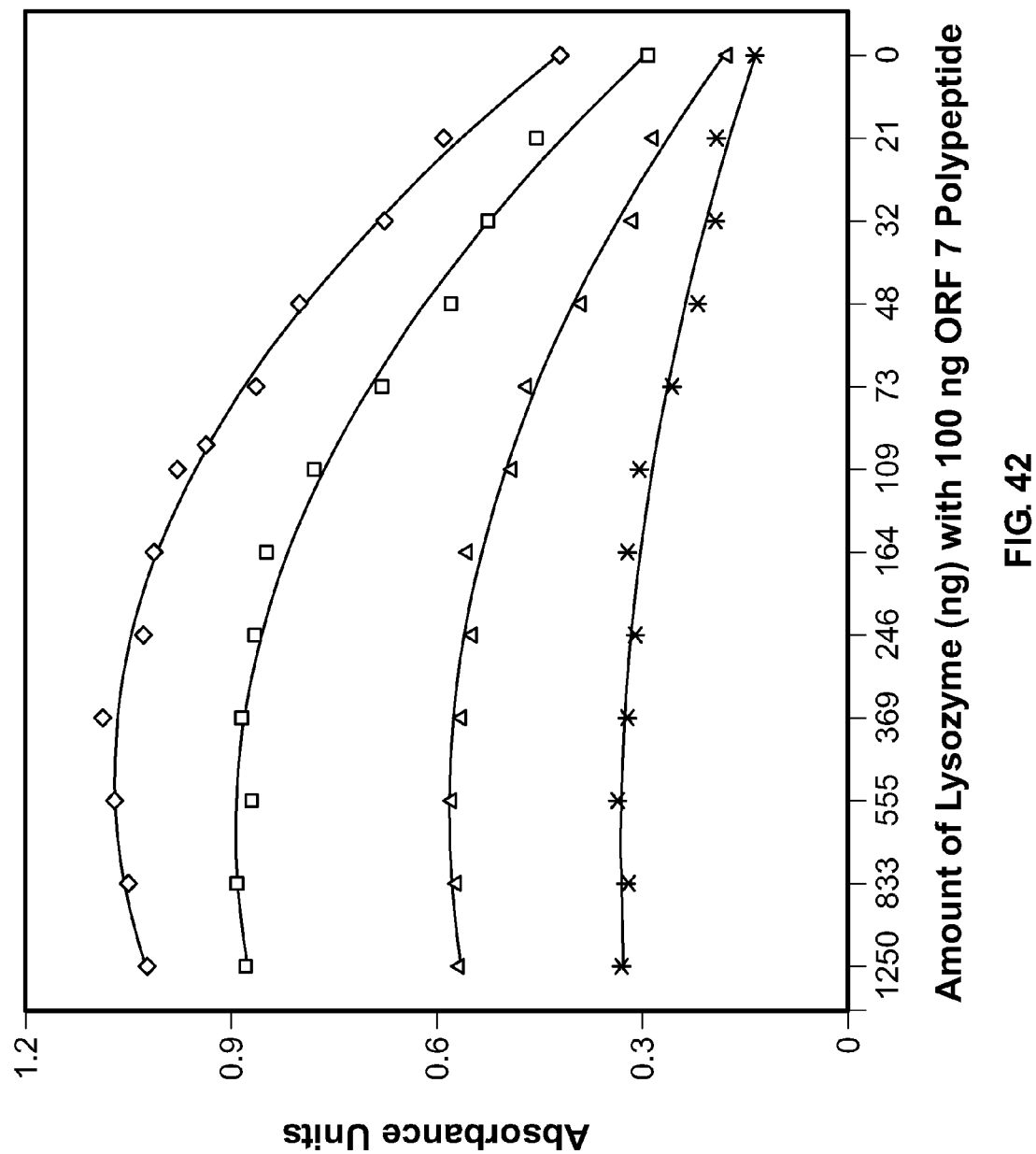
FIG. 42 is a graph plotting the absorbance versus the amount of chicken egg lysozyme added to 100 ng of refolded myc-ORF 7-His polypeptide. Values are the specific anti-ORF 7 polypeptide means after subtraction of negative serum backgrounds. Data points are from sera diluted 1/300 (diamond), 1/600 (square), 1/1200 (triangle), and 1/2400 (cross-x).

No difference was observed in the intensity of color reactions when plates were coated with various recombinant polypeptides, including myc-ORF 5-3'-His polypeptide and non-refolded myc-ORF 7-His polypeptide, in the presence or absence of lysozyme at various concentrations. Similarly, no reactivity was observed to lysozyme alone. Refolded myc-ORF 7-His polypeptide reactivity, however, was substantially increased in the presence of lysozyme. Moreover, the degree of enhancement was proportional to the amount of lysozyme added (FIG. 42). Inclusion of lysozyme in the coating step increased the specific reactivity of immune PRRS virus serum in a dose-dependent manner up to a maximum of about 200 ng of lysozyme per well (FIG. 42).

The effect was observed at all dilutions of serum examined with greater effects observed with less dilute sera. At a 1/300 dilution of serum, the average specific absorbance was about 0.42 in the absence of lysozyme, but it was greater than 1.0 in the presence of 164 ng or greater of lysozyme. The enhancing effect of lysozyme also was observed with a wide range of coating amounts, including the range of 20 to 500 ng, of refolded myc-ORF 7-His polypeptide per well. About 100 ng of lysozyme per well provided enhanced results under a variety of conditions including, for example, dilution of test serum from 1:40 to 1:5000, incubation of test serum with antigen for 45 minutes to 90 minutes, dilution of second antibody conjugate from 1:500 to 1:5000, and color development reaction time from 2 minutes to 20 minutes. The finding that lysozyme enhances the specific anti-PRRS serological reactivity to the ORF 7 polypeptide is useful since the ORF 7 polypeptide is a major antigen of the PRRS virus and is widely used in serological testing. Conditions that increase the sensitivity of detection of anti-ORF 7 polypeptide antibodies can increase the sensitivity of a diagnostic assay to early infection or exposure to PRRS virus, can increase the duration of detection following exposure or seroconversion, and can provide a basis for a more robust test since the difference between positive and negative results can be increased.

Example 14

Increased Stability of Recombinant Viral Protein-Based ELISAs

Figure 43:
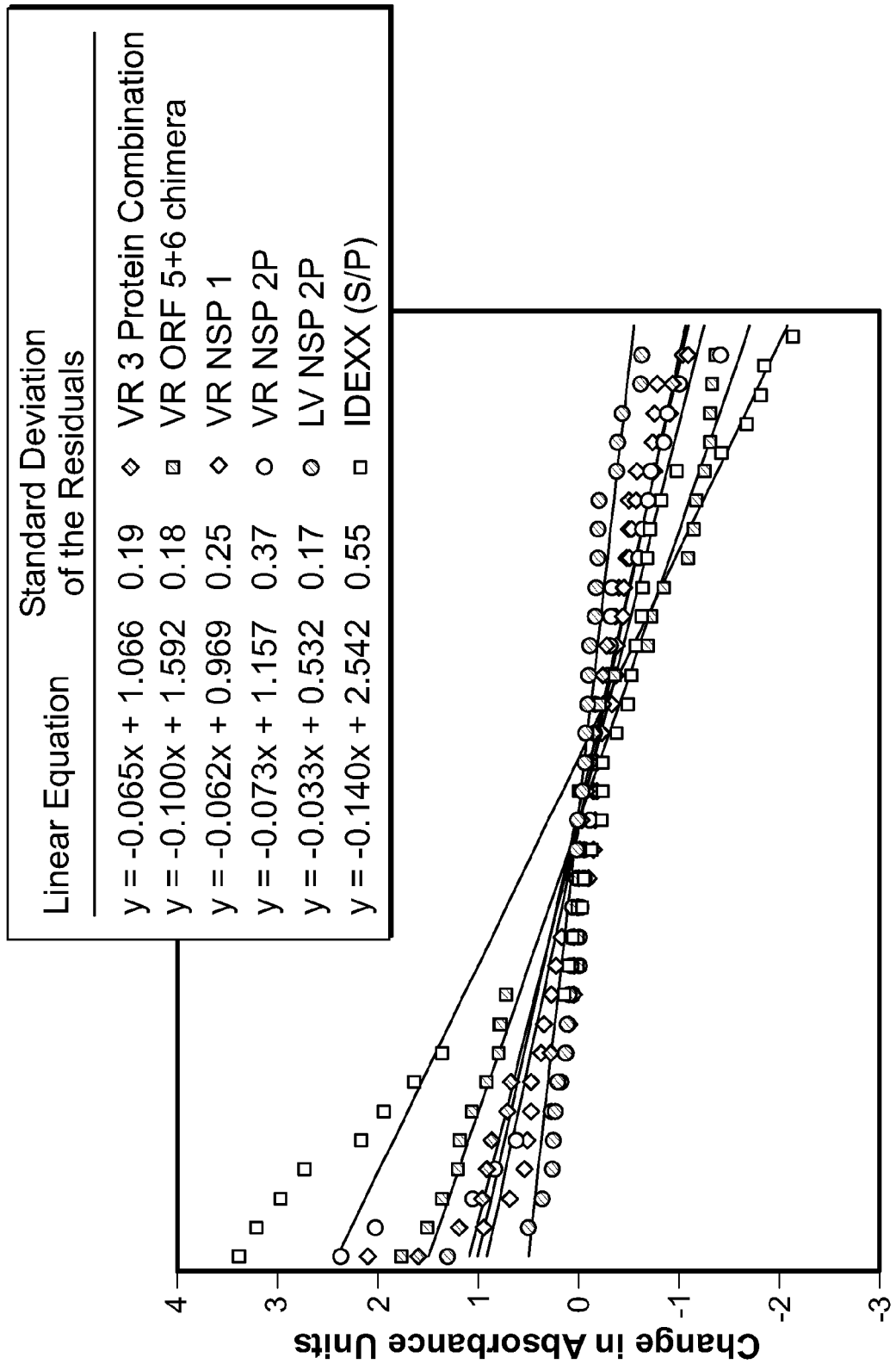
FIG. 43 is a graph plotting the change in absorbance detected in animals using the indicated ELISAs. VR indicates the polypeptide is from strain VR2332. LV indicates the polypeptide is from Lelystad virus. Standard deviation of the residuals is a measure of goodness-of-fit of the data to the equation determined by linear regression.

The ability of recombinant polypeptides to detect previous exposure to PRRS virus in pregnant sows in a commercial pig-rearing operation was evaluated in comparison to the IDEXX 2XR ELISA. Sera from 32 pregnant sows in an endemically infected herd were obtained at 35 day intervals and tested for anti-PRRS virus antibodies by IDEXX 2XR ELISA and by ELISA reactivity to a combination of three recombinant PRRS virus polypeptides (ORF 7, ORF 5-3', and ORF 6-3', all strain VR2332), or individual PRRS virus polypeptides from strain VR2332 (ORF 5+6 ectodomain chimera, NSP 1, and NSP 2P) or an individual PRRS virus polypeptide from the Lelystad virus strain (NSP 2P; FIG. 37). Briefly, serum samples diluted 1/500 were run in duplicate on ELISA plates coated with 50 ng of ORF 5+6 chimera alone, or 100 ng of a combination of ORF 7, ORF 5-3' and ORF 6-3' (33 ng each), or 100 ng of NSP 1, or 100 ng of NSP 2P. The serum samples were also analyzed by IDEXX 2XR ELISA. For each ELISA assay, the difference in average absorbance value (day 35-day 0) was calculated for all 32 pigs and ordered from positive to negative. For each set of data, a hypothetical linear regression equation and regression coefficient was calculated. The resulting values were ordered from highest to lowest value for all 32 animals for each recombinant polypeptide preparation (FIG. 43).

In each instance, a range of values from positive (higher value at interval day 35 than interval day 0) to negative (lower value at interval day 35 than interval day 0) was obtained. The greatest variation (standard deviation of the residuals=0.55) among animals in antibody levels, both positive and negative, occurred in the IDEXX 2XR ELISA test (FIG. 43). The recombinant polypeptide ELISAs exhibited more uniform results in that a hypothetical regression analysis indicated a line with a slope closer to zero, and reduced variation in the highest and lowest responses (FIG. 43). These results were on average more uniform, as indicated by the linear regression equation slope that was closer to zero and the smaller standard deviation of the residuals in each case as compared to IDEXX 2XR ELISA. The most consistent result was obtained with NSP2P derived from Lelystad virus.

Large differences in assay results in a 35 day period can be interpreted as a loss of immunity in animals that exhibit a large decrease in reactivity, and as new infection of susceptible animals in cases of large increases in reactivity. The consequence can be a potential increase in false positive and false negative interpretations of the PRRS virus status of individual animals and of commercial swine populations. The recombinant polypeptide ELISA assays exhibited less variation in animal responses, consistent with exposure of the animals to PRRS virus, the presence of an immune response in the animals, and little change in antibody status of the animals in a 35 day period. These results indicate that the recombinant polypeptide ELISAs, based on individual polypeptides or combinations of polypeptides, can provide a more uniform assessment of herd exposure to PRRS virus and can have a reduced likelihood of false positive and false negative interpretations.

Example 15

Figure 44A:
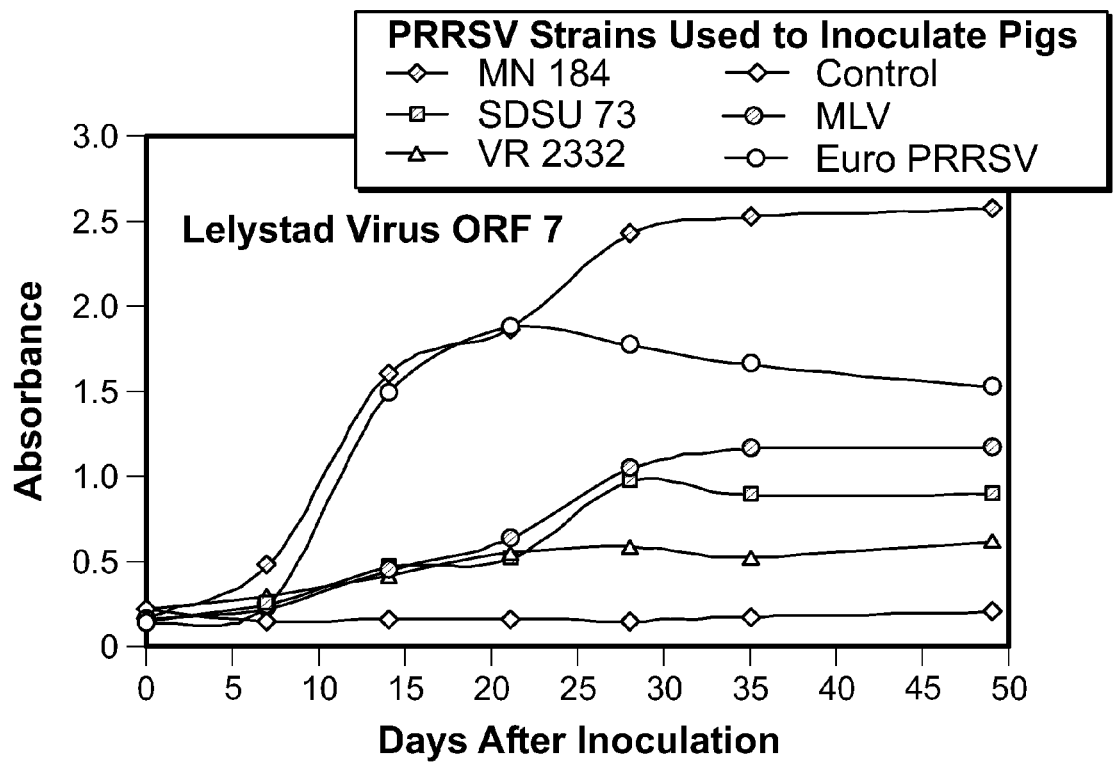
FIG. 44 contains graphs plotting the absorbance observed with samples inoculated with the indicated PRRS virus using ELISAs containing the indicated polypeptide.
Figure 44B:
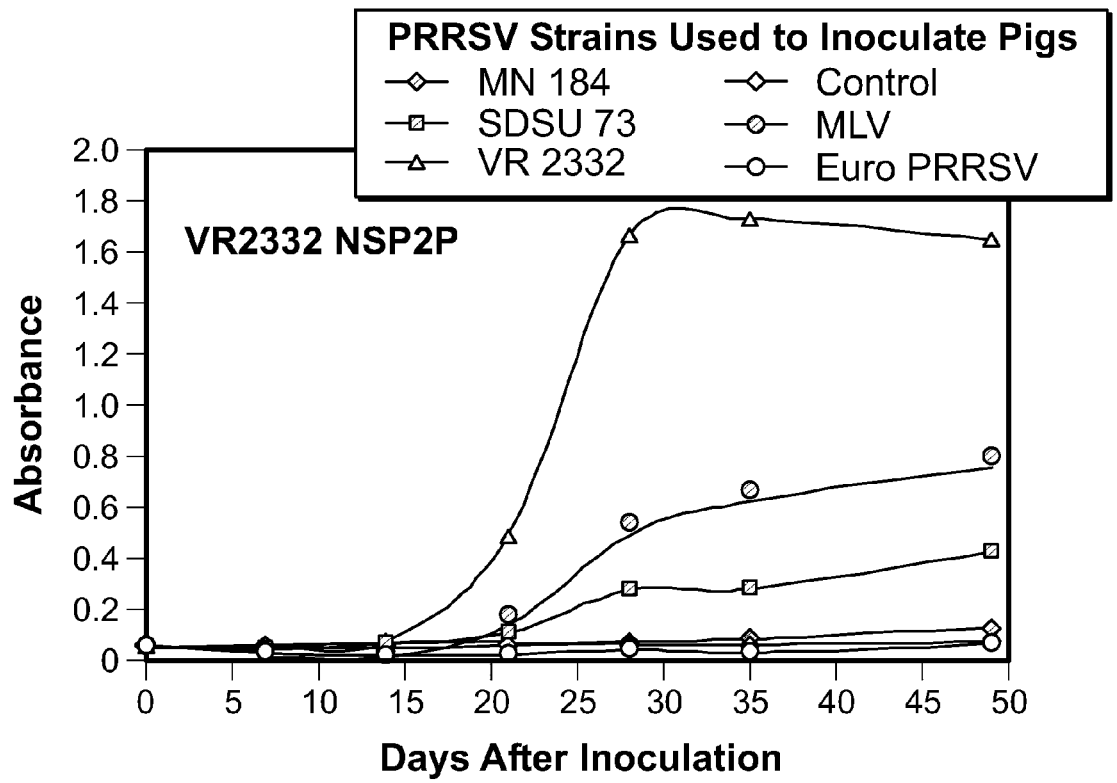

Detecting Antibodies to North American and European Genotype PRRS Viruses Using Individual PRRS Virus Polypeptides from Either Genotype The serum samples described in Example 9 as well as recombinant PRRS virus ORF 7 (from Lelystad virus, a European genotype; FIG. 36) and NSP2P (from VR2332, a North American genotype; or Lelystad virus, FIG. 37) polypeptides were used to examine the specificity of reaction for individual PRRS virus polypeptides. Serum samples from pigs inoculated with a European genotype PRRS virus and with the North American genotype virus, MN 184, reacted strongly with Lelystad virus ORF 7 polypeptides, while North American genotype strains SDSU73, VR2332, and Ingelvac MLV reacted weakly (FIG. 44). These results indicate that ORF 7 polypeptides of Lelystad virus can be used to discriminate serological responses to a subset of North American PRRS viruses as well as to European PRRS virus strains. Serum samples from pigs inoculated with a European genotype PRRS virus reacted exclusively with LV NSP 2P polypeptides and not at all with VR2332 NSP 2P polypeptides (FIG. 44, panels B and C). The VR2332 NSP 2P polypeptide reacted strongly with sera from pigs exposed to VR2332 and positively, but less strongly, with sera of pigs exposed to Ingelvac MLV and SDSU73. It appeared not to react at all with sera from pigs exposed to MN184. These findings indicate that individual PRRS virus polypeptides can detect serological responses to pigs exposed to subsets of PRRS viruses.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining whether or not a sample contains a swine anti-PRRS virus antibody, wherein said method comprises:
   (a) contacting a polypeptide with said sample under conditions wherein said polypeptide forms a polypeptide: swine anti-PRRS virus antibody complex with an antibody, if present, within said sample, wherein said polypeptide consists of:
      i. the amino acid sequence encoded by SEQ ID NO:11 or SEQ ID NO:38; or
      ii. the amino acid sequence encoded by SEQ ID NO:11 or SEQ ID NO:38 and a polypeptide tag; and
   (b) detecting the presence or absence of said complex, wherein the presence of said complex indicates that said sample contains said swine anti-PRRS virus antibody.

2. The method of claim 1, wherein said sample is a pig serum sample.

3. The method of claim 1, wherein said polypeptide t comprises a His tag or a myc tag.

4. The method of claim 1, wherein said polypeptide is a recombinant polypeptide produced by cells not infected with a PRRS virus.

5. The method of claim 1, wherein said step (b) comprises contacting said complex with an anti-swine Ig antibody.

6. The method of claim 5, wherein said anti-swine Ig antibody contains an enzyme.

7. The method of claim 1, wherein said step (a) comprises contacting said sample with polypeptides within a kit, and wherein said kit comprises a polypeptide having an amino acid sequence present in a PRRS virus ORF 5 polypeptide.

* * * * *

```
                        SEQUENCE LISTING

<160> NUMBER OF SEQ ID NOS: 105

<210> SEQ ID NO 1
<211> LENGTH: 1586
<212> TYPE: DNA
<213> ORGANISM: Porcine reproductive and respiratory syndrome virus
<220> FEATURE:
<221> NAME/KEY: CDS
<222> LOCATION: (175)..(234)

<400> SEQUENCE: 1
aggcgccagc aaccgcacct gtggcgccgg tgatgccggc cacgatgcgt ccggcgtaga       60
ggatcgagat ctcgatcccg cgaaattaat acgactcact atagggaat tgtgagcgga      120 taacaattcc cctctagaaa taattttgtt aactttaag aaggagatat acat atg         177
                                                             Met
                                                               1 gaa caa aaa ctc atc tca gaa gag gat ctg aat cga tcc atg aat tct        225
Glu Gln Lys Leu Ile Ser Glu Glu Asp Leu Asn Arg Ser Met Asn Ser
          5                  10                  15 agt gga tcc tctgggatac ttgatcggtg cacgtgtacc cccaatgcca                274
Ser Gly Ser
         20 gggtgtttat ggcggagggc caagtctact gcacacgatg cctcagtgca cggtctctcc      334 ttcccctgaa cctccaagtt tctgagctcg gggtgctagg cctattctac aggcccgaag      394 agccactccg gtggacgttg ccacgtgcat tccccactgt tgagtgctcc ccgccgggg       454 cctgctggct ttctgcaatc tttccaatcg cacgaatgac cagtggaaac ctgaacttcc      514 aacaaagaat ggtacgggtc gcagctgagc tttacagagc cggccagctc acccctgcag      574 tcttgaaggc tctacaagtt tatgaacggg gttgccgctg tacccccatt gttggacctg      634 tccctggagt ggccgttttc gccaattccc tacatgtgag tgataaacct ttcccgggag      694 caactcacgt gttgaccaac ctgccgctcc cgcagagacc caagcctgaa gacttttgcc      754 cctttgagtg tgctatggct actgtctatg acattggtca tgacgccgtc atgtatgtgg      814 ccgaaaggaa agtctcctgg gcccctcgtg gcggggatga agtgaaattt gaagctgtcc      874 ccggggagtt gaagttgatt gcgaaccggc tccgcacctc cttcccgccc caccacacag      934 tggacatgtc taagttcgcc ttcacagccc tgggtgtgg tgtttctatg cgggtcgaac       994 gccaacacgg ctgccttccc gctgacactg tccctgaagg caactgctgg tggagcttgt     1054 ttgacttgct tccactggaa gttcagaaca aagaaattcg ccatgctaac caatttggct     1114 accagaccaa gcatggtgtc tctggcaagt acctacagcg gaggctgcaa gttaatggtc     1174 tccgagcagt aactgaccta aacgaccta tcgtcgtaca gtacttctcc gttaaggaga     1234 gttggatccg ccatttgaaa ctggcgggag aacccagcta ctctgggttt gaggacctcc     1294 tcagaataag ggttgagcct aacacgtcgc cattggctga caaggaagaa aaatttttcc     1354 ggtttggcag tcacaagtgg tacggcgctc tcgagcacca ccaccaccac cactgagatc     1414 cggctgctaa caaagcccga aaggaagctg agttggctgc tgccaccgct gagcaataac     1474 tagcataacc ccttgggggcc tctaaacggg tcttgagggg tttttttgctg aaaggaggaa    1534 ctatatccgg attggcgaat gggacgcgcc ctgtagcggc gcattaagcg cg             1586
```

<210> SEQ ID NO 2
<211> LENGTH: 1149
<212> TYPE: DNA
<213> ORGANISM: Porcine reproductive and respiratory syndrome virus

<400> SEQUENCE: 2

| | | | | | |
|---|---|---|---|---|---|
| tctgggatac | ttgatcggtg | cacgtgtacc | cccaatgcca | gggtgtttat | ggcggagggc | 60 |
| caagtctact | gcacacgatg | cctcagtgca | cggtctctcc | ttcccctgaa | cctccaagtt | 120 |
| tctgagctcg | gggtgctagg | cctattctac | aggcccgaag | agccactccg | gtggacgttg | 180 |
| ccacgtgcat | tccccactgt | tgagtgctcc | cccgccgggg | cctgctggct | ttctgcaatc | 240 |
| tttccaatcg | cacgaatgac | cagtggaaac | ctgaacttcc | aacaaagaat | ggtacgggtc | 300 |
| gcagctgagc | tttacagagc | cggccagctc | acccctgcag | tcttgaaggc | tctacaagtt | 360 |
| tatgaacggg | gttgccgctg | gtaccccatt | gttggacctg | tcctggagt | ggccgttttc | 420 |
| gccaattccc | tacatgtgag | tgataaacct | ttcccgggag | caactcacgt | gttgaccaac | 480 |
| ctgccgctcc | cgcagagacc | caagcctgaa | gacttttgcc | cctttgagtg | tgctatggct | 540 |
| actgtctatg | acattggtca | tgacgccgtc | atgtatgtgg | ccgaaaggaa | agtctcctgg | 600 |
| gcccctcgtg | gcggggatga | agtgaaattt | gaagctgtcc | ccggggagtt | gaagttgatt | 660 |
| gcgaaccggc | tccgcacctc | cttcccgccc | caccacacag | tggacatgtc | taagttcgcc | 720 |
| ttcacagccc | ctgggtgtgg | tgtttctatg | cgggtcgaac | gccaacacgg | ctgccttccc | 780 |
| gctgacactg | tccctgaagg | caactgctgg | tggagcttgt | ttgacttgct | tccactggaa | 840 |
| gttcagaaca | agaaaattcg | ccatgctaac | caatttggct | accagaccaa | gcatggtgtc | 900 |
| tctggcaagt | acctacagcg | gaggctgcaa | gttaatggtc | tccgagcagt | aactgaccta | 960 |
| aacggaccta | tcgtcgtaca | gtacttctcc | gttaaggaga | gttggatccg | ccatttgaaa | 1020 |
| ctggcgggag | aacccagcta | ctctgggttt | gaggacctcc | tcagaataag | ggttgagcct | 1080 |
| aacacgtcgc | cattggctga | caaggaagaa | aaaattttcc | ggtttggcag | tcacaagtgg | 1140 |
| tacggcgct | | | | | | 1149 |

<210> SEQ ID NO 3
<211> LENGTH: 20
<212> TYPE: PRT
<213> ORGANISM: Porcine reproductive and respiratory syndrome virus

<400> SEQUENCE: 3

Met Glu Gln Lys Leu Ile Ser Glu Glu Asp Leu Asn Arg Ser Met Asn
 1               5                  10                  15

Ser Ser Gly Ser
            20

<210> SEQ ID NO 4
<211> LENGTH: 3968
<212> TYPE: DNA
<213> ORGANISM: Porcine reproductive and respiratory syndrome virus
<220> FEATURE:
<221> NAME/KEY: CDS
<222> LOCATION: (175)..(201)
<220> FEATURE:
<221> NAME/KEY: CDS
<222> LOCATION: (3766)..(3789)

<400> SEQUENCE: 4

| | | | | | |
|---|---|---|---|---|---|
| aggcgccagc | aaccgcacct | gtggcgccgg | tgatgccggc | cacgatgcgt | ccggcgtaga | 60 |
| ggatcgagat | ctcgatcccg | cgaaattaat | acgactcact | atagggggaat | tgtgagcgga | 120 |

| | |
|---|---|
| taacaattcc cctctagaaa taattttgtt taactttaag aaggagatat acat atg<br>                                                                                  Met<br>                                                                                    1 | 177 |
| gaa caa aaa ctc atc tca gaa gag gatctgaatc gatccatgaa ttctagtgga<br>Glu Gln Lys Leu Ile Ser Glu Glu<br>                 5 | 231 |
| tccgccgcgc tttgtccgtt cgtgaaaccc ggcaggccaa ggagcacgag gttgccggcc | 291 |
| aacaaggctg agcacctcaa acactactcc ccgcctgccg aagggaattg tggttggcac | 351 |
| tgcatttccg ccatcgccaa ccggatggtg aattccaaat ttgaaaccac ccttcccgaa | 411 |
| agagtgagac ctccagatga ctgggctact gacgaggatc ttgtgaatgc catccaaatc | 471 |
| ctcagactcc ctgcggcctt agacaggaac ggtgcttgta ctagcgccaa gtacgtactt | 531 |
| aagctggaag gtgagcattg gactgtcact gtgaccctg gatgtcccc ttctttgctc | 591 |
| cctcttgaat gtgttcaggg ctgttgtggg cacaagggcg gtcttggttc cccagatgca | 651 |
| gtcgaggtct ccggatttga ccctgcctgc cttgaccggc tggctgaggt gatgcacctg | 711 |
| cctagcagtg ctatcccagc cgctctggcc gaaatgtctg gcgattccga tcgttcggct | 771 |
| tctccggtca ccaccgtgtg gactgtttcg cagttctttg cccgtcacag cggagggaat | 831 |
| caccctgacc aagtgcgctt agggaaaatt atcagccttt gtcaggtgat tgaggactgc | 891 |
| tgctgttccc agaacaaaac caaccgggtc acccgaggag aggtcgcagc aaagattgac | 951 |
| ctgtacctcc gtggtgcaac aaatcttgaa gaatgcttgg ccaggcttga aaagcgcgc | 1011 |
| ccgccacgcg taatcgacac ctcctttgat tgggatgttg tgctccctgg ggttgaggcg | 1071 |
| gcaacccaga cgatcaagct gccccaggtc aaccagtgtc gtgctctggt ccctgttgtg | 1131 |
| actcaaaagt ccttggacaa caactcggtc ccctgaccg ccttttcact ggctaactac | 1191 |
| tactaccgtg cgcaaggtga cgaagttcgt caccgtgaaa gactaaccgc cgtgctctcc | 1251 |
| aagttggaaa aggttgttcg agaagaatat gggctcatgc caaccgagcc tggtccacgg | 1311 |
| cccacactgc cacgcgggct cgacgaactc aaagaccaga tggaggagga cttgctgaaa | 1371 |
| ctggctaacg cccagacgac ttcggacatg atggcctggg cagtcgagca ggttgaccta | 1431 |
| aaaacttggg tcaagaacta cccgcggtgg acaccaccac cccctccgcc aaaagttcag | 1491 |
| cctcgaaaaa cgaagcctgt caagagcttg ccggagagaa agcctgtccc cgccccgcgc | 1551 |
| aggaaggttg ggtccgattg tggcagcccg gtttcattag gcggcgatgt ccctaacagt | 1611 |
| tgggaagatt tggctgttag tagccccttt gatctcccga ccccacctga ccggcaaca | 1671 |
| ccttcaagtg agctggtgat tgtgtcctca ccgcaatgca tcttcaggcc ggcgacaccc | 1731 |
| ttgagtgagc cggctccaat tcccgcacct cgcggaactg tgtctcgacc ggtgacaccc | 1791 |
| ttgagtgagc cgatccctgt gcccgcaccg cggcgtaagt ttcagcaggt gaaaagattg | 1851 |
| agttcggcgg cggcaatccc accgtaccag gacgagcccc tggatttgtc tgcttcctca | 1911 |
| cagactgaat atgaggcctc tccccagca ccgccgcaga gcggggggcgt tctgggagta | 1971 |
| gagggggcatg aagctgagga aaccctgagt gaaatctcgg acatgtcggg taacattaaa | 2031 |
| cctgcgtccg tgtcatcaag cagctccttg tccagcgtga gaatcacacg cccaaaatac | 2091 |
| tcagctcaag ccatcatcga ctcgggcggg ccctgcagtg ggcatctcca agaggtaaag | 2151 |
| gaaacatgcc ttagtgtcat gcgcgaggca tgtgatgcga ctaagcttga tgaccctgct | 2211 |
| acgcaggaat ggctttctcg catgtgggat cgggtggaca tgctgacttg gcgcaacacg | 2271 |
| tctgtttacc aggcgatttg cacccttagat ggcaggttaa agttcctccc aaaaatgata | 2331 |
| ctcgagacac cgccgcccta tccgtgtgag tttgtgatga tgcctcacac gcctgcacct | 2391 |

```
tccgtaggtg cggagagcga ccttaccatt ggctcagttg ctactgaaga tgttccacgc    2451
atcctcgaga aaatagaaaa tgtcggcgag atggccaacc agggacccct ggccttctcc    2511
gaggataaac cggtagatga ccaacttgtc aacgaccccc ggatatcgtc gcggaggcct    2571
gacgagagca catcagctcc gtccgcaggc acaggtggcg ccggctcttt taccgatttg    2631
ccgccttcag atggcgcgga tgcggacggg ggggggccgt tcggacggt  aaaaagaaaa    2691 gctgaaaggc tctttgacca actgagccgt caggttttg  acctcgtctc ccatctccct    2751
gttttcttct cacgcctttt ctaccctggc ggtggttatt ctccgggtga ttggggtttt    2811
gcagctttta ctctattgtg cctcttttta tgttacagtt acccagcctt tggtattgct    2871
cccctcttgg gtgtgttttc tgggtcttct cggcgcgttc gaatggggt  ttttggctgc    2931 tggttggctt ttgctgttgg tctgttcaag cctgtgtccg acccagtcgg cgctgcttgt    2991
gagtttgact cgccagagtg tagaaacatc cttcattctt ttgagcttct caaaccttgg    3051
gaccctgttc gcagccttgt tgtgggcccc gtcggtctcg tcttgccat  tcttggcagg    3111 ttactgggcg gggcacgctg catctggcac ttttttgctta ggcttggcat tgttgcagac    3171
tgtatcttgg ctggagctta cgtgctttct caaggtaggt gtaaaaagtg ctggggatct    3231
tgtataagaa ctgctcctaa tgaggtcgct tttaacgtgt tccctttcac acgtgcgacc    3291
aggtcgtcac ttatcgacct gtgcgatcgg ttttgtgcgc caaaggaat  ggaccccatt    3351 tttctcgcca ctgggtggcg cgggtgctgg gccgccgaa  gccccattga caaccctct    3411 gaaaaaccca tcgcgtttgc ccaattggat gaaaagaaga ttacggctag actgtggtc    3471 gcccagcctt atgaccccaa ccaagccgta aagtgcttgc gggtattgca gtcgggtggg    3531
gcgatggtgg ctaaggcggt cccaaaaagtg gtcaaggttt ccgctgttcc attccgagcc    3591
cccttctttc ccactggagt gaaagttgac cctgattgca gggtcgtggt tgaccctgac    3651
actttcactg cagctctccg gtctggctac tccaccacaa acctcgtcct tggtgtaggg    3711
gactttgccc agctgaatgg attaaaaatc aggcaaattt ccaagccttc aggg ctc      3768
                                                                Leu
                                                                 10 gag cac cac cac cac cac cac tgagatccgg ctgctaacaa agcccgaaag         3819
Glu His His His His His His
          15 gaagctgagt tggctgctgc caccgctgag caataactag cataaccct  tggggcctct    3879 aaacgggtct tgaggggttt tttgctgaaa ggaggaacta tatccggatt ggcgaatggg    3939 acgcgccctg tagcggcgca ttaagcgcg                                      3968

<210> SEQ ID NO 5
<211> LENGTH: 3583
<212> TYPE: DNA
<213> ORGANISM: Porcine reproductive and respiratory syndrome virus

<400> SEQUENCE: 5
gctggaaaga gagcaagaaa agcacgctct tgtgcgactg ctacagtcgc tggccgcgct      60
ttgtccgttc gtgaaacccg gcaggccaag gagcacgagg ttgccggcca acaaggctga    120
gcacctcaaa cactactccc cgcctgccga agggaattgt ggttggcact gcatttccgc    180
catcgccaac cggatggtga attccaaatt tgaaaccacc cttcccgaaa gagtgagacc    240
tccagatgac tgggctactg acgaggatct tgtgaatgcc atccaaatcc tcagactccc    300
tgcggcctta gacaggaacg gtgcttgtac tagcgccaag tacgtactta agctggaagg    360
tgagcattgg actgtcactg tgaccectgg gatgtccct  tctttgctcc ctcttgaatg    420
```

```
tgttcagggc tgttgtgggc acaagggcgg tcttggttcc ccagatgcag tcgaggtctc    480
cggatttgac cctgcctgcc ttgaccggct ggctgaggtg atgcacctgc ctagcagtgc    540
tatcccagcc gctctggccg aaatgtctgg cgattccgat cgttcggctt ctccggtcac    600
caccgtgtgg actgtttcgc agttctttgc ccgtcacagc ggagggaatc accctgacca    660
agtgcgctta gggaaaatta tcagccttg tcaggtgatt gaggactgct gctgttccca    720
gaacaaaacc aaccgggtca ccccggagga ggtcgcagca aagattgacc tgtacctccg    780
tggtgcaaca atcttgaag aatgcttggc caggcttgag aaagcgcgcc cgccacgcgt    840
aatcgacacc tcctttgatt gggatgttgt gctccctggg gttgaggcgg caacccagac    900
gatcaagctg ccccaggtca accagtgtcg tgctctggtc cctgttgtga ctcaaaagtc    960
cttggacaac aactcggtcc ccctgaccgc cttttcactg gctaactact actaccgtgc   1020
gcaaggtgac gaagttcgtc accgtgaaag actaaccgcc gtgctctcca agttggaaaa   1080
ggttgttcga agaatatg ggctcatgcc aaccgagcct ggtccacggc ccacactgcc   1140
acgcgggctc gacgaactca agaccagat ggaggaggac ttgctgaaac tggctaacgc   1200
ccagacgact tcgacatga tggcctgggc agtcgagcag gttgacctaa aaacttgggt   1260
caagaactac ccgcggtgga caccaccacc ccctccgcca aaagttcagc ctcgaaaaac   1320
gaagcctgtc aagagcttgc cggagagaaa gcctgtcccc gccccgcgca ggaaggttgg   1380
gtccgattgt ggcagcccgg tttcattagg cggcgatgtc cctaacagtt gggaagattt   1440
ggctgttagt agcccctttg atctcccgac cccacctgag ccggcaacac cttcaagtga   1500
gctggtgatt gtgtcctcac cgcaatgcat cttcaggccg gcgacaccct tgagtgagcc   1560
ggctccaatt cccgcacctc gcggaactgt gtctcgaccg gtgacaccct tgagtgagcc   1620
gatccctgtg cccgcaccgc ggcgtaagtt tcagcaggtg aaaagattga gttcggcggc   1680
ggcaatccca ccgtaccagg acgagcccct ggatttgtct gcttcctcac agactgaata   1740
tgaggcctct cccccagcac cgccgcagag cggggggcgtt ctgggagtag aggggcatga   1800
agctgaggaa accctgagtg aaatctcgga catgtcgggt aacattaaac ctgcgtccgt   1860
gtcatcaagc agctccttgt ccagcgtgag aatcacacgc ccaaaatact cagctcaagc   1920
catcatcgac tcgggcggc cctgcagtgg gcatctccaa gaggtaaagg aaacatgcct   1980
tagtgtcatg cgcgaggcat gtgatgcgac taagcttgat gaccctgcta cgcaggaatg   2040
gctttctcgc atgtgggatc gggtggacat gctgacttgg cgcaacacgt ctgtttacca   2100
ggcgatttgc accttagatg gcaggttaaa gttcctccca aaaatgatac tcgagacacc   2160
gccgccctat ccgtgtgagt ttgtgatgat gcctcacacg cctgcacctt ccgtaggtgc   2220
ggagagcgac cttaccattg gctcagttgc tactgaagat gttccacgca tcctcgagaa   2280
aatagaaaat gtcggcgaga tggccaacca gggacccttg gccttctccg aggataaacc   2340
ggtagatgac caacttgtca acgaccccg gatatcgtcg cggaggcctg acgagagcac   2400
atcagctccg tccgcaggca caggtggcgc cggctctttt accgatttgc cgccttcaga   2460
tggcgcggat gcggacgggg gggggccgtt tcggacggta aaagaaaag ctgaaaggct   2520
ctttgaccaa ctgagccgtc aggtttttga cctcgtctcc catctccctg ttttcttctc   2580
acgcctttc tacccctggcg gtggttattc tccgggtgat tgggggtttg cagcttttac   2640
tctattgtgc ctcttttat gttacagtta cccagccttt ggtattgctc ccctcttggg   2700
tgtgttttct gggtcttctc ggcgcgttcg aatgggggtt tttggctgct ggttggcttt   2760
tgctgttggt ctgttcaagc ctgtgtccga cccagtcggc gctgcttgtg agtttgactc   2820
```

```
gccagagtgt agaaacatcc ttcattcttt tgagcttctc aaaccttggg accctgttcg    2880
cagccttgtt gtgggcccg tcggtctcgg tcttgccatt cttggcaggt tactgggcgg     2940
ggcacgctgc atctggcact ttttgcttag gcttggcatt gttgcagact gtatcttggc    3000
tggagcttac gtgctttctc aaggtaggtg taaaagtgc tggggatctt gtataagaac     3060
tgctcctaat gaggtcgctt ttaacgtgtt tcctttcaca cgtgcgacca ggtcgtcact    3120
tatcgacctg tgcgatcggt tttgtgcgcc aaaaggaatg acccccattt ttctcgccac    3180
tgggtggcgc gggtgctggg ccggccgaag ccccattgag caaccctctg aaaaacccat    3240
cgcgtttgcc caattggatg aaaagaagat tacggctagg actgtggtcg cccagcctta    3300 tgacccaac caagccgtaa agtgcttgcg ggtattgcag tcgggtgggg cgatggtggc     3360
taaggcggtc ccaaaagtgg tcaaggtttc cgctgttcca ttccgagccc ccttctttcc    3420
cactggagtg aaagttgacc ctgattgcag ggtcgtggtt gaccctgaca ctttcactgc    3480
agctctccgg tctggctact ccaccacaaa cctcgtcctt ggtgtagggg actttgccca    3540
gctgaatgga ttaaaaatca ggcaaatttc caagccttca ggg                      3583
```

<210> SEQ ID NO 6
<211> LENGTH: 9
<212> TYPE: PRT
<213> ORGANISM: Porcine reproductive and respiratory syndrome virus

<400> SEQUENCE: 6

```
Met Glu Gln Lys Leu Ile Ser Glu Glu
  1               5
```

<210> SEQ ID NO 7
<211> LENGTH: 1049
<212> TYPE: DNA
<213> ORGANISM: Porcine reproductive and respiratory syndrome virus
<220> FEATURE:
<221> NAME/KEY: CDS
<222> LOCATION: (175)..(870)

<400> SEQUENCE: 7

```
aggcgccagc aaccgcacct gtggcgccgg tgatgccggc cacgatgcgt ccggcgtaga    60
ggatcgagat ctcgatcccg cgaaattaat acgactcact ataggggaat tgtgagcgga   120
taacaattcc cctctagaaa taattttgtt taactttaag aaggagatat acat atg     177
                                                                Met
                                                                  1 gaa caa aaa ctc atc tca gaa gag gat ctg aat cga tcc atg aat tct    225
Glu Gln Lys Leu Ile Ser Glu Glu Asp Leu Asn Arg Ser Met Asn Ser
              5                  10                  15 agt gga tcc ggt gct ttc aga act cga aag ccc tca ctg aac acc gtc    273
Ser Gly Ser Gly Ala Phe Arg Thr Arg Lys Pro Ser Leu Asn Thr Val
         20                  25                  30 aat gtg atc ggg tcc tcc atg ggc tct ggc ggg gtg ttt acc atc gac    321
Asn Val Ile Gly Ser Ser Met Gly Ser Gly Gly Val Phe Thr Ile Asp
     35                  40                  45 ggg aaa gtc aag tgc gta act gcc gca cat gtc ctt acg ggc aat tca    369
Gly Lys Val Lys Cys Val Thr Ala Ala His Val Leu Thr Gly Asn Ser
 50                  55                  60                  65 gct cgg gtt tcc ggg gtc ggc ttc aat caa atg ctt gac ttt gac gta    417
Ala Arg Val Ser Gly Val Gly Phe Asn Gln Met Leu Asp Phe Asp Val
                 70                  75                  80 aag gga gat ttc gct ata gct gat tgc ccg aat tgg caa ggg gct gcc    465
Lys Gly Asp Phe Ala Ile Ala Asp Cys Pro Asn Trp Gln Gly Ala Ala
             85                  90                  95
```

```
ccc aag acc caa ttc tgc acg gat gga tgg act ggc cgt gcc tat tgg     513
Pro Lys Thr Gln Phe Cys Thr Asp Gly Trp Thr Gly Arg Ala Tyr Trp
        100                 105                 110 cta aca tcc tct ggc gtc gaa ccc ggc gtc att gga aaa gga ttc gcc     561
Leu Thr Ser Ser Gly Val Glu Pro Gly Val Ile Gly Lys Gly Phe Ala
    115                 120                 125 ttc tgc ttc acc gca tgt ggc gat tcc ggg tcc cca gtg atc acc gag     609
Phe Cys Phe Thr Ala Cys Gly Asp Ser Gly Ser Pro Val Ile Thr Glu
130                 135                 140                 145 gcc ggt gag ctt gtc ggc gtt cac acg gga tcg aat aaa caa ggg ggg     657
Ala Gly Glu Leu Val Gly Val His Thr Gly Ser Asn Lys Gln Gly Gly
                150                 155                 160 ggc att gtt acg cgc ccc tca ggc cag ttt tgt aat gtg gca ccc atc     705
Gly Ile Val Thr Arg Pro Ser Gly Gln Phe Cys Asn Val Ala Pro Ile
            165                 170                 175 aag cta agc gaa tta agt gaa ttc ttt gct ggg cct aag gtc ccg ctc     753
Lys Leu Ser Glu Leu Ser Glu Phe Phe Ala Gly Pro Lys Val Pro Leu
        180                 185                 190 ggt gat gtg aag gtc ggc agc cac ata att aaa gac ata agc gag gtg     801
Gly Asp Val Lys Val Gly Ser His Ile Ile Lys Asp Ile Ser Glu Val
    195                 200                 205 cct tca gat ctt tgt gcc ttg ctt gct gcc aaa cct gaa ctg gaa ctc     849
Pro Ser Asp Leu Cys Ala Leu Leu Ala Ala Lys Pro Glu Leu Glu Leu
210                 215                 220                 225 gag cac cac cac cac cac cac tgagatccgg ctgctaacaa agcccgaaag        900
Glu His His His His His His
                230 gaagctgagt tggctgctgc caccgctgag caataactag cataacccct tggggcctct   960 aaacgggtct tgaggggttt tttgctgaaa ggaggaacta tatccggatt ggcgaatggg  1020 acgcgcctg tagcggcgca ttaagcgcg                                     1049

<210> SEQ ID NO 8
<211> LENGTH: 611
<212> TYPE: DNA
<213> ORGANISM: Porcine reproductive and respiratory syndrome virus

<400> SEQUENCE: 8
ggtgctttca gaactcgaaa gccctcactg aacaccgtca atgtgatcgg gtcctccatg    60
ggctctggcg gggtgtttac catcgacggg aaagtcaagt gcgtaactgc cgcacatgtc   120
cttacgggca attcagctcg ggtttccggg gtcggcttca atcaaatgct tgactttgac   180
gtaaagggag atttcgctat agctgattgc ccgaattggc aaggggctgc ccccaagacc   240
caattctgca cggatggatg gactggccgt gcctattggc taacatcctc tggcgtcgaa   300
cccggcgtca ttggaaaagg attcgccttc tgcttcaccg catgtggcga ttccgggtcc   360
ccagtgtcac cgaggccggt gagcttgtcg cgttcacac gggatcgaat aaacaagggg   420
ggggcattgt tacgcgcccc tcaggccagt tttgtaatgt ggcacccatc aagctaagcg   480
aattaagtga attctttgct gggcctaagg tcccgctcgg tgatgtgaag gtcggcagcc   540
acataattaa agacataagc gaggtgcctt cagatctttg tgccttgctt gctgccaaac   600
ctgaactgga a                                                       611

<210> SEQ ID NO 9
<211> LENGTH: 232
<212> TYPE: PRT
<213> ORGANISM: Porcine reproductive and respiratory syndrome virus

<400> SEQUENCE: 9
```

Met Glu Gln Lys Leu Ile Ser Glu Glu Asp Leu Asn Arg Ser Met Asn
1               5                   10                  15

Ser Ser Gly Ser Gly Ala Phe Arg Thr Arg Lys Pro Ser Leu Asn Thr
            20                  25                  30

Val Asn Val Ile Gly Ser Ser Met Gly Ser Gly Gly Val Phe Thr Ile
            35                  40                  45

Asp Gly Lys Val Lys Cys Val Thr Ala Ala His Val Leu Thr Gly Asn
        50                  55                  60

Ser Ala Arg Val Ser Gly Val Gly Phe Asn Gln Met Leu Asp Phe Asp
65                  70                  75                  80

Val Lys Gly Asp Phe Ala Ile Ala Asp Cys Pro Asn Trp Gln Gly Ala
                85                  90                  95

Ala Pro Lys Thr Gln Phe Cys Thr Asp Gly Trp Thr Gly Arg Ala Tyr
                100                 105                 110

Trp Leu Thr Ser Ser Gly Val Glu Pro Gly Val Ile Gly Lys Gly Phe
            115                 120                 125

Ala Phe Cys Phe Thr Ala Cys Gly Asp Ser Gly Ser Pro Val Ile Thr
        130                 135                 140

Glu Ala Gly Glu Leu Val Gly Val His Thr Gly Ser Asn Lys Gln Gly
145                 150                 155                 160

Gly Gly Ile Val Thr Arg Pro Ser Gly Gln Phe Cys Asn Val Ala Pro
                165                 170                 175

Ile Lys Leu Ser Glu Leu Ser Glu Phe Phe Ala Gly Pro Lys Val Pro
                180                 185                 190

Leu Gly Asp Val Lys Val Gly Ser His Ile Ile Lys Asp Ile Ser Glu
            195                 200                 205

Val Pro Ser Asp Leu Cys Ala Leu Leu Ala Ala Lys Pro Glu Leu Glu
        210                 215                 220

Leu Glu His His His His His His
225                 230

<210> SEQ ID NO 10
<211> LENGTH: 2588
<212> TYPE: DNA
<213> ORGANISM: Porcine reproductive and respiratory syndrome virus
<220> FEATURE:
<221> NAME/KEY: CDS
<222> LOCATION: (175)..(234)
<220> FEATURE:
<221> NAME/KEY: CDS
<222> LOCATION: (2386)..(2409)

<400> SEQUENCE: 10
aggcgccagc aaccgcacct gtggcgccgg tgatgccggc cacgatgcgt ccggcgtaga      60
ggatcgagat ctcgatcccg cgaaattaat acgactcact atagggaat tgtgagcgga      120 taacaattcc cctctagaaa taattttgtt aactttaag aaggagatat acat atg       177
                                                                 Met
                                                                  1 gaa caa aaa ctc atc tca gaa gag gat ctg aat cga tcc atg aat tct     225
Glu Gln Lys Leu Ile Ser Glu Glu Asp Leu Asn Arg Ser Met Asn Ser
            5                   10                  15 agt gga tcc gctggaaaga gagcaagaaa agcacgctct tgtgcgactg             274
Ser Gly Ser
        20 ctacagtcgc tggccgcgct ttgtccgttc gtgaaacccg gcaggccaag gagcacgagg    334 ttgccggcgc caacaaggct gagcacctca aacactactc ccgcctgcc gaagggaatt    394

```
gtggttggca ctgcatttcc gccatcgcca accggatggt gaattccaaa tttgaaacca    454
cccttcccga aagagtgaga cctccagatg actgggctac tgacgaggat cttgtgaatg    514
ccatccaaat cctcagactc cctgcggcct tagacaggaa cggtgcttgt actagcgcca    574
agtacgtact taagctggaa ggtgagcatt ggactgtcac tgtgacccct gggatgtccc    634
cttctttgct ccctcttgaa tgtgttcagg gctgttgtgg gcacaagggc ggtcttggtt    694
ccccagatgc agtcgaggtc tccggatttg accctgcctg ccttgaccgg ctggctgagg    754
tgatgcacct gcctagcagt gctatcccag ccgctctggc cgaaatgtct ggcgattccg    814
atcgttcggt tctccggtc accaccgtgt ggactgtttc gcagttcttt gcccgtcaca    874
gcggagggaa tcaccctgac caagtgcgct tagggaaaat tatcagcctt tgtcaggtga    934
ttgaggactg ctgctgttcc cagaacaaaa ccaaccgggt caccccggag gaggtcgcag    994
caaagattga cctgtacctc cgtggtgcaa caaatcttga gaatgcttg gccaggcttg   1054
agaaagcgcg cccgccacgc gtaatcgaca cctcctttga ttgggatgtt gtgctccctg   1114
gggttgaggc ggcaacccag acgatcaagc tgccccaggt caaccagtgt cgtgctctgg   1174
tccctgttgt gactcaaaag tccttggaca caactcggt ccccctgacc gccttttcac    1234
tggctaacta ctactaccgt gcgcaaggtg acgaagttcg tcaccgtgaa agactaaccg   1294
ccgtgctctc caagttggaa aaggttgttc gagaagaata tgggctcatg ccaaccgagc   1354
ctggtccacg gcccacactg ccacgcgggc tcgacgaact caaagaccag atggaggagg   1414
acttgctgaa actggctaac gcccagacga cttcggacat gatggcctgg gcagtcgagc   1474
aggttgacct aaaaacttgg gtcaagaact acccgcggtg gacaccacca cccctccgc    1534
caaaagttca gcctcgaaaa acgaagcctg tcaagagctt gccggagaga agcctgtcc    1594
ccgccccgcg caggaaggtt gggtccgatt gtggcagccc ggtttcatta gcggcgatg   1654
tccctaacag ttgggaagat ttggctgtta gtagccccct tgatctcccg accccacctg   1714
agccggcaac accttcaagt gagctggtga ttgtgtcctc accgcaatgc atcttcaggc   1774
cggcgacacc cttgagtgag ccggctccaa ttcccgcacc tcgcggaact gtgtctcgac   1834
cggtgacacc cttgagtgag ccgatccctg tgccgcacc gcggcgtaag tttcagcagg   1894
tgaaaagatt gagttcggcg gcggcaatcc caccgtacca ggacgagccc ctggatttgt   1954
ctgcttcctc acagactgaa tatgaggcct ctccccagc accgccgcag agcggggcg   2014
ttctgggagt agaggggcat gaagctgagg aaaccctgag tgaaatctcg gacatgtcgg   2074
gtaacattaa acctgcgtcc gtgtcatcaa gcagctcctt gtccagcgtg agaatcacac   2134
gcccaaaata ctcagctcaa gccatcatcg actcgggcgg gccctgcagt gggcatctcc   2194
aagaggtaaa ggaaacatgc cttagtgtca tgcgcgaggc atgtgatgcg actaagcttg   2254
atgaccctgc tacgcaggaa tggctttctc gcatgtggga tcgggtggac atgctgactt   2314
ggcgcaacac gtctgtttac caggcgattt gcaccttaga tggcaggtta aagttcctcc   2374
caaaaatgat a ctc gag cac cac cac cac cac cac tgagatccgg              2419
             Leu Glu His His His His His His
                                25
ctgctaacaa agcccgaaag gaagctgagt tggctgctgc caccgctgag caataactag   2479
cataacccct tggggcctct aaacgggtct tgagggggttt tttgctgaaa ggaggaacta   2539
tatccggatt ggcgaatggg acgcgccctg tagcggcgca ttaagcgcg               2588
```

<210> SEQ ID NO 11
<211> LENGTH: 2151
<212> TYPE: DNA

<213> ORGANISM: Porcine reproductive and respiratory syndrome virus

<400> SEQUENCE: 11

```
gctggaaaga gagcaagaaa agcacgctct tgtgcgactg ctacagtcgc tggccgcgct      60
ttgtccgttc gtgaaacccg gcaggccaag gagcacgagg ttgccggcgc caacaaggct     120
gagcacctca acactactc cccgcctgcc gaagggaatt gtggttggca ctgcatttcc     180
gccatcgcca accggatggt gaattccaaa tttgaaacca cccttcccga aagagtgaga     240
cctccagatg actgggctac tgacgaggat cttgtgaatg ccatccaaat cctcagactc     300
cctgcgccct tagacaggaa cggtgcttgt actagcgcca agtacgtact taagctggaa     360
ggtgagcatt ggactgtcac tgtgaccct gggatgtccc cttctttgct ccctcttgaa      420
tgtgttcagg gctgttgtgg gcacaagggc ggtcttggtt ccccagatgc agtcgaggtc     480
tccggatttg accctgcctg ccttgaccgg ctggctgagg tgatgcacct gcctagcagt     540
gctatcccag ccgctctggc cgaaatgtct ggcgattccg atcgttcggc ttctccggtc     600
accaccgtgt ggactgtttc gcagttcttt gcccgtcaca gcggagggaa tcaccctgac     660
caagtgcgct tagggaaaat tatcagcctt tgtcaggtga ttgaggactg ctgctgttcc     720
cagaacaaaa ccaaccgggt cacccccgga gaggtcgcag caaagattga cctgtacctc     780
cgtggtgcaa caaatcttga agaatgcttg gccaggcttg agaaagcgcg cccgccacgc     840
gtaatcgaca cctcctttga ttgggatgtt gtgctccctg gggttgaggc ggcaacccag     900
acgatcaagc tgccccaggt caaccagtgt cgtgctctgg tccctgttgt gactcaaaag     960
tccttggaca caactcggt ccccctgacc gccttttcac tggctaacta ctactaccgt     1020
gcgcaaggtg acgaagttcg tcaccgtgaa agactaaccg ccgtgctctc caagttggaa     1080
aaggttgttc gagaagaata tgggctcatg ccaaccgagc ctggtccacg gcccacactg     1140
ccacgcgggc tcgacgaact caaagaccag atggaggagg acttgctgaa actggctaac     1200
gcccagacga cttcggacat gatggcctgg gcagtcgagc aggttgacct aaaaacttgg     1260
gtcaagaact acccgcggtg gacaccacca ccccctccgc caaaagttca gcctcgaaaa     1320
acgaagcctg tcaagagctt gccggagaga agcctgtcc cgccccgcg caggaaggtt      1380
gggtccgatt gtggcagccc ggtttcatta ggcggcgatg tccctaacag ttgggaagat     1440
ttggctgtta gtagcccctt tgatctcccg accccacctg agccggcaac accttcaagt     1500
gagctggtga ttgtgtcctc accgcaatgc atcttcaggc cggcgacacc cttgagtgag     1560
ccggctccaa ttcccgcacc tcgcggaact gtgtctcgac cggtgacacc cttgagtgag     1620
ccgatccctg tgcccgcacc gcggcgtaag tttcagcagg tgaaaagatt gagttcggcg     1680
gcggcaatcc caccgtacca ggacgagccc ctggatttgt ctgcttcctc acagactgaa     1740
tatgaggcct ctcccccagc accgccgcag agcggggcg ttctgggagt agaggggcat      1800
gaagctgagg aaaccctgag tgaaatctcg gacatgtcgg gtaacattaa acctgcgtcc     1860
gtgtcatcaa gcagctcctt gtccagcgtg agaatcacac gcccaaaata ctcagctcaa     1920
gccatcatcg actcggcgg gccctgcagt gggcatctcc aagaggtaaa ggaaacatgc     1980
cttagtgtca tgcgcgaggc atgtgatgcg actaagcttg atgaccctgc tacgcaggaa     2040
tggcttctc gcatgtggga tcgggtggac atgctgactt ggcgcaacac gtctgtttac     2100
caggcgattt gcaccttaga tggcaggtta aagttcctcc caaaaatgat a              2151
```

<210> SEQ ID NO 12
<211> LENGTH: 20
<212> TYPE: PRT

<213> ORGANISM: Porcine reproductive and respiratory syndrome virus

<400> SEQUENCE: 12

```
Met Glu Gln Lys Leu Ile Ser Glu Glu Asp Leu Asn Arg Ser Met Asn
 1               5                  10                  15
Ser Ser Gly Ser
         20
```

<210> SEQ ID NO 13
<211> LENGTH: 8
<212> TYPE: PRT
<213> ORGANISM: Porcine reproductive and respiratory syndrome virus

<400> SEQUENCE: 13

```
Leu Glu His His His His His His
 1               5
```

<210> SEQ ID NO 14
<211> LENGTH: 545
<212> TYPE: DNA
<213> ORGANISM: Porcine reproductive and respiratory syndrome virus
<220> FEATURE:
<221> NAME/KEY: CDS
<222> LOCATION: (175)..(366)

<400> SEQUENCE: 14

```
aggcgccagc aaccgcacct gtggcgccgg tgatgccggc acgatgcgt ccggcgtaga     60 ggatcgagat ctcgatcccg cgaaattaat acgactcact ataggggaat tgtgagcgga    120
taacaattcc cctctagaaa taattttgtt aactttaag aaggagatat acat atg     177
                                                            Met
                                                             1 gaa caa aaa ctc atc tca gaa gag gat ctg aat cga tcc atg aat tct     225
Glu Gln Lys Leu Ile Ser Glu Glu Asp Leu Asn Arg Ser Met Asn Ser
         5                  10                  15 agt gga tcc atg aac gcc aac agc acc agc agc tca cat ttt cag ttg     273
Ser Gly Ser Met Asn Ala Asn Ser Thr Ser Ser Ser His Phe Gln Leu
     20                  25                  30 att tat aac ttg acg cta tgc gag ctg aat ggc aca gat tgg ctg gct     321
Ile Tyr Asn Leu Thr Leu Cys Glu Leu Asn Gly Thr Asp Trp Leu Ala
 35                  40                  45 gga aag ttt gat tgg gca gtg ctc gag cac cac cac cac cac cac          366
Gly Lys Phe Asp Trp Ala Val Leu Glu His His His His His His
 50                  55                  60 tgagatccgg ctgctaacaa agcccgaaag gaagctgagt tggctgctgc caccgctgag    426
caataactag cataacccct tggggcctct aaacgggtct tgaggggttt tttgctgaaa    486
ggaggaacta tatccggatt ggcgaatggg acgcgccctg tagcggcgca ttaagcgcg     545
```

<210> SEQ ID NO 15
<211> LENGTH: 108
<212> TYPE: DNA
<213> ORGANISM: Porcine reproductive and respiratory syndrome virus

<400> SEQUENCE: 15

```
atgaacgcca acagcaccag cagctcacat tttcagttga tttataactt gacgctatgc     60
gagctgaatg gcacagattg gctggctgga aagtttgatt gggcagtg                  108
```

<210> SEQ ID NO 16
<211> LENGTH: 64
<212> TYPE: PRT
<213> ORGANISM: Porcine reproductive and respiratory syndrome virus

```
<400> SEQUENCE: 16

Met Glu Gln Lys Leu Ile Ser Glu Glu Asp Leu Asn Arg Ser Met Asn
 1               5                  10                  15

Ser Ser Gly Ser Met Asn Ala Asn Ser Thr Ser Ser Ser His Phe Gln
                20                  25                  30

Leu Ile Tyr Asn Leu Thr Leu Cys Glu Leu Asn Gly Thr Asp Trp Leu
            35                  40                  45

Ala Gly Lys Phe Asp Trp Ala Val Leu Glu His His His His His His
        50                  55                  60

<210> SEQ ID NO 17
<211> LENGTH: 545
<212> TYPE: DNA
<213> ORGANISM: Porcine reproductive and respiratory syndrome virus
<220> FEATURE:
<221> NAME/KEY: CDS
<222> LOCATION: (175)..(366)

<400> SEQUENCE: 17
aggcgccagc aaccgcacct gtggcgccgg tgatgccggc acgatgcgt  ccggcgtaga      60 ggatcgagat ctcgatcccg cgaaattaat acgactcact ataggggaat gtgagcgga     120 taacaattcc cctctagaaa taattttgtt taactttaag aaggagatat acat atg     177
                                                              Met
                                                               1 gaa caa aaa ctc atc tca gaa gag gat ctg aat cga tcc atg aat tct     225
Glu Gln Lys Leu Ile Ser Glu Glu Asp Leu Asn Arg Ser Met Asn Ser
          5                  10                  15 agt gga tcc atg aac gcc agc aac gac agc agc tcc cat cta cag ctg     273
Ser Gly Ser Met Asn Ala Ser Asn Asp Ser Ser Ser His Leu Gln Leu
        20                  25                  30 att tac aac ttg acg cta tgt gag ctg aat ggc aca gat tgg cta gct     321
Ile Tyr Asn Leu Thr Leu Cys Glu Leu Asn Gly Thr Asp Trp Leu Ala
    35                  40                  45 aac aaa ttt gat tgg gca gtg ctc gag cac cac cac cac cac cac          366
Asn Lys Phe Asp Trp Ala Val Leu Glu His His His His His His
 50                  55                  60 tgagatccgg ctgctaacaa agcccgaaag gaagctgagt tggctgctgc caccgctgag     426
caataactag cataacccct tggggcctct aaacgggtct tgaggggttt tttgctgaaa     486
ggaggaacta tatccggatt ggcgaatggg acgcgcctg tagcggcgca ttaagcgcg      545

<210> SEQ ID NO 18
<211> LENGTH: 108
<212> TYPE: DNA
<213> ORGANISM: Porcine reproductive and respiratory syndrome virus

<400> SEQUENCE: 18
atgaacgcca gcaacgacag cagctcccat ctacagctga tttacaactt gacgctatgt      60
gagctgaatg gcacagattg gctagctaac aaatttgatt gggcagtg                 108

<210> SEQ ID NO 19
<211> LENGTH: 64
<212> TYPE: PRT
<213> ORGANISM: Porcine reproductive and respiratory syndrome virus

<400> SEQUENCE: 19

Met Glu Gln Lys Leu Ile Ser Glu Glu Asp Leu Asn Arg Ser Met Asn
 1               5                  10                  15

Ser Ser Gly Ser Met Asn Ala Ser Asn Asp Ser Ser Ser His Leu Gln
                20                  25                  30
```

```
Leu Ile Tyr Asn Leu Thr Leu Cys Glu Leu Asn Gly Thr Asp Trp Leu
        35                  40                  45

Ala Asn Lys Phe Asp Trp Ala Val Leu Glu His His His His His His
    50                  55                  60

<210> SEQ ID NO 20
<211> LENGTH: 596
<212> TYPE: DNA
<213> ORGANISM: Porcine reproductive and respiratory syndrome virus
<220> FEATURE:
<221> NAME/KEY: CDS
<222> LOCATION: (175)..(417)

<400> SEQUENCE: 20
aggcgccagc aaccgcacct gtggcgccgg tgatgccggc cacgatgcgt ccggcgtaga      60
ggatcgagat ctcgatcccg cgaaattaat acgactcact ataggggaat tgtgagcgga     120
taacaattcc cctctagaaa taattttgtt aactttaag aaggagatat acat atg        177
                                                             Met
                                                              1 gaa caa aaa ctc atc tca gaa gag gat ctg aat cga tcc atg aat tct       225
Glu Gln Lys Leu Ile Ser Glu Glu Asp Leu Asn Arg Ser Met Asn Ser
        5                   10                  15 agt gga tcc atg aac gcc agc aac gac agc agc tcc cat cta cag ctg       273
Ser Gly Ser Met Asn Ala Ser Asn Asp Ser Ser His Leu Gln Leu
    20                  25                  30 att tac aac ttg acg cta tgt gag ctg aat ggc aca gat tgg cta gct       321
Ile Tyr Asn Leu Thr Leu Cys Glu Leu Asn Gly Thr Asp Trp Leu Ala
        35                  40                  45 aac aaa ttt gat tgg gca gtg ctc gag gga gga ggc ggc agc ggg ttt       369
Asn Lys Phe Asp Trp Ala Val Leu Glu Gly Gly Gly Gly Ser Gly Phe
50                  55                  60                  65 gtt cac ggg cgg tat gtc cta agt ctc gag cac cac cac cac cac cac       417
Val His Gly Arg Tyr Val Leu Ser Leu Glu His His His His His His
            70                  75                  80 tgagatccgg ctgctaacaa agcccgaaag gaagctgagt tggctgctgc caccgctgag     477
caataactag cataacccct tggggcctct aaacgggtct tgaggggttt tttgctgaaa     537
ggaggaacta tatccggatt ggcgaatggg acgcgccctg tagcggcgca ttaagcgcg      596

<210> SEQ ID NO 21
<211> LENGTH: 159
<212> TYPE: DNA
<213> ORGANISM: Porcine reproductive and respiratory syndrome virus

<400> SEQUENCE: 21
atgaacgcca gcaacgacag cagctcccat ctacagctga tttacaactt gacgctatgt      60
gagctgaatg gcacagattg gctagctaac aaatttgatt gggcagtgct cgagggagga     120
ggcggcagcg gtttgttca cgggcggtat gtcctaagt                             159

<210> SEQ ID NO 22
<211> LENGTH: 81
<212> TYPE: PRT
<213> ORGANISM: Porcine reproductive and respiratory syndrome virus

<400> SEQUENCE: 22

Met Glu Gln Lys Leu Ile Ser Glu Glu Asp Leu Asn Arg Ser Met Asn
  1               5                  10                  15

Ser Ser Gly Ser Met Asn Ala Ser Asn Asp Ser Ser His Leu Gln
            20                  25                  30
```

```
Leu Ile Tyr Asn Leu Thr Leu Cys Glu Leu Asn Gly Thr Asp Trp Leu
         35                  40                  45

Ala Asn Lys Phe Asp Trp Ala Val Leu Glu Gly Gly Gly Gly Ser Gly
 50                  55                  60

Phe Val His Gly Arg Tyr Val Leu Ser Leu Glu His His His His
 65                  70                  75                  80

His
```

```
<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      Gly-Ser linker

<400> SEQUENCE: 23

Gly Gly Gly Gly Ser
 1               5
```

```
<210> SEQ ID NO 24
<211> LENGTH: 656
<212> TYPE: DNA
<213> ORGANISM: Porcine reproductive and respiratory syndrome virus
<220> FEATURE:
<221> NAME/KEY: CDS
<222> LOCATION: (175)..(477)

<400> SEQUENCE: 24
aggcgccagc aaccgcacct gtggcgccgg tgatgccggc cacgatgcgt ccggcgtaga      60
ggatcgagat ctcgatcccg cgaaattaat acgactcact atagggggaat tgtgagcgga    120 taacaattcc cctctagaaa taattttgtt aactttaag aaggagatat acat atg      177
                                                              Met
                                                               1 gaa caa aaa ctc atc tca gaa gag gat ctg aat cga tcc atg aat tct      225
Glu Gln Lys Leu Ile Ser Glu Glu Asp Leu Asn Arg Ser Met Asn Ser
        5                  10                  15 agt gga tcc atg aag aat tgc atg tcc tgg cgc tac gcg tgt acc aga      273
Ser Gly Ser Met Lys Asn Cys Met Ser Trp Arg Tyr Ala Cys Thr Arg
 20                  25                  30 tat acc aac ttt ctt ctg gac act aag ggc aga ctc tat cgt tgg cgg      321
Tyr Thr Asn Phe Leu Leu Asp Thr Lys Gly Arg Leu Tyr Arg Trp Arg
 35                  40                  45 tcg cct gtc atc ata gag aaa agg ggc aaa gtt gag gtc gaa ggt cat      369
Ser Pro Val Ile Ile Glu Lys Arg Gly Lys Val Glu Val Glu Gly His
 50                  55                  60                  65 ctg atc gac ctc aaa aga gtt gtg ctt gat ggt tcc gtg gca acc cct      417
Leu Ile Asp Leu Lys Arg Val Val Leu Asp Gly Ser Val Ala Thr Pro
             70                  75                  80 ata acc aga gtt tca gcg gaa caa tgg ggt cgt cct ctc gag cac cac      465
Ile Thr Arg Val Ser Ala Glu Gln Trp Gly Arg Pro Leu Glu His His
         85                  90                  95 cac cac cac cac tgagatccgg ctgctaacaa agcccgaaag gaagctgagt          517
His His His His
        100 tggctgctgc caccgctgag caataactag cataacccct ggggcctct aaacgggtct     577 tgaggggttt tttgctgaaa ggaggaacta tatccggatt ggcgaatggg acgcgccctg    637 tagcggcgca ttaagcgcg                                                  656
```

```
<210> SEQ ID NO 25
```

```
<211> LENGTH: 219
<212> TYPE: DNA
<213> ORGANISM: Porcine reproductive and respiratory syndrome virus

<400> SEQUENCE: 25
atgaagaatt gcatgtcctg gcgctacgcg tgtaccagat ataccaactt tcttctggac      60
actaagggca gactctatcg ttggcggtcg cctgtcatca tagagaaaag gggcaaagtt     120
gaggtcgaag gtcatctgat cgacctcaaa agagttgtgc ttgatggttc cgtggcaacc     180
cctataacca gagtttcagc ggaacaatgg ggtcgtcct                            219

<210> SEQ ID NO 26
<211> LENGTH: 101
<212> TYPE: PRT
<213> ORGANISM: Porcine reproductive and respiratory syndrome virus

<400> SEQUENCE: 26

Met Glu Gln Lys Leu Ile Ser Glu Glu Asp Leu Asn Arg Ser Met Asn
  1               5                  10                  15

Ser Ser Gly Ser Met Lys Asn Cys Met Ser Trp Arg Tyr Ala Cys Thr
             20                  25                  30

Arg Tyr Thr Asn Phe Leu Leu Asp Thr Lys Gly Arg Leu Tyr Arg Trp
         35                  40                  45

Arg Ser Pro Val Ile Ile Glu Lys Arg Gly Lys Val Glu Val Glu Gly
     50                  55                  60

His Leu Ile Asp Leu Lys Arg Val Val Leu Asp Gly Ser Val Ala Thr
 65                  70                  75                  80

Pro Ile Thr Arg Val Ser Ala Glu Gln Trp Gly Arg Pro Leu Glu His
                 85                  90                  95

His His His His His
            100

<210> SEQ ID NO 27
<211> LENGTH: 656
<212> TYPE: DNA
<213> ORGANISM: Porcine reproductive and respiratory syndrome virus
<220> FEATURE:
<221> NAME/KEY: CDS
<222> LOCATION: (175)..(477)

<400> SEQUENCE: 27
aggcgccagc aaccgcacct gtggcgccgg tgatgccggc cacgatgcgt ccggcgtaga      60
ggatcgagat ctcgatcccg cgaaattaat acgactcact ataggggaat tgtgagcgga    120
taacaattcc cctctagaaa taattttgtt aactttaag aaggagatat acat atg       177
                                                               Met
                                                                 1 gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15 agt gga tcc atg aag aac tgc atg tcc tgg cgc tat tca tgt acc aga      273
Ser Gly Ser Met Lys Asn Cys Met Ser Trp Arg Tyr Ser Cys Thr Arg
         20                  25                  30 tac acc aac ttc ctc cta gac act aag ggc aga ctc tat cgt tgg cgg      321
Tyr Thr Asn Phe Leu Leu Asp Thr Lys Gly Arg Leu Tyr Arg Trp Arg
     35                  40                  45 tcg cct gtc att ata gag aaa ggg ggt aag gtt gag gtc gaa ggc cac      369
Ser Pro Val Ile Ile Glu Lys Gly Gly Lys Val Glu Val Glu Gly His
 50                  55                  60                  65 ctg atc gac ctc aaa aga gtt gtg ctt gat ggt tcc gtg gca aca cct      417
Leu Ile Asp Leu Lys Arg Val Val Leu Asp Gly Ser Val Ala Thr Pro
```

| | | | | | | | | | | | | | | |
|---|---|---|---|---|---|---|---|---|---|---|---|---|---|---|
| | | 70 | | | | 75 | | | | | 80 | | | |
| tta | acc | aga | gtt | tca | gcg | gaa | caa | tgg | ggt | cgt | cct | ctc | gag | cac | cac | 465 |
| Leu | Thr | Arg | Val | Ser | Ala | Glu | Gln | Trp | Gly | Arg | Pro | Leu | Glu | His | His | |
| | | 85 | | | | | 90 | | | | | 95 | | | | | cac cac cac cac tgagatccgg ctgctaacaa agcccgaaag gaagctgagt    517
His His His His
        100 tggctgctgc caccgctgag caataactag cataacccct ggggcctct aaacgggtct    577 tgagggtttt tttgctgaaa ggaggaacta tatccggatt ggcgaatggg acgcgccctg    637 tagcggcgca ttaagcgcg    656

<210> SEQ ID NO 28
<211> LENGTH: 219
<212> TYPE: DNA
<213> ORGANISM: Porcine reproductive and respiratory syndrome virus

<400> SEQUENCE: 28
atgaagaact gcatgtcctg gcgctattca tgtaccagat acaccaactt cctcctagac    60
actaagggca gactctatcg ttggcggtcg cctgtcatta tagagaaagg gggtaaggtt    120
gaggtcgaag ccacctgat cgacctcaaa agagttgtgc ttgatggttc cgtggcaaca    180
cctttaacca gagtttcagc ggaacaatgg ggtcgtcct    219

<210> SEQ ID NO 29
<211> LENGTH: 101
<212> TYPE: PRT
<213> ORGANISM: Porcine reproductive and respiratory syndrome virus

<400> SEQUENCE: 29

Met Glu Gln Lys Leu Ile Ser Glu Glu Asp Leu Asn Arg Ser Met Asn
1               5                   10                  15

Ser Ser Gly Ser Met Lys Asn Cys Met Ser Trp Arg Tyr Ser Cys Thr
            20                  25                  30

Arg Tyr Thr Asn Phe Leu Leu Asp Thr Lys Gly Arg Leu Tyr Arg Trp
        35                  40                  45

Arg Ser Pro Val Ile Ile Glu Lys Gly Gly Lys Val Glu Val Glu Gly
    50                  55                  60

His Leu Ile Asp Leu Lys Arg Val Val Leu Asp Gly Ser Val Ala Thr
65                  70                  75                  80

Pro Leu Thr Arg Val Ser Ala Glu Gln Trp Gly Arg Pro Leu Glu His
                85                  90                  95

His His His His His
        100

<210> SEQ ID NO 30
<211> LENGTH: 700
<212> TYPE: DNA
<213> ORGANISM: Porcine reproductive and respiratory syndrome virus
<220> FEATURE:
<221> NAME/KEY: CDS
<222> LOCATION: (175)..(528)

<400> SEQUENCE: 30
aggcgccagc aaccgcacct gtggcgccgg tgatgccggc cacgatgcgt ccggcgtaga    60
ggatcgagat ctcgatcccg cgaaattaat acgactcact atagggggaat tgtgagcgga    120 taacaattcc cctctagaaa taattttgtt taactttaag aaggagatat acat atg    177
                                                              Met
                                                              1

```
gaa caa aaa ctc atc tca gaa gag gat ctg aat cga tcc atg aat tct      225
Glu Gln Lys Leu Ile Ser Glu Glu Asp Leu Asn Arg Ser Met Asn Ser
          5                   10                  15 agt gga tcc atg aac gcc agc aac gac agc agc tcc cat cta cag ctg      273
Ser Gly Ser Met Asn Ala Ser Asn Asp Ser Ser His Leu Gln Leu
         20                  25                  30 att tac aac ttg acg cta tgt gag ctg aat ggc aca gat tgg cta gct      321
Ile Tyr Asn Leu Thr Leu Cys Glu Leu Asn Gly Thr Asp Trp Leu Ala
         35                  40                  45 aac aaa ttt gat tgg gca gtg ctc gag gga gga ggc ggc agc ggg ttt      369
Asn Lys Phe Asp Trp Ala Val Leu Glu Gly Gly Gly Gly Ser Gly Phe
 50                  55                  60                  65 gtt cac ggg cgg tat gtc cta agt gga gga ggc ggc agc atg ggg tcg      417
Val His Gly Arg Tyr Val Leu Ser Gly Gly Gly Gly Ser Met Gly Ser
             70                  75                  80 tcc tta gat gac ttc tgt cat gat agc acg gct cca caa aag gtg ctt      465
Ser Leu Asp Asp Phe Cys His Asp Ser Thr Ala Pro Gln Lys Val Leu
             85                  90                  95 gga gga ggc ggc agc gcg cac ttt cag agt aca aat aag ctc gag cac      513
Gly Gly Gly Gly Ser Ala His Phe Gln Ser Thr Asn Lys Leu Glu His
            100                 105                 110 cac cac cac cac cac tgagatccgg ctgctaacaa agcccgaaag gaagctgagt      568
His His His His His
        115 tggctgctgc caccgctgag caataactag cataacccct tggggcctct aaacgggtct     628 tgagggtttt tttgctgaaa ggaggaacta tatccggatt ggcgaatggg acgcgccctg     688 tagcggcgca tt                                                        700

<210> SEQ ID NO 31
<211> LENGTH: 270
<212> TYPE: DNA
<213> ORGANISM: Porcine reproductive and respiratory syndrome virus

<400> SEQUENCE: 31
atgaacgcca gcaacgacag cagctcccat ctacagctga tttacaactt gacgctatgt      60
gagctgaatg gcacagattg gctagctaac aaatttgatt gggcagtgct cgagggagga    120
ggcggcagcg ggtttgttca cgggcggtat gtcctaagtg gaggaggcgg cagcatgggg    180
tcgtccttag atgacttctg tcatgatagc acggctccac aaaaggtgct tggaggaggc    240
ggcagcgcgc actttcagag tacaaataag                                     270

<210> SEQ ID NO 32
<211> LENGTH: 118
<212> TYPE: PRT
<213> ORGANISM: Porcine reproductive and respiratory syndrome virus

<400> SEQUENCE: 32

Met Glu Gln Lys Leu Ile Ser Glu Glu Asp Leu Asn Arg Ser Met Asn
 1               5                  10                  15

Ser Ser Gly Ser Met Asn Ala Ser Asn Asp Ser Ser His Leu Gln
             20                  25                  30

Leu Ile Tyr Asn Leu Thr Leu Cys Glu Leu Asn Gly Thr Asp Trp Leu
             35                  40                  45

Ala Asn Lys Phe Asp Trp Ala Val Leu Glu Gly Gly Gly Gly Ser Gly
         50                  55                  60

Phe Val His Gly Arg Tyr Val Leu Ser Gly Gly Gly Gly Ser Met Gly
 65                  70                  75                  80

Ser Ser Leu Asp Asp Phe Cys His Asp Ser Thr Ala Pro Gln Lys Val
```

```
                     85                  90                  95
Leu Gly Gly Gly Gly Ser Ala His Phe Gln Ser Thr Asn Lys Leu Glu
            100                 105                 110
His His His His His His
        115

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
  1               5

<210> SEQ ID NO 34
<211> LENGTH: 806
<212> TYPE: DNA
<213> ORGANISM: Porcine reproductive and respiratory syndrome virus
<220> FEATURE:
<221> NAME/KEY: CDS
<222> LOCATION: (175)..(627)

<400> SEQUENCE: 34
aggcgccagc aaccgcacct gtggcgccgg tgatgccggc cacgatgcgt ccggcgtaga      60
ggatcgagat ctcgatcccg cgaaattaat acgactcact ataggggaat tgtgagcgga    120
taacaattcc cctctagaaa taattttgtt aactttaag aaggagatat acat atg       177
                                                            Met
                                                             1 gaa caa aaa ctc atc tca gaa gag gat ctg aat cga tcc atg aat tct      225
Glu Gln Lys Leu Ile Ser Glu Glu Asp Leu Asn Arg Ser Met Asn Ser
        5                  10                  15 agt gga tcc atg cca aat aac aac ggc aag cag cag aag aga aag aag      273
Ser Gly Ser Met Pro Asn Asn Asn Gly Lys Gln Gln Lys Arg Lys Lys
    20                  25                  30 ggg gat ggc cag cca gtc aat cag ctg tgc cag atg ctg ggt aag atc      321
Gly Asp Gly Gln Pro Val Asn Gln Leu Cys Gln Met Leu Gly Lys Ile
35                  40                  45 atc gct cag caa aac cag tcc aga ggc aag gga ccg gga aag aaa aat      369
Ile Ala Gln Gln Asn Gln Ser Arg Gly Lys Gly Pro Gly Lys Lys Asn
 50                  55                  60                  65 aag aag aaa aac ccg gag aag ccc cat ttt cct cta gcg act gaa gat      417
Lys Lys Lys Asn Pro Glu Lys Pro His Phe Pro Leu Ala Thr Glu Asp
                70                  75                  80 gat gtc aga cat cac ttt acc cct agt gag cgg caa ttg tgt ctg tcg      465
Asp Val Arg His His Phe Thr Pro Ser Glu Arg Gln Leu Cys Leu Ser
            85                  90                  95 tca atc cag acc gcc ttt aat caa ggc gct ggg act tgc acc ctg tca      513
Ser Ile Gln Thr Ala Phe Asn Gln Gly Ala Gly Thr Cys Thr Leu Ser
        100                 105                 110 gat tca ggg agg ata agt tac act gtg gag ttt agt ttg cct acg cat      561
Asp Ser Gly Arg Ile Ser Tyr Thr Val Glu Phe Ser Leu Pro Thr His
    115                 120                 125 cat act gtg cgc ctg atc cgc gtc aca gca tca ccc tca gca ctc gag      609
His Thr Val Arg Leu Ile Arg Val Thr Ala Ser Pro Ser Ala Leu Glu
130                 135                 140                 145 cac cac cac cac cac cac tgagatccgg ctgctaacaa agcccgaaag             657
His His His His His His
                150
```

```
gaagctgagt tggctgctgc caccgctgag caataactag cataacccct tggggcctct      717
aaacgggtct tgaggggttt tttgctgaaa ggaggaacta tatccggatt ggcgaatggg      777
acgcgccctg tagcggcgca ttaagcgcg                                        806
```

<210> SEQ ID NO 35
<211> LENGTH: 369
<212> TYPE: DNA
<213> ORGANISM: Porcine reproductive and respiratory syndrome virus

<400> SEQUENCE: 35

```
atgccaaata caacggcaa gcagcagaag agaaagaagg gggatggcca gccagtcaat       60
cagctgtgcc agatgctggg taagatcatc gctcagcaaa accagtccag aggcaaggga      120
ccgggaaaga aaataagaa gaaaaacccg gagaagcccc attttcctct agcgactgaa       180
gatgatgtca gacatcactt taccctagt gagcggcaat tgtgtctgtc gtcaatccag       240
accgccttta tcaaggcgc tgggacttgc accctgtcag attcagggag gataagttac       300
actgtggagt ttagtttgcc tacgcatcat actgtgcgcc tgatccgcgt cacagcatca      360
ccctcagca                                                              369
```

<210> SEQ ID NO 36
<211> LENGTH: 151
<212> TYPE: PRT
<213> ORGANISM: Porcine reproductive and respiratory syndrome virus

<400> SEQUENCE: 36

```
Met Glu Gln Lys Leu Ile Ser Glu Glu Asp Leu Asn Arg Ser Met Asn
1               5                   10                  15

Ser Ser Gly Ser Met Pro Asn Asn Gly Lys Gln Gln Lys Arg Lys
            20                  25                  30

Lys Gly Asp Gly Gln Pro Val Asn Gln Leu Cys Gln Met Leu Gly Lys
        35                  40                  45

Ile Ile Ala Gln Gln Asn Gln Ser Arg Gly Lys Gly Pro Gly Lys Lys
    50                  55                  60

Asn Lys Lys Lys Asn Pro Glu Lys Pro His Phe Pro Leu Ala Thr Glu
65                  70                  75                  80

Asp Asp Val Arg His His Phe Thr Pro Ser Glu Arg Gln Leu Cys Leu
                85                  90                  95

Ser Ser Ile Gln Thr Ala Phe Asn Gln Gly Ala Gly Thr Cys Thr Leu
            100                 105                 110

Ser Asp Ser Gly Arg Ile Ser Tyr Thr Val Glu Phe Ser Leu Pro Thr
        115                 120                 125

His His Thr Val Arg Leu Ile Arg Val Thr Ala Ser Pro Ser Ala Leu
    130                 135                 140

Glu His His His His His His
145                 150
```

<210> SEQ ID NO 37
<211> LENGTH: 907
<212> TYPE: DNA
<213> ORGANISM: Porcine reproductive and respiratory syndrome virus
<220> FEATURE:
<221> NAME/KEY: CDS
<222> LOCATION: (175)..(735)

<400> SEQUENCE: 37

```
aggcgccagc aaccgcacct gtggcgccgg tgatgccggc acgatgcgt ccggcgtaga       60
```

```
ggatcgagat ctcgatcccg cgaaattaat acgactcact ataggggaat tgtgagcgga        120
taacaattcc cctctagaaa taattttgtt taactttaag aaggagatat acat atg          177
                                                            Met
                                                              1 gaa caa aaa ctc atc tca gaa gag gat ctg aat cga tcc atg aat tct          225
Glu Gln Lys Leu Ile Ser Glu Glu Asp Leu Asn Arg Ser Met Asn Ser
          5                  10                  15 agt gga tcc ggc agc ccg gtt tca tta ggc ggc gat gtc cct aac agt          273
Ser Gly Ser Gly Ser Pro Val Ser Leu Gly Gly Asp Val Pro Asn Ser
         20                  25                  30 tgg gaa gat ttg gct gtt agt agc ccc ttt gat ctc ccg acc cca cct          321
Trp Glu Asp Leu Ala Val Ser Ser Pro Phe Asp Leu Pro Thr Pro Pro
 35                  40                  45 gag ccg gca aca cct tca agt gag ctg gtg att gtg tcc tca ccg caa          369
Glu Pro Ala Thr Pro Ser Ser Glu Leu Val Ile Val Ser Ser Pro Gln
 50                  55                  60                  65 tgc atc ttc agg ccg gcg aca ccc ttg agt gag ccg gct cca att ccc          417
Cys Ile Phe Arg Pro Ala Thr Pro Leu Ser Glu Pro Ala Pro Ile Pro
                 70                  75                  80 gca cct cgc gga act gtg tct cga ccg gtg aca ccc ttg agt gag ccg          465
Ala Pro Arg Gly Thr Val Ser Arg Pro Val Thr Pro Leu Ser Glu Pro
             85                  90                  95 atc cct gtg ccc gca ccg cgg cgt aag ttt cag cag gtg aaa aga ttg          513
Ile Pro Val Pro Ala Pro Arg Arg Lys Phe Gln Gln Val Lys Arg Leu
        100                 105                 110 agt tcg gcg gcg gca atc cca ccg tac cag gac gag ccc ctg gat ttg          561
Ser Ser Ala Ala Ala Ile Pro Pro Tyr Gln Asp Glu Pro Leu Asp Leu
    115                 120                 125 tct gct tcc tca cag gct gaa tat gag gcc tct ccc cca gca ccg ccg          609
Ser Ala Ser Ser Gln Ala Glu Tyr Glu Ala Ser Pro Pro Ala Pro Pro
130                 135                 140                 145 cag agc ggg ggc gtt ctg gga gta gag ggg cat gaa gct gag gaa acc          657
Gln Ser Gly Gly Val Leu Gly Val Glu Gly His Glu Ala Glu Glu Thr
                150                 155                 160 ctg agt gaa atc tcg gac atg tcg ggt aac att aaa cct gcg tcc gtg          705
Leu Ser Glu Ile Ser Asp Met Ser Gly Asn Ile Lys Pro Ala Ser Val
            165                 170                 175 tca tca ctc gag cac cac cac cac cac cac tgagatccgg ctgctaacaa           755
Ser Ser Leu Glu His His His His His His
        180                 185 agcccgaaag gaagctgagt tggctgctgc caccgctgag caataactag cataacccct       815
tggggcctct aaacgggtct tgaggggttt tttgctgaaa ggaggaacta tatccggatt       875
ggcgaatggg acgcgccctg tagcggcgca tt                                     907

<210> SEQ ID NO 38
<211> LENGTH: 477
<212> TYPE: DNA
<213> ORGANISM: Porcine reproductive and respiratory syndrome virus

<400> SEQUENCE: 38
ggcagcccgg tttcattagg cggcgatgtc cctaacagtt gggaagattt ggctgttagt        60 agccccttttg atctcccgac cccacctgag ccggcaacac cttcaagtga gctggtgatt      120
gtgtcctcac cgcaatgcat cttcaggccg gcgacaccct tgagtgagcc ggctccaatt      180
cccgcacctc gcggaactgt gtctcgaccg gtgacaccct tgagtgagcc gatccctgtg      240
cccgcaccgc ggcgtaagtt tcagcaggtg aaaagattga gttcggcggc ggcaatccca      300
ccgtaccagg acgagcccct ggatttgtct gcttcctcac aggctgaata tgaggcctct      360
```

```
cccccagcac cgccgcagag cgggggcgtt ctgggagtag aggggcatga agctgaggaa      420
accctgagtg aaatctcgga catgtcgggt aacattaaac ctgcgtccgt gtcatca         477
```

<210> SEQ ID NO 39
<211> LENGTH: 187
<212> TYPE: PRT
<213> ORGANISM: Porcine reproductive and respiratory syndrome virus

<400> SEQUENCE: 39

```
Met Glu Gln Lys Leu Ile Ser Glu Glu Asp Leu Asn Arg Ser Met Asn
 1               5                  10                  15

Ser Ser Gly Ser Gly Ser Pro Val Ser Leu Gly Gly Asp Val Pro Asn
            20                  25                  30

Ser Trp Glu Asp Leu Ala Val Ser Ser Pro Phe Asp Leu Pro Thr Pro
        35                  40                  45

Pro Glu Pro Ala Thr Pro Ser Ser Glu Leu Val Ile Val Ser Ser Pro
    50                  55                  60

Gln Cys Ile Phe Arg Pro Ala Thr Pro Leu Ser Glu Pro Ala Pro Ile
65                  70                  75                  80

Pro Ala Pro Arg Gly Thr Val Ser Arg Pro Val Thr Pro Leu Ser Glu
                85                  90                  95

Pro Ile Pro Val Pro Ala Pro Arg Arg Lys Phe Gln Gln Val Lys Arg
            100                 105                 110

Leu Ser Ser Ala Ala Ala Ile Pro Pro Tyr Gln Asp Glu Pro Leu Asp
        115                 120                 125

Leu Ser Ala Ser Ser Gln Ala Glu Tyr Glu Ala Ser Pro Pro Ala Pro
    130                 135                 140

Pro Gln Ser Gly Gly Val Leu Gly Val Glu Gly His Glu Ala Glu Glu
145                 150                 155                 160

Thr Leu Ser Glu Ile Ser Asp Met Ser Gly Asn Ile Lys Pro Ala Ser
                165                 170                 175

Val Ser Ser Leu Glu His His His His His His
            180                 185
```

<210> SEQ ID NO 40
<211> LENGTH: 532
<212> TYPE: DNA
<213> ORGANISM: Porcine reproductive and respiratory syndrome virus
<220> FEATURE:
<221> NAME/KEY: CDS
<222> LOCATION: (175)..(360)

<400> SEQUENCE: 40

```
aggcgccagc aaccgcacct gtggcgccgg tgatgccggc cacgatgcgt ccggcgtaga      60
ggatcgagat ctcgatcccg cgaaattaat acgactcact ataggggaat tgtgagcgga     120
taacaattcc cctctagaaa taattttgtt aactttaag aaggagatat acat atg        177
                                                             Met
                                                               1 gaa caa aaa ctc atc tca gaa gag gat ctg aat cga tcc atg aat tct       225
Glu Gln Lys Leu Ile Ser Glu Glu Asp Leu Asn Arg Ser Met Asn Ser
            5                  10                  15 agt gga tcc gcg act gct aca gtc gct ggc cgc gct ttg tcc gtt cgt       273
Ser Gly Ser Ala Thr Ala Thr Val Ala Gly Arg Ala Leu Ser Val Arg
        20                  25                  30 gaa acc cgg cag gcc aag gag cac gag gtt gcc ggc gcc aac aag gct       321
Glu Thr Arg Gln Ala Lys Glu His Glu Val Ala Gly Ala Asn Lys Ala
    35                  40                  45 gag cac ctc aaa cac ctc gag cac cac cac cac cac cac tgagatccgg       370
Glu His Leu Lys His Leu Glu His His His His His His
```

```
Glu His Leu Lys His Leu Glu His His His His His
 50              55              60 ctgctaacaa agcccgaaag gaagctgagt tggctgctgc caccgctgag caataactag    430
cataacccct ggggcctct aaacgggtct tgaggggttt tttgctgaaa ggaggaacta    490
tatccggatt ggcgaatggg acgcgccctg tagcggcgca tt                      532

<210> SEQ ID NO 41
<211> LENGTH: 102
<212> TYPE: DNA
<213> ORGANISM: Porcine reproductive and respiratory syndrome virus

<400> SEQUENCE: 41
gcgactgcta cagtcgctgg ccgcgctttg tccgttcgtg aaacccggca ggccaaggag    60
cacgaggttg ccggcgccaa caaggctgag cacctcaaac ac                      102

<210> SEQ ID NO 42
<211> LENGTH: 62
<212> TYPE: PRT
<213> ORGANISM: Porcine reproductive and respiratory syndrome virus

<400> SEQUENCE: 42

Met Glu Gln Lys Leu Ile Ser Glu Glu Asp Leu Asn Arg Ser Met Asn
 1               5                  10                  15

Ser Ser Gly Ser Ala Thr Ala Thr Val Ala Gly Arg Ala Leu Ser Val
             20                  25                  30

Arg Glu Thr Arg Gln Ala Lys Glu His Glu Val Ala Gly Ala Asn Lys
         35                  40                  45

Ala Glu His Leu Lys His Leu Glu His His His His His His
     50                  55                  60

<210> SEQ ID NO 43
<211> LENGTH: 538
<212> TYPE: DNA
<213> ORGANISM: Porcine reproductive and respiratory syndrome virus
<220> FEATURE:
<221> NAME/KEY: CDS
<222> LOCATION: (175)..(366)

<400> SEQUENCE: 43
aggcgccagc aaccgcacct gtggcgccgg tgatgccggc cacgatgcgt ccggcgtaga    60
ggatcgagat ctcgatcccg cgaaattaat acgactcact ataggggaat gtgagcgga   120 taacaattcc cctctagaaa taattttgtt aactttaag aaggagatat acat atg     177
                                                              Met
                                                               1 gaa caa aaa ctc atc tca gaa gag gat ctg aat cga tcc atg aat tct    225
Glu Gln Lys Leu Ile Ser Glu Glu Asp Leu Asn Arg Ser Met Asn Ser
          5                  10                  15 agt gga tcc gca aag att gac ctg tac ctc cgt ggt gca aca aat ctt    273
Ser Gly Ser Ala Lys Ile Asp Leu Tyr Leu Arg Gly Ala Thr Asn Leu
             20                  25                  30 gaa gaa tgc ttg gcc agg ctt gag aaa gcg cgc ccg cca cgc gta atc    321
Glu Glu Cys Leu Ala Arg Leu Glu Lys Ala Arg Pro Pro Arg Val Ile
         35                  40                  45 gac acc tcc ttt gat tgg gat ctc gag cac cac cac cac cac cac        366
Asp Thr Ser Phe Asp Trp Asp Leu Glu His His His His His His
     50                  55                  60 tgagatccgg ctgctaacaa agcccgaaag gaagctgagt tggctgctgc caccgctgag   426
caataactag cataacccct ggggcctct aaacgggtct tgaggggttt tttgctgaaa   486
```

```
ggaggaacta tatccggatt ggcgaatggg acgcgccctg tagcggcgca tt          538

<210> SEQ ID NO 44
<211> LENGTH: 108
<212> TYPE: DNA
<213> ORGANISM: Porcine reproductive and respiratory syndrome virus

<400> SEQUENCE: 44
gcaaagattg acctgtacct ccgtggtgca acaaatcttg aagaatgctt ggccaggctt   60
gagaaagcgc gcccgccacg cgtaatcgac acctcctttg attgggat              108

<210> SEQ ID NO 45
<211> LENGTH: 64
<212> TYPE: PRT
<213> ORGANISM: Porcine reproductive and respiratory syndrome virus

<400> SEQUENCE: 45

Met Glu Gln Lys Leu Ile Ser Glu Glu Asp Leu Asn Arg Ser Met Asn
 1               5                  10                  15

Ser Ser Gly Ser Ala Lys Ile Asp Leu Tyr Leu Arg Gly Ala Thr Asn
            20                  25                  30

Leu Glu Glu Cys Leu Ala Arg Leu Glu Lys Ala Arg Pro Pro Arg Val
        35                  40                  45

Ile Asp Thr Ser Phe Asp Trp Asp Leu Glu His His His His His His
    50                  55                  60

<210> SEQ ID NO 46
<211> LENGTH: 526
<212> TYPE: DNA
<213> ORGANISM: Porcine reproductive and respiratory syndrome virus
<220> FEATURE:
<221> NAME/KEY: CDS
<222> LOCATION: (175)..(354)

<400> SEQUENCE: 46
aggcgccagc aaccgcacct gtggcgccgg tgatgccggc acgatgcgt ccggcgtaga    60 ggatcgagat ctcgatcccg cgaaattaat acgactcact ataggggaat tgtgagcgga  120
taacaattcc cctctagaaa taattttgtt aactttaag aaggagatat acat atg     177
                                                              Met
                                                                1 gaa caa aaa ctc atc tca gaa gag gat ctg aat cga tcc atg aat tct    225
Glu Gln Lys Leu Ile Ser Glu Glu Asp Leu Asn Arg Ser Met Asn Ser
          5                  10                  15 agt gga tcc atg ggg tcg tcc tta gat gac ttc tgt cat gat agc acg    273
Ser Gly Ser Met Gly Ser Ser Leu Asp Asp Phe Cys His Asp Ser Thr
         20                  25                  30 gct cca caa aag gtg ctt gga gga ggc ggc agc gcg cac ttt cag agt    321
Ala Pro Gln Lys Val Leu Gly Gly Gly Gly Ser Ala His Phe Gln Ser
     35                  40                  45 aca aat aag ctc gag cac cac cac cac cac cac tgagatccgg ctgctaacaa  374
Thr Asn Lys Leu Glu His His His His His His
 50                  55                  60 agcccgaaag gaagctgagt tggctgctgc caccgctgag caataactag cataacccct  434
tggggcctct aaacgggtct tgaggggttt tttgctgaaa ggaggaacta tatccggatt  494
ggcgaatggg acgcgccctg tagcggcgca tt                                526

<210> SEQ ID NO 47
<211> LENGTH: 96
<212> TYPE: DNA
<213> ORGANISM: Porcine reproductive and respiratory syndrome virus
```

<400> SEQUENCE: 47

```
atggggtcgt ccttagatga cttctgtcat gatagcacgg ctccacaaaa ggtgcttgga      60
ggaggcggca gcgcgcactt tcagagtaca aataag                                96
```

<210> SEQ ID NO 48
<211> LENGTH: 60
<212> TYPE: PRT
<213> ORGANISM: Porcine reproductive and respiratory syndrome virus

<400> SEQUENCE: 48

```
Met Glu Gln Lys Leu Ile Ser Glu Glu Asp Leu Asn Arg Ser Met Asn
  1               5                  10                  15

Ser Ser Gly Ser Met Gly Ser Ser Leu Asp Asp Phe Cys His Asp Ser
             20                  25                  30

Thr Ala Pro Gln Lys Val Leu Gly Gly Gly Ser Ala His Phe Gln
         35                  40                  45

Ser Thr Asn Lys Leu Glu His His His His His His
         50                  55                  60
```

<210> SEQ ID NO 49
<211> LENGTH: 694
<212> TYPE: DNA
<213> ORGANISM: Porcine reproductive and respiratory syndrome virus
<220> FEATURE:
<221> NAME/KEY: CDS
<222> LOCATION: (175)..(522)

<400> SEQUENCE: 49

```
aggcgccagc aaccgcacct gtggcgccgg tgatgccggc cacgatgcgt ccggcgtaga      60
ggatcgagat ctcgatcccg cgaaattaat acgactcact ataggggaat gtgagcgga     120 taacaattcc cctctagaaa taattttgtt taactttaag aaggagatat acat atg      177
                                                            Met
                                                              1 gaa caa aaa ctc atc tca gaa gag gat ctg aat cga tcc atg aat tct      225
Glu Gln Lys Leu Ile Ser Glu Glu Asp Leu Asn Arg Ser Met Asn Ser
              5                  10                  15 agt gga tcc tca gcc ata gaa acc tgg aaa ttc atc acc tcc aga tgc      273
Ser Gly Ser Ser Ala Ile Glu Thr Trp Lys Phe Ile Thr Ser Arg Cys
         20                  25                  30 cgt ttg tgc ttg cta ggc cgc aag tac att ctg gcc cct gcc cac cac      321
Arg Leu Cys Leu Leu Gly Arg Lys Tyr Ile Leu Ala Pro Ala His His
     35                  40                  45 gtt gaa agt gcc gca cgg ttt cat ccg att gcg gca aat gat aac cac      369
Val Glu Ser Ala Ala Arg Phe His Pro Ile Ala Ala Asn Asp Asn His
 50                  55                  60                  65 gca ttt gtc gtc cgg cgt ccc ggc tcc act acg gtc aac ggc aca ttg      417
Ala Phe Val Val Arg Arg Pro Gly Ser Thr Thr Val Asn Gly Thr Leu
                 70                  75                  80 gtg ccc ggg tta aaa agc ctc gtg ttg ggt ggc aga aaa gct gtt aaa      465
Val Pro Gly Leu Lys Ser Leu Val Leu Gly Gly Arg Lys Ala Val Lys
             85                  90                  95 cag gga gtg gta aac ctt gtc aaa tat gcc aaa ctc gag cac cac cac      513
Gln Gly Val Val Asn Leu Val Lys Tyr Ala Lys Leu Glu His His His
         100                 105                 110 cac cac cac tgagatccgg ctgctaacaa agcccgaaag gaagctgagt              562
His His His
     115 tggctgctgc caccgctgag caataactag cataaccccct tggggcctct aaacgggtct   622
```

```
tgaggggttt tttgctgaaa ggaggaacta tatccggatt ggcgaatggg acgcgccctg      682
tagcggcgca tt                                                          694

<210> SEQ ID NO 50
<211> LENGTH: 264
<212> TYPE: DNA
<213> ORGANISM: Porcine reproductive and respiratory syndrome virus

<400> SEQUENCE: 50
tcagccatag aaacctggaa attcatcacc tccagatgcc gtttgtgctt gctaggccgc       60
aagtacattc tggcccctgc ccaccacgtt gaaagtgccg cacggtttca tccgattgcg      120
gcaaatgata ccacgcatt tgtcgtccgg cgtcccggct ccactacggt caacggcaca      180
ttggtgcccg ggttaaaaag cctcgtgttg ggtggcagaa aagctgttaa acagggagtg      240
gtaaaccttg tcaaatatgc caaa                                             264

<210> SEQ ID NO 51
<211> LENGTH: 116
<212> TYPE: PRT
<213> ORGANISM: Porcine reproductive and respiratory syndrome virus

<400> SEQUENCE: 51

Met Glu Gln Lys Leu Ile Ser Glu Glu Asp Leu Asn Arg Ser Met Asn
  1               5                  10                  15

Ser Ser Gly Ser Ser Ala Ile Glu Thr Trp Lys Phe Ile Thr Ser Arg
             20                  25                  30

Cys Arg Leu Cys Leu Leu Gly Arg Lys Tyr Ile Leu Ala Pro Ala His
         35                  40                  45

His Val Glu Ser Ala Ala Arg Phe His Pro Ile Ala Ala Asn Asp Asn
     50                  55                  60

His Ala Phe Val Val Arg Arg Pro Gly Ser Thr Thr Val Asn Gly Thr
 65                  70                  75                  80

Leu Val Pro Gly Leu Lys Ser Leu Val Leu Gly Gly Arg Lys Ala Val
                 85                  90                  95

Lys Gln Gly Val Val Asn Leu Val Lys Tyr Ala Lys Leu Glu His His
            100                 105                 110

His His His His
        115

<210> SEQ ID NO 52
<211> LENGTH: 821
<212> TYPE: DNA
<213> ORGANISM: Porcine reproductive and respiratory syndrome virus
<220> FEATURE:
<221> NAME/KEY: CDS
<222> LOCATION: (175)..(642)

<400> SEQUENCE: 52
aggcgccagc aaccgcacct gtggcgccgg tgatgccggc cacgatgcgt ccggcgtaga       60
ggatcgagat ctcgatcccg cgaaattaat acgactcact ataggggaat tgtgagcgga      120
taacaattcc cctctagaaa taattttgtt aactttaag aaggagatat acat atg         177
                                                             Met
                                                               1 gaa caa aaa ctc atc tca gaa gag gat ctg aat cga tcc atg aat tct       225
Glu Gln Lys Leu Ile Ser Glu Glu Asp Leu Asn Arg Ser Met Asn Ser
              5                  10                  15 agt gga tcc atg gcc ggt aaa aac cag agc cag aag aaa aag aaa agt       273
Ser Gly Ser Met Ala Gly Lys Asn Gln Ser Gln Lys Lys Lys Lys Ser
         20                  25                  30
```

-continued

```
aca gct ccg atg ggg aat ggc cag cca gtc aat caa ctg tgc cag ttg      321
Thr Ala Pro Met Gly Asn Gly Gln Pro Val Asn Gln Leu Cys Gln Leu
         35                  40                  45 ctg ggt gca atg ata aag tcc cag cgc cag caa cct agg gga gga cag      369
Leu Gly Ala Met Ile Lys Ser Gln Arg Gln Gln Pro Arg Gly Gly Gln
 50                  55                  60                  65 gcc aaa aag aaa aag cct gag aag cca cat ttt ccc ctg gct gct gaa      417
Ala Lys Lys Lys Lys Pro Glu Lys Pro His Phe Pro Leu Ala Ala Glu
                 70                  75                  80 gat gac atc cgg cac cac ctc acc cag act gaa cgc tcc ctc tgc ttg      465
Asp Asp Ile Arg His His Leu Thr Gln Thr Glu Arg Ser Leu Cys Leu
             85                  90                  95 caa tcg atc cag acg gct ttc aat caa ggc gca gga act gcg tcg ctt      513
Gln Ser Ile Gln Thr Ala Phe Asn Gln Gly Ala Gly Thr Ala Ser Leu
        100                 105                 110 tca tcc agc ggg aag gtc agt ttt cag gtt gag ttt atg ctg ccg gtt      561
Ser Ser Ser Gly Lys Val Ser Phe Gln Val Glu Phe Met Leu Pro Val
115                 120                 125 gct cat aca gtg cgc ctg att cgc gtg act tct aca tcc gcc agt cag      609
Ala His Thr Val Arg Leu Ile Arg Val Thr Ser Thr Ser Ala Ser Gln
130                 135                 140                 145 ggt gca agt ctc gag cac cac cac cac cac cac tgagatccgg ctgctaacaa    662
Gly Ala Ser Leu Glu His His His His His His
                150                 155 agcccgaaag gaagctgagt tggctgctgc caccgctgag caataactag cataacccct    722
tggggcctct aaacgggtct tgaggggttt tttgctgaaa ggaggaacta tatccggatt    782
ggcgaatggg acgcgccctg tagcggcgca ttaagcgcg                           821

<210> SEQ ID NO 53
<211> LENGTH: 384
<212> TYPE: DNA
<213> ORGANISM: Porcine reproductive and respiratory syndrome virus

<400> SEQUENCE: 53
atggccggta aaaccagag ccagaagaaa aagaaaagta cagctccgat ggggaatggc       60
cagccagtca atcaactgtg ccagttgctg ggtgcaatga taaagtccca gcgccagcaa     120
cctaggggag acaggccaa aaagaaaaag cctgagaagc acatttttcc cctggctgct      180
gaagatgaca tccggcacca cctcacccag actgaacgct ccctctgctt gcaatcgatc     240
cagacggctt tcaatcaagg cgcaggaact gcgtcgcttt catccagcgg gaaggtcagt     300
tttcaggttg agtttatgct gccggttgct catacagtgc gcctgattcg cgtgacttct     360
acatccgcca gtcagggtgc aagt                                            384

<210> SEQ ID NO 54
<211> LENGTH: 156
<212> TYPE: PRT
<213> ORGANISM: Porcine reproductive and respiratory syndrome virus

<400> SEQUENCE: 54

Met Glu Gln Lys Leu Ile Ser Glu Glu Asp Leu Asn Arg Ser Met Asn
  1               5                  10                  15

Ser Ser Gly Ser Met Ala Gly Lys Asn Gln Ser Gln Lys Lys Lys Lys
                 20                  25                  30

Ser Thr Ala Pro Met Gly Asn Gly Gln Pro Val Asn Gln Leu Cys Gln
             35                  40                  45

Leu Leu Gly Ala Met Ile Lys Ser Gln Arg Gln Gln Pro Arg Gly Gly
     50                  55                  60
```

-continued

```
Gln Ala Lys Lys Lys Pro Glu Lys Pro His Phe Pro Leu Ala Ala
 65                  70                  75                  80

Glu Asp Asp Ile Arg His His Leu Thr Gln Thr Glu Arg Ser Leu Cys
             85                  90                  95

Leu Gln Ser Ile Gln Thr Ala Phe Asn Gln Gly Ala Gly Thr Ala Ser
            100                 105                 110

Leu Ser Ser Ser Gly Lys Val Ser Phe Gln Val Glu Phe Met Leu Pro
        115                 120                 125

Val Ala His Thr Val Arg Leu Ile Arg Val Thr Ser Thr Ser Ala Ser
    130                 135                 140

Gln Gly Ala Ser Leu Glu His His His His His His
145                 150                 155

<210> SEQ ID NO 55
<211> LENGTH: 2336
<212> TYPE: DNA
<213> ORGANISM: Porcine reproductive and respiratory syndrome virus
<220> FEATURE:
<221> NAME/KEY: CDS
<222> LOCATION: (175)..(234)
<220> FEATURE:
<221> NAME/KEY: CDS
<222> LOCATION: (2134)..(2157)

<400> SEQUENCE: 55
aggcgccagc aaccgcacct gtggcgccgg tgatgccggc cacgatgcgt ccggcgtaga      60
ggatcgagat ctcgatcccg cgaaattaat acgactcact atagggggaat gtgagcgga    120 taacaattcc cctctagaaa taattttgtt aactttaag aaggagatat acat atg       177
                                                            Met
                                                             1 gaa caa aaa ctc atc tca gaa gag gat ctg aat cga tcc atg aat tct      225
Glu Gln Lys Leu Ile Ser Glu Glu Asp Leu Asn Arg Ser Met Asn Ser
        5                  10                  15 agt gga tcc gctgccggca acgggctcg tgctaagcgt gccgctaaaa                274
Ser Gly Ser
        20 gtgagaagga ttcggctccc accccaagg ttgcctgcc ggtccccacc tgtggaatta       334 ccacctactc tccaccgaca gacgggtctt gtggttggca tgtccttgcc gccataatga    394 accggatgat aaatggtgac ttcacgtccc ctctgactca gtacaacaga ccagaggatg    454 attgggcttc tgattatgat cttgttcagg cgattcaatg tctacgactg cctgctaccg    514 tggttcggaa tcgcgcctgt cctaacgcca agtaccttat aaaacttaac ggagttcact    574 gggaggtaga ggtgaggtct ggaatggctc ctcgctccct ttctcgtgaa tgtgtggttg    634 gcgtttgctc tgaaggctgt gtcgcaccgc cttatccagc agacgggcta cctaaacgtg    694 cactcgaggc cttggcgtct gcttacagac taccctccga ttgtgttagc tctggtattg    754 ctgactttct tgctaatcca cctcctcagg aattctggac cctcgacaaa atgttgacct    814 ccccgtcacc agagcggtcc ggcttctcta gtttgtataa attactatta gaggttgttc    874 cgcaaaaatg cggtgccacg gaagggggctt tcatctatgc tgttgagagg atgttgaagg    934 attgtccgag ctccaaacag gccatggccc ttctggcaaa aattaaagtt ccatcctcaa    994 aggccccgtc tgtgtccctg gacgagtgtt tccctacgga tgttttagcc gacttcgagc   1054 cagcatctca ggaaaggccc caaagttccg gcgctgctgt tgtcctgtgt tcaccggatg   1114 caaaagagtt cgaggaagca gccccggaag aagttcaaga gagtggccac aaggccgtcc   1174 actctgcact ccttgccgag ggtcctaaca tgagcaggt acaggtggtt gccggtgagc    1234
```

```
aactgaagct cggcggttgt ggtttggcag tcgggaatgc tcatgaaggt gctctggtct    1294
cagctggtct aattaacctg gtaggcggga atttgtcccc ctcagacccc atgaaagaaa    1354
acatgctcaa tagccgggaa gacgaaccac tggatttgtc ccaaccagca ccagcttcca    1414
caacgaccct tgtgagagag caaacacccg acaacccagg ttctgatgcc ggtgccctcc    1474
ccgtcaccgt tcgagaattt gtcccgacgg ggcctatact ctgtcatgtt gagcactgcg    1534
gcacggagtc gggcgacagc agttcgcctt tggatctatc tgatgcgcaa accctggacc    1594
agcctttaaa tctatccctg ccgcttggc cagtgagggc caccgcgtct gaccctggct     1654
gggtccacgg taggcgcgag cctgtctttg taaagcctcg aaatgctttc tctgatggcg    1714
attcagccct tcagttcggg gagctttctg aatccagctc tgtcatcgag tttgaccgga    1774
caaaagatgc tccggtggtt gacgcccctg tcgacttgac gacttcgaac gaggccctct    1834
ctgtagtcga tcctttcgaa tttgccgaac tcaagcgccc gcgtttctcc gcacaagcct    1894
taattgaccg aggcggtcca cttgccgatg tccatgcaaa aataaagaac cgggtatatg    1954
aacagtgcct ccaagcttgt gagcccggta gtcgtgcaac cccagccacc agggagtggc    2014
tcgacaaaat gtgggatagg gtggacatga aaacttggcg ctgcacctcg cagttccaag    2074
ctggtcgcat tcttgcgtcc ctcaaattcc tccctgacat gattcaagac acaccgcct    2133 ctc gag cac cac cac cac cac cac tgagatccgg ctgctaacaa agcccgaaag    2187
Leu Glu His His His His His His
        25 gaagctgagt tggctgctgc caccgctgag caataactag cataaccct tggggcctct     2247 aaacgggtct tgaggggttt tttgctgaaa ggaggaacta tatccggatt ggcgaatggg    2307 acgcgccctg tagcggcgca ttaagcgcg                                      2336

<210> SEQ ID NO 56
<211> LENGTH: 1899
<212> TYPE: DNA
<213> ORGANISM: Porcine reproductive and respiratory syndrome virus

<400> SEQUENCE: 56
gctgccggca acgggctcg tgctaagcgt gccgctaaaa gtgagaagga ttcggctccc      60
acccccaagg ttgccctgcc ggtccccacc tgtggaatta ccactactc tccaccgaca     120 gacgggtctt gtggttggca tgtccttgcc gccataatga accggatgat aaatggtgac    180
ttcacgtccc ctctgactca gtacaacaga ccagaggatg attgggcttc tgattatgat    240
cttgttcagg cgattcaatg tctacgactg cctgctaccg tggttcggaa tcgcgcctgt    300
cctaacgcca agtaccttat aaaacttaac ggagttcact gggaggtaga ggtgaggtct    360
ggaatggctc ctcgctccct ttctcgtgaa tgtgtggttg gcgtttgctc tgaaggctgt    420
gtcgcaccgc cttatccagc agacgggcta cctaaacgtg cactcgaggc cttggcgtct    480
gcttacagac taccctccga ttgtgttagc tctggtattg ctgactttct tgctaatcca    540
cctcctcagg aattctggac cctcgacaaa atgttgacct cccgtcacc agagcggtcc     600 ggcttctcta gtttgtataa attactatta gaggttgttc cgcaaaaatg cggtgccacg    660
gaagggcttt tcatctatgc tgttgagagg atgttgaagg attgtccgag ctccaaacag    720 gccatgccc ttctggcaaa aattaaagtt ccatcctcaa ggccccgtc tgtgtccctg      780 gacgagtgtt tccctacgga tgttttagcc gacttcgagc cagcatctca ggaaaggccc    840
caaagttccg gcgctgctgt tgtcctgtgt tcaccggatg caaaagagtt cgaggaagca    900
gccccggaag aagttcaaga gagtggccac aaggccgtcc actctgcact ccttgccgag    960
```

```
ggtcctaaca atgagcaggt acaggtggtt gccggtgagc aactgaagct cggcggttgt    1020
ggtttggcag tcgggaatgc tcatgaaggt gctctggtct cagctggtct aattaacctg    1080
gtaggcggga atttgtcccc ctcagacccc atgaaagaaa acatgctcaa tagccgggaa    1140
gacgaaccac tggatttgtc ccaaccagca ccagcttcca caacgaccct tgtgagagag    1200
caaacacccg acaacccagg ttctgatgcc ggtgccctcc ccgtcaccgt tcgagaattt    1260
gtcccgacgg ggcctatact ctgtcatgtt gagcactgcg gcacggagtc gggcgacagc    1320
agttcgcctt tggatctatc tgatgcgcaa accctggacc agcctttaaa tctatccctg    1380
gccgcttggc cagtgagggc caccgcgtct gaccctggct gggtccacgg taggcgcgag    1440
cctgtctttg taaagcctcg aaatgctttc tctgatggcg attcagccct tcagttcggg    1500
gagctttctg aatccagctc tgtcatcgag tttgaccgga caaaagatgc tccggtggtt    1560 gacgccctg tcgacttgac gacttcgaac gaggccctct ctgtagtcga tcctttcgaa    1620
tttgccgaac tcaagcgccc gcgtttctcc gcacaagcct taattgaccg aggcggtcca    1680
cttgccgatg tccatgcaaa aataaagaac cgggtatatg aacagtgcct ccaagcttgt    1740
gagcccggta gtcgtgcaac cccagccacc agggagtggc tcgacaaaat gtgggatagg    1800
gtggacatga aaacttggcg ctgcacctcg cagttccaag ctggtcgcat tcttgcgtcc    1860
ctcaaattcc tccctgacat gattcaagac acaccgcct                           1899
```

<210> SEQ ID NO 57
<211> LENGTH: 2588
<212> TYPE: DNA
<213> ORGANISM: Porcine reproductive and respiratory syndrome virus
<220> FEATURE:
<221> NAME/KEY: CDS
<222> LOCATION: (175)..(234)
<220> FEATURE:
<221> NAME/KEY: CDS
<222> LOCATION: (2386)..(2409)

<400> SEQUENCE: 57

```
aggcgccagc aaccgcacct gtggcgccgg tgatgccggc cacgatgcgt ccggcgtaga     60
ggatcgagat ctcgatcccg cgaaattaat acgactcact ataggggaat tgtgagcgga    120
taacaattcc cctctagaaa taattttgtt taactttaag aaggagatat acat atg     177
                                                                Met
                                                                 1 gaa caa aaa ctc atc tca gaa gag gat ctg aat cga tcc atg aat tct    225
Glu Gln Lys Leu Ile Ser Glu Glu Asp Leu Asn Arg Ser Met Asn Ser
         5                  10                  15 agt gga tcc gctggaaaga gagcaaggaa agcacgctct ggtatgacca             274
Ser Gly Ser
        20 ccacagtcgc tcaccgcgcc ttgcccgctc gtgaaatcca gcaagccaaa agcacgagg    334 atgccggcgc tgataaggct gtgcatctca ggcactattc tccgcctgcc gacgggaact    394 gtggttggca ctgcatttcc gccatcgcca accgaatggt gaattccaaa tttgaaacta    454 ctcttcccga gagggtgaga ccttcagatg actgggctac tgacgaggac cttgtgaaca    514 ccatccaaat tctcaagctc cctgcggcct tggacaggaa cggtgcttgt gttggcgcca    574 aatacgtgct taagctggaa ggcgagcatt ggactgtctc tgtgacccct gggatgtccc    634 cttctttgct cccccttgaa tgtgttcagg gctgttgtga gcataagagc ggacttggtc    694 ccccagatgc ggtcgaagtt tcggatttga acctgcctg ccttgaccga ctggctgagg    754 taatgcactt gcctagcagt gtcatcccag ctgctctggc cgaaatgtcc ggcgaccca    814
```

```
actgtccggc ttccccggtc actactgtgt ggactgtttc acaattcttt gcccgccaca      874
gaggaggaga gcaccctgat caggtgcgct taggaaaaat catcagcctt tgtcaagttg      934
ttgaggaatg ctgttgccat cagaataaaa ccaaccgggc caccccggaa gaggttgcgg      994
caaggattga tcagtacctc catggtgcaa caagtcttga agaatgcttg attaggcttg     1054
agagggtttg cccgccgagc gctgcggaca ccttctttga ttggaatgtt gtgctccctg     1114
gggttgggc ttcaactcag acaaccaaac agctccatgt caaccagtgc cgcgctctgg      1174
ttcctgtcgt gactcaagag cctttggaca aagactcagt ccctctgacc gccttctcgc     1234
tgtccaattg ctactatcct gcacaaggtg acgaggttcg tcaccgtgag aggctaaact     1294
ccgtactctc taagctggag ggggttgttc gtgaggaata tgggctcacg ccaactgaac     1354
ctggcccgcg acccgcacta ccgaacgggc tcgtcgaact taaagaccag atggaggagg     1414
atctgctgaa actagtcaac gcccaggcaa cttcagaaat gatggcctgg gcagccgagc     1474
aggttgatct gaaagcttgg gtcaaaaact acccacggtg gacaccgcca cccctccac     1534
caagagttca gcctcgaaaa acaaagtctg tcaagagctt gccagggaac aaacctgtcc     1594
ccgctccacg caggaaggtc agatctgatt gtggcagccc gattttgatg ggcgacaatg     1654
ttcctgacgg tcgggaagat ttgactgttg gtggccccct tgatctttcg acaccatccg     1714
agccgatgac acctctgagt gagcctgcac ttatgcccgc gttgcaatat atttctaggc     1774
cagtgacatc tttgagtgtg ctggccccag ttcctgcacc gcgtagaact gtgtcccgac     1834
cggtgacgcc cttgagtgag ccaattttg tgtctgcacc gcgacacaaa tttcagcagg      1894
tggaagaagc gaatctggcg gcaacaacgc tgacgcacca ggacgaacct ctagatttgt     1954
ctgcatcctc acagactgaa tatgaggctt ctccctaac accactgcag aacatgggta      2014
ttctggaggt gggggggcaa gaagctgagg aagttctgag tgaaatctcg gatacactga     2074
atgacatcaa ccctgcacct gtgtcatcaa gcagctccct gtcaagtgtt aagatcacac     2134
gcccaaaaca ctctgctcaa gccatcattg actcgggcgg gccctgcagt gggcatctcc     2194
gaagggaaaa agaagcatgc ctcagcatca tgcgtgaggc ttgtgatgcg ctaagctta      2254
gtgaccctgc cacgcaggaa tggctttctc gcatgtggga taggttgac atgctgactt      2314
ggcgcaacac gtctgcttac caggcgttcc gcatcttaga tggtaggttt gagtttctcc     2374
caaagatgat a ctc gag cac cac cac cac cac cac tgagatccgg              2419
              Leu Glu His His His His His His
                           25
ctgctaacaa agcccgaaag gaagctgagt tggctgctgc caccgctgag caataactag      2479
cataacccct tggggcctct aaacgggtct tgagggtttt tttgctgaaa ggaggaacta     2539
tatccggatt ggcgaatggg acgcgccctg tagcggcgca ttaagcgcg               2588
```

<210> SEQ ID NO 58
<211> LENGTH: 2151
<212> TYPE: DNA
<213> ORGANISM: Porcine reproductive and respiratory syndrome virus

<400> SEQUENCE: 58

```
gctggaaaga gagcaaggaa agcacgctct ggtatgacca ccacagtcgc tcaccgcgcc       60
ttgcccgctc gtgaaatcca gcaagccaaa aagcacgagg atgccggcgc tgataaggct      120
gtgcatctca ggcactattc tccgcctgcc gacgggaact gtggttggca ctgcatttcc      180
gccatcgcca accgaatggt gaattccaaa tttgaaacta ctcttcccga gagggtgaga      240
ccttcagatg actgggctac tgacgaggac cttgtgaaca ccatccaaat tctcaagctc      300
```

```
cctgcggcct tggacaggaa cggtgcttgt gttggcgcca aatacgtgct taagctggaa    360
ggcgagcatt ggactgtctc tgtgacccct gggatgtccc cttctttgct ccccttgaa     420 tgtgttcagg gctgttgtga gcataagagc ggacttggtc ccccagatgc ggtcgaagtt    480
ttcggatttg accctgcctg ccttgaccga ctggctgagg taatgcactt gcctagcagt    540
gtcatcccag ctgctctggc cgaaatgtcc ggcgacccca actgtccggc ttccccggtc    600
actactgtgt ggactgtttc acaattcttt gcccgccaca gaggaggaga gcaccctgat    660
caggtgcgct taggaaaaat catcagcctt tgtcaagttg ttgaggaatg ctgttgccat    720
cagaataaaa ccaaccgggc caccccggaa gaggttgcgg caaggattga tcagtacctc    780
catggtgcaa caagtcttga agaatgcttg attaggcttg agagggtttg cccgccgagc    840
gctgcggaca ccttctttga ttggaatgtt gtgctccctg ggttggggc ttcaactcag     900 acaaccaaac agctccatgt caaccagtgc cgcgctctgg ttcctgtcgt gactcaagag    960
cctttggaca aagactcagt ccctctgacc gccttctcgc tgtccaattg ctactatcct   1020
gcacaaggtg acgaggttcg tcaccgtgag aggctaaact ccgtactctc taagctggag   1080
ggggttgttc gtgaggaata tgggctcacg ccaactgaac ctggcccgcg acccgcacta   1140
ccgaacgggc tcgtcgaact aaagaccag atggaggagg atctgctgaa actagtcaac    1200
gcccaggcaa cttcagaaat gatggcctgg gcagccgagc aggttgatct gaaagcttgg   1260
gtcaaaaact acccacggtg gacaccgcca ccccctccac caagagttca gcctcgaaaa   1320
acaaagtctg tcaagagctt gccagggaac aaacctgtcc ccgctccacg caggaaggtc   1380
agatctgatt gtggcagccc gattttgatg ggcgacaatg ttcctgacgg tcgggaagat   1440
ttgactgttg gtggccccct tgatctttcg acaccatccg agccgatgac acctctgagt   1500
gagcctgcac ttatgcccgc gttgcaatat atttctaggc cagtgacatc tttgagtgtg   1560
ctggccccag ttcctgcacc gcgtagaact gtgtcccgac cggtgacgcc cttgagtgag   1620
ccaatttttg tgtctgcacc gcgacacaaa tttcagcagg tggaagaagc gaatctggcg   1680
gcaacaacgc tgacgcacca ggacgaacct ctagatttgt ctgcatcctc acagactgaa   1740
tatgaggctt ctcccctaac accactgcag aacatgggta ttctggaggt ggggggcaa    1800 gaagctgagg aagttctgag tgaaatctcg gatacactga atgacatcaa ccctgcacct   1860
gtgtcatcaa gcagctccct gtcaagtgtt aagatcacac gcccaaaaca ctctgctcaa   1920
gccatcattg actcgggcgg gccctgcagt gggcatctcc gaagggaaaa agaagcatgc   1980
ctcagcatca tgcgtgaggc ttgtgatgcg gctaagctta gtgaccctgc cacgcaggaa   2040 tggcttctc gcatgtggga tagggttgac atgctgactt ggcgcaacac gtctgcttac    2100
caggcgttcc gcatcttaga tggtaggttt gagtttctcc caaagatgat a            2151
```

<210> SEQ ID NO 59
<211> LENGTH: 907
<212> TYPE: DNA
<213> ORGANISM: Porcine reproductive and respiratory syndrome virus
<220> FEATURE:
<221> NAME/KEY: CDS
<222> LOCATION: (175)..(735)

<400> SEQUENCE: 59

```
aggcgccagc aaccgcacct gtggcgccgg tgatgccggc cacgatgcgt ccggcgtaga     60
ggatcgagat ctcgatcccg cgaaattaat acgactcact ataggggaat tgtgagcgga    120
taacaattcc cctctagaaa taattttgtt taactttaag aaggagatat acat atg      177
                                                                   Met
```

```
gaa caa aaa ctc atc tca gaa gag gat ctg aat cga tcc atg aat tct      225
Glu Gln Lys Leu Ile Ser Glu Glu Asp Leu Asn Arg Ser Met Asn Ser
          5                  10                  15 agt gga tcc ggc agc ccg att ttg atg ggc gac aat gtt cct gac ggt      273
Ser Gly Ser Gly Ser Pro Ile Leu Met Gly Asp Asn Val Pro Asp Gly
         20                  25                  30 cgg gaa gat ttg cct gtt ggt ggc ccc ctt gat ctt tcg aca cca tcc      321
Arg Glu Asp Leu Pro Val Gly Gly Pro Leu Asp Leu Ser Thr Pro Ser
     35                  40                  45 gag ccg atg aca cct ctg agt gag cct gca cct atg ccc gcg ttg caa      369
Glu Pro Met Thr Pro Leu Ser Glu Pro Ala Pro Met Pro Ala Leu Gln
 50                  55                  60                  65 tat att tct agg cca gtg aca cct ttg agt gag ctg gcc cca gta cct      417
Tyr Ile Ser Arg Pro Val Thr Pro Leu Ser Glu Leu Ala Pro Val Pro
             70                  75                  80 gca ccg cgt aga act gtg tcc cga ccg gtg acg ccc ttg agt gag cca      465
Ala Pro Arg Arg Thr Val Ser Arg Pro Val Thr Pro Leu Ser Glu Pro
         85                  90                  95 att ttt gtg tct gca ccg cga cac aaa ttt cgg cag gtg gaa gaa gcg      513
Ile Phe Val Ser Ala Pro Arg His Lys Phe Arg Gln Val Glu Glu Ala
    100                 105                 110 aat ctg gcg gca aca atg ctg acg cac cag gac gaa cct cta gat ttg      561
Asn Leu Ala Ala Thr Met Leu Thr His Gln Asp Glu Pro Leu Asp Leu
115                 120                 125 tct gca tcc tca cag act gaa tat gag gct tct ccc cta aca cca ctg      609
Ser Ala Ser Ser Gln Thr Glu Tyr Glu Ala Ser Pro Leu Thr Pro Leu
130                 135                 140                 145 cag aac atg ggt att ctt gag gtg ggg ggg caa gaa gct gag gaa gtt      657
Gln Asn Met Gly Ile Leu Glu Val Gly Gly Gln Glu Ala Glu Glu Val
                150                 155                 160 ctg agt gaa aac tcg gat aca ctg aat gac atc aac cct gca cct gtg      705
Leu Ser Glu Asn Ser Asp Thr Leu Asn Asp Ile Asn Pro Ala Pro Val
            165                 170                 175 tca tca ctc gag cac cac cac cac cac cac tgagatccgg ctgctaacaa      755
Ser Ser Leu Glu His His His His His His
        180                 185 agcccgaaag gaagctgagt tggctgctgc caccgctgag caataactag cataacccct     815
tggggcctct aaacgggtct tgagggtttt tttgctgaaa ggaggaacta tatccggatt     875
ggcgaatggg acgcgccctg tagcggcgca tt                                   907

<210> SEQ ID NO 60
<211> LENGTH: 477
<212> TYPE: DNA
<213> ORGANISM: Porcine reproductive and respiratory syndrome virus

<400> SEQUENCE: 60
ggcagcccga ttttgatggg cgacaatgtt cctgacggtc gggaagattt gcctgttggt      60 ggccccttg atctttcgac accatccgag ccgatgacac tctgagtga gcctgcacct     120 atgcccgcgt tgcaatatat ttctaggcca gtgacacctt tgagtgagct ggccccagta     180
cctgcaccgc gtagaactgt gtcccgaccg gtgacgccct tgagtgagcc aattttttgtg    240 tctgcaccgc gacacaaatt tcggcaggtg gaagaagcga atctggcggc aacaatgctg     300
acgcaccagg acgaacctct agatttgtct gcatcctcac agactgaata tgaggcttct     360
cccctaacac cactgcagaa catgggtatt cttgaggtgg gggggcaaga agctgaggaa     420
gttctgagtg aaaactcgga tacactgaat gacatcaacc ctgcacctgt gtcatca        477
```

-continued

<210> SEQ ID NO 61
<211> LENGTH: 187
<212> TYPE: PRT
<213> ORGANISM: Porcine reproductive and respiratory syndrome virus

<400> SEQUENCE: 61

Met Glu Gln Lys Leu Ile Ser Glu Glu Asp Leu Asn Arg Ser Met Asn
1               5                   10                  15

Ser Ser Gly Ser Gly Ser Pro Ile Leu Met Gly Asp Asn Val Pro Asp
            20                  25                  30

Gly Arg Glu Asp Leu Pro Val Gly Gly Pro Leu Asp Leu Ser Thr Pro
        35                  40                  45

Ser Glu Pro Met Thr Pro Leu Ser Glu Pro Ala Pro Met Pro Ala Leu
    50                  55                  60

Gln Tyr Ile Ser Arg Pro Val Thr Pro Leu Ser Glu Leu Ala Pro Val
65              70                  75                  80

Pro Ala Pro Arg Arg Thr Val Ser Arg Pro Val Thr Pro Leu Ser Glu
                85                  90                  95

Pro Ile Phe Val Ser Ala Pro Arg His Lys Phe Arg Gln Val Glu Glu
            100                 105                 110

Ala Asn Leu Ala Ala Thr Met Leu Thr His Gln Asp Glu Pro Leu Asp
        115                 120                 125

Leu Ser Ala Ser Ser Gln Thr Glu Tyr Glu Ala Ser Pro Leu Thr Pro
    130                 135                 140

Leu Gln Asn Met Gly Ile Leu Glu Val Gly Gly Gln Glu Ala Glu Glu
145                 150                 155                 160

Val Leu Ser Glu Asn Ser Asp Thr Leu Asn Asp Ile Asn Pro Ala Pro
                165                 170                 175

Val Ser Ser Leu Glu His His His His His His
            180                 185

<210> SEQ ID NO 62
<211> LENGTH: 644
<212> TYPE: DNA
<213> ORGANISM: Porcine reproductive and respiratory syndrome virus
<220> FEATURE:
<221> NAME/KEY: CDS
<222> LOCATION: (175)..(465)

<400> SEQUENCE: 62
aggcgccagc aaccgcacct gtggcgccgg tgatgccggc cacgatgcgt ccggcgtaga      60
ggatcgagat ctcgatcccg cgaaattaat acgactcact ataggggaat tgtgagcgga     120
taacaattcc cctctagaaa taattttgtt aactttaag aaggagatat acat atg        177
                                                             Met
                                                             1 gaa caa aaa ctc atc tca gaa gag gat ctg aat cga tcc atg aat tct       225
Glu Gln Lys Leu Ile Ser Glu Glu Asp Leu Asn Arg Ser Met Asn Ser
                5                   10                  15 agt gga tcc tgc atg gcc tgc cgc tat gcc cgt acc cgg ttt acc aac       273
Ser Gly Ser Cys Met Ala Cys Arg Tyr Ala Arg Thr Arg Phe Thr Asn
            20                  25                  30 ttc att gtg gac gac cgg ggg aga gtt cat cga tgg aag tct cca ata       321
Phe Ile Val Asp Asp Arg Gly Arg Val His Arg Trp Lys Ser Pro Ile
        35                  40                  45 gtg gta gaa aaa ttg ggc aaa gcc gaa gtc gat ggc aac ctc gtc acc       369
Val Val Glu Lys Leu Gly Lys Ala Glu Val Asp Gly Asn Leu Val Thr
    50                  55                  60                  65 atc aaa cat gtc gtc ctc gaa ggg gtt aaa gct caa ccc ttg acg agg       417

```
Ile Lys His Val Val Leu Glu Gly Val Lys Ala Gln Pro Leu Thr Arg
            70                  75                  80 act tcg gct gag caa tgg gag gcc ctc gag cac cac cac cac cac cac    465
Thr Ser Ala Glu Gln Trp Glu Ala Leu Glu His His His His His His
            85                  90                  95 tgagatccgg ctgctaacaa agcccgaaag gaagctgagt tggctgctgc caccgctgag    525
caataactag cataaccect tgggcctct aaacgggtct tgaggggttt tttgctgaaa    585
ggaggaacta tatccggatt ggcgaatggg acgcgccctg tagcggcgca ttaagcgcg    644

<210> SEQ ID NO 63
<211> LENGTH: 207
<212> TYPE: DNA
<213> ORGANISM: Porcine reproductive and respiratory syndrome virus

<400> SEQUENCE: 63
tgcatggcct gccgctatgc ccgtacccgg tttaccaact tcattgtgga cgaccggggg    60
agagttcatc gatggaagtc tccaatagtg gtagaaaaat tgggcaaagc cgaagtcgat    120
ggcaacctcg tcaccatcaa acatgtcgtc ctcgaagggg ttaaagctca accettgacg    180 aggacttcgg ctgagcaatg ggaggcc                                       207

<210> SEQ ID NO 64
<211> LENGTH: 97
<212> TYPE: PRT
<213> ORGANISM: Porcine reproductive and respiratory syndrome virus

<400> SEQUENCE: 64

Met Glu Gln Lys Leu Ile Ser Glu Glu Asp Leu Asn Arg Ser Met Asn
  1               5                  10                  15

Ser Ser Gly Ser Cys Met Ala Cys Arg Tyr Ala Arg Thr Arg Phe Thr
            20                  25                  30

Asn Phe Ile Val Asp Asp Arg Gly Arg Val His Arg Trp Lys Ser Pro
        35                  40                  45

Ile Val Val Glu Lys Leu Gly Lys Ala Glu Val Asp Gly Asn Leu Val
    50                  55                  60

Thr Ile Lys His Val Val Leu Glu Gly Val Lys Ala Gln Pro Leu Thr
 65                  70                  75                  80

Arg Thr Ser Ala Glu Gln Trp Glu Ala Leu Glu His His His His
                85                  90                  95

His

<210> SEQ ID NO 65
<211> LENGTH: 694
<212> TYPE: DNA
<213> ORGANISM: Porcine reproductive and respiratory syndrome virus
<220> FEATURE:
<221> NAME/KEY: CDS
<222> LOCATION: (175)..(522)

<400> SEQUENCE: 65
aggcgccagc aaccgcacct gtggcgccgg tgatgccggc cacgatgcgt ccggcgtaga    60
ggatcgagat ctcgatcccg cgaaattaat acgactcact atagggaat tgtgagcgga   120 taacaattcc cctctagaaa taattttgtt taactttaag aaggagatat acat atg    177
                                                              Met
                                                                1 gaa caa aaa ctc atc tca gaa gag gat ctg aat cga tcc atg aat tct    225
Glu Gln Lys Leu Ile Ser Glu Glu Asp Leu Asn Arg Ser Met Asn Ser
          5                  10                  15
```

```
agt gga tcc agc ttc aca gag tca tgg aag ttt atc act tcc aga tgc    273
Ser Gly Ser Ser Phe Thr Glu Ser Trp Lys Phe Ile Thr Ser Arg Cys
         20                  25                  30 aga ttg tgt tgc ctt ggc cgg cga tac att ctg gcc cct gcc cat cac    321
Arg Leu Cys Cys Leu Gly Arg Arg Tyr Ile Leu Ala Pro Ala His His
         35                  40                  45 gta gaa agt gct gca ggt ctc cat tca atc tca gcg tct ggt aac cga    369
Val Glu Ser Ala Ala Gly Leu His Ser Ile Ser Ala Ser Gly Asn Arg
 50                  55                  60                  65 gca tac gct gtg aga aag ccc gga cta aca tca gtg aac ggc act cta    417
Ala Tyr Ala Val Arg Lys Pro Gly Leu Thr Ser Val Asn Gly Thr Leu
                 70                  75                  80 gta cca gga ctt cgg agc ctc gtg ctg ggc ggc aaa cga gct gtt aaa    465
Val Pro Gly Leu Arg Ser Leu Val Leu Gly Gly Lys Arg Ala Val Lys
             85                  90                  95 cga gga gtg gtt aac ctc gtc aag tat ggc cgg ctc gag cac cac cac    513
Arg Gly Val Val Asn Leu Val Lys Tyr Gly Arg Leu Glu His His His
100                 105                 110 cac cac cac tgagatccgg ctgctaacaa agcccgaaag gaagctgagt            562
His His His
        115 tggctgctgc caccgctgag caataactag cataacccct tggggcctct aaacgggtct  622 tgaggggttt tttgctgaaa ggaggaacta tatccggatt ggcgaatggg acgcgccctg  682 tagcggcgca tt                                                     694

<210> SEQ ID NO 66
<211> LENGTH: 264
<212> TYPE: DNA
<213> ORGANISM: Porcine reproductive and respiratory syndrome virus

<400> SEQUENCE: 66
agcttcacag agtcatggaa gtttatcact tccagatgca gattgtgttg ccttggccgg   60
cgatacattc tggcccctgc ccatcacgta gaaagtgctg caggtctcca ttcaatctca  120
gcgtctggta accgagcata cgctgtgaga aagcccggac taacatcagt gaacggcact  180
ctagtaccag gacttcggag cctcgtgctg ggcggcaaac gagctgttaa acgaggagtg  240
gttaacctcg tcaagtatgg ccgg                                        264

<210> SEQ ID NO 67
<211> LENGTH: 116
<212> TYPE: PRT
<213> ORGANISM: Porcine reproductive and respiratory syndrome virus

<400> SEQUENCE: 67

Met Glu Gln Lys Leu Ile Ser Glu Glu Asp Leu Asn Arg Ser Met Asn
 1               5                  10                  15

Ser Ser Gly Ser Ser Phe Thr Glu Ser Trp Lys Phe Ile Thr Ser Arg
             20                  25                  30

Cys Arg Leu Cys Cys Leu Gly Arg Arg Tyr Ile Leu Ala Pro Ala His
         35                  40                  45

His Val Glu Ser Ala Ala Gly Leu His Ser Ile Ser Ala Ser Gly Asn
     50                  55                  60

Arg Ala Tyr Ala Val Arg Lys Pro Gly Leu Thr Ser Val Asn Gly Thr
 65                  70                  75                  80

Leu Val Pro Gly Leu Arg Ser Leu Val Leu Gly Gly Lys Arg Ala Val
                 85                  90                  95

Lys Arg Gly Val Val Asn Leu Val Lys Tyr Gly Arg Leu Glu His His
            100                 105                 110
```

His His His His
    115

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 68
aggtcgtgta ctgtcagtca                                              20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 69
acgtggtgaa ctgccagtga                                              20

<210> SEQ ID NO 70
<211> LENGTH: 719
<212> TYPE: PRT
<213> ORGANISM: Porcine reproductive and respiratory syndrome virus

<400> SEQUENCE: 70

Ala Gly Lys Arg Ala Arg Lys Ala Arg Ser Gly Ala Thr Ala Thr Val
 1               5                  10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
65                  70                  75                  80

Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Glu His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asn Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

```
Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Ser Phe Asp Trp
        275                 280                 285

Asp Val Val Leu Pro Gly Val Glu Ala Ala Thr Gln Thr Thr Lys Leu
        290                 295                 300

Pro Gln Val Asn Gln Cys Arg Ala Leu Val Pro Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Gly Val Val Arg Glu Glu Tyr Gly
            355                 360                 365

Leu Met Pro Thr Glu Pro Gly Pro Arg Pro Thr Leu Pro Arg Gly Leu
370                 375                 380

Asp Glu Leu Lys Asp Gln Met Glu Glu Asp Leu Leu Lys Leu Ala Asn
385                 390                 395                 400

Ala Gln Ala Thr Ser Asp Met Met Ala Trp Ala Ala Glu Gln Val Asp
            405                 410                 415

Leu Lys Thr Trp Val Lys Asn Tyr Pro Arg Trp Thr Pro Pro Pro
        420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
        450                 455                 460

Gly Ser Pro Val Leu Leu Gly Gly Asn Val Pro Asn Ser Trp Glu Asp
465                 470                 475                 480

Leu Ala Val Gly Gly Pro Leu Asp Leu Pro Thr Pro Glu Pro Ala
            485                 490                 495

Thr Pro Leu Ser Glu Pro Val Leu Val Ser Ala Pro Gln Cys Ile Phe
            500                 505                 510

Arg Pro Val Thr Pro Leu Ser Glu Pro Ala Pro Val Pro Ala Pro Arg
        515                 520                 525

Gly Thr Val Ser Arg Pro Val Thr Pro Leu Ser Glu Pro Ile Pro Val
        530                 535                 540

Pro Ala Pro Arg Arg Lys Phe Gln Gln Val Glu Arg Ala Asn Ser Ala
545                 550                 555                 560

Ala Ala Thr Pro Thr Tyr Gln Asp Glu Pro Leu Asp Leu Ser Ala Ser
            565                 570                 575

Ser Gln Thr Glu Tyr Glu Ala Ser Pro Leu Ala Pro Pro Gln Asn Gly
        580                 585                 590

Gly Val Leu Glu Val Glu Gly Gln Glu Ala Glu Val Leu Ser Glu
            595                 600                 605

Ile Ser Asp Met Leu Gly Asp Ile Lys Pro Ala Ser Val Ser Ser Ser
610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
            645                 650                 655
```

```
Lys Glu Ala Cys Leu Ser Ile Met Arg Glu Ala Cys Asp Ala Thr Lys
                660                 665                 670

Leu Asp Asp Pro Ala Thr Gln Glu Trp Leu Ser Arg Met Trp Asp Arg
            675                 680                 685

Val Asp Met Leu Thr Trp Arg Asn Thr Ser Val Tyr Gln Ala Ile Arg
        690                 695                 700

Thr Leu Asp Gly Arg Leu Lys Phe Leu Pro Lys Met Ile Leu Glu
705                 710                 715

<210> SEQ ID NO 71
<211> LENGTH: 719
<212> TYPE: PRT
<213> ORGANISM: Porcine reproductive and respiratory syndrome virus

<400> SEQUENCE: 71

Ala Gly Lys Arg Ala Arg Lys Ala Arg Ser Cys Ala Thr Ala Thr Val
  1               5                  10                  15

Ala Gly Arg Ala Leu Ser Val Arg Glu Thr Arg Gln Ala Lys Glu His
             20                  25                  30

Glu Val Ala Gly Ala Asn Lys Ala Glu His Leu Lys His Tyr Ser Pro
         35                  40                  45

Pro Ala Glu Gly Asn Cys Gly Trp His Cys Ile Ser Ala Ile Ala Asn
     50                  55                  60

Arg Met Val Asn Ser Lys Phe Glu Thr Thr Leu Pro Glu Arg Val Arg
 65                  70                  75                  80

Pro Pro Asp Asp Trp Ala Thr Asp Glu Asp Leu Val Asn Ala Ile Gln
                 85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Phe
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Pro Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Val Thr Gln Lys
305                 310                 315                 320
```

Ser Leu Asp Asn Asn Ser Val Pro Leu Thr Ala Phe Ser Leu Ala Asn
            325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Lys Val Val Arg Glu Glu Tyr Gly
            355                 360                 365

Leu Met Pro Thr Lys Pro Gly Pro Arg Pro Thr Leu Pro Arg Gly Leu
370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Ala Glu Gln Val Asp
            405                 410                 415

Leu Lys Thr Trp Val Lys Asn Tyr Pro Arg Trp Thr Pro Pro Pro
            420                 425                 430

Ser Pro Lys Val Gln Leu Arg Lys Thr Lys Pro Val Lys Ser Leu Pro
            435                 440                 445

Lys Arg Lys Pro Val Pro Ala Pro Arg Arg Lys Val Gly Ser Asp Cys
450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Pro Glu Pro Ala
            485                 490                 495

Ile Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
            515                 520                 525

Gly Thr Val Ser Arg Pro Val Thr Pro Leu Ser Glu Pro Ile Pro Val
            530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
            565                 570                 575

Ser Gln Thr Glu Tyr Glu Ala Ser Pro Pro Ala Pro Pro Gln Ser Gly
            580                 585                 590

Gly Val Leu Gly Val Glu Gly His Glu Ala Glu Glu Thr Leu Ser Glu
            595                 600                 605

Ile Ser Asp Met Ser Gly Asn Ile Lys Pro Ala Ser Val Ser Ser Ser
610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
            645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
            675                 680                 685

Val Asp Met Leu Thr Trp Arg Asn Thr Ser Val Tyr Gln Val Ile Cys
            690                 695                 700

Thr Leu Asp Gly Met Leu Lys Phe Leu Pro Lys Met Ile Leu Glu
705                 710                 715

<210> SEQ ID NO 72
<211> LENGTH: 719
<212> TYPE: PRT

<213> ORGANISM: Porcine reproductive and respiratory syndrome virus

<400> SEQUENCE: 72

Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
65                  70                  75                  80

Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Phe Phe Asp Trp
        275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Lys Val Val Arg Glu Glu Tyr Gly
        355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp

```
                    405                 410                 415
Leu Lys Thr Trp Val Lys Asn Tyr Pro Arg Trp Thr Pro Pro Pro
            420                 425                 430

Pro Pro Lys Val Gln Pro Arg Lys Thr Lys Pro Val Lys Ser Leu Pro
        435                 440                 445

Glu Arg Lys Pro Val Pro Ala Pro Arg Arg Lys Val Gly Ser Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Glu Pro Ala
            485                 490                 495

Thr Pro Ser Ser Glu Leu Val Ile Val Ser Ser Pro Gln Cys Ile Phe
        500                 505                 510

Arg Pro Ala Thr Pro Leu Ser Glu Pro Ala Pro Ile Pro Ala Pro Arg
    515                 520                 525

Gly Thr Val Ser Arg Pro Val Thr Pro Leu Ser Glu Pro Ile Pro Val
530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
            565                 570                 575

Ser Gln Thr Glu Tyr Glu Ala Ser Pro Ala Pro Pro Gln Ser Gly
        580                 585                 590

Gly Val Leu Gly Val Glu Gly His Glu Ala Glu Glu Thr Leu Ser Glu
    595                 600                 605

Ile Ser Asp Met Ser Gly Asn Ile Lys Pro Ala Ser Val Ser Ser Ser
610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
            645                 650                 655

Lys Glu Thr Cys Leu Ser Val Met Arg Glu Ala Cys Asp Ala Thr Lys
        660                 665                 670

Leu Asp Asp Pro Ala Thr Gln Glu Trp Leu Ser Arg Met Trp Asp Arg
    675                 680                 685

Val Asp Met Leu Thr Trp Arg Asn Thr Ser Val Tyr Gln Ala Ile Cys
690                 695                 700

Thr Leu Asn Gly Arg Leu Lys Phe Leu Pro Lys Met Ile Leu Glu
705                 710                 715

<210> SEQ ID NO 73
<211> LENGTH: 719
<212> TYPE: PRT
<213> ORGANISM: Porcine reproductive and respiratory syndrome virus

<400> SEQUENCE: 73

Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
```

```
                65                  70                  75                  80
Pro Pro Asp Asp Trp Ala Thr Asp Glu Asp Leu Val Asn Ala Ile Gln
                    85                  90                  95

Ile Leu Arg Leu Pro Ala Ala Leu Asp Arg Asn Gly Ala Cys Thr Ser
                100                 105                 110

Ala Lys Tyr Val Leu Lys Leu Glu Gly Glu His Trp Thr Val Thr Val
                115                 120                 125

Thr Pro Gly Met Ser Pro Ser Leu Leu Pro Leu Glu Cys Val Gln Gly
                130                 135                 140

Cys Cys Gly His Lys Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Ser Gly Asp
                180                 185                 190

Ser Asp Arg Ser Ala Ser Pro Val Thr Thr Val Trp Thr Val Ser Gln
                195                 200                 205

Phe Phe Ala Arg His Ser Gly Gly Asn His Pro Asp Gln Val Arg Leu
                210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
                260                 265                 270

Leu Glu Lys Ala Arg Pro Pro Arg Val Ile Asp Thr Phe Phe Asp Trp
                275                 280                 285

Asp Val Val Leu Pro Gly Val Glu Ala Ala Thr Gln Thr Ile Lys Leu
                290                 295                 300

Pro Gln Val Asn Gln Cys Arg Ala Leu Val Pro Val Thr Gln Lys
305                 310                 315                 320

Ser Leu Asp Asn Asn Ser Val Pro Leu Thr Ala Phe Ser Leu Ala Asn
                325                 330                 335

His Tyr Tyr Arg Ala Gln Gly Asp Glu Val Arg His Arg Glu Arg Leu
                340                 345                 350

Thr Ala Val Leu Ser Asn Leu Glu Lys Val Val Arg Glu Tyr Gly
                355                 360                 365

Leu Met Pro Thr Glu Pro Gly Pro Arg Pro Thr Leu Pro Arg Gly Leu
                370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro
                420                 425                 430

Pro Pro Lys Val Gln Pro Arg Lys Thr Lys Pro Val Lys Ser Leu Pro
                435                 440                 445

Glu Arg Lys Pro Val Pro Ala Pro Arg Arg Lys Val Gly Ser Asp Cys
                450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Pro Glu Pro Ala
                485                 490                 495
```

-continued

```
Thr Pro Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
        515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asn Glu Pro Leu Asp Leu Ser Ala Ser
                565                 570                 575

Ser Gln Thr Glu Tyr Glu Ala Ser Pro Ala Pro Gln Ser Gly
            580                 585                 590

Gly Val Leu Gly Val Glu Gly His Glu Ala Glu Thr Leu Ser Glu
    595                 600                 605

Ile Ser Asp Met Ser Gly Asn Ile Lys Pro Ala Ser Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
                645                 650                 655

Lys Glu Ala Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
        675                 680                 685

Val Asp Met Leu Thr Trp Arg Asn Thr Ser Val Tyr Gln Ala Ile Cys
    690                 695                 700

Thr Leu Asp Gly Arg Leu Lys Phe Leu Pro Lys Met Ile Leu Glu
705                 710                 715

<210> SEQ ID NO 74
<211> LENGTH: 719
<212> TYPE: PRT
<213> ORGANISM: Porcine reproductive and respiratory syndrome virus

<400> SEQUENCE: 74

Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asn Lys Ala Glu His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Lys Phe Glu Thr Thr Leu Pro Glu Arg Val Arg
65                  70                  75                  80

Pro Pro Asp Asp Trp Ala Thr Asp Glu Asp Leu Val Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Gly His Lys Gly Gly Leu Gly Ser Pro Asp Ala Val Glu Val
145                 150                 155                 160
```

-continued

```
Ser Gly Phe Asp Pro Ala Cys Leu Asp Arg Leu Ala Glu Val Met His
            165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
            195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Ser Phe Asp Trp
            275                 280                 285

Asp Val Val Leu Pro Gly Val Glu Ala Ala Thr Gln Thr Ile Lys Leu
    290                 295                 300

Pro Gln Val Asn Gln Cys Arg Ala Leu Val Pro Val Thr Gln Lys
305                 310                 315                 320

Ser Leu Asp Asn Asn Ser Val Pro Leu Thr Ala Phe Ser Leu Ala Asn
            325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Lys Val Val Arg Glu Glu Tyr Gly
            355                 360                 365

Leu Met Pro Thr Glu Pro Gly Pro Arg Pro Thr Leu Pro Arg Gly Leu
    370                 375                 380

Asp Glu Leu Lys Asp Gln Met Glu Glu Asp Leu Leu Lys Leu Ala Asn
385                 390                 395                 400

Ala Gln Thr Thr Ser Asp Met Met Ala Trp Ala Val Glu Gln Val Asp
                405                 410                 415

Leu Lys Thr Trp Val Lys Asn Tyr Pro Arg Trp Thr Pro Pro Pro
            420                 425                 430

Pro Pro Lys Val Gln Pro Arg Lys Thr Lys Pro Val Lys Ser Leu Pro
            435                 440                 445

Glu Arg Lys Pro Val Pro Ala Pro Arg Arg Lys Val Gly Ser Asp Cys
    450                 455                 460

Gly Ser Pro Val Ser Leu Gly Gly Asp Val Pro Asn Ser Trp Glu Asp
465                 470                 475                 480

Leu Ala Val Ser Ser Pro Phe Asp Leu Pro Thr Pro Glu Pro Ala
                485                 490                 495

Thr Pro Ser Ser Glu Leu Val Ile Val Ser Ser Pro Gln Cys Ile Phe
            500                 505                 510

Arg Pro Ala Thr Pro Leu Ser Glu Pro Ala Ile Pro Ala Pro Arg
            515                 520                 525

Gly Thr Val Ser Arg Pro Val Thr Pro Leu Ser Glu Pro Ile Pro Val
    530                 535                 540

Pro Ala Pro Arg Arg Lys Phe Gln Gln Val Lys Arg Leu Ser Ser Ala
545                 550                 555                 560

Ala Ala Ile Pro Pro Tyr Gln Asp Glu Pro Leu Asp Leu Ser Ala Ser
                565                 570                 575

Ser Gln Thr Glu Tyr Glu Ala Ser Pro Pro Ala Pro Pro Gln Ser Gly
            580                 585                 590
```

```
Gly Val Leu Gly Val Glu Gly His Glu Ala Glu Thr Leu Ser Glu
            595                 600                 605

Ile Ser Asp Met Ser Gly Asn Ile Lys Pro Ala Ser Val Ser Ser Ser
610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Glu Val
            645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
            675                 680                 685

Val Asp Met Leu Thr Trp Arg Asn Thr Ser Val Tyr Gln Ala Ile Cys
            690                 695                 700

Thr Leu Asp Gly Arg Leu Lys Phe Leu Pro Lys Met Ile Leu Glu
705                 710                 715

<210> SEQ ID NO 75
<211> LENGTH: 719
<212> TYPE: PRT
<213> ORGANISM: Porcine reproductive and respiratory syndrome virus

<400> SEQUENCE: 75

Ala Gly Lys Arg Ala Arg Lys Ala Arg Ser Cys Ala Thr Ala Thr Val
1               5                   10                  15

Ala Gly Arg Ala Leu Ser Val Arg Glu Thr Arg Gln Ala Lys Glu His
            20                  25                  30

Glu Val Ala Gly Ala Asp Lys Ala Glu His Leu Lys His Tyr Ser Pro
        35                  40                  45

Pro Ala Glu Gly Asn Cys Gly Trp His Cys Ile Ser Ala Ile Ala Asn
    50                  55                  60

Arg Met Val Asn Ser Ile Phe Glu Thr Thr Leu Pro Glu Arg Val Arg
65                  70                  75                  80

Pro Pro Asp Asp Trp Ala Thr Asp Asp Asp Leu Ala Asn Ala Ile Gln
                85                  90                  95

Ile Leu Arg Leu Pro Ala Ala Leu Asp Arg Asn Gly Ala Cys Thr Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Glu His Lys Gly Gly Leu Gly Ser Pro Asp Ala Ile Glu Val
145                 150                 155                 160

Ser Gly Phe Asp Pro Ala Cys Leu Asp Trp Leu Ala Glu Val Met His
                165                 170                 175

Leu Pro Ser Ser Ala Ile Pro Ala Ala Leu Ala Glu Met Ser Gly Asp
            180                 185                 190

Ser Asp Arg Ser Ala Ser Pro Val Thr Thr Val Trp Thr Val Ser Gln
        195                 200                 205

Phe Phe Ala Arg His Ser Gly Gly Asn His Pro Asp Gln Val Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255
```

```
Asp Leu Tyr Leu Arg Gly Ala Thr Asn Leu Glu Glu Cys Leu Ala Arg
            260                 265                 270

Leu Glu Lys Ala Arg Pro Pro Arg Val Ile Asp Thr Ser Phe Asp Trp
            275                 280                 285

Asp Val Val Leu Pro Gly Val Glu Ala Ala Thr Gln Thr Asn Lys Leu
            290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
            325                 330                 335

Tyr Tyr Tyr Arg Ala Gln Gly Asp Glu Val Arg His Arg Glu Arg Leu
            340                 345                 350

Thr Ala Val Leu Ser Lys Leu Glu Glu Val Val Arg Glu Glu Tyr Gly
            355                 360                 365

Leu Met Pro Thr Glu Pro Gly Pro Arg Pro Thr Leu Pro Arg Gly Leu
            370                 375                 380

Asp Glu Leu Lys Asp Gln Met Glu Glu Asp Leu Leu Arg Leu Ala Asn
385                 390                 395                 400

Ala Gln Ala Thr Ser Asp Met Met Ala Trp Ala Val Glu Gln Val Asp
            405                 410                 415

Leu Lys Thr Trp Val Lys Asn Tyr Pro Arg Trp Thr Pro Pro Pro
            420                 425                 430

Pro Pro Lys Val Gln Pro Arg Lys Thr Lys Pro Val Lys Ser Leu Pro
            435                 440                 445

Glu Arg Lys Pro Val Pro Ala Pro Arg Arg Lys Val Gly Pro Asp Cys
            450                 455                 460

Gly Ser Pro Val Ser Leu Gly Gly Asp Val Pro Asn Ser Trp Glu Asp
465                 470                 475                 480

Leu Ala Val Ser Ser Pro Leu Asp Leu Pro Thr Pro Pro Glu Pro Ala
            485                 490                 495

Thr Leu Ser Ser Glu Leu Val Ile Val Ser Ser Pro Gln Cys Ile Phe
            500                 505                 510

Arg Pro Ala Thr Pro Leu Ser Glu Pro Ala Pro Ile Pro Ala Pro Arg
            515                 520                 525

Gly Thr Val Ser Arg Pro Val Thr Pro Leu Ser Glu Pro Ile Pro Val
            530                 535                 540

Pro Ala Pro Arg Arg Lys Phe Gln Gln Val Lys Arg Leu Ser Ser Ala
545                 550                 555                 560

Ala Ala Val Pro Leu His Gln Asn Glu Pro Leu Asp Leu Ser Ala Ser
            565                 570                 575

Ser Gln Thr Glu Tyr Glu Ala Ser Pro Ser Ala Pro Pro Gln Ser Gly
            580                 585                 590

Gly Val Leu Gly Val Glu Gly His Glu Ala Glu Glu Thr Leu Ser Glu
            595                 600                 605

Ile Ser Asp Met Ser Gly Asn Ile Lys Pro Ala Ser Val Ser Ser Ser
            610                 615                 620

Ser Ser Leu Ser Ser Val Glu Ile Thr Arg Pro Lys Tyr Ser Ala Gln
625                 630                 635                 640

Ala Ile Ile Asp Ser Gly Gly Pro Cys Ser Gly His Leu Gln Gly Val
            645                 650                 655

Lys Glu Thr Cys Leu Ser Val Met Arg Glu Ala Cys Asp Ala Thr Lys
            660                 665                 670

Leu Asp Asp Pro Ala Thr Gln Glu Trp Leu Ser Arg Met Trp Asp Arg
```

```
                675                 680                 685
Val Asp Met Leu Thr Trp Arg Asn Thr Ser Val Cys Gln Ala Ile Arg
690                 695                 700

Thr Leu Asp Gly Arg Leu Lys Phe Leu Pro Lys Met Ile Leu Glu
705                 710                 715

<210> SEQ ID NO 76
<211> LENGTH: 719
<212> TYPE: PRT
<213> ORGANISM: Porcine reproductive and respiratory syndrome virus

<400> SEQUENCE: 76

Ala Gly Lys Arg Ala Arg Lys Ala Arg Ser Ser Ala Thr Ala Thr Val
  1               5                  10                  15

Ala Gly Arg Ala Leu Pro Val Arg Glu Thr Arg Gln Val Glu Glu His
                 20                  25                  30

Glu Val Ala Gly Ala Asn Lys Ala Glu His Leu Lys His Tyr Ser Pro
             35                  40                  45

Pro Ala Glu Gly Asn Cys Gly Trp His Cys Ile Ser Ala Ile Gly Asn
         50                  55                  60

Arg Met Leu Asn Ser Lys Phe Glu Thr Thr Leu Pro Glu Arg Val Arg
 65                  70                  75                  80

Pro Pro Asp Asp Trp Ala Thr Asp Glu Asp Leu Val Asn Ala Ile Gln
                 85                  90                  95

Ile Leu Arg Leu Pro Ala Ala Leu Asp Arg Asn Gly Ala Cys Ala Ser
            100                 105                 110

Ala Lys Tyr Val Leu Lys Leu Glu Gly Glu His Trp Thr Val Thr Val
        115                 120                 125

Thr Pro Gly Met Ser Pro Ser Leu Leu Pro Leu Glu Cys Val Gln Gly
    130                 135                 140

Cys Cys Glu His Lys Gly Gly Leu Gly Ser Pro Asp Ala Val Glu Val
145                 150                 155                 160

Pro Gly Phe Asp Pro Ala Cys Leu Asp Trp Leu Ala Glu Val Met His
                165                 170                 175

Leu Pro Ser Asn Ala Ile Pro Ala Ala Leu Ala Glu Met Ser Gly Asp
            180                 185                 190

Ser Asn Arg Pro Ala Ser Pro Val Thr Thr Val Trp Thr Val Ser Gln
        195                 200                 205

Phe Leu Ala Arg His Asn Gly Gly Asn His Pro Asp Gln Ile Arg Leu
    210                 215                 220

Gly Lys Ile Ile Ser Leu Cys Gln Val Ile Glu Asp Cys Cys Cys Ser
225                 230                 235                 240

Gln Asn Lys Thr Asn Arg Val Thr Pro Glu Glu Val Ala Ala Lys Ile
                245                 250                 255

Asp Leu Tyr Leu Arg Gly Ala Thr Asn Leu Glu Glu Cys Leu Ala Arg
            260                 265                 270

Leu Glu Lys Ala Arg Pro Pro Arg Val Met Asp Thr Ser Phe Asp Trp
        275                 280                 285

Asp Val Val Leu Pro Gly Val Glu Ala Ala Thr Gln Thr Thr Glu Leu
    290                 295                 300

Pro Gln Val Asn Gln Cys Arg Ala Leu Val Pro Val Val Thr Gln Lys
305                 310                 315                 320

Ser Leu Asp Asn Asn Ser Val Pro Leu Thr Ala Phe Ser Leu Ala Asn
                325                 330                 335

Tyr Tyr Tyr Arg Ala Gln Gly Asp Glu Val Arg His Arg Glu Arg Leu
```

```
                    340             345             350
Thr Ala Val Leu Ser Lys Leu Glu Gly Val Val Arg Glu Glu Tyr Gly
            355                 360                 365
Leu Met Pro Thr Gly Pro Gly Pro Arg Pro Thr Leu Pro Arg Gly Leu
    370                 375                 380
Asp Glu Leu Lys Asp Gln Met Glu Val Asp Leu Leu Lys Leu Ala Asn
385                 390                 395                 400
Ala Gln Met Thr Ser Asp Met Met Ala Trp Ala Val Glu Gln Val Asp
                405                 410                 415
Leu Lys Thr Trp Val Lys Asn Tyr Pro Arg Trp Thr Pro Pro Pro Pro
            420                 425                 430
Pro Pro Ile Val Gln Pro Arg Lys Thr Lys Leu Val Lys Ser Leu Pro
        435                 440                 445
Glu Ser Lys Pro Val Pro Ala Pro Arg Arg Lys Val Arg Ser Asp Cys
        450                 455                 460
Asp Cys Pro Thr Leu Ser Gly Asn Asn Leu Pro Asp Ser Trp Glu Asp
465                 470                 475                 480
Leu Ala Val Gly Cys Pro Ser Asp Leu Pro Thr Ser Pro Glu Pro Val
                485                 490                 495
Thr Pro Leu Ser Glu Pro Ala Ser Val Ser Ala Pro Arg Arg Ser Phe
            500                 505                 510
Arg Pro Val Lys Pro Leu Ser Glu Pro Val Pro Val Pro Ala Pro Arg
            515                 520                 525
Lys Thr Val Ser Arg Pro Ala Thr Pro Leu Ser Glu Pro Ile Pro Val
        530                 535                 540
Pro Ala Pro Arg Arg Lys Phe Gln Gln Val Glu Lys Val Asn Pro Ala
545                 550                 555                 560
Ala Ala Thr Leu Gly Cys Gln Asp Glu Phe Pro Asp Leu Ser Ala Ser
                565                 570                 575
Ser His Thr Glu Tyr Glu Ala Ser Pro Leu Val Leu Pro Gln Asn Gly
            580                 585                 590
Asp Val Leu Glu Val Glu Glu Arg Glu Ala Glu Glu Ile Leu Ser Gly
            595                 600                 605
Ile Ser Asp Ile Leu Asp Ala Ile Lys Pro Ala Ser Ala Ser Ser Ser
        610                 615                 620
Ser Ser Leu Ser Ser Val Ala Ile Thr Arg Pro Lys Tyr Ser Ala Gln
625                 630                 635                 640
Ala Ile Ile Asp Ser Gly Gly Pro Tyr Ser Gly His Leu Gln Glu Val
                645                 650                 655
Lys Glu Thr Cys Leu Ser Ile Met Ser Glu Ala Cys Asp Val Thr Lys
            660                 665                 670
Leu Asp Asp Pro Ala Thr Gln Glu Trp Leu Ser Arg Met Trp Asp Arg
        675                 680                 685
Val Asp Met Leu Thr Trp Arg Asn Thr Ser Val His Gln Ala Ser Arg
        690                 695                 700
Thr Leu Asp Asp Arg Phe Lys Phe Leu Pro Lys Met Ile Leu Glu
705                 710                 715

<210> SEQ ID NO 77
<211> LENGTH: 719
<212> TYPE: PRT
<213> ORGANISM: Porcine reproductive and respiratory syndrome virus

<400> SEQUENCE: 77

Ala Gly Lys Arg Ala Arg Lys Ala Arg Ser Gly Met Thr Thr Thr Val
```

```
  1               5                  10                 15
Ala His Arg Ala Leu Pro Ala Arg Glu Ile Gln Gln Ala Lys Lys His
                 20                 25                 30

Glu Asp Ala Gly Ala Asp Lys Ala Val His Leu Arg His Tyr Ser Pro
             35                 40                 45

Pro Ala Asp Gly Asn Cys Gly Trp His Cys Ile Ser Ala Ile Ala Asn
         50                 55                 60

Arg Met Val Asn Ser Lys Phe Glu Thr Thr Leu Pro Glu Arg Val Arg
 65                 70                 75                 80

Pro Ser Asp Asp Trp Ala Thr Asp Glu Asp Leu Val Asn Thr Ile Gln
                 85                 90                 95

Ile Leu Lys Leu Pro Ala Ala Leu Asp Arg Asn Gly Ala Cys Val Gly
                100                105                110

Ala Lys Tyr Val Leu Lys Leu Glu Gly Glu His Trp Thr Val Ser Val
            115                120                125

Thr Leu Gly Met Ser Pro Ser Leu Leu Pro Leu Glu Cys Val Gln Gly
        130                135                140

Cys Cys Glu His Lys Ser Gly Leu Gly Pro Asp Ala Val Glu Val
145                150                155                160

Phe Gly Phe Asp Pro Ala Cys Leu Asp Arg Leu Ala Glu Val Met His
                165                170                175

Leu Pro Ser Ser Val Ile Pro Ala Ala Leu Ala Glu Met Ser Gly Asp
                180                185                190

Pro Asn Cys Pro Ala Ser Pro Val Thr Thr Val Trp Thr Val Ser Gln
            195                200                205

Phe Phe Ala Arg His Arg Gly Glu His Pro Asp Gln Val Arg Leu
        210                215                220

Gly Lys Ile Ile Ser Leu Cys Gln Val Val Glu Cys Cys Cys His
225                230                235                240

Gln Asn Lys Thr Asn Arg Ala Thr Pro Glu Glu Val Ala Ala Arg Ile
                245                250                255

Asp Gln Tyr Leu His Gly Ala Thr Ser Leu Glu Glu Cys Leu Ile Arg
            260                265                270

Leu Glu Arg Val Cys Pro Pro Ser Ala Ala Asp Thr Phe Phe Asp Trp
        275                280                285

Asn Val Val Leu Pro Gly Val Gly Ala Ser Thr Gln Thr Thr Lys Gln
    290                295                300

Leu His Val Asn Gln Cys Arg Ala Leu Val Pro Val Val Thr Gln Glu
305                310                315                320

Pro Leu Asp Lys Asp Ser Val Pro Leu Thr Ala Phe Ser Leu Ser Asn
                325                330                335

Cys Tyr Tyr Pro Ala Gln Gly Asp Glu Val Arg His Arg Glu Arg Leu
            340                345                350

Asn Ser Val Leu Ser Lys Leu Glu Gly Val Val Arg Glu Glu Tyr Gly
        355                360                365

Leu Thr Pro Thr Glu Pro Gly Pro Arg Pro Ala Leu Pro Asn Gly Leu
    370                375                380

Val Glu Leu Lys Asp Gln Met Glu Glu Asp Leu Leu Lys Leu Val Asn
385                390                395                400

Ala Gln Ala Thr Ser Glu Met Met Ala Trp Ala Ala Glu Gln Val Asp
                405                410                415

Leu Lys Ala Trp Val Lys Asn Tyr Pro Arg Trp Thr Pro Pro Pro
                420                425                430
```

```
Pro Pro Arg Val Gln Pro Arg Lys Thr Lys Ser Val Lys Ser Leu Pro
            435                 440                 445

Gly Asn Lys Pro Val Pro Ala Pro Arg Arg Lys Val Arg Ser Asp Cys
            450                 455                 460

Gly Ser Pro Ile Leu Met Gly Asp Asn Val Pro Asp Gly Arg Glu Asp
465                 470                 475                 480

Leu Thr Val Gly Gly Pro Leu Asp Leu Ser Thr Pro Ser Glu Pro Met
                485                 490                 495

Thr Pro Leu Ser Glu Pro Ala Leu Met Pro Ala Leu Gln Tyr Ile Ser
            500                 505                 510

Arg Pro Val Thr Ser Leu Ser Val Leu Ala Pro Val Pro Ala Pro Arg
            515                 520                 525

Phe Thr Val Ser Arg Pro Val Thr Pro Leu Ser Glu Pro Ile Phe Val
            530                 535                 540

Ser Ala Pro Arg His Lys Phe Gln Val Glu Glu Ala Asn Leu Ala
545                 550                 555                 560

Ala Thr Thr Leu Thr His Gln Asp Glu Pro Leu Asp Leu Ser Ala Ser
                565                 570                 575

Ser Gln Thr Glu Tyr Glu Ala Ser Pro Leu Thr Pro Leu Gln Asn Met
            580                 585                 590

Gly Ile Leu Glu Val Gly Gly Gln Glu Ala Glu Glu Val Leu Ser Glu
            595                 600                 605

Ile Ser Asp Thr Leu Asn Asp Ile Asn Pro Ala Pro Val Ser Ser Ser
            610                 615                 620

Ser Ser Leu Ser Ser Val Lys Ile Thr Arg Pro Lys His Ser Ala Gln
625                 630                 635                 640

Ala Ile Ile Asp Ser Gly Gly Pro Cys Ser Gly His Leu Arg Arg Glu
                645                 650                 655

Lys Glu Ala Cys Leu Ser Ile Met Arg Glu Ala Cys Asp Ala Ala Lys
            660                 665                 670

Leu Ser Asp Pro Ala Thr Gln Glu Trp Leu Ser Arg Met Trp Asp Arg
            675                 680                 685

Val Asp Met Leu Thr Trp Arg Asn Thr Ser Ala Tyr Gln Ala Phe Arg
            690                 695                 700

Ile Leu Asp Gly Arg Phe Glu Phe Leu Pro Lys Met Ile Leu Glu
705                 710                 715

<210> SEQ ID NO 78
<211> LENGTH: 719
<212> TYPE: PRT
<213> ORGANISM: Porcine reproductive and respiratory syndrome virus

<400> SEQUENCE: 78

Ala Gly Lys Arg Ala Arg Lys Ala Arg Ser Gly Met Thr Thr Thr Val
1               5                   10                  15

Ala His Arg Ala Leu Pro Ala Arg Glu Ile Gln Ala Lys Lys His
            20                  25                  30

Glu Asp Ala Gly Ala Asp Lys Ala Val His Leu Arg His Tyr Ser Pro
            35                  40                  45

Pro Ala Asp Gly Asn Cys Gly Trp His Cys Ile Ser Ala Ile Ala Asn
        50                  55                  60

Arg Met Val Asn Ser Lys Phe Glu Thr Thr Leu Pro Glu Arg Val Arg
65                  70                  75                  80

Pro Ser Asp Asp Trp Ala Thr Asp Glu Asp Leu Val Asn Thr Ile Gln
                85                  90                  95
```

-continued

```
Ile Leu Lys Leu Pro Ala Ala Leu Asp Arg Asn Gly Ala Cys Val Gly
            100                 105                 110

Ala Lys Tyr Val Leu Lys Leu Glu Gly Glu His Trp Thr Val Ser Val
        115                 120                 125

Thr Leu Gly Met Ser Pro Ser Leu Leu Pro Leu Glu Cys Val Gln Gly
        130                 135                 140

Cys Cys Glu His Lys Ser Gly Leu Gly Pro Asp Ala Val Glu Val
145                 150                 155                 160

Phe Gly Phe Asp Pro Ala Cys Leu Asp Arg Leu Ala Glu Val Met His
                165                 170                 175

Leu Pro Ser Ser Val Ile Pro Ala Ala Leu Ala Glu Met Ser Gly Asp
                180                 185                 190

Pro Asn Cys Pro Ala Ser Pro Val Thr Thr Val Trp Thr Val Ser Gln
            195                 200                 205

Phe Phe Ala Arg His Arg Gly Gly Glu His Pro Asp Gln Val Arg Leu
            210                 215                 220

Gly Lys Ile Ile Ser Leu Cys Gln Val Val Glu Cys Cys Cys His
225                 230                 235                 240

Gln Asn Lys Thr Asn Arg Ala Thr Pro Glu Glu Val Ala Ala Arg Ile
                245                 250                 255

Asp Gln Tyr Leu His Gly Ala Thr Ser Leu Glu Glu Cys Leu Ile Arg
                260                 265                 270

Leu Glu Arg Val Cys Pro Pro Ser Ala Ala Asp Thr Phe Phe Asp Trp
        275                 280                 285

Asn Val Val Leu Pro Gly Val Gly Ala Ser Thr Gln Thr Thr Lys Gln
        290                 295                 300

Leu His Val Asn Gln Cys Arg Ala Leu Val Pro Val Val Thr Gln Glu
305                 310                 315                 320

Pro Leu Asp Lys Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
            340                 345                 350

Asn Ser Val Leu Ser Lys Leu Glu Gly Val Val Arg Glu Glu Tyr Gly
            355                 360                 365

Leu Thr Pro Thr Glu Pro Gly Pro Arg Pro Ala Leu Pro Asn Gly Leu
        370                 375                 380

Val Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
            405                 410                 415

Leu Lys Ala Trp Val Lys Asn Tyr Pro Arg Trp Thr Pro Pro Pro
            420                 425                 430

Pro Pro Arg Val Gln Pro Arg Lys Thr Lys Ser Val Lys Ser Leu Pro
        435                 440                 445

Gly Asn Lys Pro Val Pro Ala Pro Arg Arg Lys Val Arg Ser Asp Cys
        450                 455                 460

Gly Ser Pro Ile Leu Met Gly Asp Asn Val Pro Asp Gly Arg Glu Asp
465                 470                 475                 480

Leu Thr Val Gly Gly Pro Leu Asp Leu Ser Thr Pro Ser Glu Pro Met
                485                 490                 495

Thr Pro Leu Ser Glu Pro Ala Leu Met Pro Ala Leu Gln Tyr Ile Ser
            500                 505                 510

Arg Pro Val Thr Ser Leu Ser Val Leu Ala Pro Val Pro Ala Pro Arg
            515                 520                 525
```

Arg Thr Val Ser Arg Pro Val Thr Pro Leu Ser Glu Pro Ile Phe Val
    530                 535                 540

Ser Ala Pro Arg His Lys Phe Gln Gln Val Glu Glu Ala Asn Leu Ala
545                 550                 555                 560

Ala Thr Thr Leu Thr His Gln Asp Glu Pro Leu Asp Leu Ser Ala Ser
                565                 570                 575

Ser Gln Thr Glu Tyr Glu Ala Ser Pro Leu Thr Pro Leu Gln Asn Met
            580                 585                 590

Gly Ile Leu Glu Val Gly Gly Gln Glu Ala Glu Glu Val Leu Ser Glu
        595                 600                 605

Ile Ser Asp Thr Leu Asn Asp Ile Asn Pro Ala Pro Val Ser Ser Ser
    610                 615                 620

Ser Ser Leu Ser Ser Val Lys Ile Thr Arg Pro Lys His Ser Ala Gln
625                 630                 635                 640

Ala Ile Ile Asp Ser Gly Gly Pro Cys Ser Gly His Leu Arg Arg Glu
                645                 650                 655

Lys Glu Ala Cys Leu Ser Ile Met Arg Lys Ala Cys Asp Ala Ala Lys
            660                 665                 670

Leu Ser Asp Pro Ala Thr Gln Glu Trp Leu Ser Arg Met Trp Asp Arg
        675                 680                 685

Val Asp Met Leu Thr Trp Arg Asn Thr Ser Ala Tyr Gln Ala Phe Arg
    690                 695                 700

Ile Leu Asp Gly Arg Phe Glu Phe Leu Pro Lys Met Ile Leu Glu
705                 710                 715

<210> SEQ ID NO 79
<211> LENGTH: 719
<212> TYPE: PRT
<213> ORGANISM: Porcine reproductive and respiratory syndrome virus

<400> SEQUENCE: 79

Ala Gly Lys Arg Ala Lys Lys Ala Arg Ser Gly Ala Thr Ala Thr Val
  1               5                  10                  15

Ala His Arg Ala Ser Pro Val Arg Glu Thr Gln Gln Ala Lys Lys His
                20                  25                  30

Glu Val Ala Asn Ala Asn Arg Ala Gly His Phe Lys Arg Tyr Ser Pro
            35                  40                  45

Pro Ala Asp Gly Asn Cys Gly Trp His Cys Ile Ser Ala Ile Ala Asn
        50                  55                  60

Arg Met Val Asn Ser Lys Phe Glu Thr Thr Leu Pro Glu Arg Val Arg
 65                  70                  75                  80

Pro Ser Asp Asp Trp Ala Thr Asp Glu Asp Leu Val Asn Thr Ile Gln
                 85                  90                  95

Ile Leu Arg Leu Pro Ala Ala Leu Asp Arg Asn Gly Ala Cys Ala Ser
            100                 105                 110

Ala Lys Tyr Val Leu Lys Leu Glu Gly Glu His Trp Thr Val Ser Val
        115                 120                 125

Thr Pro Gly Thr Ser Pro Ser Leu Leu Pro Leu Glu Cys Val Gln Gly
    130                 135                 140

Cys Cys Glu His Lys Gly Gly Leu Gly Ser Pro Asp Ala Val Glu Ile
145                 150                 155                 160

Ser Gly Phe Asp Pro Ala Cys Leu Asp Arg Leu Ala Glu Ile Met His
                165                 170                 175

Leu Pro Ser Ser Val Ile Pro Ala Ala Leu Ala Glu Met Ser Gly Asp
            180                 185                 190

```
Pro Asn Arg Pro Ala Ser Pro Val Thr Thr Val Trp Thr Val Ser Gln
            195                 200                 205

Phe Phe Ala Arg His Arg Gly Gly Glu His Pro Asp Gln Val Arg Leu
            210                 215                 220

Gly Lys Ile Ile Ser Leu Cys Gln Val Ile Glu Glu Cys Cys Cys Arg
225                 230                 235                 240

Gln Asn Asp Thr Asn Arg Val Thr Pro Glu Glu Val Ala Val Lys Ile
            245                 250                 255

Asn Gln Tyr Leu Arg Gly Ala Thr Asn Leu Glu Glu Cys Leu Thr Arg
            260                 265                 270

Leu Glu Arg Ala Cys Pro Pro Ser Ala Ala Asp Thr Ser Phe Asp Trp
            275                 280                 285

Asn Val Val Leu Pro Gly Ile Glu Ala Ala Thr Gln Thr Thr Lys Gln
            290                 295                 300

Leu His Val Asn Gln Cys Arg Ala Leu Val Pro Val Val Thr Gln Glu
305                 310                 315                 320

Pro Leu Asp Lys Asp Ser Val Pro Leu Thr Ala Phe Ser Leu Ser Asn
            325                 330                 335

Cys Tyr Tyr Pro Ala Gln Gly Asp Glu Val Arg His Arg Glu Arg Leu
            340                 345                 350

Asn Ser Val Leu Ser Lys Leu Glu Gly Val Val Arg Glu Glu Tyr Gly
            355                 360                 365

Leu Thr Pro Thr Glu Pro Gly Pro Arg Pro Ala Leu Pro Asn Gly Leu
            370                 375                 380

Asp Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
            405                 410                 415

Leu Lys Ala Trp Val Lys Asn Tyr Pro Arg Trp Thr Pro Pro Pro Pro
            420                 425                 430

Pro Pro Arg Val Gln Pro Arg Lys Thr Lys Ser Val Lys Ser Leu Pro
            435                 440                 445

Gly Asp Lys Pro Val Pro Ala Pro Arg Arg Lys Val Arg Ser Asp Cys
450                 455                 460

Gly Ser Pro Ile Leu Met Gly Asp Asn Asp Pro Asn Gly Arg Glu Asp
465                 470                 475                 480

Leu Thr Val Asp Gly Pro Leu Asp Leu Ser Thr Pro Ser Glu Pro Met
            485                 490                 495

Thr Pro Leu Gly Glu Pro Ala Leu Leu Pro Ala Leu Gln His Ile Ser
            500                 505                 510

Arg Pro Val Thr Ser Leu Ser Val Pro Ala Pro Val Pro Ala Pro Arg
            515                 520                 525

Arg Ala Val Ser Arg Pro Val Thr Pro Leu Ser Glu Pro Ile Phe Glu
            530                 535                 540

Ser Ala Pro Arg His Lys Leu Gln Gln Val Glu Glu Ala Asn Leu Val
545                 550                 555                 560

Ala Thr Thr Leu Thr His Gln Asp Glu Pro Leu Asp Leu Ser Ala Ser
            565                 570                 575

Ser Gln Thr Glu Tyr Glu Ala Ser Pro Leu Ala Pro Leu Gln Asn Met
            580                 585                 590

Gly Val Leu Glu Val Gly Gly Gln Glu Ala Glu Glu Val Leu Ser Glu
            595                 600                 605

Ile Ser Asp Ile Leu Asn Asp Ile Asn Pro Ala Pro Val Ser Ser Ser
```

```
                610                 615                 620
Ser Ser Leu Ser Ser Val Lys Ile Thr Arg Pro Lys Tyr Ser Ala Gln
625                 630                 635                 640

Ala Ile Ile Asp Ser Gly Gly Pro Cys Ser Gly His Leu Arg Arg Glu
                645                 650                 655

Lys Glu Ala Cys Leu Ser Ile Met Arg Lys Ala Cys Asp Ala Ala Lys
                660                 665                 670

Leu Ser Asp Pro Ala Thr Gln Glu Trp Leu Ser Arg Met Trp Asp Arg
                675                 680                 685

Val Asp Met Leu Thr Trp Arg Asn Thr Ser Ala Tyr Gln Ala Leu Arg
                690                 695                 700

Val Leu Asp Gly Arg Phe Gly Phe Leu Pro Lys Met Ile Leu Glu
705                 710                 715

<210> SEQ ID NO 80
<211> LENGTH: 725
<212> TYPE: PRT
<213> ORGANISM: Porcine reproductive and respiratory syndrome virus

<400> SEQUENCE: 80

Ala Gly Lys Arg Ala Arg Arg Ala Arg Ser Gly Ala Thr Ala Thr Val
1               5                   10                  15

Ala His Cys Ala Leu Pro Ala Arg Glu Ala Gln Gln Ala Lys Lys Leu
                20                  25                  30

Glu Val Ala Ser Ala Asn Arg Ala Glu His Leu Lys Tyr Tyr Ser Pro
                35                  40                  45

Pro Ala Asp Gly Asn Cys Gly Trp His Cys Ile Ser Ala Ile Thr Asn
            50                  55                  60

Arg Met Val Asn Ser Lys Phe Glu Thr Thr Leu Pro Glu Arg Val Arg
65                  70                  75                  80

Pro Ser Asp Asp Trp Ala Thr Asp Glu Asp Leu Val Asn Thr Ile Gln
                85                  90                  95

Ile Leu Arg Leu Pro Ala Ala Leu Asp Arg Asn Gly Ala Cys Ala Gly
                100                 105                 110

Ala Lys Tyr Val Leu Lys Leu Glu Gly Glu His Trp Thr Val Ser Val
            115                 120                 125

Thr Pro Gly Met Thr Pro Ser Leu Leu Pro Leu Glu Cys Val Gln Gly
130                 135                 140

Cys Cys Glu His Lys Ser Gly Leu Gly Phe Pro Asp Val Val Glu Val
145                 150                 155                 160

Ser Gly Phe Asp Pro Ala Cys Leu Asp Arg Leu Ala Glu Ile Met His
                165                 170                 175

Leu Pro Ser Ser Val Ile Pro Ala Ala Leu Ala Glu Met Ser Asp Asp
            180                 185                 190

Phe Asn Arg Leu Ala Ser Pro Ala Ala Thr Val Trp Thr Val Ser Gln
            195                 200                 205

Phe Phe Ala Arg His Arg Gly Gly Glu His Pro Asp Gln Val Cys Leu
            210                 215                 220

Gly Lys Ile Ile Asn Leu Cys Gln Val Ile Glu Cys Cys Cys Ser
225                 230                 235                 240

Arg Asn Lys Ala Asn Arg Ala Thr Pro Glu Glu Val Ala Ala Lys Val
                245                 250                 255

Asp Gln Tyr Leu Arg Gly Ala Ala Ser Leu Gly Glu Cys Leu Ala Lys
            260                 265                 270

Leu Glu Arg Ala Arg Pro Pro Ser Ala Met Asp Thr Ser Phe Asp Trp
```

```
                    275                 280                 285
Asn Val Val Leu Pro Gly Val Glu Thr Ala Asp Gln Thr Thr Lys Gln
    290                 295                 300

Leu His Val Asn Gln Cys Arg Ala Leu Val Pro Val Thr Gln Glu
305                 310                 315                 320

Pro Leu Asp Arg Asp Ser Val Pro Leu Thr Ala Phe Ser Leu Ser Asn
                    325                 330                 335

Cys Tyr Tyr Pro Ala Gln Gly Asp Glu Val Arg His Arg Glu Arg Leu
                340                 345                 350

Asn Ser Val Leu Ser Lys Leu Glu Gly Val Val Arg Glu Glu Tyr Gly
            355                 360                 365

Leu Thr Pro Thr Gly Pro Gly Pro Arg Pro Ala Leu Pro Asn Gly Leu
        370                 375                 380

Asp Glu Leu Lys Asp Gln Met Glu Glu Asp Leu Leu Lys Leu Val Asn
385                 390                 395                 400

Ala Gln Ala Thr Ser Glu Met Met Ala Trp Ala Ala Glu Gln Val Asp
                405                 410                 415

Leu Lys Ala Trp Val Lys Asn Tyr Pro Arg Trp Thr Pro Pro Pro
                420                 425                 430

Pro Pro Arg Val Gln Pro Arg Lys Thr Lys Ser Val Lys Ser Leu Leu
            435                 440                 445

Glu Asn Lys Pro Val Pro Ala Pro Arg Arg Lys Val Arg Ser Asp Tyr
    450                 455                 460

Gly Ser Pro Ile Leu Met Gly Asp Asn Val Pro Asn Gly Trp Glu Asp
465                 470                 475                 480

Ser Thr Val Gly Gly Pro Leu Asp Leu Ser Ala Pro Ser Glu Pro Met
                485                 490                 495

Thr Pro Leu Ser Glu Pro Val Leu Val Ser Ala Pro Gln Cys Ile Ser
            500                 505                 510

Arg Pro Val Thr Ser Leu Ser Val Pro Ala Pro Val Pro Ala Pro Arg
        515                 520                 525

Arg Ala Val Ser Arg Pro Met Thr Pro Ser Ser Glu Pro Ile Phe Val
    530                 535                 540

Ser Ala Leu Arg His Lys Phe Gln Gln Val Glu Lys Ala Asn Leu Ala
545                 550                 555                 560

Ala Ala Ala Pro Met Tyr Gln Asp Glu Pro Leu Asp Leu Ser Ala Ser
                565                 570                 575

Ser Gln Thr Glu Tyr Gly Ala Ser Pro Leu Thr Pro Gln Asn Val
            580                 585                 590

Gly Ile Leu Glu Val Arg Gly Gln Glu Ala Glu Glu Val Leu Ser Glu
        595                 600                 605

Ile Ser Asp Ile Leu Asn Asp Thr Asn Pro Ala Pro Val Ser Ser Ser
    610                 615                 620

Ser Ser Leu Ser Ser Val Arg Ile Thr Arg Pro Lys Tyr Ser Ala Gln
625                 630                 635                 640

Ala Ile Ile Asp Leu Gly Gly Pro Cys Ser Gly His Leu Gln Arg Glu
                645                 650                 655

Lys Glu Ala Cys Leu Arg Ile Met Arg Glu Ala Cys Asp Ala Ala Lys
            660                 665                 670

Leu Ser Asp Pro Ala Thr Gln Glu Trp Leu Ser Arg Met Trp Asp Arg
        675                 680                 685

Val Asp Met Leu Thr Trp Arg Asn Thr Ser Ala Tyr Gln Ala Phe Arg
    690                 695                 700
```

```
Thr Leu Asp Gly Arg Phe Gly Phe Leu Pro Lys Met Ile Leu Glu Thr
705                 710                 715                 720

Pro Pro Pro Tyr Pro
                725

<210> SEQ ID NO 81
<211> LENGTH: 719
<212> TYPE: PRT
<213> ORGANISM: Porcine reproductive and respiratory syndrome virus

<400> SEQUENCE: 81

Ala Gly Lys Arg Ala Arg Lys Ala Arg Ser Gly Ala Thr Thr Met Val
 1               5                  10                  15

Ala His Arg Ala Leu Ser Ala Arg Glu Thr Arg Gln Ala Lys Lys His
                20                  25                  30

Glu Gly Ala Asp Ala Asn Lys Ala Glu His Leu Glu His Tyr Ser Pro
            35                  40                  45

Pro Ala Glu Gly Asn Cys Gly Trp His Cys Ile Ser Ala Ile Ala Asn
        50                  55                  60

Arg Met Val Asn Ser Asn Phe Glu Thr Thr Leu Pro Glu Arg Ala Arg
 65                  70                  75                  80

Pro Leu Asp Asp Trp Ala Thr Asp Glu Asp Leu Val Asn Thr Ile Gln
                 85                  90                  95

Ile Leu Arg Leu Pro Ala Ala Leu Asp Arg Asn Gly Ala Cys Thr Ser
                100                 105                 110

Ala Lys Tyr Val Leu Arg Leu Glu Gly Glu His Trp Thr Val Ser Val
            115                 120                 125

Thr Pro Gly Met Ser Pro Ser Leu Leu Pro Leu Glu Cys Val Gln Gly
        130                 135                 140

Cys Cys Glu His Lys Gly Gly Leu Gly Ser Pro Asp Ala Val Glu Val
145                 150                 155                 160

Ser Gly Phe Asp Pro Ala Cys Leu Asp Arg Leu Ala Glu Val Met His
                165                 170                 175

Leu Pro Ser Ser Ala Ile Pro Ala Ala Leu Ala Glu Met Pro Val Asp
                180                 185                 190

Ser Asn Arg Pro Ala Ser Pro Val Thr Thr Ala Trp Thr Val Ser Gln
            195                 200                 205

Phe Tyr Ala Arg His Arg Gly Gly Asn His Arg Asp Gln Val Cys Leu
        210                 215                 220

Gly Lys Ile Ile Ser Leu Cys Gln Val Ile Glu Asp Cys Cys Cys His
225                 230                 235                 240

Gln Asn Lys Thr Asn Arg Ala Thr Pro Glu Glu Val Ala Ala Lys Ile
                245                 250                 255

Asp Gln Tyr Leu Arg Gly Ala Thr Ser Leu Glu Glu Cys Leu Ile Lys
                260                 265                 270

Leu Glu Arg Val Ser Pro Pro Ser Ala Ala Asp Thr Ser Phe Asp Trp
            275                 280                 285

Asn Val Val Leu Pro Gly Val Glu Ala Ala Asn Gln Thr Thr Lys Gln
        290                 295                 300

Leu His Val Asn Gln Cys Arg Ala Leu Val Pro Val Val Thr Gln Glu
305                 310                 315                 320

Pro Leu Asp Lys Asp Ser Val Pro Leu Thr Ala Phe Ser Leu Ser Asn
                325                 330                 335

Cys Tyr Tyr Pro Ala Gln Gly Asp Glu Val Arg His Arg Glu Arg Leu
                340                 345                 350
```

```
Asn Ser Val Leu Ser Lys Leu Glu Gly Val Val Leu Glu Glu Tyr Gly
        355                 360                 365

Leu Met Ser Thr Gly Leu Gly Pro Arg Pro Val Leu Pro Ser Gly Leu
    370                 375                 380

Asp Glu Leu Lys Asp Gln Met Glu Glu Asp Leu Leu Lys Leu Ala Asn
385                 390                 395                 400

Ala Gln Ala Thr Ser Glu Met Met Ala Trp Ala Ala Glu Gln Val Asp
                405                 410                 415

Leu Lys Ala Trp Val Lys Ser Tyr Pro Arg Trp Thr Pro Pro Pro Pro
                420                 425                 430

Pro Pro Arg Val Gln Pro Arg Lys Thr Lys Pro Val Lys Ser Leu Pro
            435                 440                 445

Glu Asn Lys Pro Val Pro Ala Pro Arg Arg Lys Val Gly Ser Asp Cys
        450                 455                 460

Gly Ser Pro Ile Leu Met Gly Asp Asn Val Pro Asn Gly Trp Glu Asp
465                 470                 475                 480

Phe Ala Val Gly Gly Pro Leu Asp Phe Pro Thr Pro Ser Glu Pro Met
                485                 490                 495

Thr Pro Leu Ser Glu Pro Val Leu Met Pro Ala Ser Gln His Ile Pro
            500                 505                 510

Arg Pro Val Thr Pro Leu Ser Gly Pro Ala Pro Val Pro Ala Pro Arg
        515                 520                 525

Arg Thr Val Ser Arg Pro Met Thr Pro Leu Ser Glu Pro Ile Phe Val
    530                 535                 540

Ser Ala Pro Arg His Lys Phe Gln Gln Val Glu Ala Asn Pro Ala
545                 550                 555                 560

Ala Thr Thr Leu Thr Tyr Gln Asp Glu Pro Leu Asp Leu Ser Ala Phe
                565                 570                 575

Ser Gln Thr Glu Cys Glu Ala Ser Pro Leu Ala Pro Leu Gln Asn Met
            580                 585                 590

Gly Ile Leu Glu Ala Gly Gly Gln Glu Ala Glu Glu Val Leu Ser Gly
        595                 600                 605

Ile Ser Asp Ile Leu Asn Asp Ile Asn Pro Ala Pro Val Ser Ser Ser
610                 615                 620

Ser Ser Leu Ser Ser Val Arg Ile Thr Arg Pro Lys Tyr Ser Ala Gln
625                 630                 635                 640

Ala Ile Ile Asp Ser Gly Gly Pro Cys Ser Gly His Leu Gln Arg Glu
                645                 650                 655

Lys Glu Ala Cys Leu Ser Ile Met Arg Glu Ala Cys Asp Ala Ala Lys
                660                 665                 670

Leu Ser Asp Pro Ala Thr Gln Glu Trp Leu Ser Arg Met Trp Asp Arg
            675                 680                 685

Val Asp Met Leu Thr Trp Arg Asn Thr Ser Ala Tyr Gln Ala Leu His
        690                 695                 700

Thr Leu Asp Gly Arg Ser Gly Phe Leu Pro Lys Met Ile Leu Glu
705                 710                 715

<210> SEQ ID NO 82
<211> LENGTH: 200
<212> TYPE: PRT
<213> ORGANISM: Porcine reproductive and respiratory syndrome virus

<400> SEQUENCE: 82

Met Leu Gly Lys Cys Leu Thr Ala Gly Cys Cys Ser Arg Leu Leu Ser
  1               5                  10                  15
```

```
Leu Trp Cys Ile Val Pro Phe Cys Phe Ala Val Leu Ala Asn Ala Ser
            20                  25                  30

Asn Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Ile Cys Phe Val Ile Arg Leu Ala
            115                 120                 125

Lys Asn Cys Met Ser Trp Arg Tyr Ser Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Pro
            195                 200

<210> SEQ ID NO 83
<211> LENGTH: 200
<212> TYPE: PRT
<213> ORGANISM: Porcine reproductive and respiratory syndrome virus

<400> SEQUENCE: 83

Met Leu Gly Lys Cys Leu Thr Ala Gly Trp Cys Ser Gln Leu Leu Ser
 1               5                  10                  15

Leu Gly Cys Ile Val Pro Phe Cys Phe Ala Val Leu Ala Asn Ala Ser
            20                  25                  30

Asn Asp Ser Ser Ser His Val Gln Leu Ile Tyr Asn Leu Thr Leu Cys
        35                  40                  45

Glu Leu Asn Gly Thr Asp Trp Leu Ala Asn Lys Phe Asp Trp Ala Val
 50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
            115                 120                 125

Lys Asn Cys Met Ser Trp Arg Tyr Ala Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190
```

Ser Ala Glu Gln Trp Gly Arg Pro
        195                 200

<210> SEQ ID NO 84
<211> LENGTH: 200
<212> TYPE: PRT
<213> ORGANISM: Porcine reproductive and respiratory syndrome virus

<400> SEQUENCE: 84

Met Leu Glu Lys Cys Leu Thr Ala Gly Cys Cys Ser Gln Leu Leu Ser
 1               5                  10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
    130                 135                 140

Leu Leu Asp Thr Lys Gly Gly Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 85
<211> LENGTH: 200
<212> TYPE: PRT
<213> ORGANISM: Porcine reproductive and respiratory syndrome virus

<400> SEQUENCE: 85

Met Leu Glu Lys Cys Leu Thr Ala Gly Cys Cys Ser Gln Leu Leu Ser
 1               5                  10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala

```
            115                 120                 125
Lys Asn Cys Met Ser Trp Arg Tyr Ala Cys Thr Arg Tyr Thr Asn Phe
        130                 135                 140
Leu Leu Asp Thr Lys Gly Arg Leu Tyr Arg Trp Arg Ser Pro Val Ile
145                 150                 155                 160
Ile Glu Lys Arg Gly Lys Val Glu Val Glu Gly His Leu Ile Asp Leu
                165                 170                 175
Lys Arg Val Val Leu Asp Gly Ser Val Ala Thr Pro Ile Thr Arg Val
            180                 185                 190
Ser Ala Glu Gln Trp Gly Arg Pro
            195                 200

<210> SEQ ID NO 86
<211> LENGTH: 200
<212> TYPE: PRT
<213> ORGANISM: Porcine reproductive and respiratory syndrome virus

<400> SEQUENCE: 86

Met Leu Glu Lys Cys Leu Thr Ala Gly Cys Cys Ser Arg Leu Leu Ser
1               5                   10                  15
Leu Trp Cys Ile Val Pro Phe Cys Phe Ala Val Leu Ala Asn Ala Ser
            20                  25                  30
Asn Asp Ser Ser Ser His Leu Gln Leu Ile Tyr Asn Leu Thr Leu Cys
        35                  40                  45
Glu Leu Asn Gly Thr Asp Trp Leu Ala Asn Lys Phe Asp Trp Ala Val
    50                  55                  60
Glu Ser Phe Val Ile Phe Pro Val Leu Thr His Ile Val Ser Tyr Gly
65                  70                  75                  80
Ala Leu Thr Thr Ser His Phe Leu Asp Thr Val Ala Leu Val Thr Val
                85                  90                  95
Ser Thr Ala Gly Phe Val His Gly Arg Tyr Val Leu Ser Ser Ile Tyr
            100                 105                 110
Ala Val Cys Ala Leu Ala Ala Leu Thr Cys Phe Val Ile Arg Phe Ala
        115                 120                 125
Lys Asn Cys Met Ser Trp Arg Tyr Ala Cys Thr Arg Tyr Thr Asn Phe
    130                 135                 140
Leu Leu Asp Thr Lys Gly Arg Leu Tyr Arg Trp Arg Ser Pro Val Ile
145                 150                 155                 160
Ile Glu Lys Arg Gly Lys Val Glu Val Glu Gly His Leu Ile Asp Leu
                165                 170                 175
Lys Arg Val Val Leu Asp Gly Ser Val Ala Thr Pro Ile Thr Arg Val
            180                 185                 190
Ser Ala Glu Gln Trp Gly Arg Pro
        195                 200

<210> SEQ ID NO 87
<211> LENGTH: 200
<212> TYPE: PRT
<213> ORGANISM: Porcine reproductive and respiratory syndrome virus

<400> SEQUENCE: 87

Met Leu Glu Lys Cys Leu Thr Ala Gly Cys Cys Ser Arg Leu Leu Ser
1               5                   10                  15
Leu Trp Cys Ile Val Pro Phe Cys Phe Ala Val Leu Ala Asn Ala Ser
            20                  25                  30
Asn Ser Ser Ser Ser His Leu Gln Leu Ile Tyr Asn Leu Thr Leu Cys
        35                  40                  45
```

```
Glu Leu Asn Gly Thr Asp Trp Leu Ala Asn Arg Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
        115                 120                 125

Lys Asn Cys Met Ser Trp Arg Tyr Ala Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
        195                 200

<210> SEQ ID NO 88
<211> LENGTH: 200
<212> TYPE: PRT
<213> ORGANISM: Porcine reproductive and respiratory syndrome virus

<400> SEQUENCE: 88

Met Leu Gly Lys Cys Leu Thr Ala Gly Cys Cys Ser Arg Leu Leu Ser
 1               5                  10                  15

Phe Trp Cys Ile Val Pro Phe Cys Phe Ala Val Leu Val Asn Ala Ser
                20                  25                  30

Tyr Ser Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
     50                  55                  60

Glu Ser Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                 85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Ser His Leu Ile Asp Leu
                165                 170                 175

Lys Arg Val Val Leu Asp Gly Ser Ala Ala Thr Pro Leu Thr Arg Val
            180                 185                 190

Ser Ala Glu Gln Trp Gly Arg Pro
        195                 200

<210> SEQ ID NO 89
```

```
<211> LENGTH: 200
<212> TYPE: PRT
<213> ORGANISM: Porcine reproductive and respiratory syndrome virus

<400> SEQUENCE: 89

Met Leu Gly Arg Cys Leu Thr Ala Gly Cys Cys Ser Arg Leu Leu Ser
 1               5                  10                  15

Leu Trp Cys Ile Val Pro Phe Cys Phe Ala Ala Leu Val Asn Ala Asn
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Lys Asp Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 90
<211> LENGTH: 200
<212> TYPE: PRT
<213> ORGANISM: Porcine reproductive and respiratory syndrome virus

<400> SEQUENCE: 90

Met Leu Gly Arg Cys Leu Thr Ala Gly Cys Cys Ser Arg Leu Leu Ser
 1               5                  10                  15

Leu Trp Cys Ile Val Pro Phe Cys Phe Ala Ala Leu Val Asn Ala Asn
            20                  25                  30

Ser Asn Ser Ser Ser His Leu Gln Leu Ile Tyr Asn Leu Thr Leu Cys
        35                  40                  45

Glu Leu Asn Gly Thr Asp Trp Leu Lys Asp Lys Phe Asp Trp Ala Val
 50                  55                  60

Glu Thr Phe Val Ile Phe Pro Val Leu Thr His Ile Val Ser Tyr Gly
 65                  70                  75                  80

Ala Leu Thr Thr Ser His Phe Leu Asp Thr Val Gly Leu Val Thr Val
                85                  90                  95

Ser Thr Ala Gly Phe Tyr His Gly Arg Tyr Val Leu Ser Ser Ile Tyr
            100                 105                 110

Ala Val Cys Ala Leu Ala Ala Leu Ile Cys Phe Val Ile Arg Leu Ala
        115                 120                 125

Lys Asn Cys Met Ser Trp Arg Tyr Ser Cys Thr Arg Tyr Thr Asn Phe
    130                 135                 140
```

```
Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
            180                 185                 190

Ser Ala Glu Gln Trp Gly Arg Leu
        195                 200

<210> SEQ ID NO 91
<211> LENGTH: 200
<212> TYPE: PRT
<213> ORGANISM: Porcine reproductive and respiratory syndrome virus

<400> SEQUENCE: 91

Met Leu Glu Lys Cys Leu Thr Ala Gly Cys Cys Leu Arg Leu Pro Ser
1               5                   10                  15

Leu Trp Cys Ile Val Pro Phe Cys Phe Ala Val Leu Val Asn Ala Asn
            20                  25                  30

Asn Ser Ser Ser Ser His Phe Gln Ser Ile Tyr Asn Leu Thr Leu Cys
        35                  40                  45

Glu Leu Asn Gly Thr Glu Trp Leu Ser Glu Lys Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Leu His Arg Arg Tyr Val Leu Ser Ser Val Tyr
            100                 105                 110

Ala Val Cys Ala Leu Ala Ala Leu Ile Cys Phe Ile Ile Arg Leu Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Lys Leu Tyr Arg Trp Arg Ser Pro Val Ile
145                 150                 155                 160

Ile Glu Lys Gly Gly Arg Val Glu Val Glu Gly His Leu Ile Asp Leu
                165                 170                 175

Lys Arg Val Val Leu Asp Gly Ser Ala Ala Thr Pro Leu Thr Arg Val
            180                 185                 190

Ser Ala Glu Gln Trp Gly Arg Leu
        195                 200

<210> SEQ ID NO 92
<211> LENGTH: 200
<212> TYPE: PRT
<213> ORGANISM: Porcine reproductive and respiratory syndrome virus

<400> SEQUENCE: 92

Met Leu Gly Lys Cys Leu Thr Ala Gly Cys Cys Ser Arg Leu Leu Ser
1               5                   10                  15

Leu Trp Cys Ile Val Pro Phe Cys Phe Ala Val Leu Gly Ser Ala Asn
            20                  25                  30

Ser Ser Ser Ser Ser His Phe Gln Leu Ile Tyr Asn Leu Thr Leu Cys
        35                  40                  45

Glu Leu Asn Gly Thr Asp Trp Leu Ala Glu Lys Phe Asp Trp Ala Val
    50                  55                  60

Glu Thr Phe Val Ile Phe Pro Val Leu Thr His Ile Val Ser Tyr Gly
```

```
                65                  70                  75                  80
Ala Leu Thr Thr Ser His Phe Leu Asp Thr Val Gly Leu Val Thr Val
                        85                  90                  95

Ser Thr Ala Gly Phe Tyr His Gly Arg Tyr Val Leu Ser Ser Ile Tyr
                100                 105                 110

Ala Val Cys Ala Leu Ala Ala Leu Ile Cys Phe Val Ile Arg Leu Ala
                115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
                180                 185                 190

Ser Ala Glu Gln Trp Gly Arg Leu
                195                 200

<210> SEQ ID NO 93
<211> LENGTH: 200
<212> TYPE: PRT
<213> ORGANISM: Porcine reproductive and respiratory syndrome virus

<400> SEQUENCE: 93

Met Leu Gly Lys Cys Leu Thr Thr Gly Cys Cys Ser Arg Leu Leu Ser
1               5                   10                  15

Leu Trp Cys Ile Val Pro Phe Cys Phe Ala Val Leu Val Asn Ala Asn
                20                  25                  30

Ser Asn Ser Ser Ser His Phe Gln Leu Ile Tyr Asn Leu Thr Leu Cys
            35                  40                  45

Glu Leu Asn Gly Thr Asp Trp Leu Ala Asn Lys Phe Asp Trp Ala Val
        50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                        85                  90                  95

Ser Thr Ala Gly Phe Tyr His Gly Arg Tyr Val Leu Ser Ser Ile Tyr
                100                 105                 110

Ala Val Cys Ala Leu Ala Ala Leu Ile Cys Phe Val Ile Arg Leu Ala
                115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Val Glu Lys Gly Gly Lys Val Glu Val Glu Gly His Leu Ile Asp Leu
                165                 170                 175

Lys Arg Val Val Leu Asp Gly Ser Val Ala Thr Pro Leu Thr Arg Val
                180                 185                 190

Ser Ala Glu Gln Trp Gly Arg Leu
                195                 200

<210> SEQ ID NO 94
<211> LENGTH: 123
<212> TYPE: PRT
<213> ORGANISM: Porcine reproductive and respiratory syndrome virus

<400> SEQUENCE: 94
```

```
Met Pro Asn Asn Gly Lys Gln Gln Lys Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His Thr Val
            100                 105                 110

Arg Leu Ile Arg Val Thr Ala Ser Pro Ser Ala
        115                 120
```

<210> SEQ ID NO 95
<211> LENGTH: 123
<212> TYPE: PRT
<213> ORGANISM: Porcine reproductive and respiratory syndrome virus

<400> SEQUENCE: 95

```
Met Pro Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120
```

<210> SEQ ID NO 96
<211> LENGTH: 123
<212> TYPE: PRT
<213> ORGANISM: Porcine reproductive and respiratory syndrome virus

<400> SEQUENCE: 96

```
Met Pro Asn Asn Gly Lys Gln Gln Lys Arg Lys Lys Gly Asp Gly
  1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80
```

```
Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 97
<211> LENGTH: 123
<212> TYPE: PRT
<213> ORGANISM: Porcine reproductive and respiratory syndrome virus

<400> SEQUENCE: 97

Met Pro Asn Asn Gly Lys Gln Gln Lys Arg Lys Lys Gly Asp Gly
 1               5                  10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Lys Lys Lys
            35                  40                  45

Asn Pro Glu Lys Pro His Phe Pro Leu Ala Thr Glu Asp Asp Val Arg
        50                  55                  60

His His Phe Thr Pro Ser Glu Arg Gln Leu Cys Leu Ser Ser Ile Gln
 65                 70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 98
<211> LENGTH: 123
<212> TYPE: PRT
<213> ORGANISM: Porcine reproductive and respiratory syndrome virus

<400> SEQUENCE: 98

Met Pro Asn Asn Gly Lys Gln Gln Lys Arg Lys Lys Gly Asp Gly
 1               5                  10                  15

Gln Pro Val Asn Gln Leu Cys Gln Met Leu Gly Lys Ile Ile Ala Gln
                20                  25                  30

Gln Asn Gln Ser Arg Gly Lys Gly Pro Gly Lys Lys Asn Lys Lys Lys
            35                  40                  45

Asn Pro Glu Lys Pro His Phe Pro Leu Ala Thr Glu Asp Asp Val Arg
        50                  55                  60

His His Phe Thr Pro Ser Glu Arg Gln Leu Cys Leu Ser Ser Ile Gln
 65                 70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
        115                 120

<210> SEQ ID NO 99
<211> LENGTH: 123
<212> TYPE: PRT
<213> ORGANISM: Porcine reproductive and respiratory syndrome virus

<400> SEQUENCE: 99
```

```
Met Pro Asn Asn Gly Lys Gln Gln Lys Arg Lys Gly Asp Gly
1               5                  10                 15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
                35                  40                  45

Asn Pro Glu Lys Pro His Phe Pro Leu Ala Thr Glu Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
                100                 105                 110

Arg Leu Ile Arg Val Thr Ala Ser Pro Ser Ala
            115                 120
```

<210> SEQ ID NO 100
<211> LENGTH: 123
<212> TYPE: PRT
<213> ORGANISM: Porcine reproductive and respiratory syndrome virus

<400> SEQUENCE: 100

```
Met Pro Asn Asn Gly Lys Gln Gln Lys Lys Lys Gly Asp Gly
1               5                  10                 15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
                35                  40                  45

Asn Pro Glu Lys Pro His Phe Pro Leu Ala Thr Glu Tyr Asp Val Arg
    50                  55                  60

His His Phe Thr Pro Ser Glu Arg Gln Leu Cys Leu Ser Ser Ile Gln
65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
                100                 105                 110

Arg Leu Ile Arg Val Thr Ala Ser Pro Ser Ala
            115                 120
```

<210> SEQ ID NO 101
<211> LENGTH: 123
<212> TYPE: PRT
<213> ORGANISM: Porcine reproductive and respiratory syndrome virus

<400> SEQUENCE: 101

```
Met Pro Asn Asn Gly Lys Gln Gln Lys Lys Lys Arg Gly Asn Gly
1               5                  10                 15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Ile Lys Asn Lys
                35                  40                  45

Asn Pro Glu Lys Pro His Phe Pro Leu Ala Thr Glu Asp Asp Val Arg
    50                  55                  60

His His Phe Thr Pro Ser Glu Arg Gln Leu Cys Leu Ser Ser Ile Gln
65                  70                  75                  80
```

```
Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Pro Ser Ser Ala
        115                 120
```

<210> SEQ ID NO 102
<211> LENGTH: 123
<212> TYPE: PRT
<213> ORGANISM: Porcine reproductive and respiratory syndrome virus

<400> SEQUENCE: 102

```
Met Pro Asn Asn Gly Lys Gln Gln Lys Lys Lys Arg Gly Asn Gly
 1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Ile Lys Asn Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Pro Ser Ser Ala
        115                 120
```

<210> SEQ ID NO 103
<211> LENGTH: 123
<212> TYPE: PRT
<213> ORGANISM: Porcine reproductive and respiratory syndrome virus

<400> SEQUENCE: 103

```
Met Pro Asn Asn Gly Lys Gln Gln Lys Lys Lys Gly Asn Gly
 1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Ile Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Pro Pro Ser Ala
        115                 120
```

<210> SEQ ID NO 104
<211> LENGTH: 123
<212> TYPE: PRT
<213> ORGANISM: Porcine reproductive and respiratory syndrome virus

<400> SEQUENCE: 104

-continued

```
Met Pro Asn Asn Gly Lys Gln Gln Lys Lys Lys Gly Asn Gly
 1               5                  10                 15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Ser Lys Lys Lys
            35                  40                  45

Asn Pro Glu Lys Pro His Phe Pro Leu Ala Thr Glu Asp Asp Val Arg
        50                  55                  60

His His Phe Thr Pro Gly Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
            115                 120

<210> SEQ ID NO 105
<211> LENGTH: 123
<212> TYPE: PRT
<213> ORGANISM: Porcine reproductive and respiratory syndrome virus

<400> SEQUENCE: 105

Met Pro Asn Asn Gly Lys Gln Arg Lys Lys Lys Gly Asn Gly
 1               5                  10                 15

Gln Pro Val Asn Gln Leu Cys Gln Met Leu Gly Lys Ile Ile Ala Gln
            20                  25                  30

Gln Asn Gln Ser Arg Gly Lys Gly Pro Gly Lys Lys Asn Lys Lys Lys
            35                  40                  45

Ser Pro Glu Lys Pro His Phe Pro Leu Ala Thr Glu Asp Asp Val Arg
        50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                85                  90                  95

Arg Ile Ser Tyr Thr Val Glu Phe Ser Leu Pro Thr His His Thr Val
            100                 105                 110

Arg Leu Ile Arg Val Thr Ala Ser Pro Ser Ala
            115                 120
```